United States Patent
Sau et al.

(10) Patent No.: US 12,083,187 B2
(45) Date of Patent: Sep. 10, 2024

(54) METHOD OF TREATMENT FOR SOLID TUMORS CONTAINING HYPOXIA AND/OR STROMA FEATURES

(71) Applicant: Wayne State University, Detroit, MI (US)

(72) Inventors: Samaresh Sau, Detroit, MI (US); Arun K. Iyer, Troy, MI (US); Hashem Alsaab, Dearborn, MI (US)

(73) Assignee: WAYNE STATE UNIVERSITY, Detroit, MI (US)

( * ) Notice: Subject to any disclaimer, the term of this patent is extended or adjusted under 35 U.S.C. 154(b) by 0 days.

(21) Appl. No.: 16/958,636

(22) PCT Filed: Dec. 28, 2018

(86) PCT No.: PCT/US2018/068019
§ 371 (c)(1),
(2) Date: Jun. 26, 2020

(87) PCT Pub. No.: WO2019/133914
PCT Pub. Date: Jul. 4, 2019

(65) Prior Publication Data
US 2020/0338211 A1 Oct. 29, 2020

Related U.S. Application Data

(60) Provisional application No. 62/612,122, filed on Dec. 29, 2017.

(51) Int. Cl.
| | | |
|---|---|---|
| A61K 47/69 | (2017.01) | |
| A61K 47/55 | (2017.01) | |
| A61K 49/00 | (2006.01) | |
| A61P 35/00 | (2006.01) | |

(52) U.S. Cl.
CPC ........ *A61K 47/6935* (2017.08); *A61K 47/551* (2017.08); *A61K 47/6911* (2017.08); *A61K 49/0045* (2013.01); *A61K 49/0052* (2013.01); *A61K 49/0084* (2013.01); *A61K 49/0093* (2013.01); *A61P 35/00* (2018.01)

(58) Field of Classification Search
CPC .............. A61K 47/6935; A61K 47/551; A61K 47/6911; A61K 49/0045; A61K 49/0052; A61K 49/0084; A61K 49/0093; A61K 9/1075; A61K 47/22; A61K 47/32; A61K 47/34; A61K 49/0041; A61P 35/00
See application file for complete search history.

(56) References Cited

U.S. PATENT DOCUMENTS

| | | |
|---|---|---|
| 9,598,441 B2 | 3/2017 | Rishi et al. |
| 2011/0020242 A1 | 1/2011 | Zheng et al. |
| 2011/0195030 A1 | 8/2011 | Mumper et al. |
| 2014/0161725 A1 | 6/2014 | Morse |
| 2016/0015661 A1 | 1/2016 | Pini et al. |
| 2017/0224831 A1 | 8/2017 | Krall et al. |
| 2017/0285040 A1 | 10/2017 | Kularatne et al. |

FOREIGN PATENT DOCUMENTS

WO  WO2016123675 A1  8/2016

OTHER PUBLICATIONS

Alsaab, et al., "PD-1 and PD-L1 Checkpoint Signaling Inhibition for Cancer Immunotherapy: Mechanism, Combinations, and Clinical Outcome," Front Pharmacology, vol. 8, 2017, 15 pgs.
Alsaab, et al., "Tumor hypoxia directed multimodal nanotherapy for overcoming drug resistance in renal cell carcinoma and reprogramming macrophages," Biomaterials, vol. 183, 2018, pp. 280-294.
Ashour, et al., "CARP-1 Functional Mimetics: A Novel Class of Small Molecule Inhibitors of Medulloblastoma Cell Growth," PLoS One, vol. 8, No. 6, 2013, 14 pgs.
Bao, et al., "In vivo imaging and quantification of carbonic anhydrase IX expression as an endogenous biomarker of tumor hypoxia," PLoS One, vol. 7, No. 11, 2012, 12 pgs.
Bellmunt, et al., "Sequential targeted therapy after pazopanib therapy in patients with metastatic renal cell cancer: efficacy and toxicity," Clin. Genitourin. Cancer, vol. 12, No. 4, 2014, pp. 262-269.
Brouwers, et al., "Carbonic anhydrase IX expression in clear cell renal cell carcinoma and normal tissues: experiences from (radio) immunotherapy," J. Clin. Oncol., vol. 26, No. 22, 2008, pp. 3808-3809.
Calvo, et al., "Improvement in survival end points of patients with metastatic renal cell carcinoma through sequential targeted therapy," Cancer Treat. Rev., vol. 50, 2016, pp. 109-117.
Cazzamlli, et al., "Linker stability influences the anti-tumor activity of acetazolamide-drug conjugates for the therapy of renal cell carcinoma," J. Control. Release, vol. 246, 2017, 18 pgs.
Cheriyan, et al., "A CARP-1 functional mimetic compound is synergistic with BRAF-targeting in non-small cell lung cancers," Oncotarget, vol. 9, No. 51, 2018, pp. 29680-29697.
Choudhury, et al., "Recent advances in TPGS-based nanoparticles of docetaxel for improved chemotherapy," International Journal of Pharmaceutics, vol. 529, No. 1-2, 2017, pp. 506-522.
Choueiri, et al., "Carbonic anhydrase IX and pathological features as predictors of outcome in patients with metastatic clear-cell renal cell carcinoma receiving vascular endothelial growth factor-targeted therapy," BJU. Int., vol. 106, No. 6, 2010, pp. 772-778.

(Continued)

*Primary Examiner* — Robert S Cabral
(74) *Attorney, Agent, or Firm* — Lee & Hayes P.C.

(57) ABSTRACT

Advancements in solid tumor (e.g., renal cell carcinoma) treatments and imaging are described. The advancements are based on nanoformulations that: (i) overcome deliverability issues associated with anti-cancer compounds; (ii) have increased targeted delivery to tumors, and hypoxic cores of tumors due to the presence of targeting ligands; (iii) have increased delivery to the hypoxic cores of tumors due to engineered shapes; (iv) provide synergistic treatment combinations; and/or (v) overcome cancer cell resistance to therapeutic treatments.

10 Claims, 65 Drawing Sheets

(56) References Cited

OTHER PUBLICATIONS

Choueiri, et al., "Carbonic anhydrase IX as a potential biomarker of efficacy in metastatic clear-cell renal cell carcinoma patients receiving sorafenib or placebo: analysis from the treatment approaches in renal cancer global evaluation trial (TARGET)," Urol. Oncol., vol. 31, No. 8, 2013, pp. 1788-1793.
De Jesus, et al., "Comparison of Folate Receptor Targeted Optical Contrast Agents for Intraoperative Molecular Imaging," Int. J. Mol. Imaging, vol. 2015, 2015, 10 pgs.
Gibney, et al., "c-Met is a prognostic marker and potential therapeutic target in clear cell renal cell carcinoma," Ann. Oncol., vol. 24, No. 2, 2013, pp. 343-349.
Hatfield, et al., "Modifications of human carboxylesterase for improved prodrug activation," Expert Opin. Drug Metab. Toxicol., vol. 4, No. 9, 2008, pp. 1153-1165.
Hsieh & Cheng, "A braided cancer river connects tumor heterogeneity and precision medicine," Clinical and Translational Medicine, vol. 5, No. 42, 2016, 3 pgs.
Hsieh, et al., "Overcome tumor heterogeneity-imposed therapeutic barriers through convergent genomic biomarker discovery: A braided cancer river model of kidney cancer," Semin. Cell Dev. Biol., vol. 64, 2017, pp. 98-106.
Iyer, et al., "Polymeric micelles of zinc protoporphyrin for tumor targeted delivery based on EPR effect and singlet oxygen generation," J. Drug Targeting, vol. 15, No. 7-8, 2007, pp. 496-506.
Kesharwani, et al., "Hyaluronic Acid Engineered Nanomicelles Loaded with 3,4-Difluorobenzylidene Curcumin for Targeted Killing of CD44+ Stem-Like Pancreatic Cancer Cells," Biomacromolecules, vol. 16, No. 9, 2015, pp. 3042-3053.
Kim, et al., "CCAR1, a key regulator of mediator complex recruitment to nuclear receptor transcription complexes," Mol. Cell., vol. 31, No. 4, 2008, pp. 510-519.
Krall, et al., "A 99mTc-Labeled Ligand of Carbonic Anhydrase IX Selectively Targets Renal Cell Carcinoma In Vivo," J. Nucl. Med., vol. 57, No. 6, 2016, pp. 943-949.
Krusch, et al., "The kinase inhibitors sunitinib and sorafenib differentially affect NK cell antitumor reactivity in vitro," J. Immunol., vol. 183, No. 12, 2009, pp. 8286-8294.
Liao, et al., "Identification of the MN/CA9 protein as a reliable diagnostic biomarker of clear cell carcinoma of the kidney," Cancer Res., vol. 57, No. 14, 1997, pp. 2827-2831.
Luong, et al., "Folic acid conjugated polymeric micelles loaded with a curcumin difluorinated analog for targeting cervical and ovarian cancers," Colloids. Surf. B. Biointerfaces, vol. 157, 2017, pp. 490-502.
Lv, et al., "Evaluation of a Carbonic Anhydrase IX-Targeted Near-Infrared Dye for Fluorescence-Guided Surgery of Hypoxic Tumors," Mol. Pharm., vol. 13, No. 5, 2016, pp. 1618-1625.
Maeda, et al., "Tumor vascular permeability and the EPR effect in macromolecular therapeutics: a review," J. Control. Release, vol. 65, No. 1-2, 2000, pp. 271-284.
Maresca, et al., "Deciphering the mechanism of carbonic anhydrase inhibition with coumarins and thiocoumarins," J. Med. Chem., vol. 53, No. 1, 2010, pp. 335-344.
McDonald & Dedhar, "Carbonic anhydrase IX (CAIX) as a mediator of hypoxia-induced stress response in cancer cells," Subcell Biochem., vol. 75, 2014, pp. 255-269.
McDonald, et al., "Recent developments in targeting carbonic anhydrase IX for cancer therapeutics, " Oncotarget, vol. 3, No. 1, 2012, pp. 84-97.
Minn, et al., "[64Cu]XYIMSR-06: A dual-motif CAIX ligand for PET imaging of clear cell renal cell carcinoma," Oncotarget, vol. 7, No. 35, 2016, pp. 56471-56479.
Muselaers, et al., "Optical Imaging of Renal Cell Carcinoma with Anti-Carbonic Anhydrase IX Monoclonal Antibody Girentuximab," J. Nucl. Med., vol. 55, No. 6, 2014, pp. 1035-1040.

O'Shannessy, et al., "Characterization of the human folate receptor alpha via novel antibody-based probes," Oncotarget, vol. 2, No. 12, 2011, pp. 1227-1243.
Oosterwijk-Wakka, et al., "Effect of tyrosine kinase inhibitor treatment of renal cell carcinoma on the accumulation of carbonic anhydrase IX-specific chimeric monoclonal antibody cG250," BJU. Int., vol. 107, No. 1, 2011, pp. 118-125.
Pena, et al., "Biomarkers predicting outcome in patients with advanced renal cell carcinoma: Results from sorafenib phase III Treatment Approaches in Renal Cancer Global Evaluation Trial," Clin. Cancer Res., vol. 16, No. 19, 2010, pp. 4853-4363.
Rishi, et al., "Cell cycle- and apoptosis-regulatory protein-1 is involved in apoptosis signaling by epidermal growth factor receptor," J. Biol. Chem., vol. 281, No. 19, 2006, pp. 13188-13198.
Rishi, et al., "Identification and characterization of a cell cycle and apoptosis regulatory protein-1 as a novel mediator of apoptosis signaling by retinoid CD437," J. Biol. Chem., vol. 278, No. 35, 2003, pp. 33422-33435.
Rivet, et al., "VEGF and VEGFR-1 are coexpressed by epithelial and stromal cells of renal cell carcinoma," Cancer, vol. 112, No. 2, 2008, pp. 433-442.
Sahu, et al., "Assessment of penetration potential of pH responsive double walled biodegradable nanogels coated with eucalyptus oil for the controlled delivery of 5-fluorouracil: In vitro and ex vivo studies," J. Control. Release, vol. 253, 2017, pp. 122-136.
Sanchez-Gastaldo, et al., "Systemic treatment of renal cell cancer: A comprehensive review," Cancer Treat. Rev., vol. 60, 2017, pp. 77-89.
Sau, et al., "Multifunctional nanoparticles for cancer immunotherapy: A groundbreaking approach for reprogramming malfunctioned tumor environment," J. Control Release., vol. 274, 2018, pp. 24-34.
Smaldone & Maranchie, "Clinical implications of hypoxia inducible factor in renal cell carcinoma," Urologic Oncology, vol. 27, No. 3, 2009, pp. 238-245.
Sosman & Puzanov, "Combination targeted therapy in advanced renal cell carcinoma," Cancer, vol. 115, No. 10, 2009, pp. 2368-2375.
Soyupak, et al., "CA9 expression as a prognostic factor in renal clear cell carcinoma," Urol. Int., vol. 74, No. 1, 2005, pp. 68-73.
Supuran, Claudiu, "Bacterial carbonic anhydrases as drug targets: toward novel antibiotics?," Front. Pharmacol., vol. 2, No. 34, 2011, 6 pgs.
Tostain, et al., "Carbonic anhydrase 9 in clear cell renal cell carcinoma: a marker for diagnosis, prognosis and treatment," Eur. J. Cancer, vol. 46, No. 18, 2010, pp. 3141-3148.
Uemura, et al., "A phase I trial of vaccination of CA9-derived peptides for HLA-A24-positive patients with cytokine-refractory metastatic renal cell carcinoma," Clin. Cancer Res., vol. 12, No. 6, 2006, pp. 1768-1775.
Voss, et al., "mTOR Inhibitors in Advanced Renal Cell Carcinoma," Hematol. Oncol. Clin. North Am., vol. 25, No. 4, 2011, pp. 835-852.
Wang, et al., "CD44 directed nanomicellar payload delivery platform for selective anticancer effect and tumor specific imaging of triple negative breast cancer," Nanomedicine, vol. 14, No. 4, 2018, pp. 1441-1454.
Weiss, et al., "First-in-human phase 1/2a trial of CRLX101, a cyclodextrin-containing polymer-camptothecin nanopharmaceutical in patients with advanced solid tumor malignancies," Invest New Drugs, vol. 31, No. 4, 2013, pp. 986-1000.
Wilhelm, et al., "Analysis of nanoparticle delivery to tumours," Nat. Rev. Mater., vol. 1, 2016, 12 pgs.
Cheriyan, et al., "A CARP-1 functional mimetic loaded vitamin E-TPGS micellar nano-formulation for inhibition of renal cell carcinoma", Oncotarget, vol. 8, No. 62, 2017, pp. 104928-104945.
Invitation to pay additional fees for Application PCT/US2018/068019, mailed on Mar. 6, 2019, 2 pgs.
PCT Search Report & Written Opinion for Application No. PCT/US19/68019, mailed on May 1, 2019, 14 pgs.
Yang, et al., "MDR1 siRNA loaded hyaluronic acid-based CD44 targeted nanoparticle systems circumvent paclitaxel resistance in ovarian cancer," Sci. Rep., vol. 5, No. 8509, 2015, 9 pgs.

(56) References Cited

OTHER PUBLICATIONS

Yu, et al., "Self-assembled methoxy poly(ethylene glycol)-cholesterol micelles for hydrophobic drug delivery," J. Pharm. Sci., vol. 102, No. 3, 2013, pp. 1054-1062.

Zhang, et al., "Nanotechnology-based combination therapy for overcoming multidrug-resistant cancer," Cancer Biol. Med., vol. 14, No. 3, 2017, pp. 212-227.

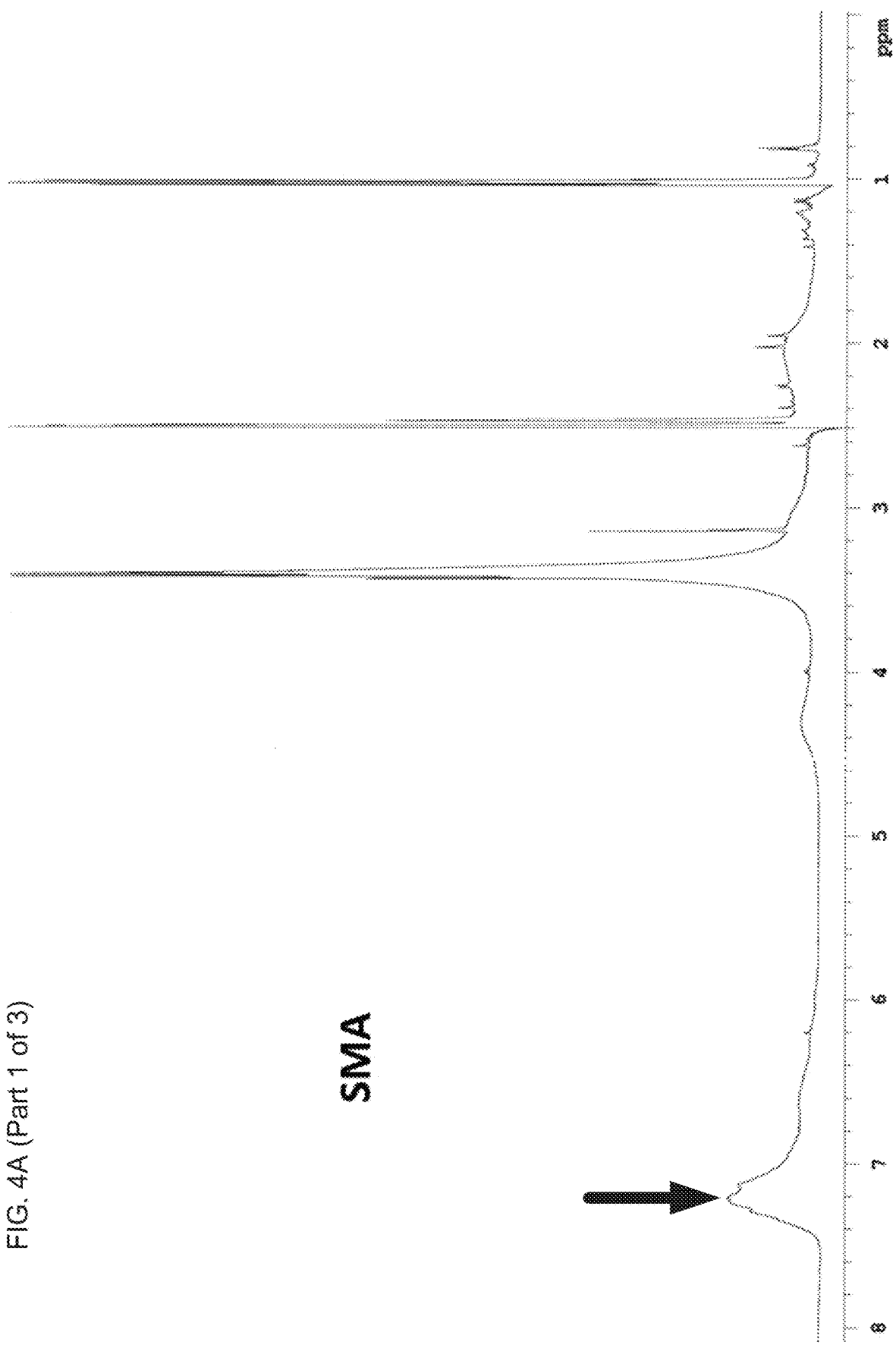
FIG. 4A (Part 1 of 3)

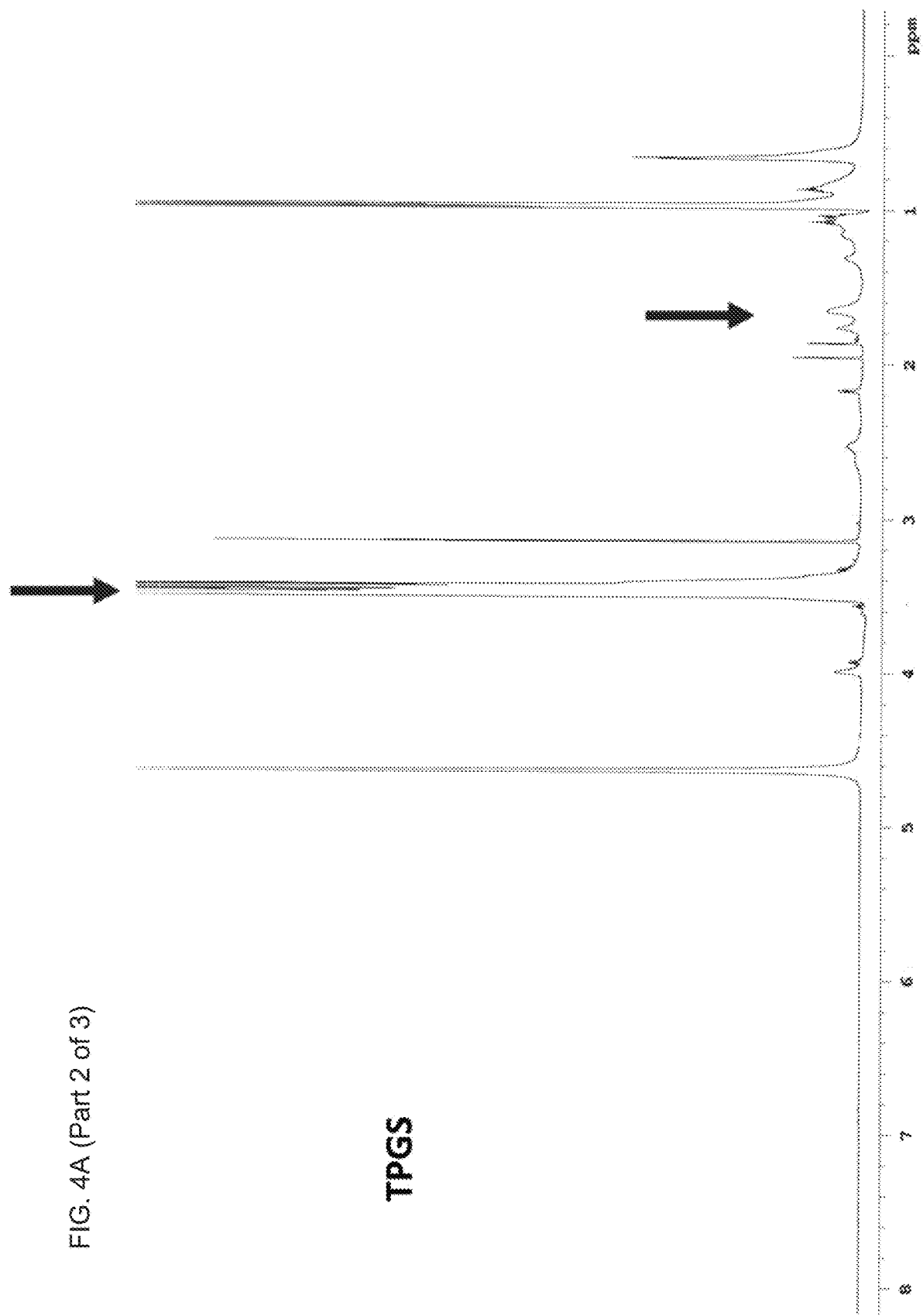
FIG. 4A (Part 2 of 3)

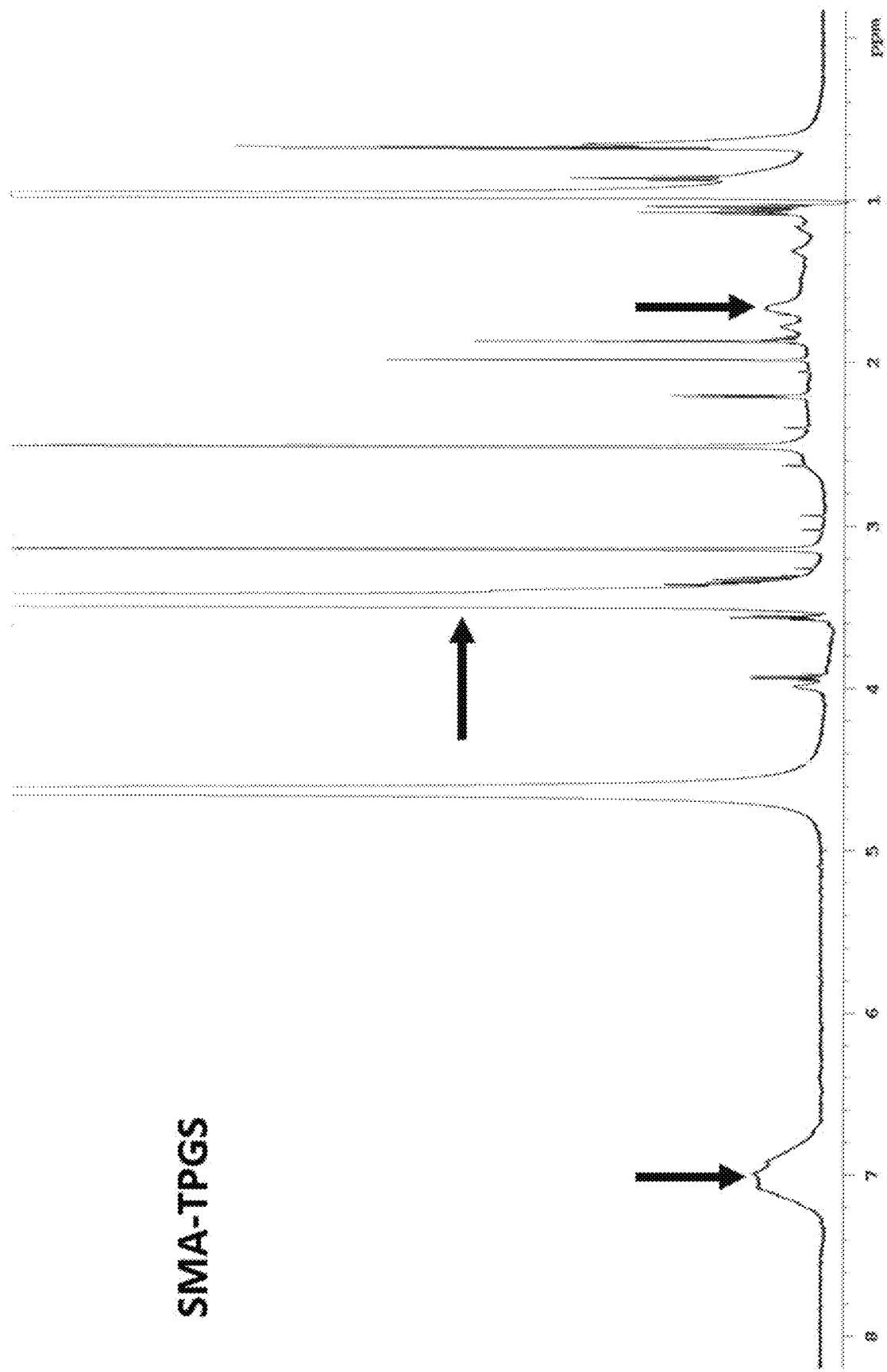
FIG. 4A (Part 3 of 3)

FIG. 4B
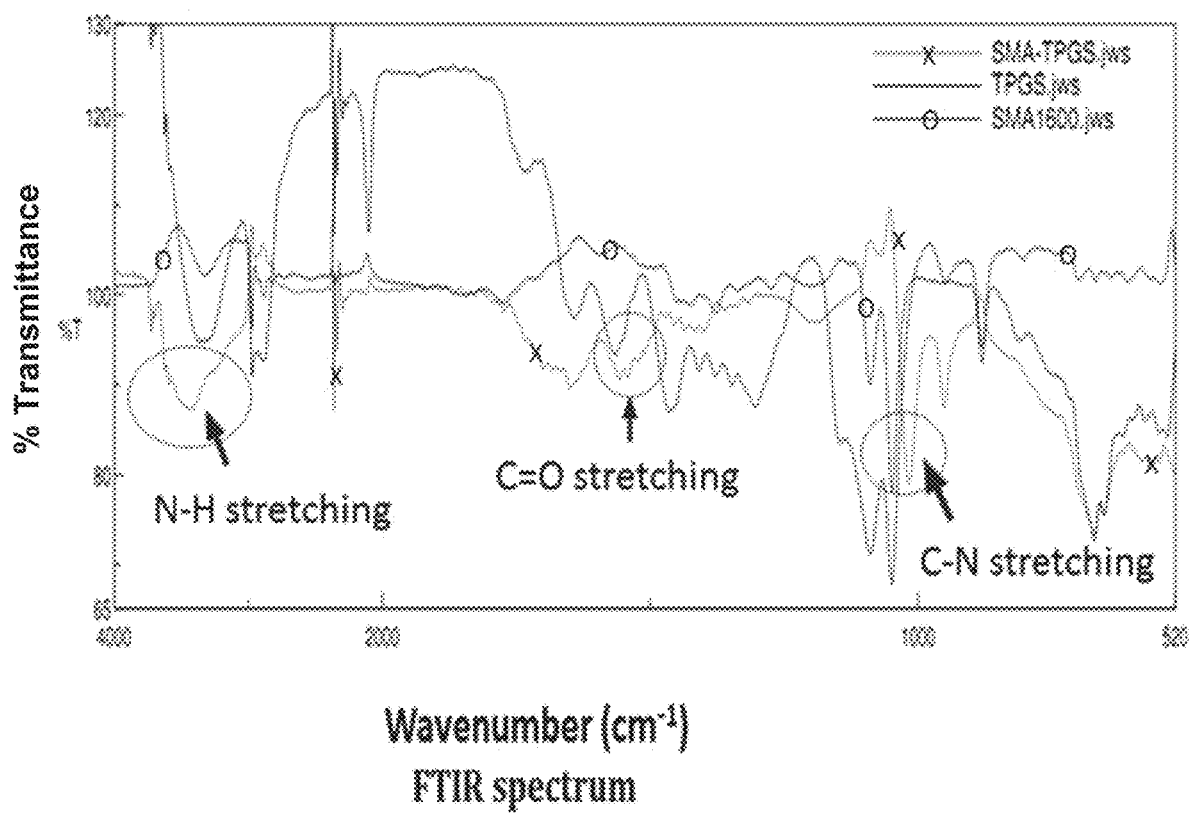
Wavenumber (cm⁻¹)
FTIR spectrum
FIG. 4C  SMA-TPGS-CFM4.16
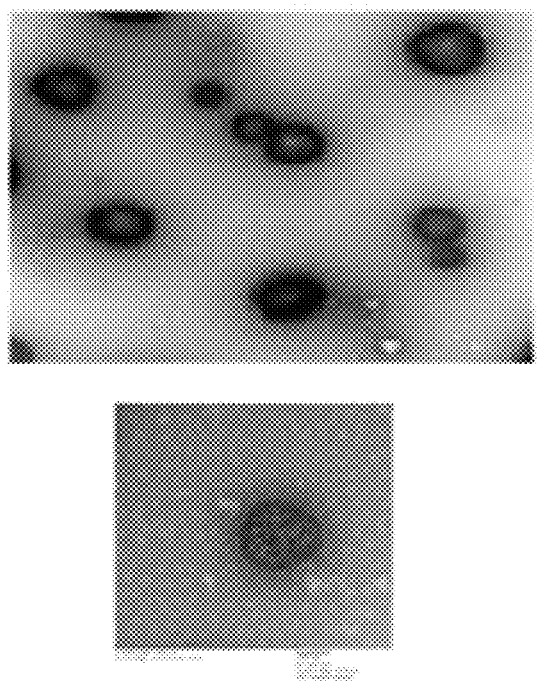

Zeta Potential : -7.86 (mV)

Amount of Drug Remaining in the Blood

FIG. 11
Patient Derived tumor Xenograft (PDX) and A498 RCC NIR-imaging and therapy
After 4 hrs
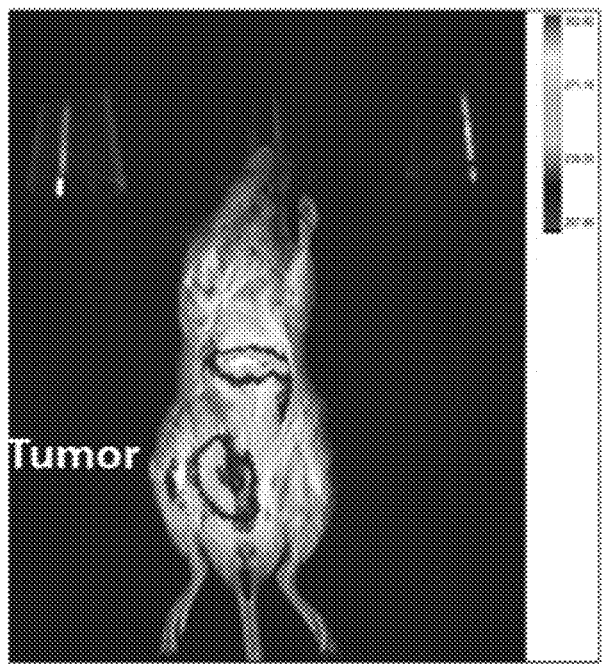
After 24hrs
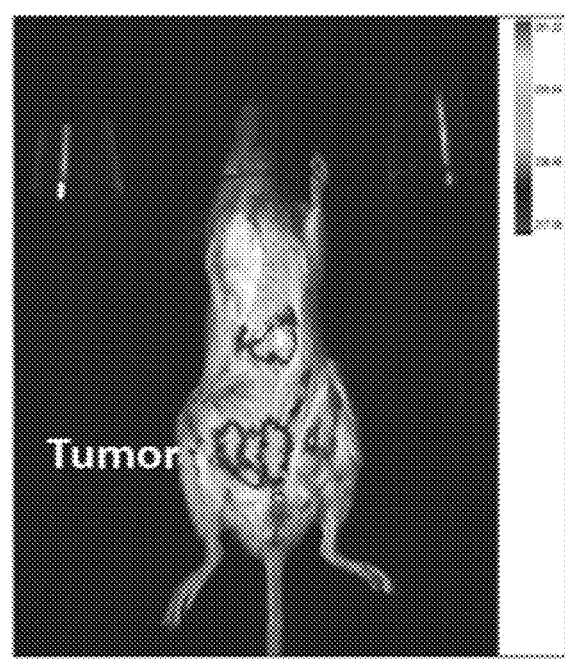
A498 RCC cells
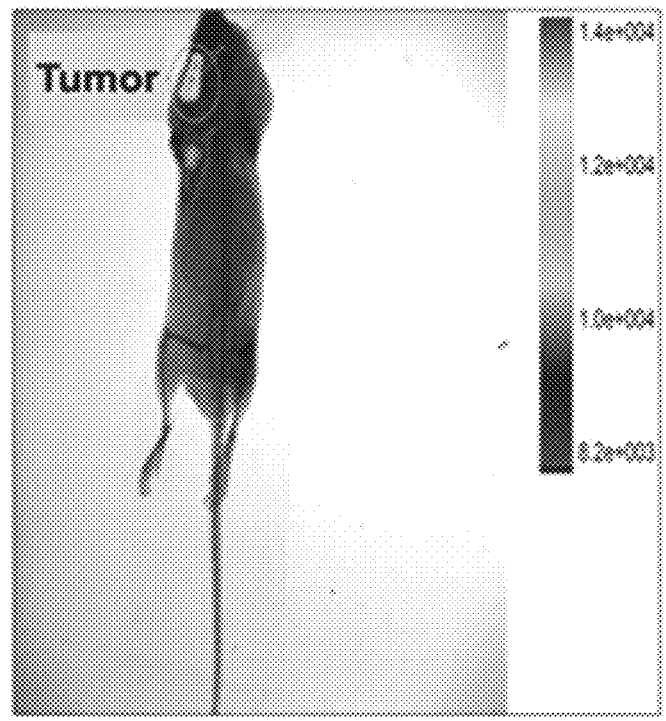
Bio-distribution study
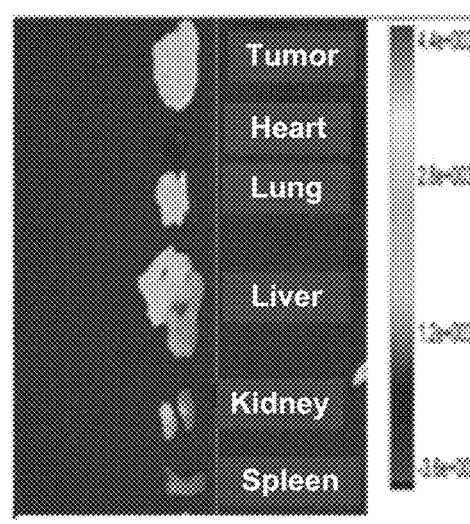

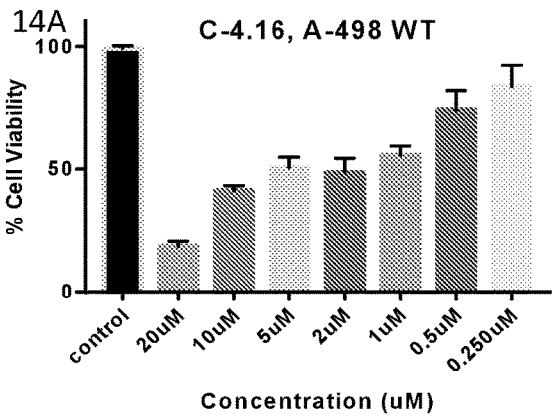
FIG. 14A C-4.16, A-498 WT
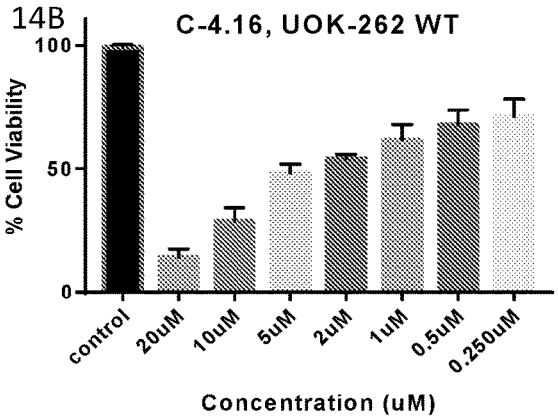
FIG. 14B C-4.16, UOK-262 WT
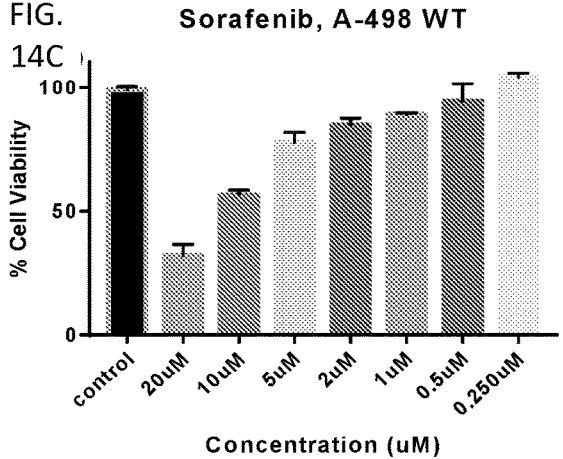
FIG. 14C Sorafenib, A-498 WT
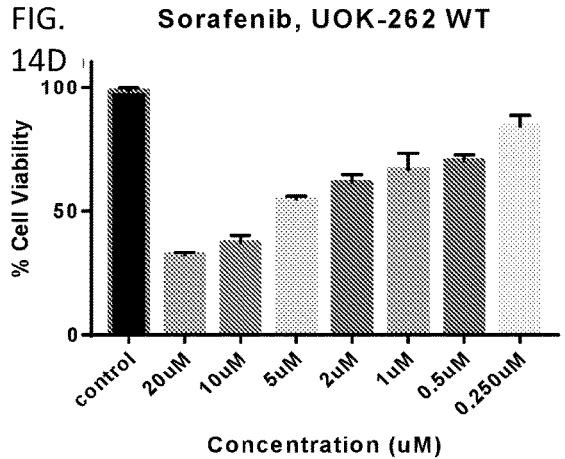
FIG. 14D Sorafenib, UOK-262 WT
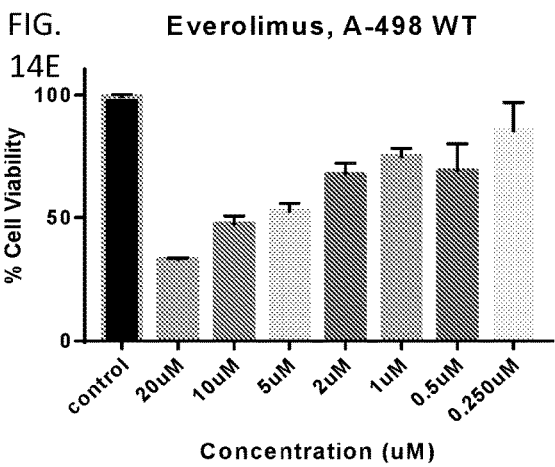
FIG. 14E Everolimus, A-498 WT
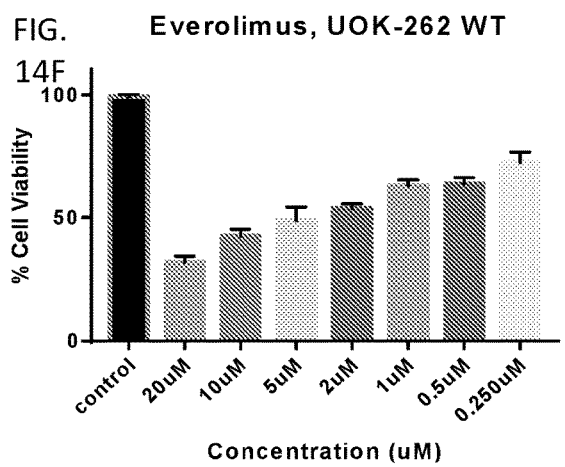
FIG. 14F Everolimus, UOK-262 WT

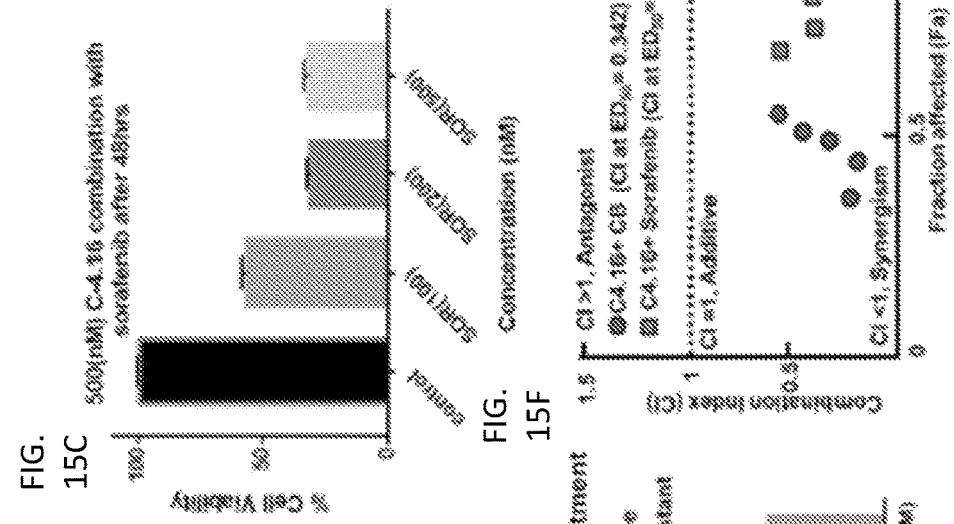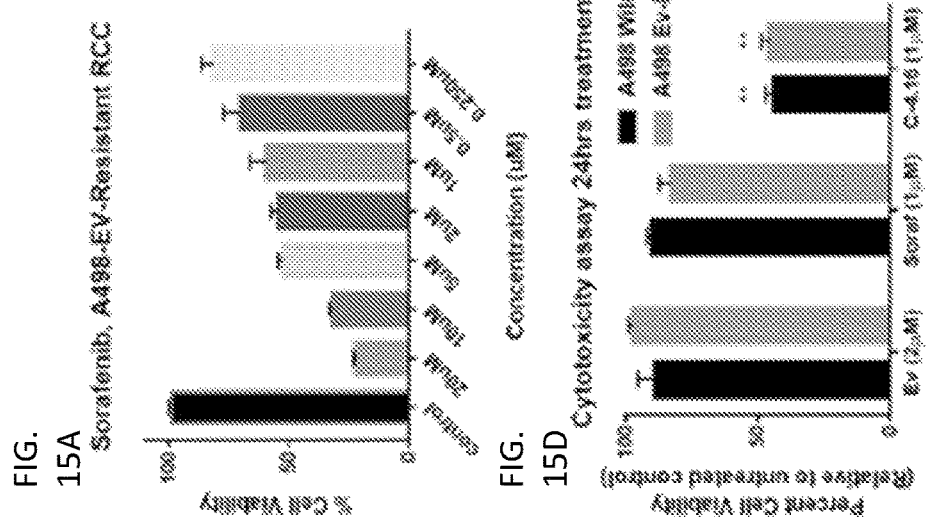
FIG. 15A FIG. 15B FIG. 15C
FIG. 15D FIG. 15E FIG. 15F

FIG. 22A  FIG. 22B  FIG. 22C
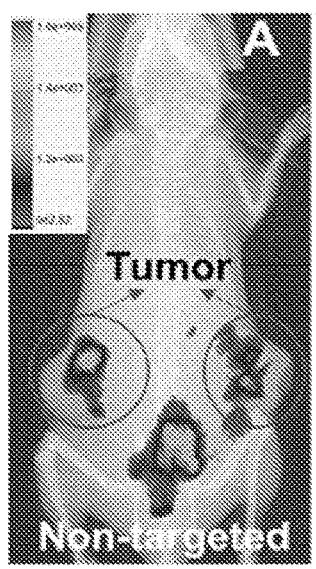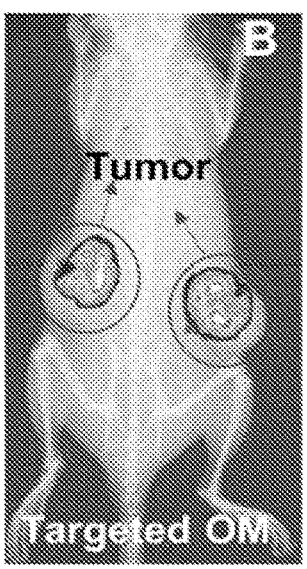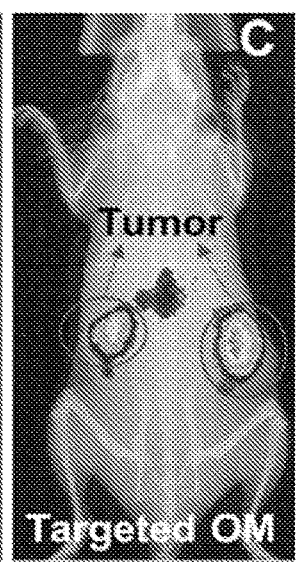
FIG. 22D
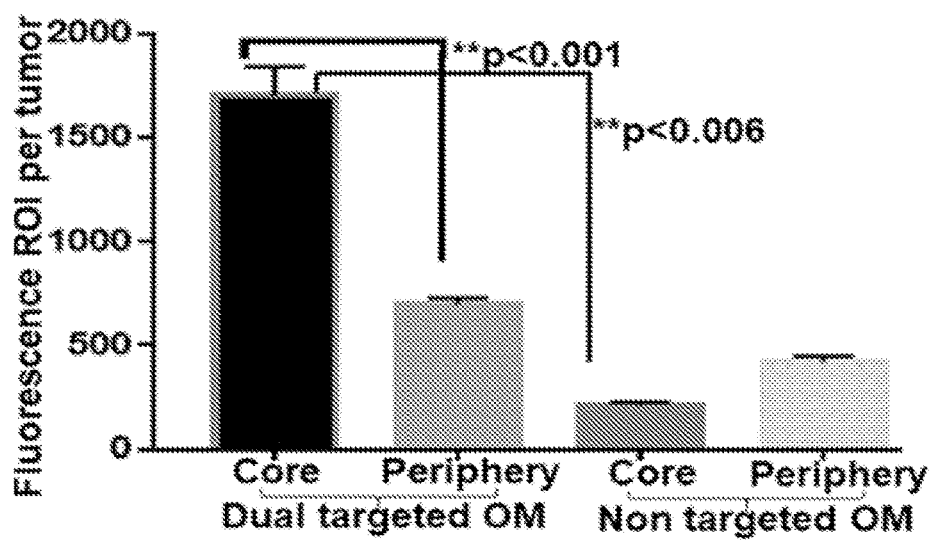
FIG. 22E
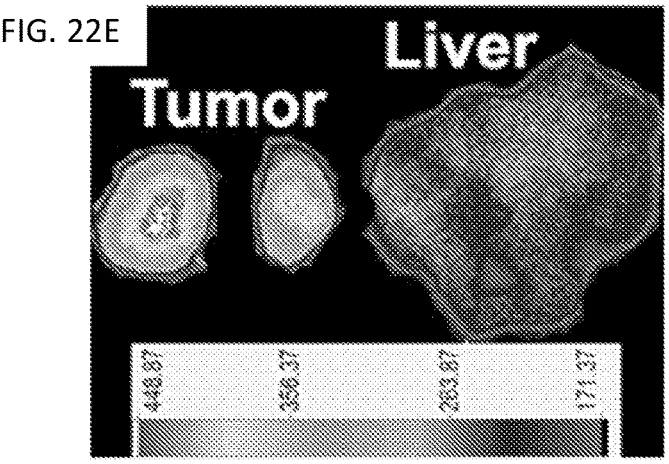

FIG. 26A
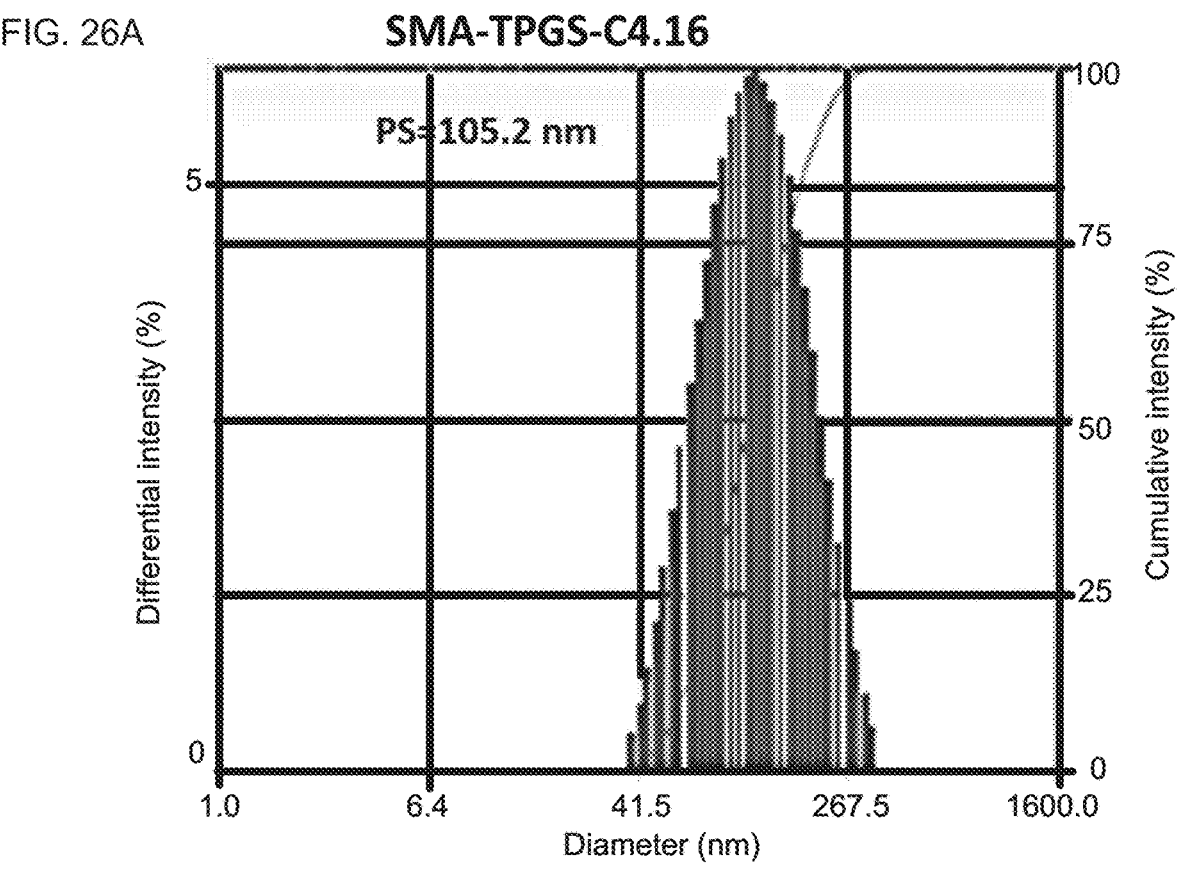
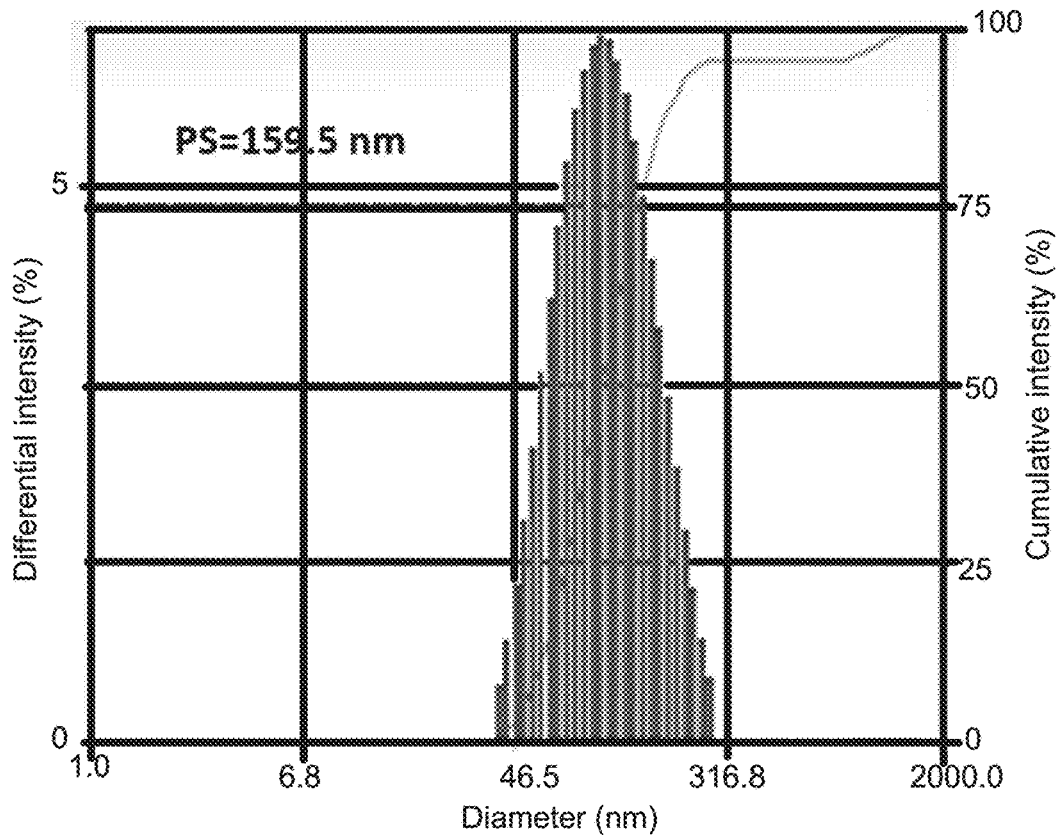

FIG. 26B
SMA-TPGS-C4.16
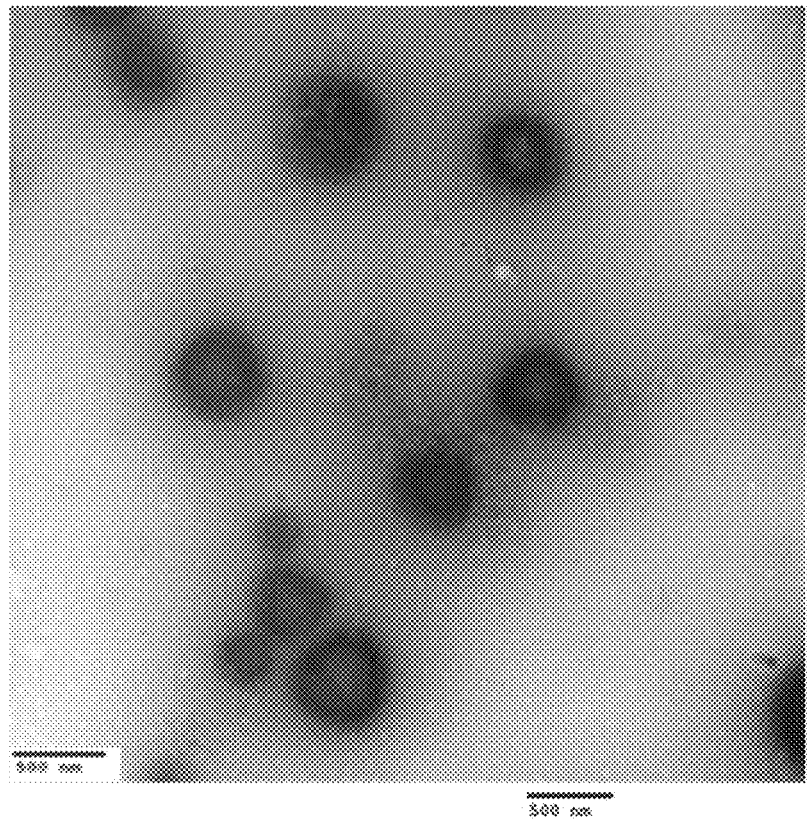
CAIX-SMA-TPGS-C4.16
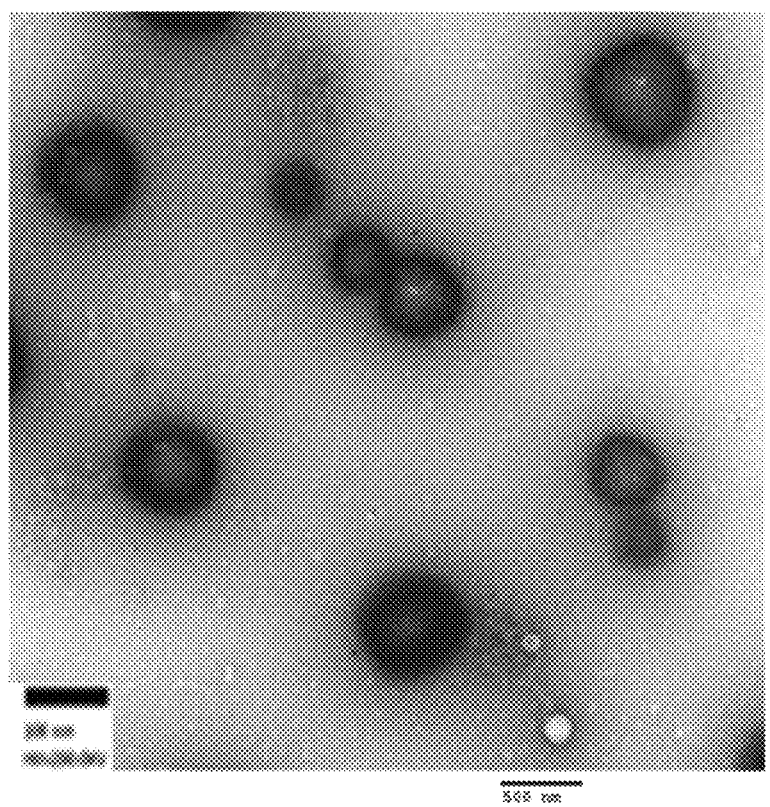

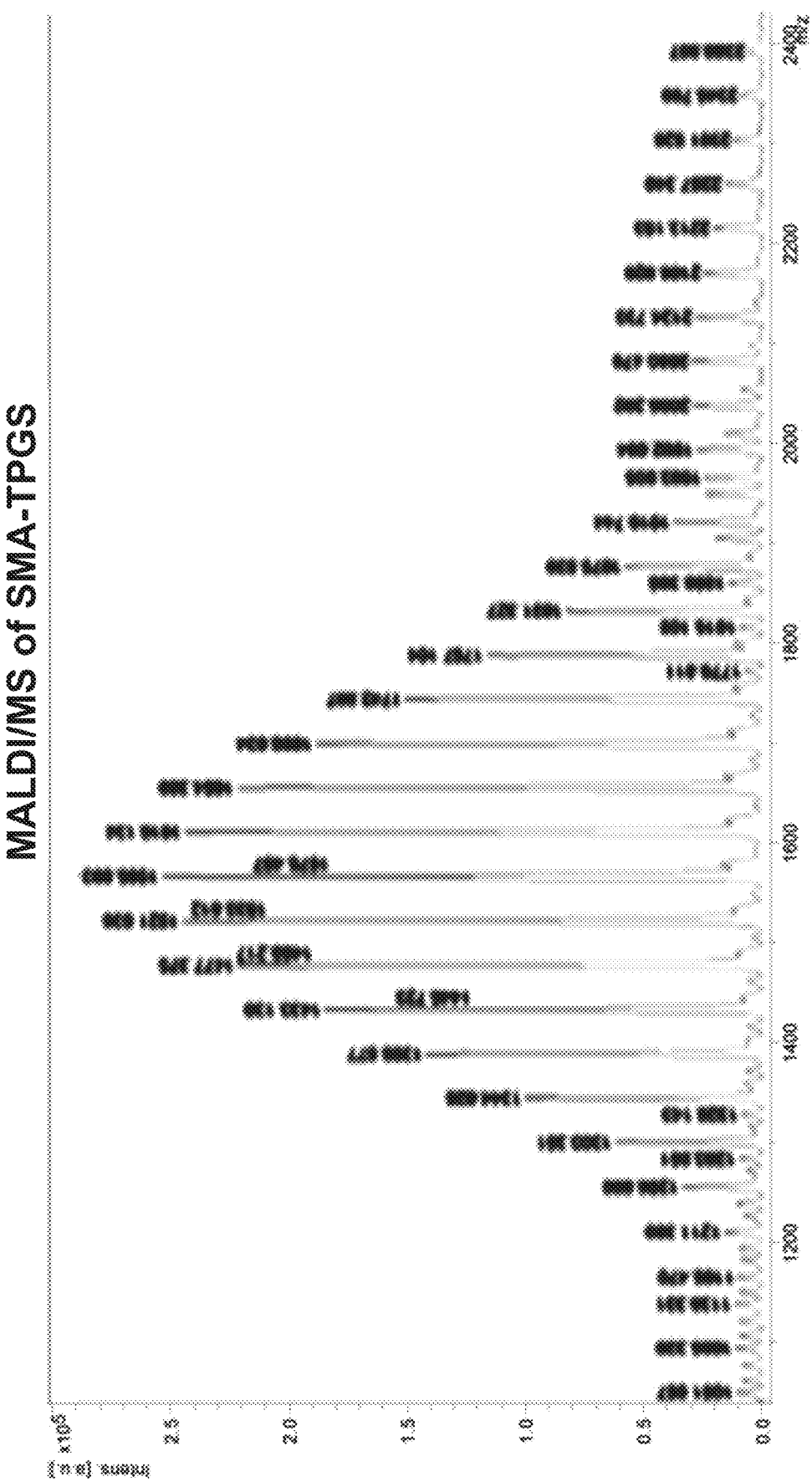
FIG. 26D (Part 1 of 2)

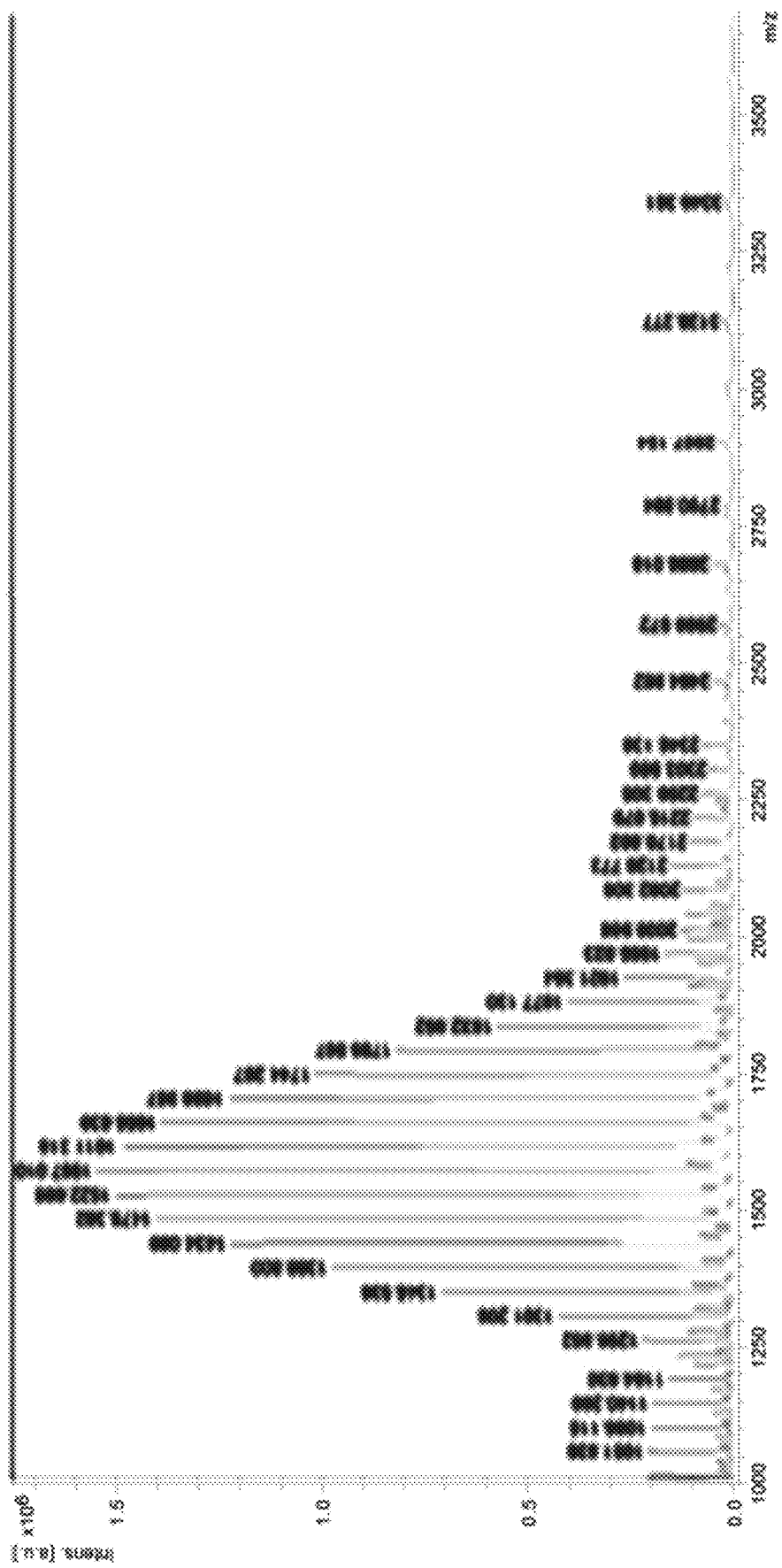
FIG. 26D (Part 2 of 2)
MALDI/MS of CAIX-SMA-TPGS

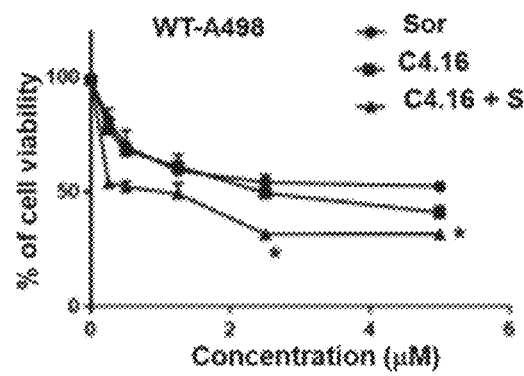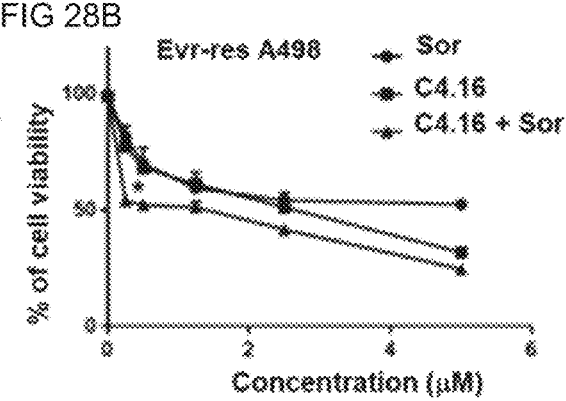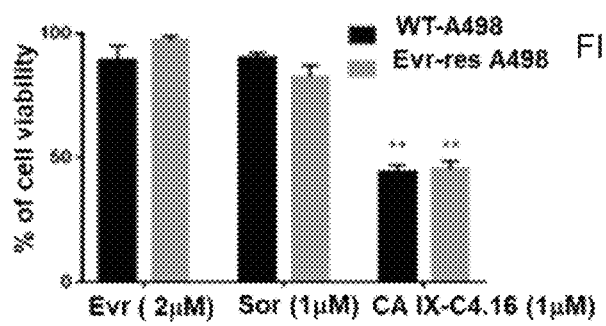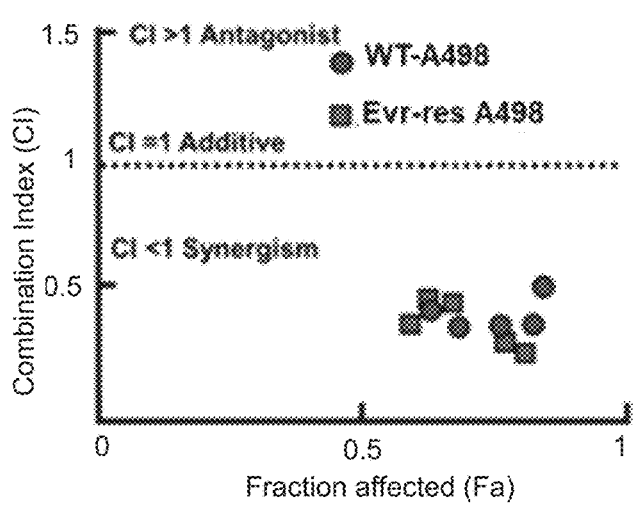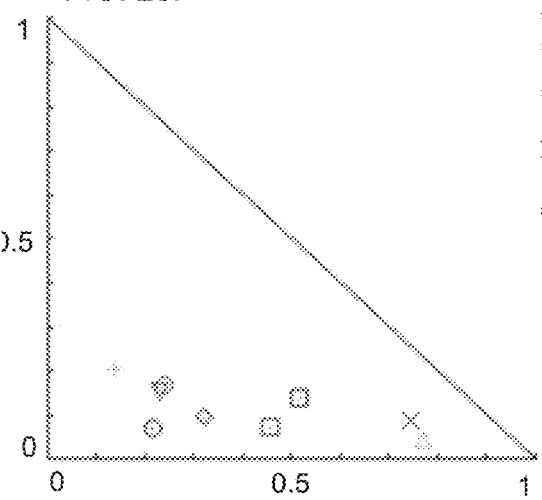

FIG. 33A
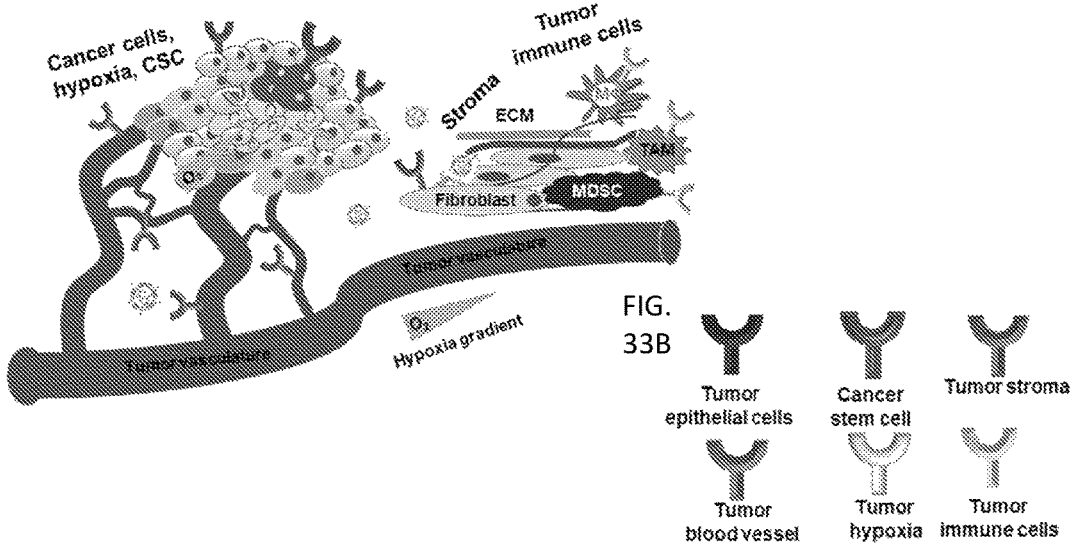
FIG. 33B
FIG. 34
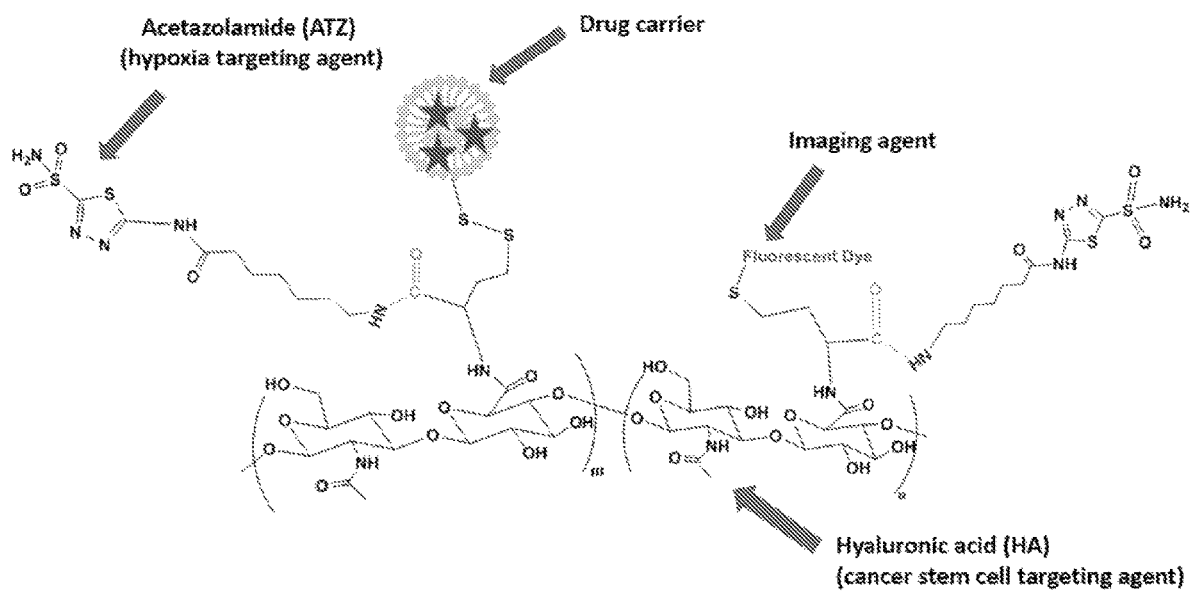

CAIX and CD44 targeting nanoformulation conjugated with Fluorescent dye

Bio-D of CAIX and CD44 targeting nanoformulation conjugated with Fluorescent dye Lung PDX Tumor

CAIX and CD44 targeting nanoformulation conjugated with Fluorescent dye

Bio-D of CAIX and CD44 targeting nanoformulation conjugated with Fluorescent dye breast PDX Tumor Receptor competition study of CAIX and CD44 targeting nanoformulation conjugated with Fluorescent dye Bio-D of Receptor competition study of CAIX and CD44 targeting nanoformulation conjugated with Fluorescent dye in PDX tumor Control FA-CA9-Rhodamine Free Rhodamine (A) SMA-TPGS-PEG-Azide

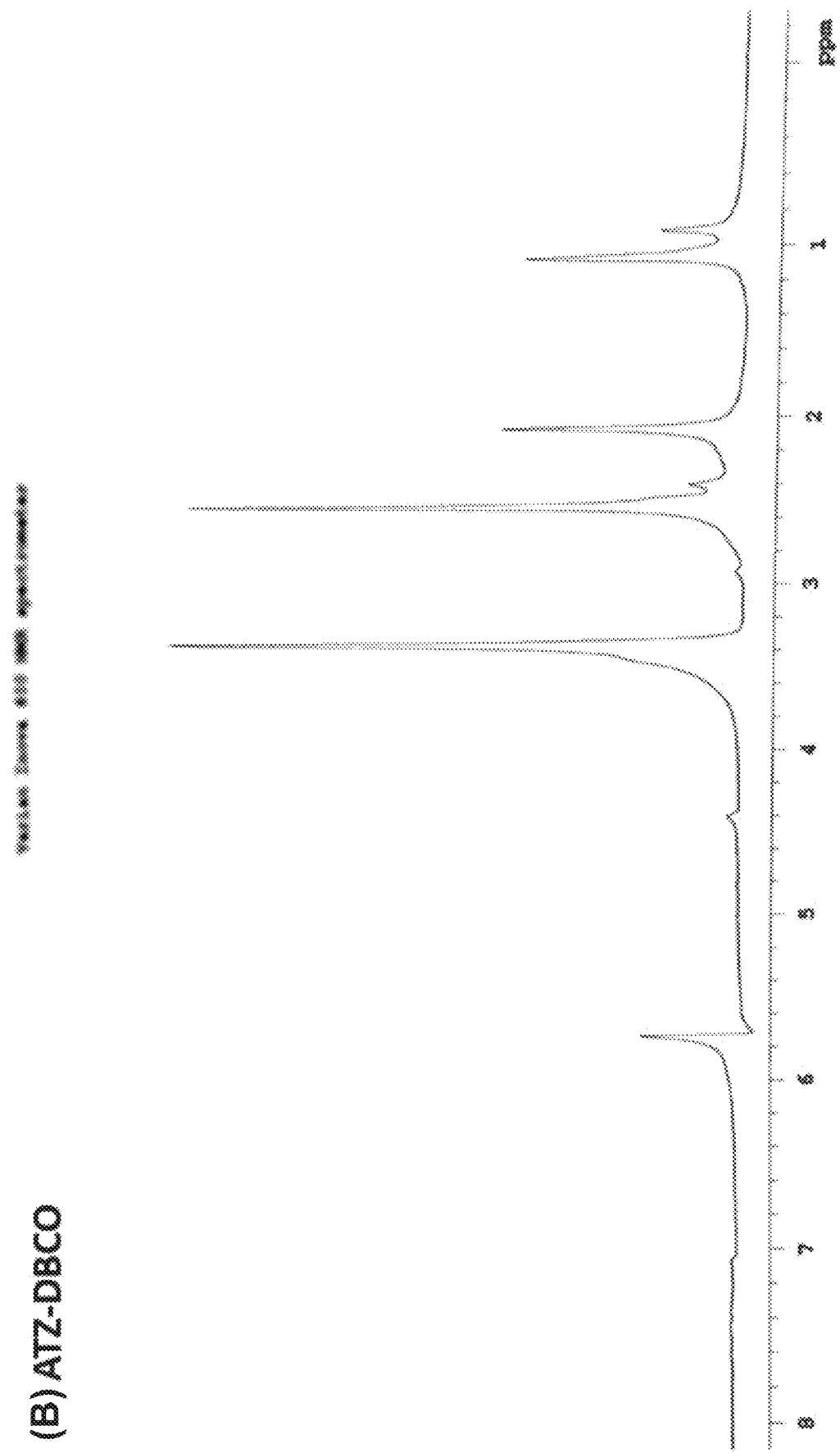
FIG. 46B (B) ATZ-DBCO

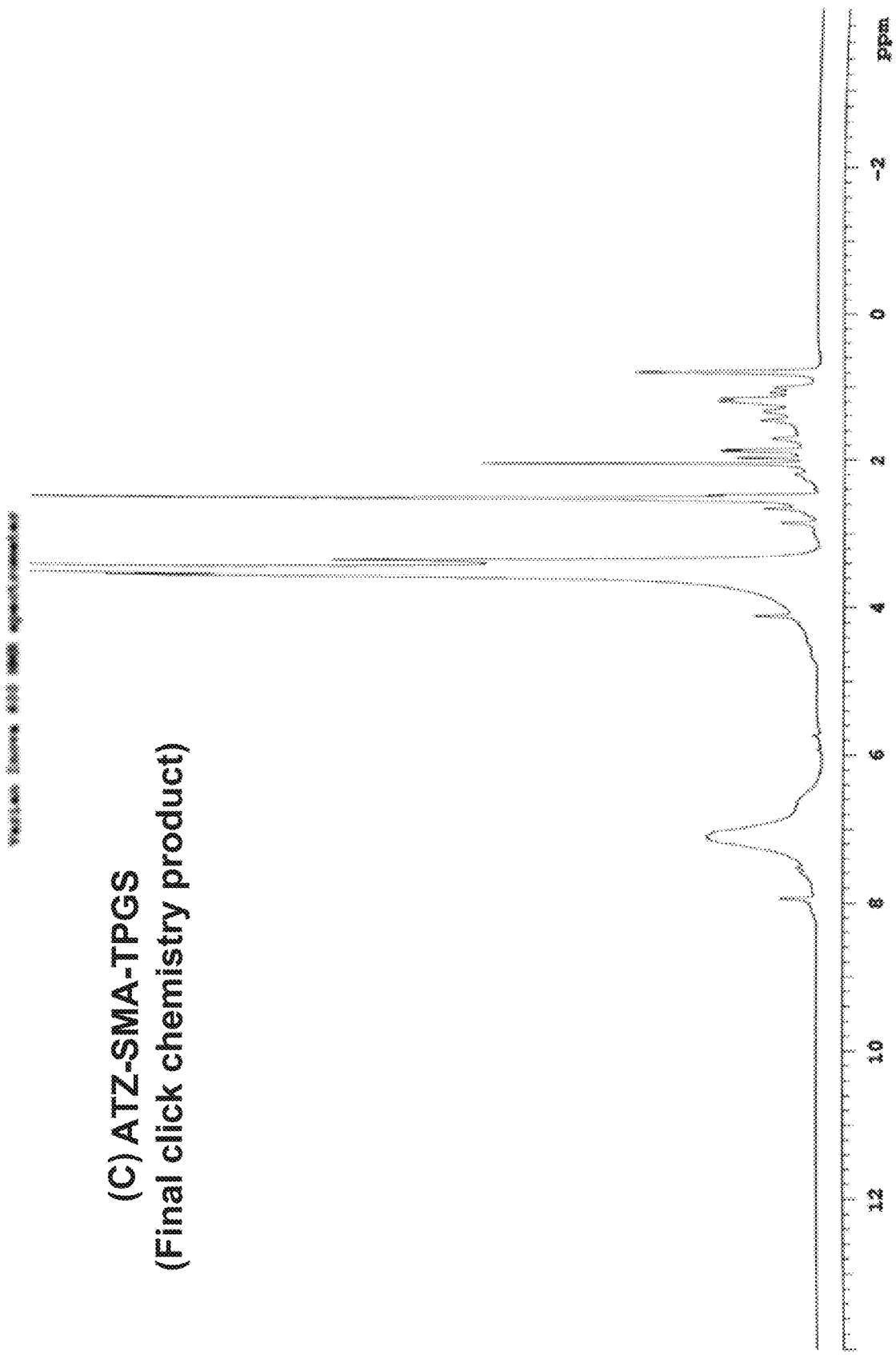
FIG. 46C (C) ATZ-SMA-TPGS (Final click chemistry product)

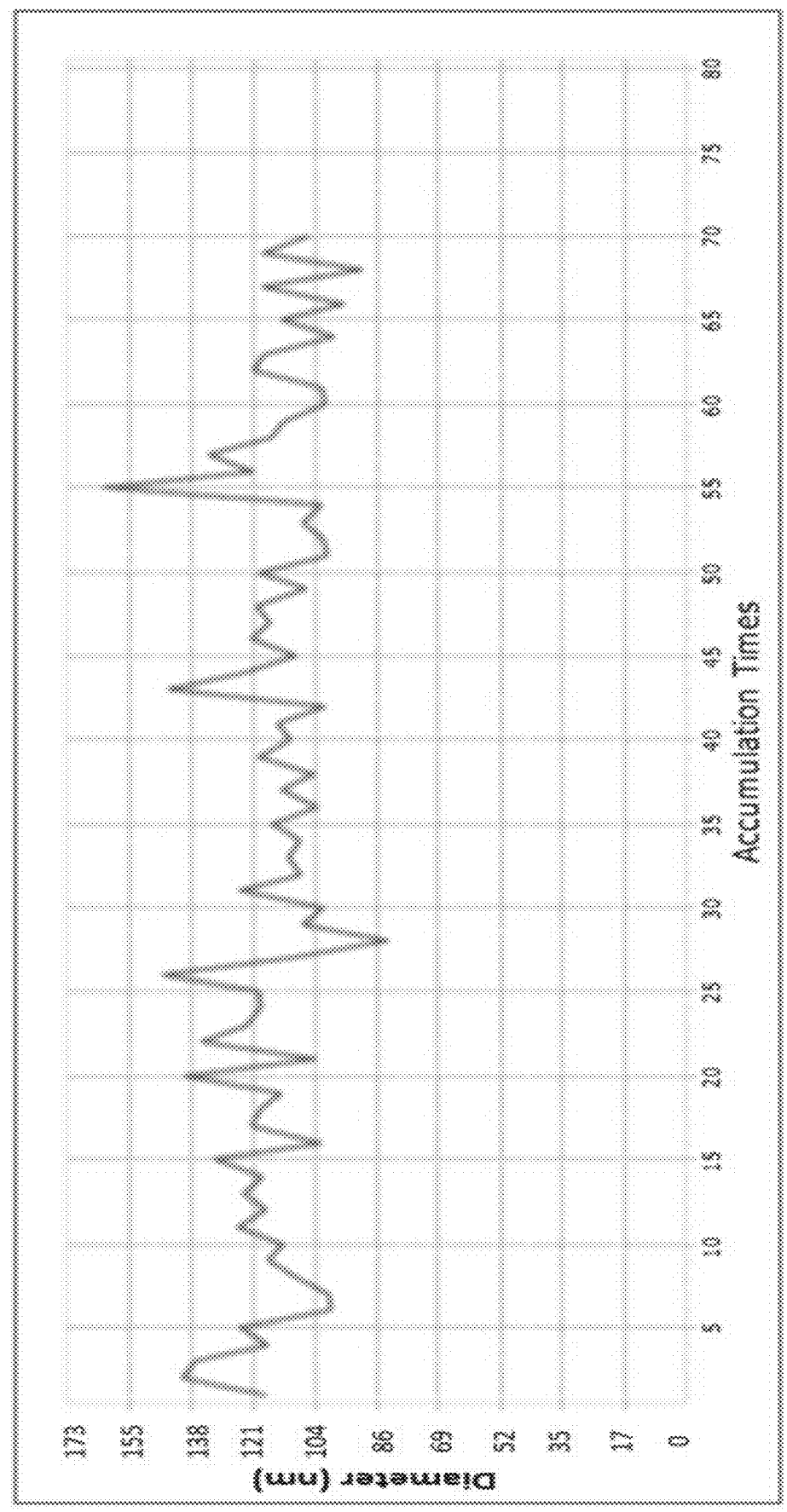
FIG. 48 (part 2 of 2)

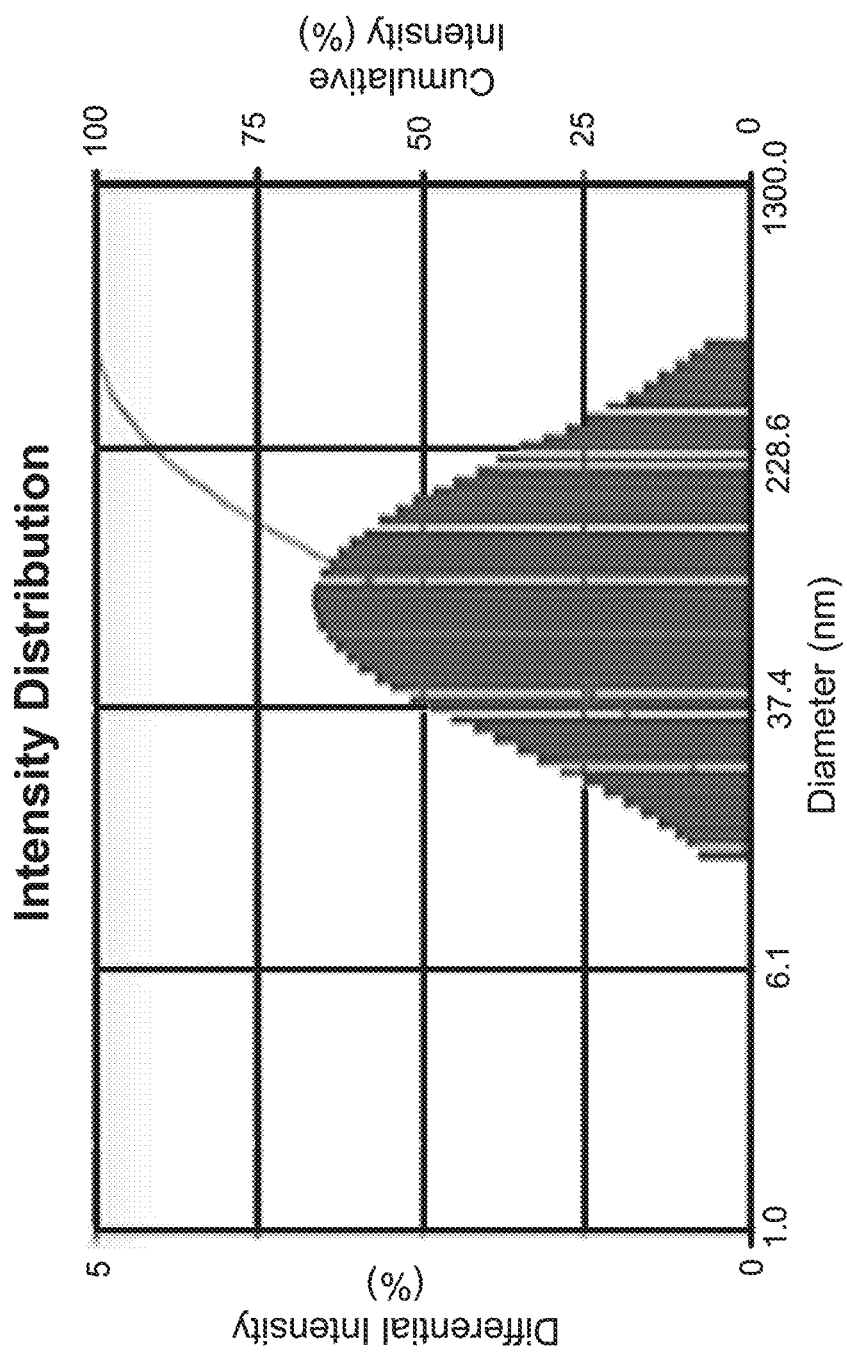
FIG. 48 (part 2 of 2)

METHOD OF TREATMENT FOR SOLID TUMORS CONTAINING HYPOXIA AND/OR STROMA FEATURES

CROSS-REFERENCE TO RELATED APPLICATIONS

This application is the 35 U.S.C. § 371 U.S. National Phase Application based on International Patent Application No. PCT/US2018/068019, which was filed on Dec. 28, 2018, which claims priority to 62/612,122 filed on Dec. 29, 2017, each of which is incorporated herein by reference in its entirety as if fully set forth herein.

FIELD OF THE DISCLOSURE

The current disclosure provides advancement of nanoformulations for therapy, and small molecule conjugates for imaging of solid tumors (including renal cell carcinoma), that: (i) overcome delivery issues associated with anti-cancer compounds; (ii) have increased targeted delivery to tumor epithelial cells, stroma, and hypoxic regions/cores of tumors due to the presence of tumor multicomponent targeting ligands; (iii) have increased delivery to the hypoxic cores of tumors due to engineered shapes; (iv) provide synergistic treatment combinations; (v) reprogram tumor immune cells to kill tumor cells; (vii) distinguish cancer lesion from non-cancer tissue by imaging; (vi) provide imaging of tumor, pre-tumor, polyps for early diagnosis and imaging guided surgery and/or (vi) overcome cancer cell resistance to therapeutic treatments.

BACKGROUND OF THE DISCLOSURE

Renal cell carcinoma (RCC) is one of the most common and deadly malignancies, and its occurrence is expected to rise in coming years. Surgery remains the best treatment option, although 20-30% of patients progress to develop metastatic disease. Currently, FDA approved treatments for metastatic RCC include tyrosine kinase inhibitors (TKIs) such as sorafenib and sunitinib and mammalian target of rapamycin (mTOR) inhibitors such as temsiorlimus and everolimus. RCC is generally very difficult to treat, however, as the cancerous cells are (or become) largely resistant to currently available therapies. When RCC fails to respond to first line therapies there are very limited secondary options. For example, everolimus is the first drug that was recently developed as a secondary treatment option for resistant RCC. To anyone affected by RCC, it is very clear that newer and more effective treatment strategies are needed. There are similar issues with the treatment of other solid tumors.

SUMMARY OF THE DISCLOSURE

The current disclosure provides important advancements in the treatment of solid tumors including RCC. Aspects of the disclosure are related to improving the deliverability of compounds that have shown promising results in pre-clinical development. Aspects of the disclosure are related to more targeted deliverability of RCC therapeutics by including targeting ligands for proteins preferentially expressed on the surface of RCC cells. Aspects of the disclosure are related to therapeutic formulations that more effectively penetrate into the hypoxic core environment of RCC tumors either through the use of targeting ligands and/or non-spherical micelles. Synergistic combination therapies as well as the ability to overcome drug resistance to treatments are also described. The current disclosure additionally provides for new imaging approaches for diagnosis and care management of RCC by utilizing targeting ligands associated with appropriate dyes.

The current disclosure is organized into several overall sections detailing the advancements disclosed herein. There is overlap between and among the sections, however, each section includes a distinct aspect of the disclosure. While not limiting the teaching of any individual section, the following are described:

SMA-TPGS block polymers to encapsulate RCC therapeutics; CA9 expression in hypoxic environments; CA9 targeting ligands; combination therapies; efficacy of various administration routes; and imaging with CA9 targeting ligands attached to an appropriate dye.

dual targeting with folate receptor and CA9 targeted oligomicelles and small molecule imaging agent; the ability of such oligomicelles to penetrate into the hypoxic core and tumor stroma of RCC tumors; and additional combination therapies; and RCC tumor imaging with small molecule imaging agent.

the ability of non-spherical oligomicelles to penetrate into the hypoxic core and tumor stroma of RCC tumors; additional combination therapies; the use of tumor cell stimuli-responsive linkers; and imaging.

There is provided herein a first embodiment that is a substantially rod-shaped nanoformulation including: up to 30% CFM-4.16; a styrene maleic anhydride (SMA)—vitamin E tocopheryl polyethylene glycol succinate (TPGS) co-polymer; and one or more of: the CAIX targeting ligand acetazolamide (ATZ); the folate receptor targeting ligand folic acid; both ATZ and folic acid; one or more of sorafenib, everolimus, and/or cabozantinib; and/or a tumor cell stimuli-responsive linker.

Another embodiment is a nanoformulation including up to 30% w/w of a CARP-1 functional mimetic (CFM) and a styrene maleic anhydride (SMA)—vitamin E tocopheryl polyethylene glycol succinate (TPGS) co-polymer.

Also provided are rod-shaped nanoformulation including: CFM-4.16; a CAIX targeting ligand (such as ATZ); a folate receptor targeting ligand (such as folic acid); and one or more polymer(s) selected from the group consisting of: DBCO-conjugated vitamin E TPSG, SMA-TPGS; 2-hydroxypropyl-β-cyclodextrin (HP-β-CD), sulfobutylether-β-cyclodextrin (SBE-β-CD), phosphatidylethanolamine (PC), ceramide, Pluronic® F127, and PLA-PEG.

Yet additional embodiments are nanoformulations including: a polymer selected from one or more of: DBCO-conjugated vitamin E TPSG, SMA-TPGS; HP-β-CD, SBE-β-CD, PC, ceramide, Pluronic® F127, and PLA-PEG; a CAIX-targeting ligand (such as ATZ); and a dye (such as S0456 NIR dye).

Also provided are imaging composition including any nanoformulation described herein, as well as use of such imaging compositions to visualize a solid tumor in a subject in need thereof. By way of example, such uses include visualizing a solid tumor that is renal cell carcinoma (RCC).

Yet another embodiment is a method of treating a subject with a solid tumor exhibiting hypoxia and/or stromal components, including administering to the subject a nanoformulation described herein, or a pharmaceutical composition including such a nanoformulation.

Another embodiment is a method of treating a subject with a solid tumor (such as a carcinoma, a sarcoma, a lymphoma, a melanoma, a mesothelioma, or an adenocarcinoma) exhibiting hypoxia and/or stromal components, which method includes administering to the subject: (i) a nanoformulation encapsulated with a chemotherapeutic agent (such as a kinase inhibitor) for therapy; and/or (ii) a small molecule-based imaging agent for early diagnosis of tumor, pre-tumor/pre-cancerous lesion, polyp and imaging guided surgery. In specific examples of this method of treatment embodiment the cancer expresses one or more of carbonic anhydrase-IX, XII in a hypoxia/hypoxic region; folate receptor isotypes in tumor and tumor immune cells; and/or CD44 in cancer stem cells or stem like cells.

Another provided embodiment is a method of treating a subject with a solid tumor using a nanoformulation, wherein the nanoformulation is a rod-shaped nanoformulation including CFM-4.16, a CAIX targeting ligand, a folate receptor targeting ligand, and a polymer selected from one or more of: DBCO-conjugated vitamin E TPSG, SMA-TPGS; 2-hydroxypropyl-β-cyclodextrin (HP-β-CD), sulfobutylether-β-cyclodextrin (SBE-β-CD), phosphatidylethanolamine (PC), ceramide, Pluronic® F127, or PLA-PEG. Optionally, the nanoformulation further includes one or more of Valine-citrulline (Val-Cit); Hydrazone; alpha-dialky substituted hydrazine; polyethylene glycol unit 2-30 (PEG2-30), (PEG2-40); rigid cyclic hexyl, pentyl groups; non-rigid alkyl groups; Saccharo-peptides; Dithiol (S—S); alpha-dialky substituted [(R1R2HC—S—S—), R1 or R2 are alkyl groups)]; Zwitterionic; or Thiol-maleimide.

Also provided herein are methods of treating a subject with a solid tumor using a small molecule-based imaging agent, wherein the small molecule-based imaging agent used for the treatment provides early diagnosis of a tumor, a pre-tumor, or a polyp, and/or enables imaging guided surgery. In examples of such embodiments, the small molecule-based imaging agent includes one, two, or more than two different types of receptor targeting ligand(s) (such as ligand(s) that target hypoxia, stromal components, epithelial cell components, and/or angiogenic blood vessel cell components). In additional examples, the small molecule-based imaging agent includes: one or more rigid cyclic hexyl, pentyl groups; non-rigid alkyl groups; saccharo-peptides; oligomeric, polymeric, Zwitterionic; or Thiol-maleimide linkers; one or more of carbonic anhydrase-IX, XII targeting ligand including imidazole, sulfoimidazole derivative, acetazolamide; methazolamide; ethoxzolamide; dichlorphenamide; dorzolamide; brinzolamide; benzolamide; topiramate; zonisamide; sulpiride; indisulam; celecoxib; valdecoxib; antibody, or peptides; one or more of folate receptor isotypes targeting ligands including folic acid, methotrexate, aminopterin, antibody, or peptides; one or more of CD44 targeting hyaluronic acid (HA), hyaluronan, antibody, or peptides; a CMET targeting GE137 peptide; and/or a near infrared (NIR) dye (such as S0456), a NIR-II dye, or a maleimide, dibenzocyclooctyne (DBCO), thiol, carboxylic acid (—COOH), amine (—NH$_2$), or azide (N$_3$) functionalized derivative thereof.

BRIEF DESCRIPTION OF THE DRAWINGS

Many of the drawings submitted herein are better understood in color. Applicants consider the color versions of the drawings as part of the original submission and reserve the right to present color images of the drawings in later proceedings.

FIGS. 4A-4F illustrate characterization of nanoformulations, as described in Example 1. FIG. 4A: H$^1$-NMR profile for polymers used (SMA and TPGS) and the conjugate polymer (SMA-TPGS). The structure of the synthesized SMA-TPGS copolymer was detected by $^1$H NMR in D$_2$O. The —C—H protons and ring protons of SMA segment had signals at 1.69 ppm and 7.3 ppm, respectively. The —CH$_2$ protons of TPGS had the peak at 3.65 ppm. We noted the lower peaks in the aliphatic region that belong to various moieties of vitamin E tails. These peaks have been identified as well in the conjugate polymer as indicated by arrows. FIG. 4B: FTIR data for polymers used (SMA and TPGS) and the conjugate polymer (SMA-TPGS). The arrows indicated forming an amide bond between the conjugate polymer (SMA-TPGS). Peaks were identified for C—N bond, C=O stretching, and N—H stretching at around 1100, 1640-1690, and 3100-3500 cm−1, respectively. FIG. 4C: TEM images of SMA-TPGS-CFM4.16 indicates spherical and nanosized micelles. FIG. 4D: Critical micellar concentration (CMC) for SMA-TPGS-CFM4.16 nanomicelles was 0.010 mg/ml, indicating high stability even on dilution of the sample in in vivo conditions. FIG. 4E Particle size distribution of SMA-TPGS-CFM4.16 and SMA-CFM4.16 in dynamic light scattering instrument and their representative bright light images. FIG. 4F: Moderately negative zeta potential of nanomicelle indicating favorable particle characteristics for in vivo application.

FIG. 9A Overexpression of CA9 protein in A498 tumor tissue section. The intense bright green fluorescence (right panel) indicates the rational of choosing CA9 as a marker for RCC targeted therapy. FIG. 9B Fold up-regulation of CA9 expression in hypoxic WT and Evr-res A498 cells compared to normoxia provides solid foundation for delivering the payload to hypoxic core of RCC.

FIG. 11 shows In vivo animal imaging for Patient Derived tumor Xenograft (PDX) and A498 RCC cell-derived xenografts. The polymeric nanoparticles were conjugated with NIR dye. Bio-distribution study indicates high accumulation of NIR dye inside the tumor microenvironments.

(FIGS. 13A and 13B) Hydrodynamic size of SMA-TPGS-C-4.16 and ATZ-SMA-TPGS-C-4.16 oligomicelles by Dynamic Light Scattering (DLS) are shown. (FIG. 13C) The morphology of representative oligomicelles is characterized by TEM as shown. Scale bar=100 nm.

FIGS. 14A-14F Cell cultures studies and in vitro cytotoxicity assay of C-4.16, sorafenib, Everolimus on A498 and UOK-262 renal cell carcinoma cell lines. (FIG. 14A, 14C, 14E) Cytotoxicity data indicates C-4.16 is more potent than FDA approved drugs (sorafenib and everolimus) in WT or EV-res A498 and (FIG. 14B, 14D, 14F) WT or EV-res UOK262.

FIGS. 15A-15F are a series of graphs illustrating cell cultures studies and in vitro cytotoxicity assay of C-4.16, sorafenib, Everolimus on A498 and UOK-262 renal cell carcinoma cell lines. (FIGS. 15A, 15C, 15E) Cytotoxicity data indicates C-4.16 is more potent than FDA approved drugs (sorafenib and everolimus) in WT or EV-res A498 and (FIGS. 15B, 15D, 15F) WT or EV-res UOK262. Note High synergistic CI value of C-4.16 with sorafenib combination.

FIG. 17 is a western blot analysis, showing that CFM-4.16 stimulates apoptosis in parental and Everolimus-resistant RCC cells in part by upregulating pro-apoptotic CARP-1 and activating SAPKs. The combination of C4.16+Sor completely wiped out P-AKT level both in WT and Evr-res A498 cells. Cells were either kept untreated (control, C) or treated with Evr, Sor, C4.16 or C4.16+Sor. Indicated RCC cells were either untreated (Control, denoted as 0), treated with CFM-4, or CFM-4.16 for the noted doses and times.

Cell lysates were analyzed by Western blotting (WB) as in Methods for levels of CARP-1, cyclin B1, cleaved PARP and caspase-8, and activation (phosphorylation) of pro-apoptotic p38 and JNK1/2 SAPKs Parental or Everolimus-resistant UOK262 cells were either untreated (Control), treated with Everolimus, CFM-4, or CFM-4.16 for the noted doses and times. Cell lysates were analyzed by Western blotting (WB) for expression and/or activation of pro-apoptotic proteins as in panel A. Free oligomer, SMA-TPGS-C-4.16 oligomicelles and ATZ-SMA-TPGS-C-4.16 oligomicelles with an increasing apoptosis. See FIG. 3 as published in Cheriyan et al., *Oncotarget*. 8(62): 104928-104945, 2017.

Figure 18:
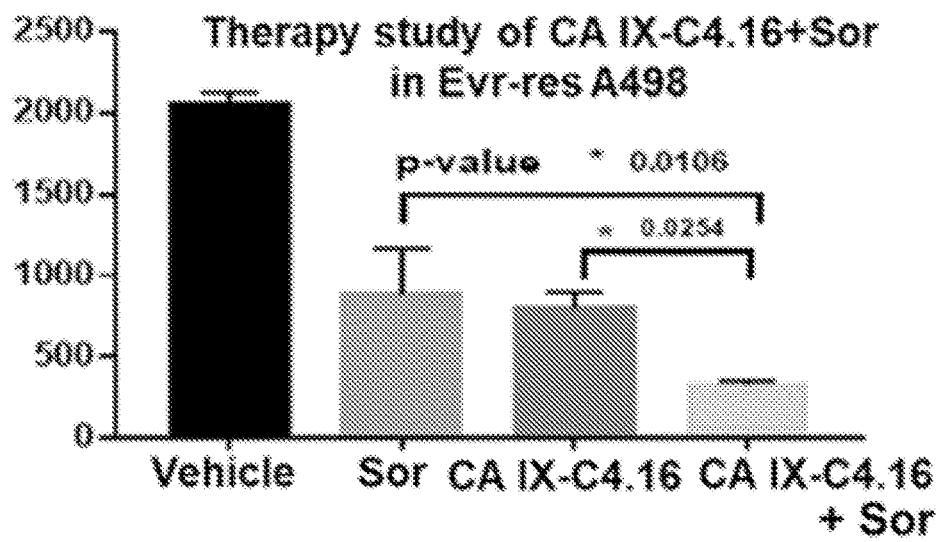

FIG. 18 is a bar graph illustrating results of an animal antitumor efficacy study. Nanomicellar formulation of CA9 targeted C-4.16 inhibits growth of RCC cell-derived xenografts. Histogram showing tumor size in the vehicle-treated (indicated as Control), free drug C-4.16, free drug sorafenib, or CA9-C-4.16 combined with sorafenib (iv) treated, RCC (A498) xenograft-bearing animals. The xenograft establishment, treatment and analysis procedures were carried out essentially as detailed in Example 2. The bars represent average values from a total of five animals in respective group, bars, SE, significant where *p=0.05 vs Control. Significant anti-tumor effect of CA9 targeting C-4.16 and sorafenib combination oligomicelles treatment than single agent in WT A498 xenograft nu/nu model. Tumor growth inhibition of (CA IX-C4.16+Sor) is significantly higher compared to vehicle(control), Sor, and CA IX-C4.16 in Evr-res A498 xenograft tumor. Significant tumor growth suppression of combination therapy supports the rationale of using CA IX targeting nanoformulation as the delivery vehicle of potent drugs, C4.16. The data represented as average values from whole four animals in the respective group, bars, SE, significant where *p<0.05 vs. Control.

Figure 19A:
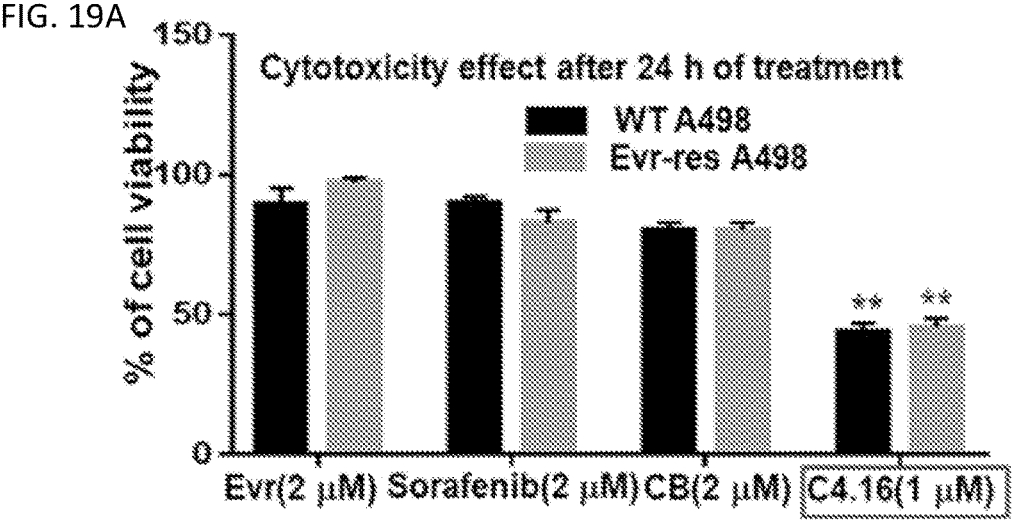
Figure 19B:
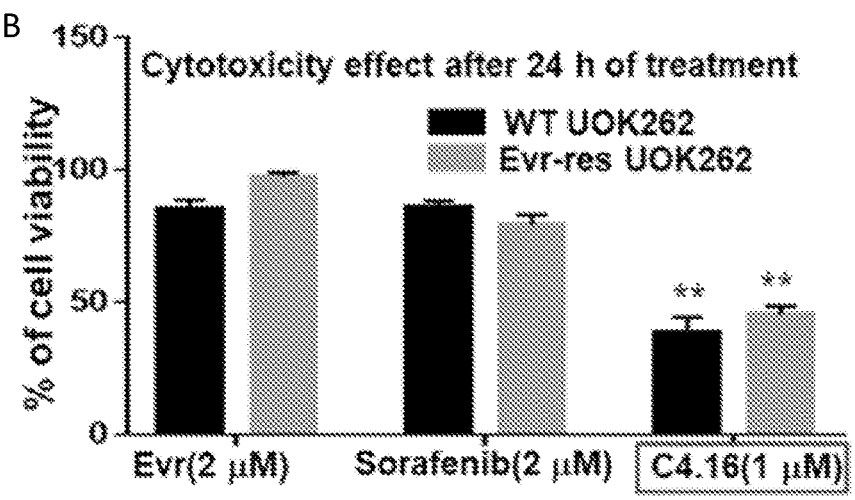

FIGS. 19A and 19B are bar graphs showing the anticancer effect of C4.16 in strain A498 (FIG. 19A), and in strain UOK262 (FIG. 19B). Cytotoxicity data indicates CF.16 is more potent than FDA approved drugs in WT and Evr-res RCC cells even at half of their dose used. ** p<0.001

Figure 20:
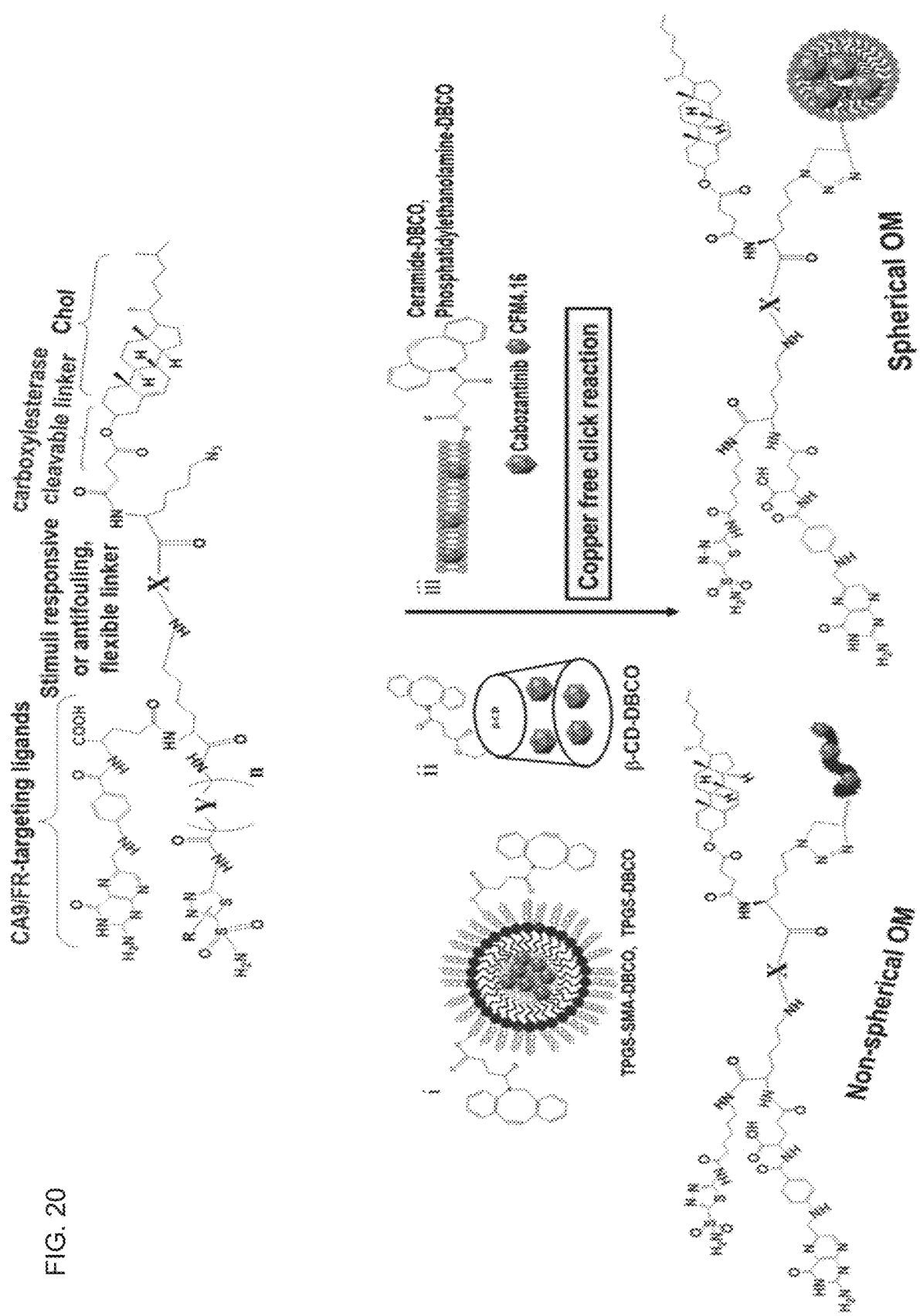

FIG. 20 is a scheme illustrating dual tumor stroma and hypoxia targeting nanomicelle library using folate receptor (FR) and carbonic anhydrase-9 (CA9) for delivery of combination of drugs. Key: X (various linker)=valine-citrulline (Val-Cit); Hydrazone; alpha-dialky substitute hydrazine; Polyethylene glycol unit 2-30 (PEG2-30); rigid cyclic hexyl, pentyl groups; non-rigid alkyl groups; Saccharo-peptides; Dithiol (S—S); alpha dialky substitute [(R1R2HC—S—S—), R1 or R2 are alkyl groups)]; Zwitterionic; Thiol-maleimide. These linkers will selectively release the payload in tumor stimuli-condition. The cholesterol (Chol) was linked through and carboxyl esterase responsive ester linker. The dual tumor responsive linkers (X and carboxyl esterase responsive ester) will play as a stepwise disintegrating nanoparticle for superior tumor penetration. The FR and CA9 targeting oligomicelle (OM) can be developed using copper free click reaction to obtain spherical and non-spherical OMs.

Figure 21A:
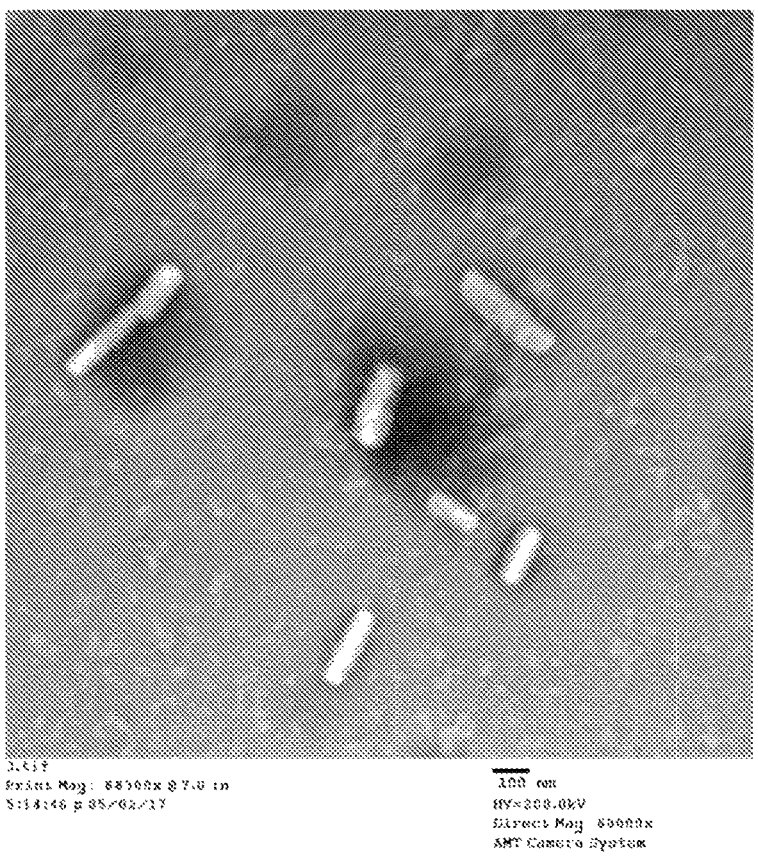
Figure 21B:
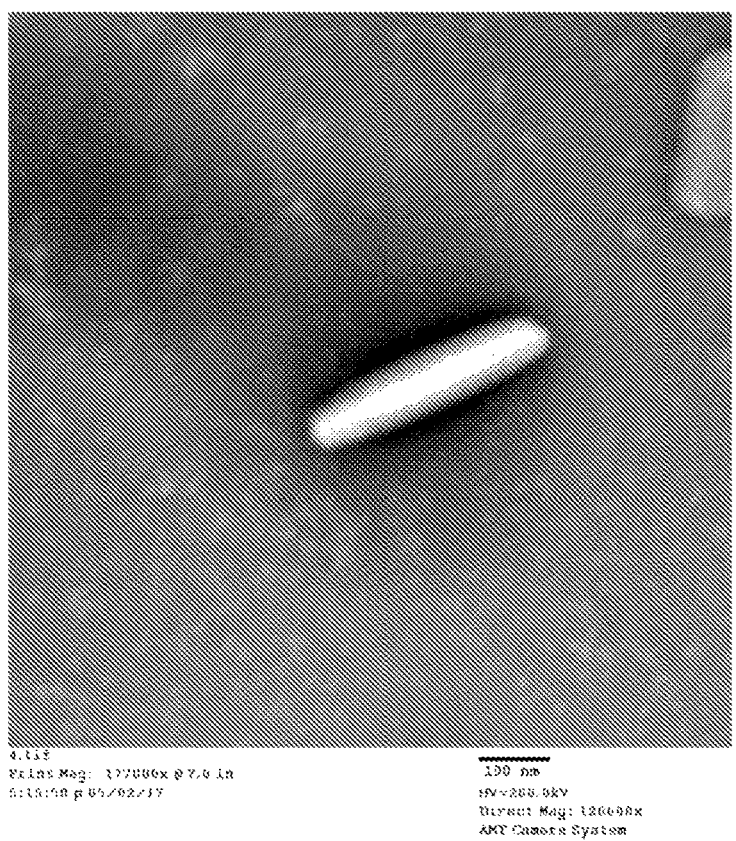

FIG. 21A, FIG. 21B are a pair of TEM images of rod-shaped OMs; magnification 6000× and 12,000× (respectively). These particles showed superior tumor core penetration in the PDx tumor and potent therapy outcome.

FIGS. 22A-22E illustrate tumor core penetration. NIR imaging of (FIG. 22A) non-targeted (NT), dual CA9 and CSC targeting non-spherical OM in (FIG. 22B) lung and (FIG. 22C) breast PDx tumor. Quantification of NIR-dye (FIG. 22D) suggests that the targeted OM penetrates 2.4- fold higher in the tumor core than its periphery and 8-fold higher than the core of the NT OM treated tumor. (FIG. 22E) superior tumor accumulation compared to liver for targeted oligomer. See also FIGS. 37A-37D, 38A-38C, and 39.

Figure 23:
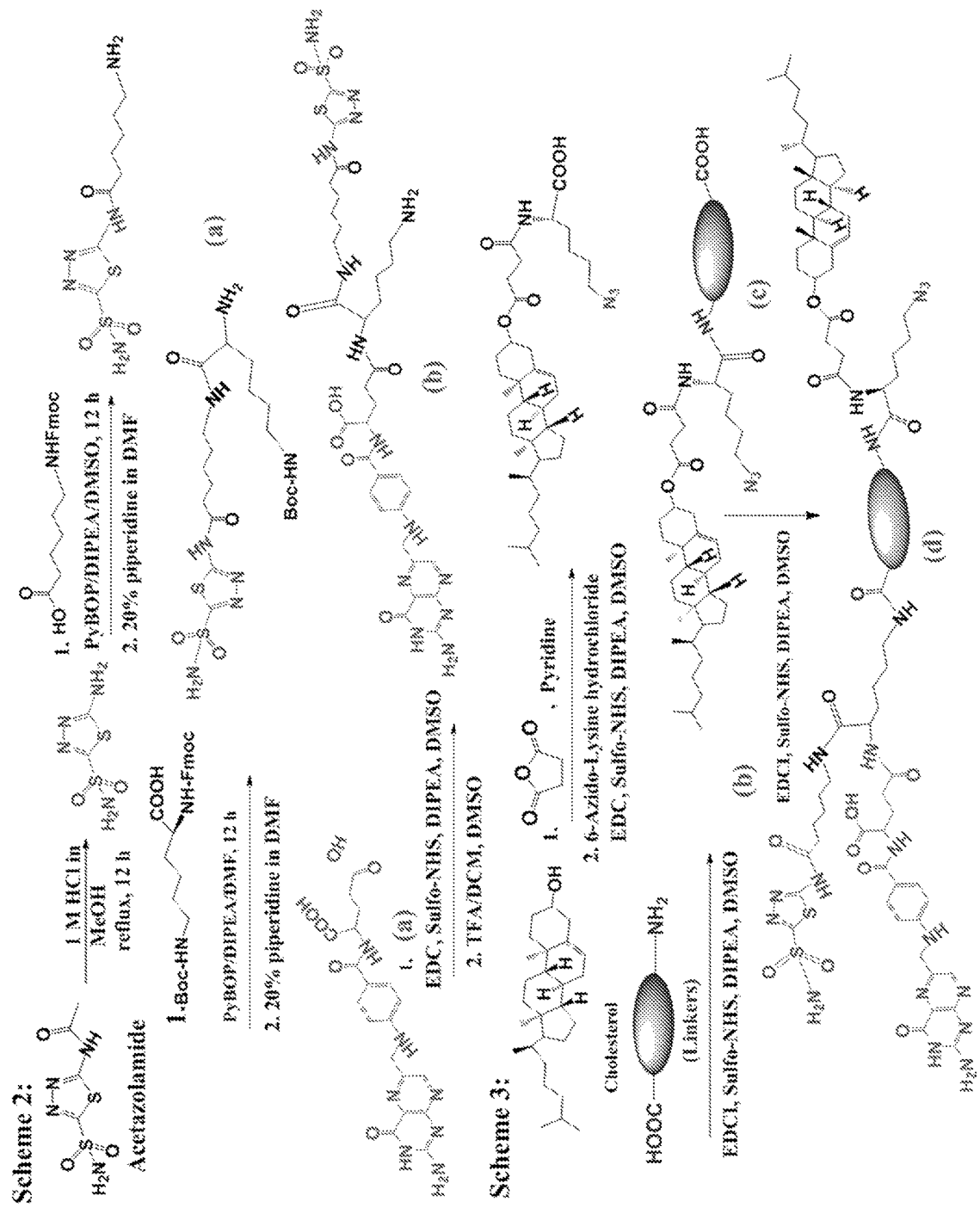

FIG. 23 includes a scheme showing stepwise synthesis of FA-ATZ small molecule fragment (b). The NIR dye (S0456) will be conjugated with compound b to yield FA-ATZ-S0456. FIG. 23 also includes a scheme showing conjugation between various linkers and Azide-cholesterol, followed by coupling with compound b to yield oligomers (d).

Figure 24:
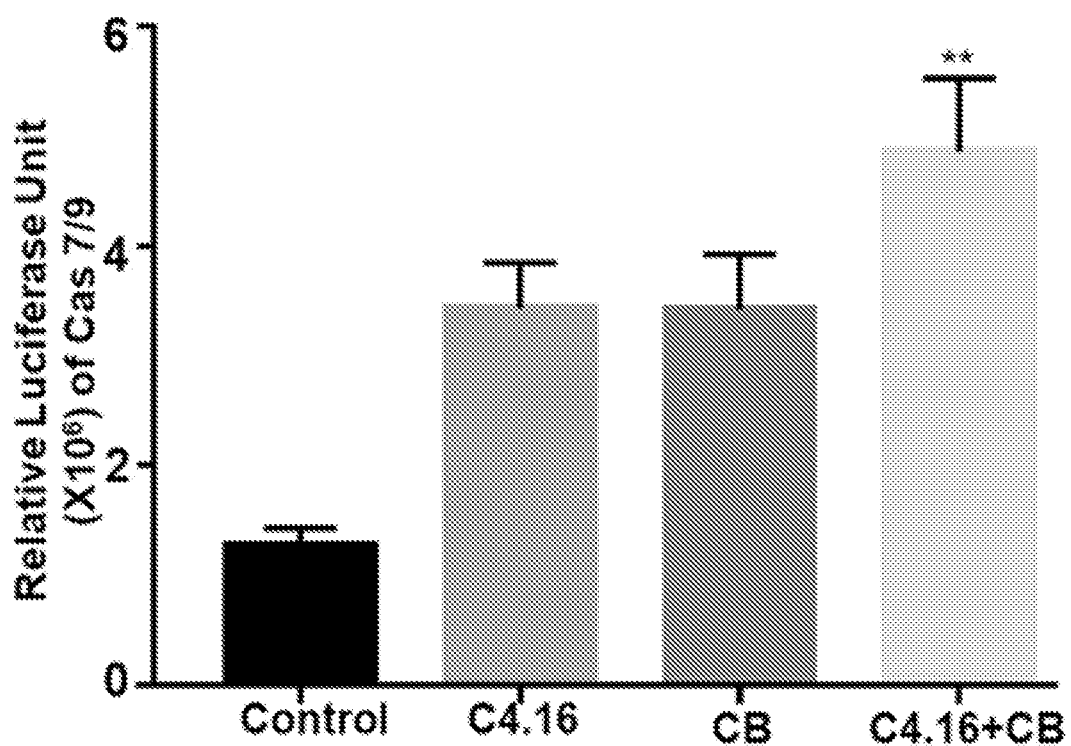

FIG. 24 is a graph illustrating that RAW264.7 cells induce apoptosis of Evr-res A498 cells treated with C4.16+CB.

Figure 25:
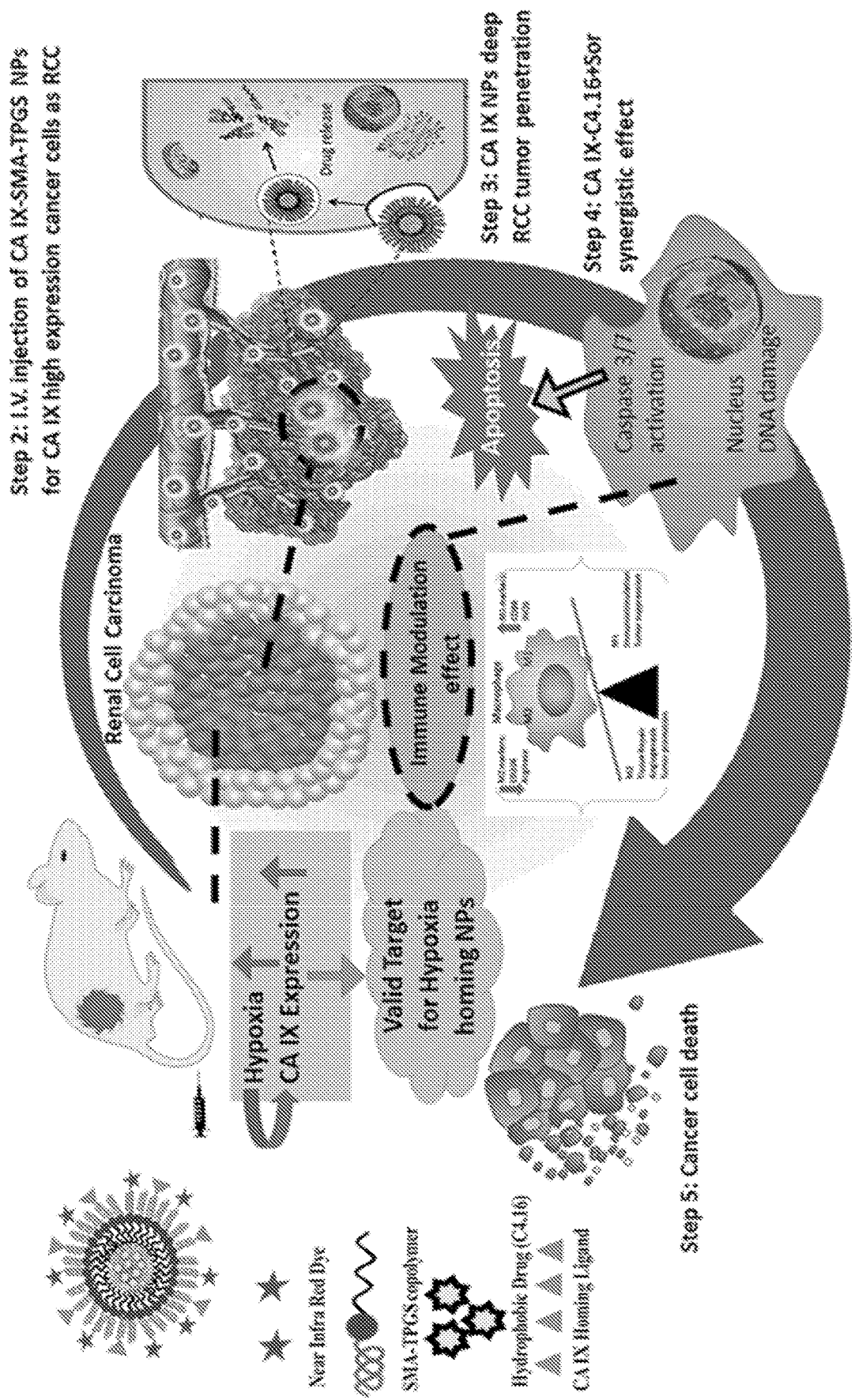

FIG. 25 is a representative illustration of tumor hypoxia directed nano-therapy in combination with Sorafenib for achieving multiple benefits against cancer, such as reversing drug resistance, inducing apoptosis and reprogramming macrophages.

Figure 13A:
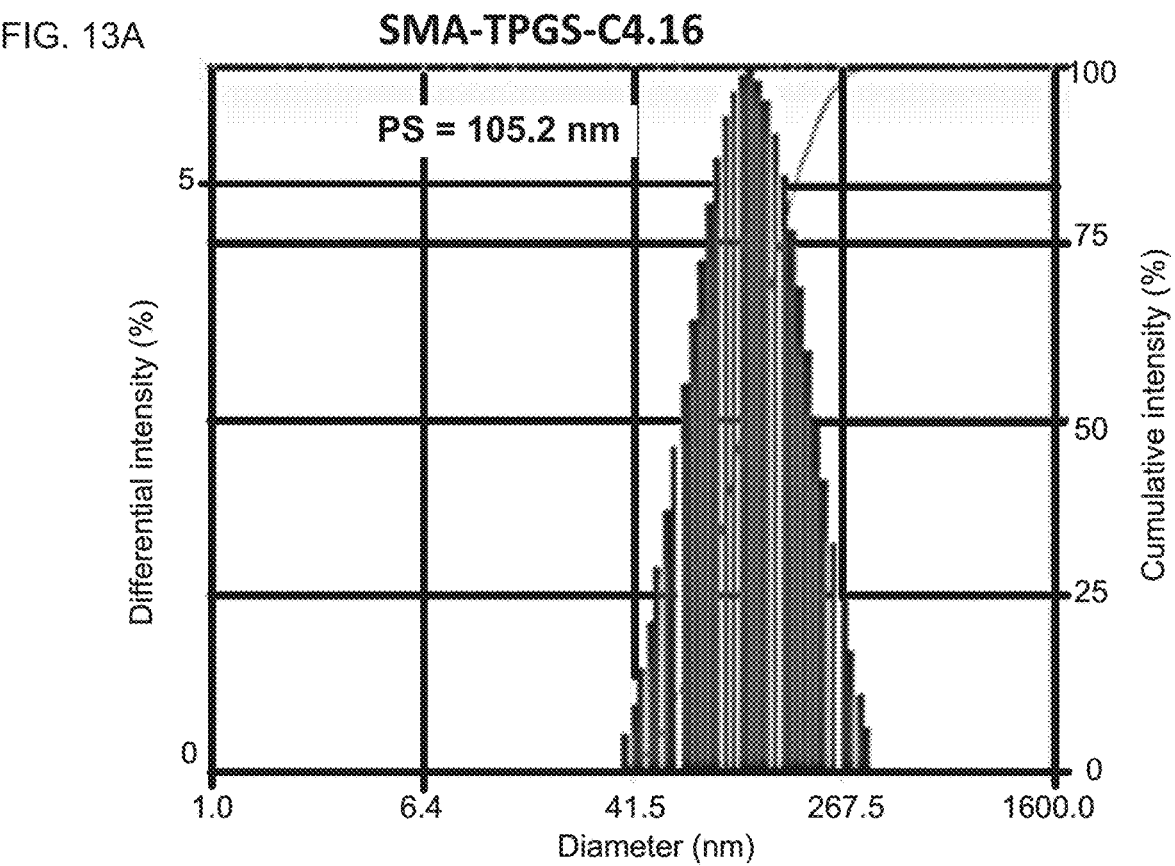
FIGS. 13A-13C illustrate oligomicelles formulation and characterization.
Figure 13B:
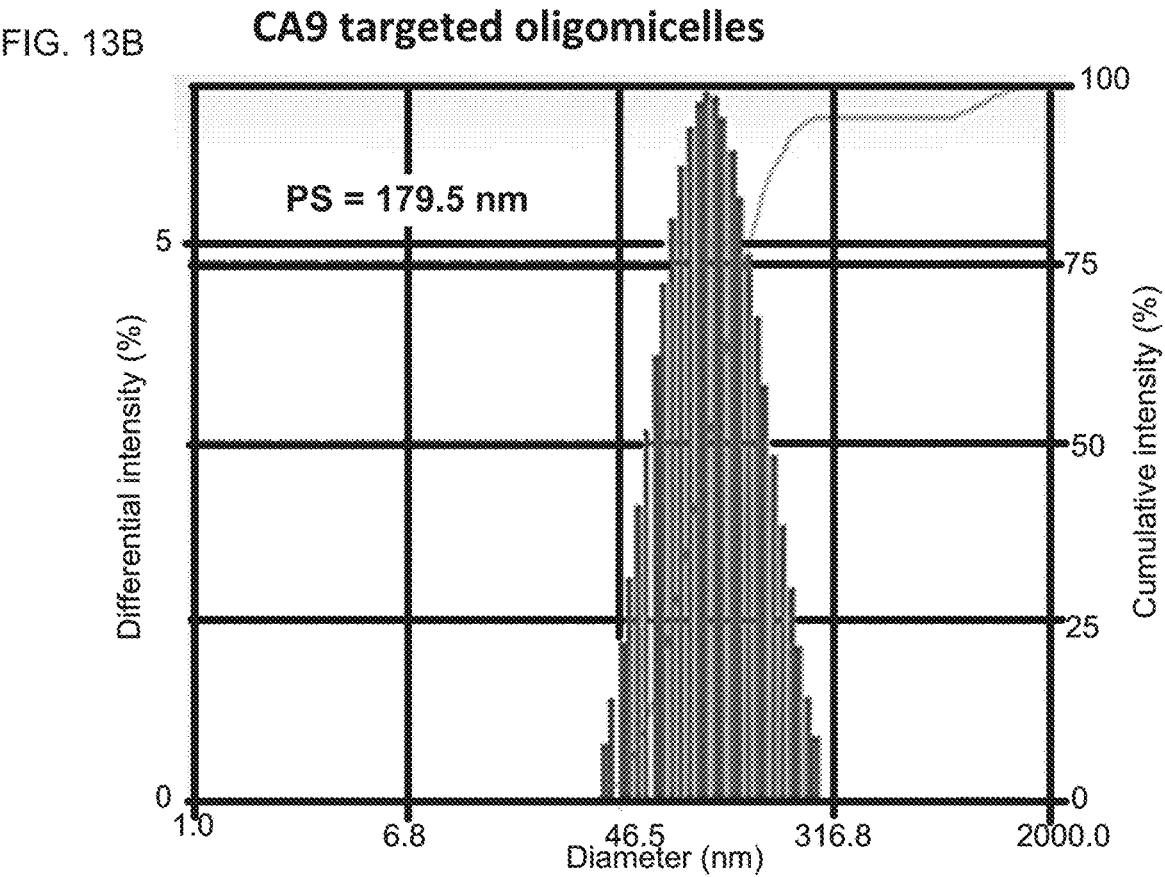
Figure 13C:
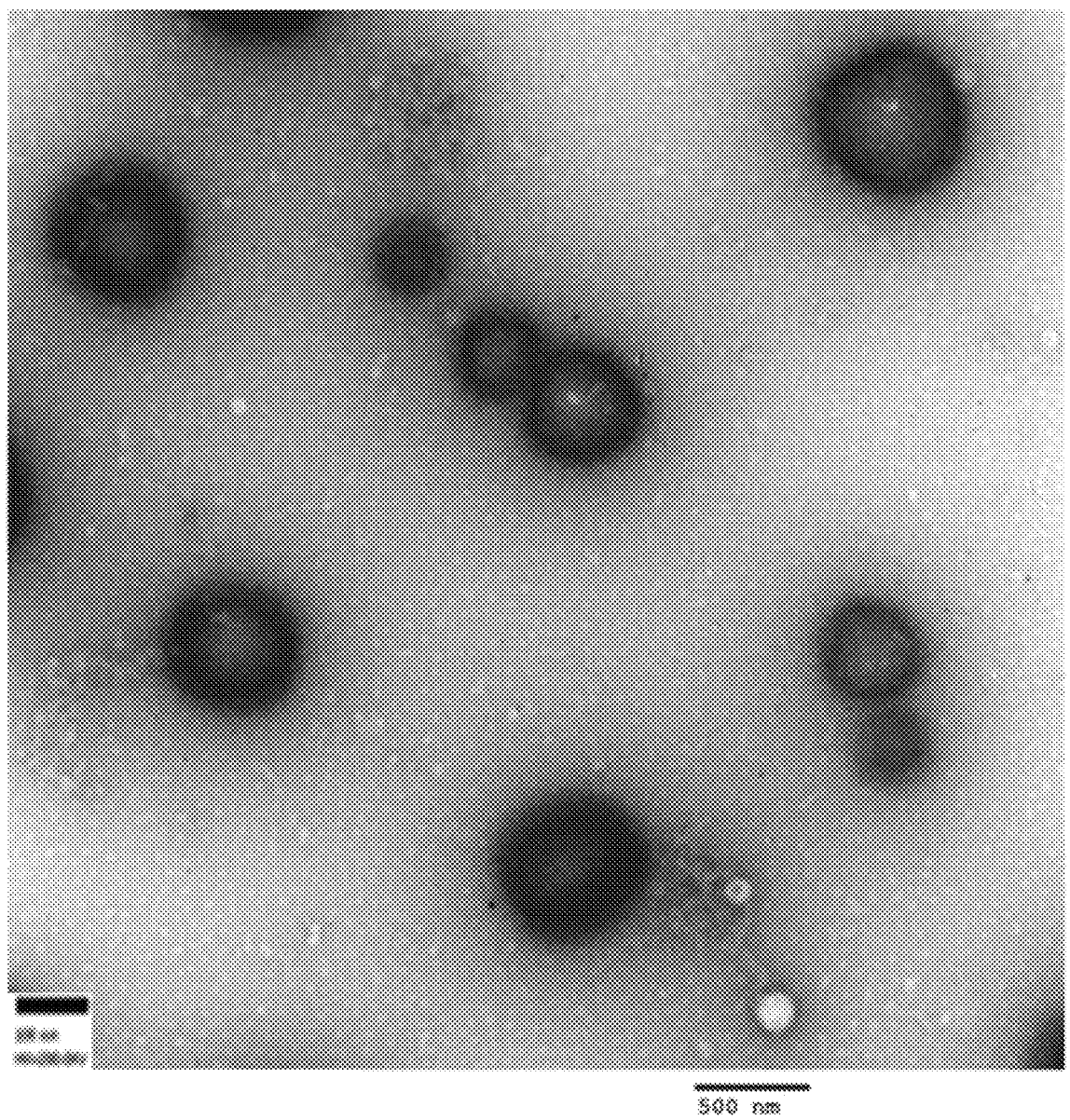

FIGS. 26A-26E illustrate nanoparticles formulation and characterization. (FIG. 26A) Hydrodynamic size of targeted non-targeted SMA-TPGS-C4.16 and hypoxia targeting CA IX-SMA-TPGS-C4.16 NP. (FIG. 26B) The Transmission electron microscopic morphology of non-targeted and targeted NP. (FIG. 26C) Zeta potential by Dynamic Light Scattering (DLS) is shown. (Representative histogram of hydrodynamic particle size and zeta potential (n=3). (FIG. 26D) MALDI/MS analysis of CA IX-SMA-TPGS and SMA-TPGS are shown. The increment of molecular weight in CA IX-SMA-TPGS (m/z 3126) compared to SMA-TPGS (m/z 2399), and their corresponding fragmented peaks indicates the successful conjugation of ATZ to the SMA-TPGS polymers. (FIG. 26E) In vitro drug release kinetics of CAIX-SMA-TPGS-C4.16 in PBS indicates that the sustained release of C4.16 from the CAIX-SMA-TPGS-C4.16 NP as compared to free C4.16 with excipient, such as KOLLIPHOR® in PBS is shown. At least some of the data in FIG. 26 is also included in FIG. 13.

Figure 9A:
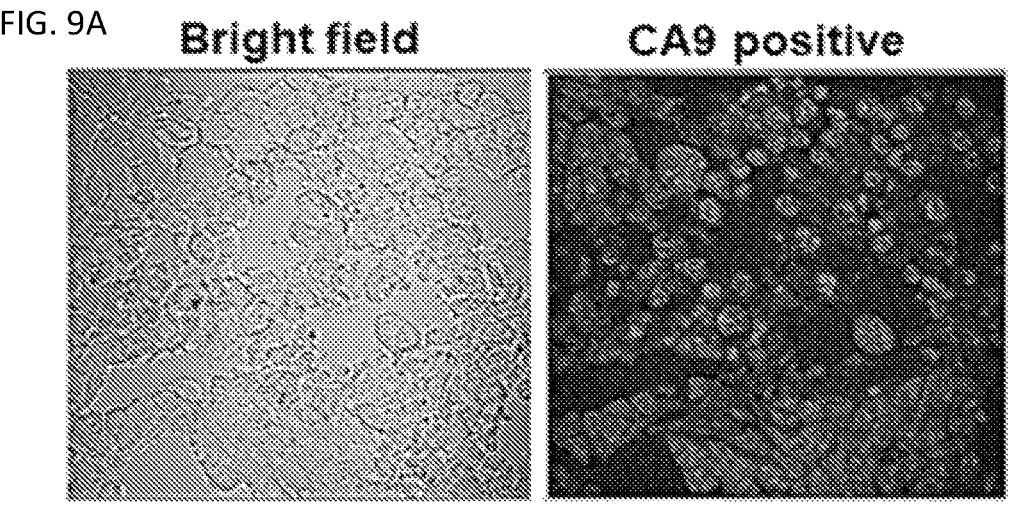
FIGS. 9A-9B shows that CAIX expression increases after hypoxia is induced RCC cells and tumor.
Figure 27A:
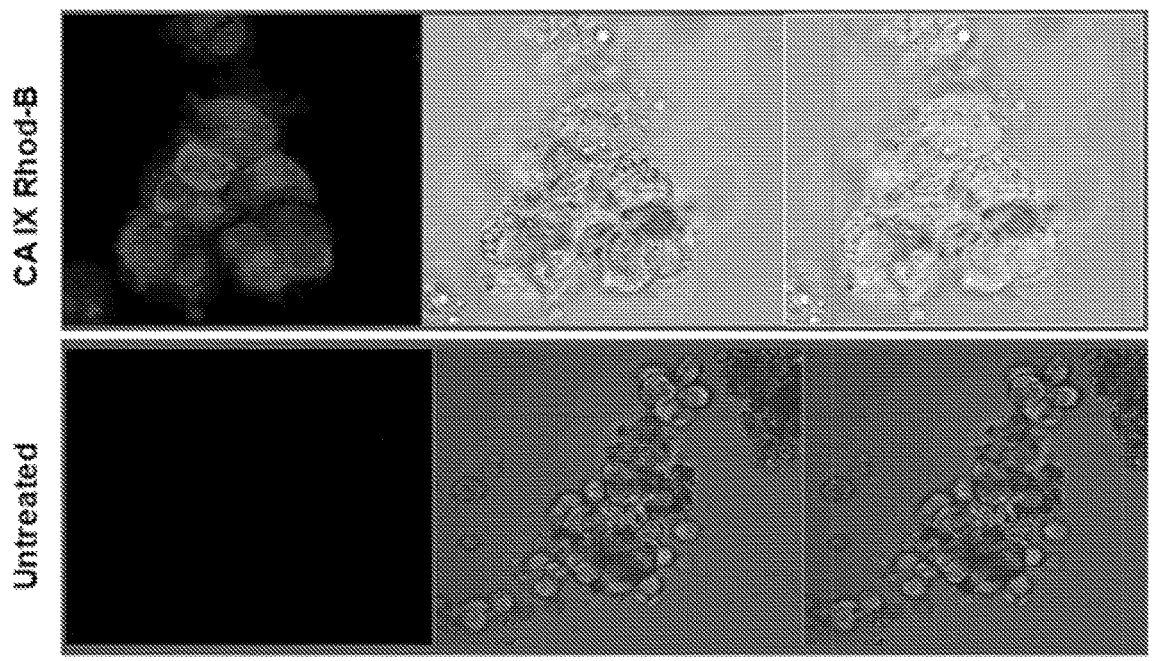
Figure 27B:
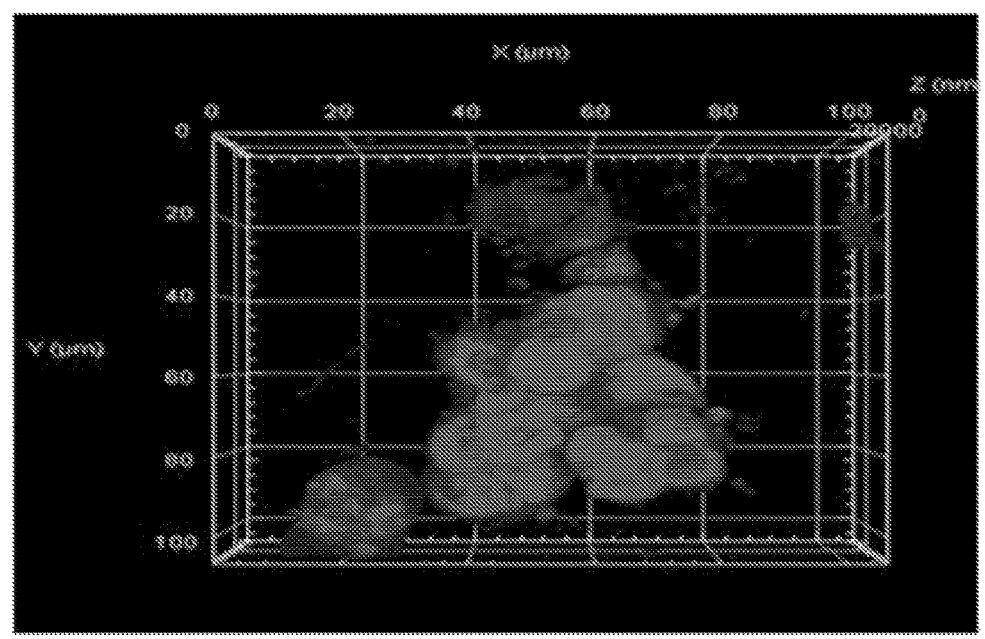

FIGS. 27A-27B illustrate hypoxia induced CA IX-overexpression in A498 cells and tumors to enable tumor core penetration of CA IX oligomer. (FIG. 9A) Immunohistochemistry of CA IX-positive A498 RCC tumor xenografts collected from tumor tissue section is shown. The intense bright green fluorescence indicates the rationale for choosing CA IX as an excellent biomarker for RCC specific payload delivery. (FIG. 9B) Western blot detection of CA IX protein in A498 and EV-A498 RCC cells lysates after normoxia and hypoxia (treated with cobalt chloride for 72 h) are shown. The fold up-regulation of CA IX expression in hypoxic WT and EV-res A498 RCC cells compared to normoxia provides a solid foundation for delivering the payload into oxygen-deprived regions and the hypoxic core of RCC tumor. (FIG. 16B) 3D spheroid uptake studies of hypoxia targeted-oligomer (CA IX Rhod-B). Confocal microscope images of CA IX Rhod-B treated hypoxic A498 spheroid indicates tumor matrix penetration of CA IX-oligomer. The untreated and treated spheres were then photographed as noted in the methods section. Z-stacking of the spheroid clearly indicates that fluorescence intensity is superior in 40-60 μm section (core) as compared to 10 or 100 μm (periphery). The highest fluorescence intensity at the center (as indicated by arrow) of 3D-plot suggests that CA IX-Rhod oligomer is highly efficient to reach deep into the core of the tumor spheroid. (FIG. 16A) Z-stacking of the spheroid at different sections from 10-100 μm with CA IX targeted formulations also reveals similar findings as noted for the 40-60 μm that had superior fluorescence intensity. FIG. 27A shows the untreated control experiments in comparison with CA IX-Rhod oligomer and FIG. 27B shows the overall shape of the spheroid from along the three dimensions (x, y, and z).

FIGS. 28A-28F illustrate that C4.16 and CA IX-C4.16 are more efficient in inhibiting the growth of WT and Evr-res A498 cells. In vitro cytotoxicity assay of C4.16 and Sor on (FIG. 28A) WT and (FIG. 28B) Evr-res A498 indicates C4.16 was more potent than the FDA approved drug, Sor and combining both drugs C4.16+Sor demonstrated significantly lower cell viability. (FIG. 28C) The results also showed that CA IX-C4.16 is more effective in inhibiting the growth of A498 (WT and Evr-res) RCC cell lines compared to Sor and Evr and support the notion that C4.16 is more potent than FDA approved drugs in the RCC model. (FIG. 28D) Summary of $IC_{50}$ value for all the tested drugs with the tested RCC cell lines are shown in a tabular fashion. The data in the IC50 columns represent the mean of three independent experiments. Indicated A498 WT and their respective Evr-res A498 cells were either untreated (control) or treated with a noted dose of C4.16, Sor, Evr, and CA IX-C4.16 for 48 h. (FIG. 28E) High synergistic CI value of C4.16 in combination with Sor supports the hypothesis of selecting the combination to treat RCC for reversing the drug resistance. This data builds a rationale for using hypoxic core penetrating CA IX-C4.16+Sor to sensitize the drug resistant RCC. (FIG. 28F) Isobologram of CA IX-C4.16+Sor suggests high synergism combination treatment in RCC cells.

Figure 29A:
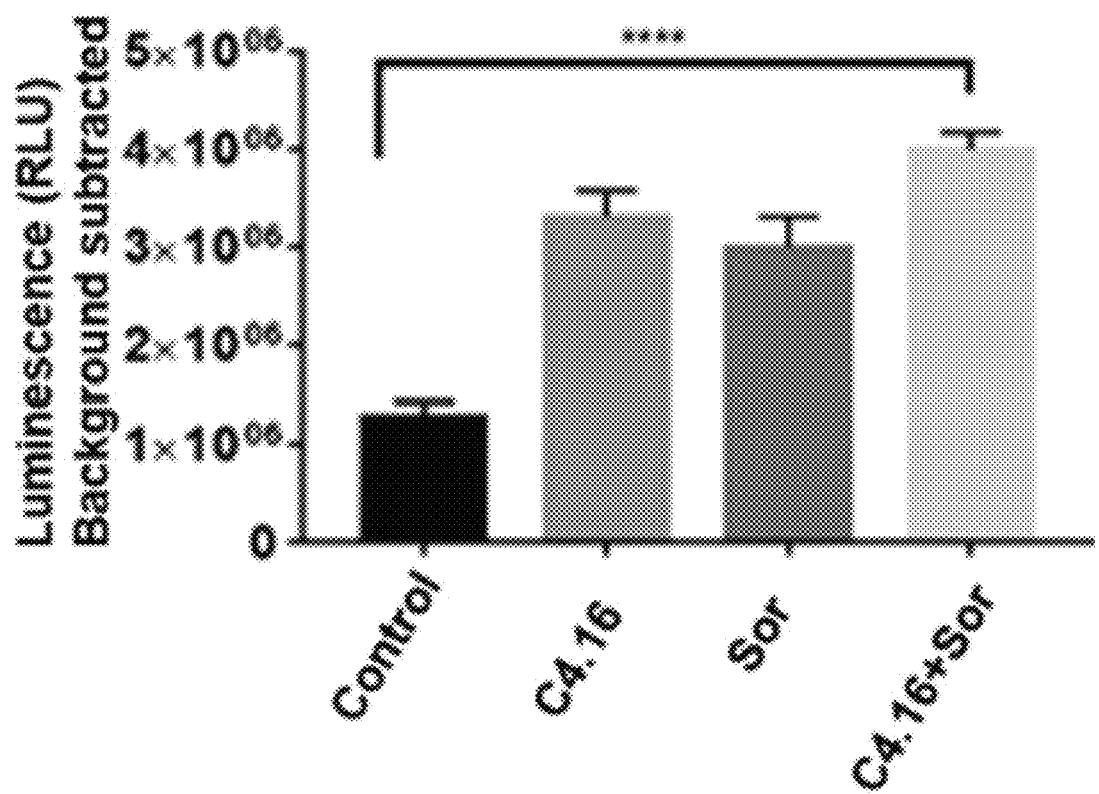
Figure 29B:
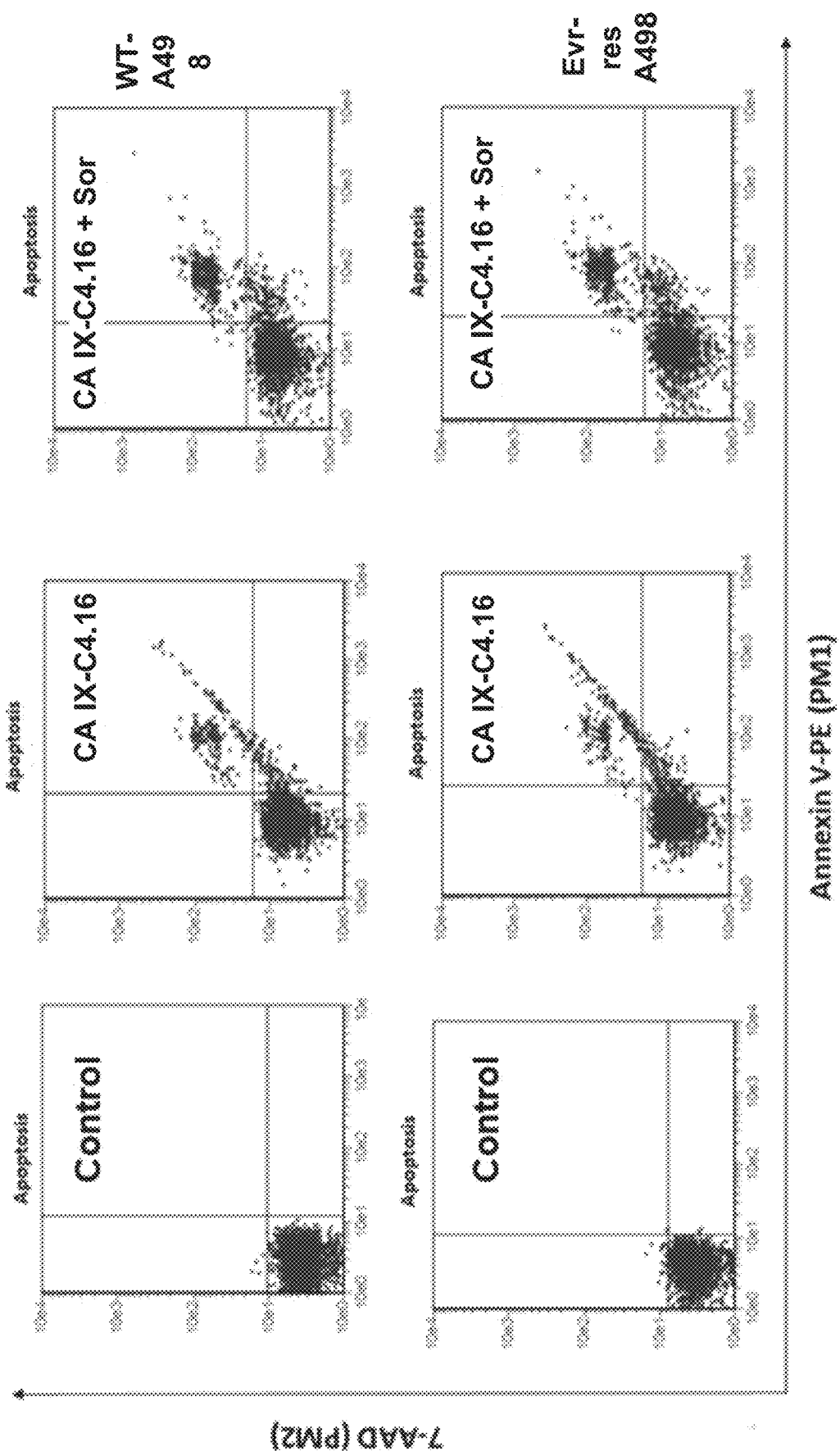
Figure 29C:
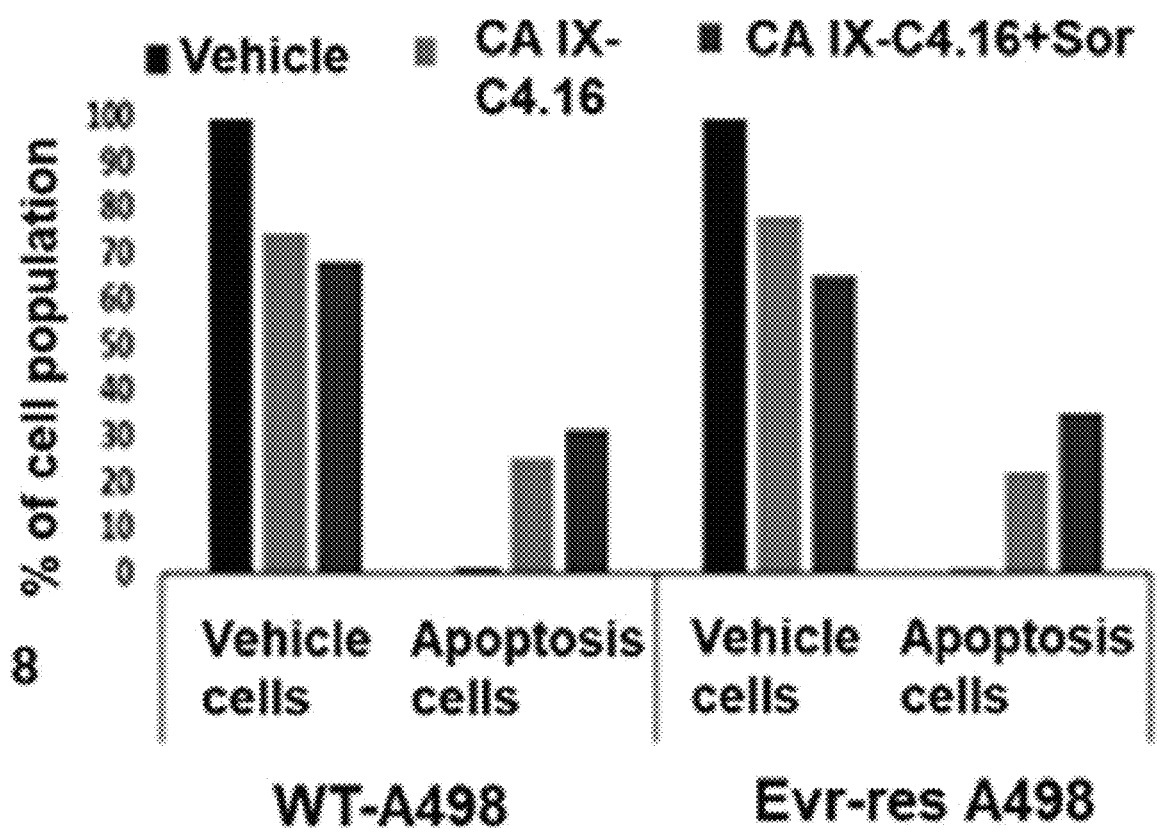

FIG. 29A is a histogram showing upregulation of caspase 7/9 with (C4.16+Sor) treatment in Evr-res A498 cells indicates effective induction of apoptosis to drug resistant cells as compared to control or individual treatment. The results support the notion that (C4.16+Sor) combination is more effective in resurrecting apoptosis mediated cell death. Data represent mean±SD, n=3 per group, ****p<0.01 vs. control. FIG. 29B shows apoptosis analysis of WT and Evr-res A498 cell by FACS using dual Annexin-V and 7-AAD staining. The data indicates CA IX-C4.16+Sor is superior in inducing apoptosis as compared to control; CA IX-C4.16 NP treated cells. FIG. 29C is a histogram of both viable cells and apoptotic cells indicates that CA IX-C4.16+Sor has more % apoptotic cell compared to CA IX-C4.16 alone which support our hypothesis of the synergism in RCC cell killing.

FIGS. 30A-30E illustrate targeting tumor stroma with CA IX-C4.16 nanoparticle. (FIG. 30A) Schematic diagram of the procedure. Raw-264.7 cells were placed into the insert. Then, cells were polarized to M1-macrophage using IFN-g and LPS, and to M2-macrophage using IL-4 recombinant protein. Scheme modified from the original protocol by Smith et al. (FIG. 30B) Change of morphology of M1 and M2 macrophages supports the polarization of Raw-264.7. (FIG. 30C) RT-PCR data clearly demonstrates the up-modulation of the tumoricidal M1-macrophage marker (CD86, iNOS) and down-modulation of the tumorigenic M2-macrophage marker (CD206, Arginase I) in CA IX-C4.16+Sor as compared to control and C4.16. The macrophage reprogramming ability of CA IX-targeting NP builds a rational of using (CA IX-C-4.16+Sor) as a potent antitumor immunestimulatory agent of RCC. (FIG. 30D) Change of morphology and reduction of Evr-res A498 density in M1-macrophage and Evr-res A498 co-cultured condition, treated with CA XI+Sor suggesting activated M1-macrophage mediated RCC cell death. (FIG. 30E) Treatment of CA IX+Sor educate the Raw-264.7 in inducing caspase 3/7 mediated apoptosis of Evr-res A498.

FIGS. 31A-31H illustrate superior tumor specificity of CA IX-oligomer and antitumor efficacy study of combination therapy in Evr-res A498 xenograft and RCC PDx model. (FIG. 31A and FIG. 31C) Superior tumor accumulation of CAIX oligomer (CA IX-S0456) as compared to control (S0456) in Evr-res A498 tumor xenograft model. (FIG. 31B) Biodistribution (Bio-D) study of CA IX-S0456 showed superior tumor specificity and low non-specific liver uptake in Evr-res A498 tumor bearing mice. The control, S0456 showed poor tumor accumulation with high off-target activity. (FIG. 31D) Further to demonstrate the tumor core penetration of NIR dye, isolated Evr-res A498 tumor was transversely sectioned, and brightest fluorescence intensity at the middle section confirmed of CA IX-S0456 has an excellent hypoxic tumor core penetration ability as compared to control. (FIG. 31E) Significantly high tumor/liver accumulation (more than 3-fold) of CA IX-oligomer solve the non-specificity effect of the oligomer. (FIG. 31F) Quantification of fluorescent ROI indicates CA IX-oligomer is significantly penetrating higher in tumor core contained as compared to its periphery. The results suggest the importance of CA IX-oligomer in selective tumor targetability of RCC tumor model. (FIG. 31G) Histopathologic (H&E staining) examination to determine the toxicity of therapeutic drugs on livers and kidneys at the end of the experiments. Images indicate there is no significant sign of necrosis or loss of tissue architectural difference in vehicle control and CA IX-C4.16+Sor treated tissues.

Figure 32:
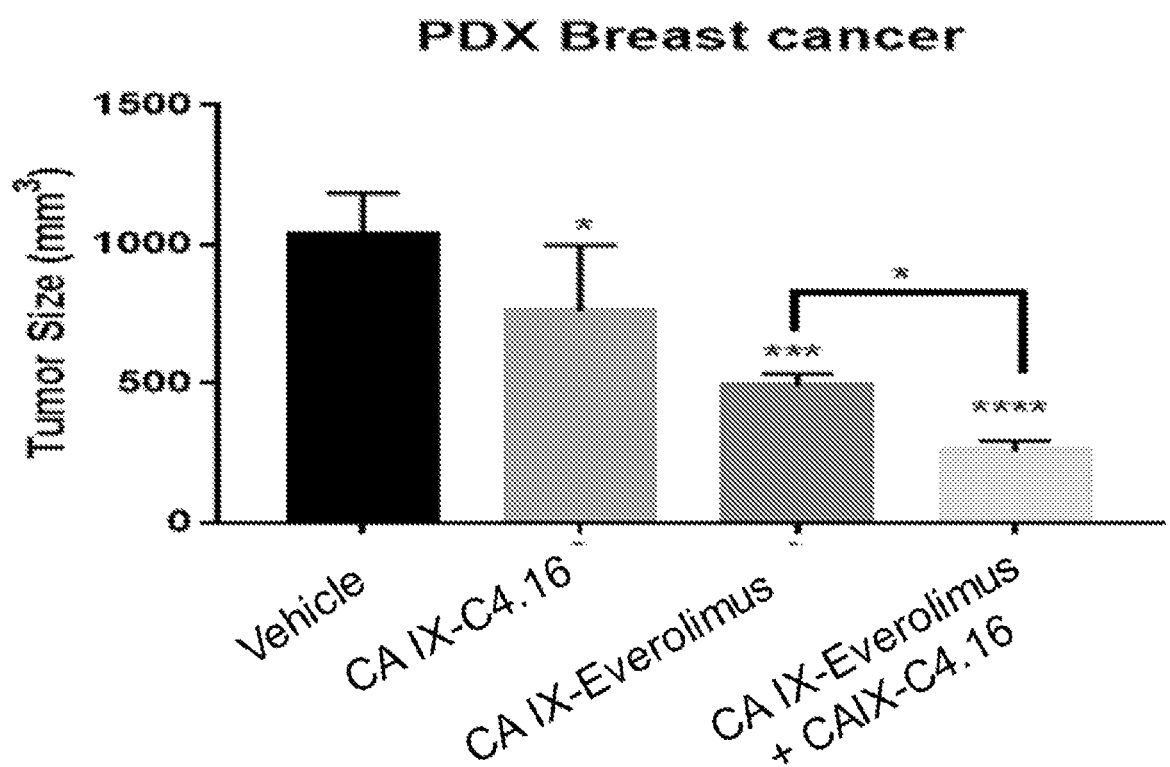

FIG. 32 is a graph showing that tumor growth inhibition of CA IX-C4.16+CAIX-Everolimus is significantly higher compared to controls in breast patient derived tumor model.

FIG. 33A is an illustration of tumor microenvironment and overexpression of tumor cell type specific receptors that can be selectively targeted together for delivering therapeutic and diagnostic agents. FIG. 33B shows representative receptors that are overexpressed in tumor components. We are targeting multicomponent of tumor environment by using nanoformulation and small molecule imaging agent. This will improve the therapeutics outcome of cancer.

FIG. 34 is a representative carbonic anhydrase IX (for hypoxia) and CD44 (cancer stem cells) by using Acetazolamide and hyaluronic acid nanoformulation for therapeutic drug delivery and tumor imaging.

Figure 35:
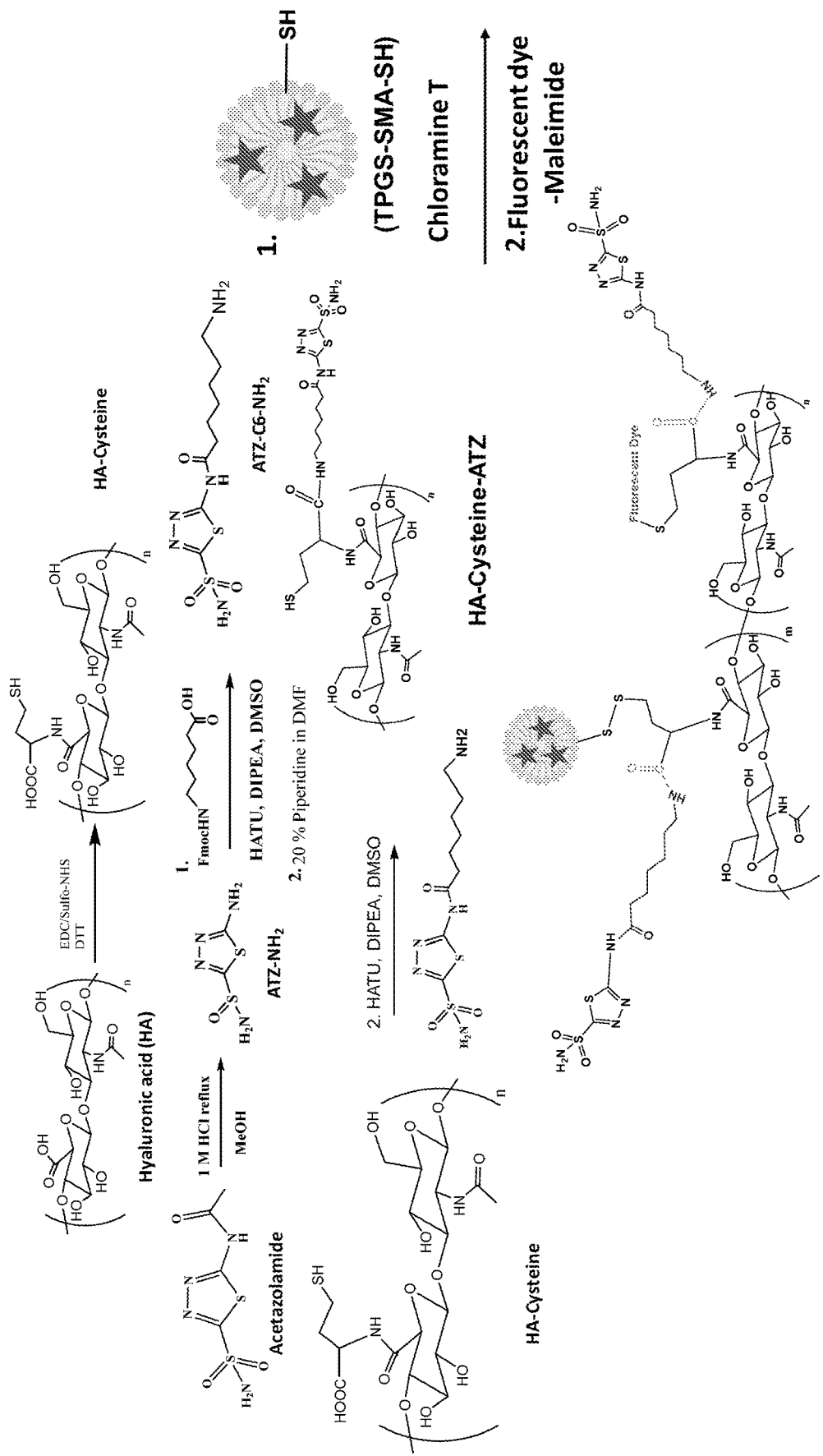

FIG. 35 is a scheme illustrating production of the compounds in FIG. 34.

Figure 36:
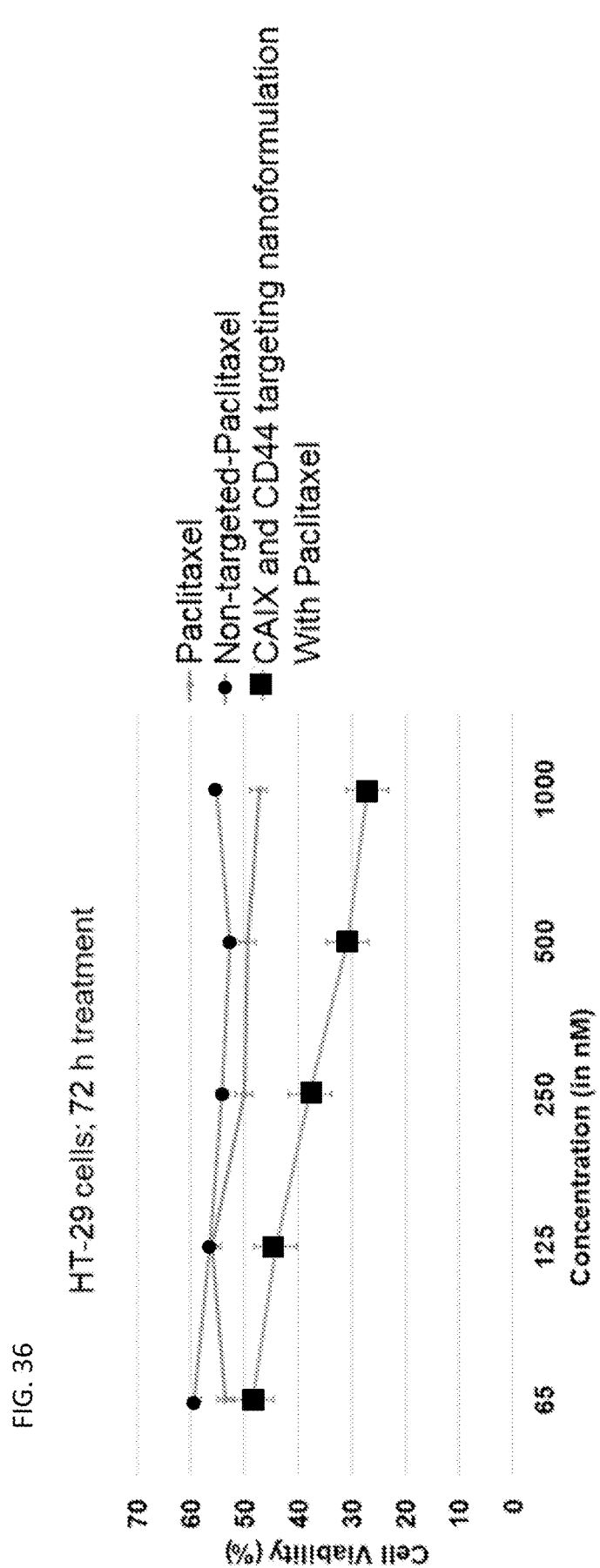
Figure 37A:
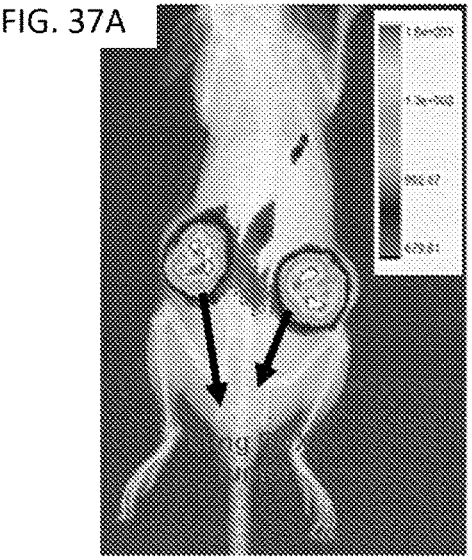
Figure 37B:
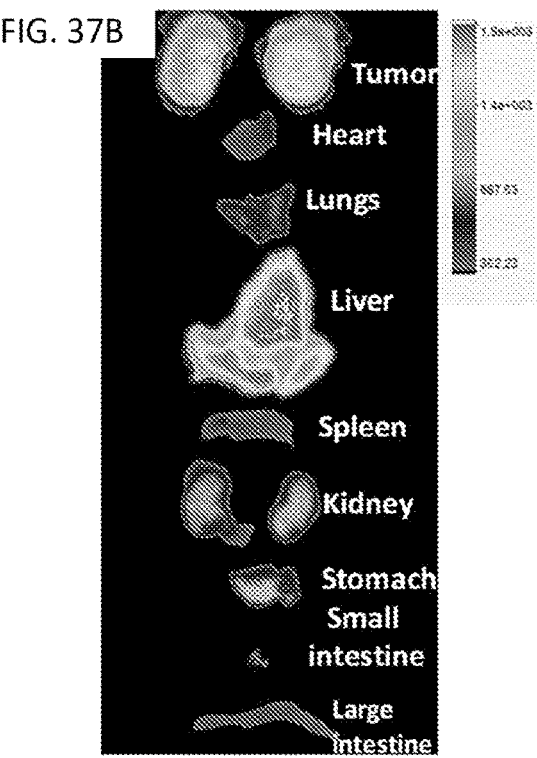
Figure 37C:
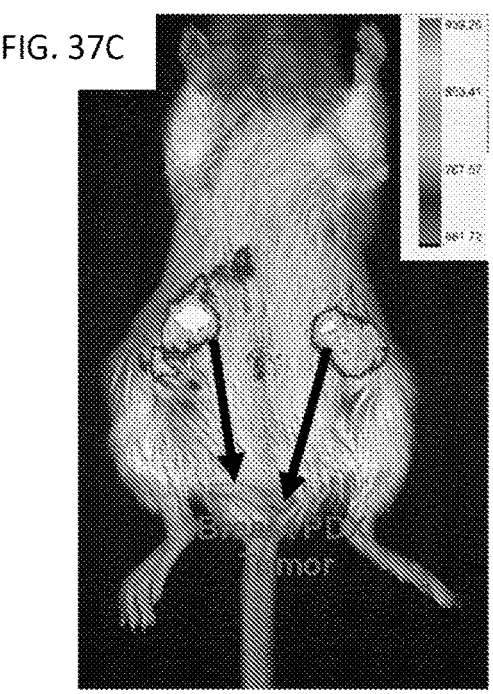
Figure 37D:
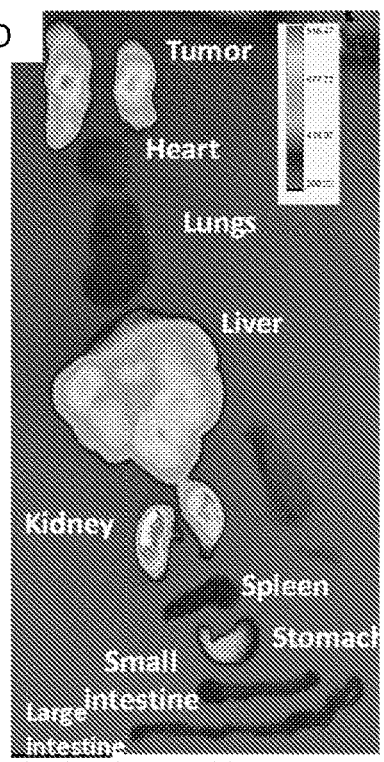

FIG. 36 is a graph showing the CAIX and CD44 targeting nanoformulation encapsulated paclitaxel demonstrated superior HT-29 tumor killing effect compared to control.

FIGS. 37A-38D illustrates that the CAIX and CD44 targeting nanoformulation conjugated with Nera infrared fluorescent dye showed superior tumor core penetration in (FIG. 37A) lung PDX tumor, (FIG. 37B) tumor targeting bio-distribution (Bio-D) in lung PDX tumor, (FIG. 37C) breast tumor, and (FIG. 37D) tumor targeting bio-distribution (Bio-D) in breast PDX tumor. CAIX and CD44 targeting nanoformulation demonstrated superior tumor core penetration.

Figure 38A:
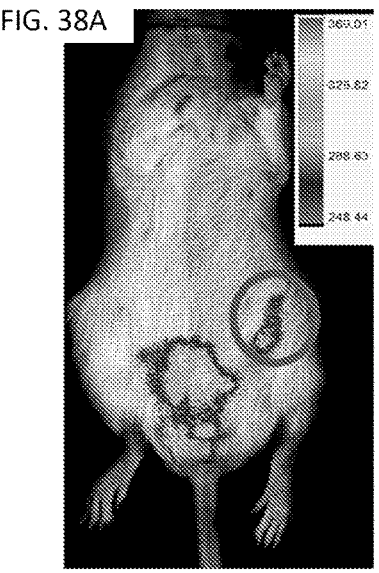
Figure 38B:
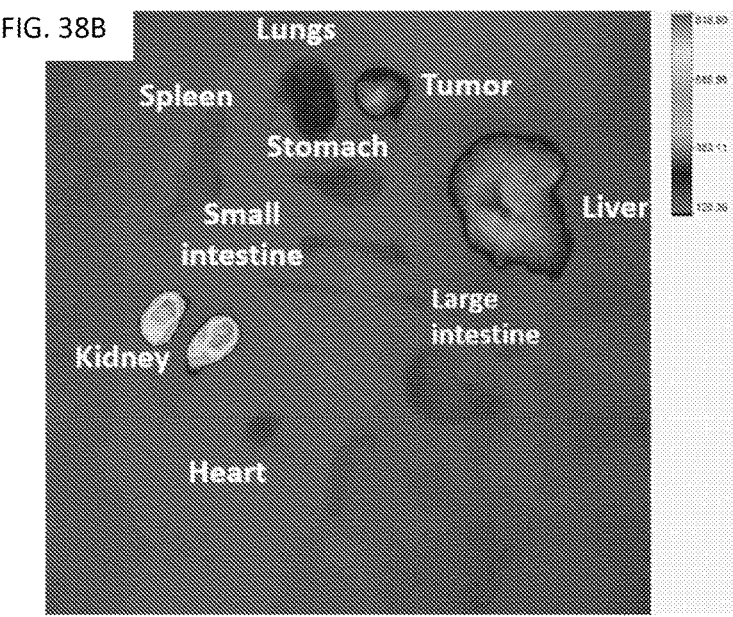
Figure 38C:
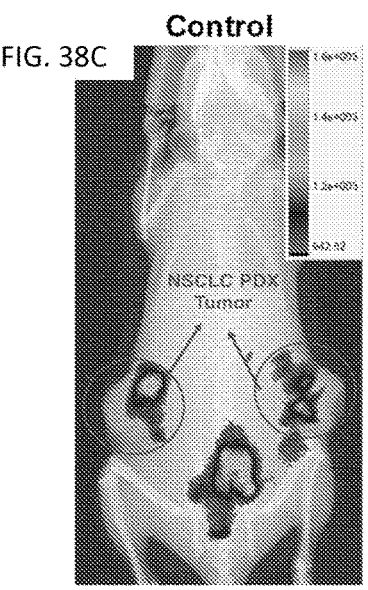

FIGS. 38A-38C illustrates re-blocking of CAIX and CD44 receptor inhibits the tumor accumulation of CAIX-CD44 targeting nanoformulation, thus competing the receptor in (FIG. 38A) lung PDX tumor, (FIG. 38B) insignificant tumor accumulation of tumor targeting CAIX-CD44 targeting nanoformulation after receptor blocking in bio-distribution (Bio-D) study of in lung PDX tumor, (FIG. 38C) control dye treated mice has no-significant tumor uptake as compared to CAIX-CD44 targeting nanoformulation.

Figure 39:
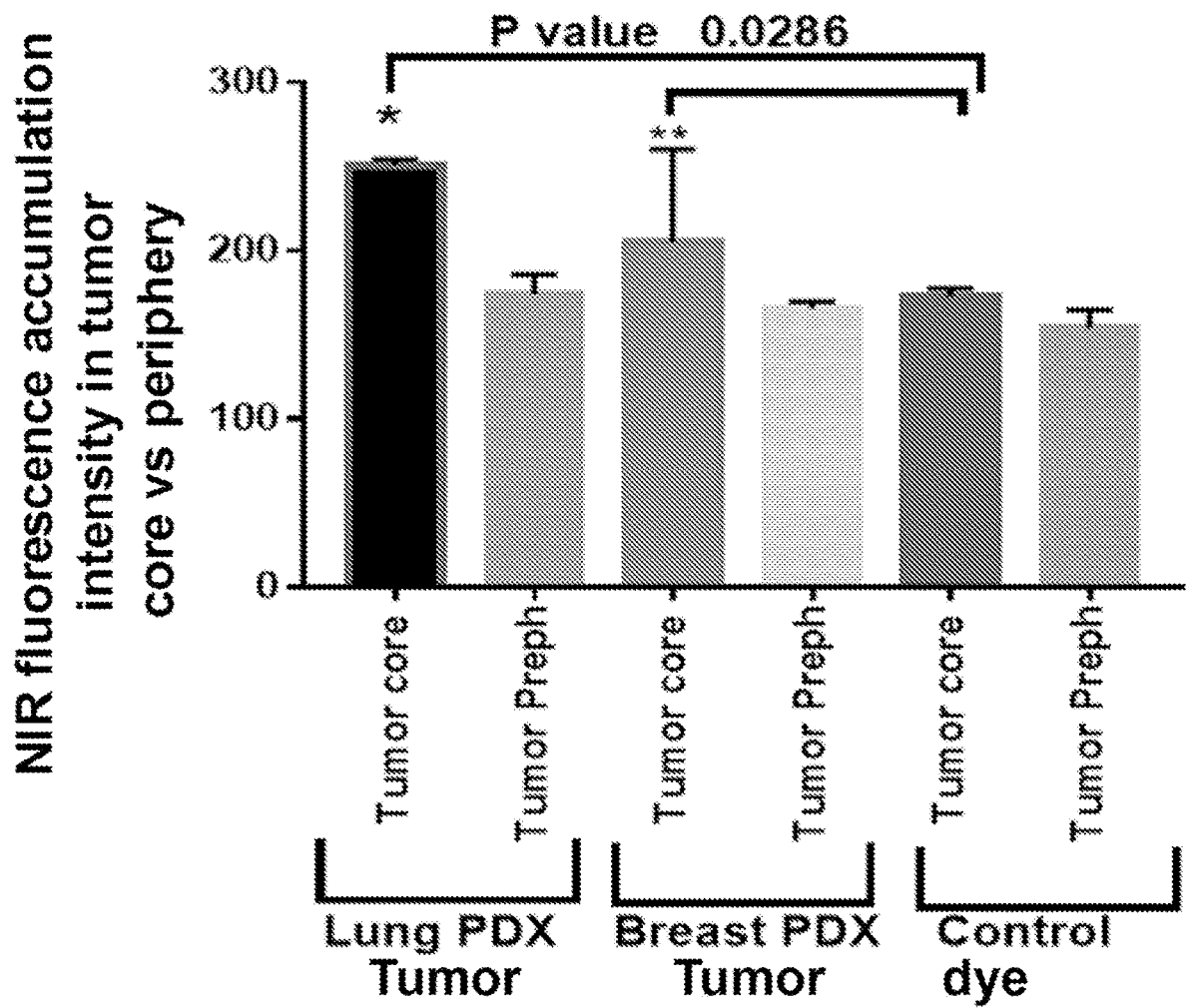

FIG. 39 is a graph, showing the quantification of fluorescent intensities in CAIX and CD44 targeting nanoformulation treated tumor showed higher tumor core penetration than tumor periphery in lung, breast PDX tumor model, whereas control dye fails to reach tumor core as compared to its periphery.

Figure 40:
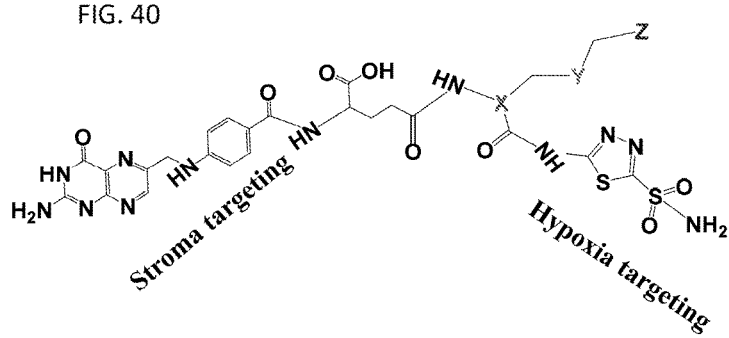

FIG. 40 shows a hypoxia and tumor stroma targeting small molecule imaging agent for imaging guided surgery. Key: X: Click chemistry linker, thiol-maleimide, amide linker, ester bond; Y: Cleavable, non-cleavable, zwitterionic, polyethylene glycol; Saccharo-peptide, dimethylated dithiol linker; Z: Fluorescent dyes (UV, Visible and near infrared dyes); Rhodamine, FITC, S0456, IR 800, ICG FIG. 41 shows a hypoxia (targeting CAIX) and tumor stroma (folate receptor) targeting small molecule conjugated with rhodamine dye (namely FA-CAIX Rhodamine) for imaging and detection of tumor, pre-tumor, polyps and imaging guided surgery.

Figure 41:
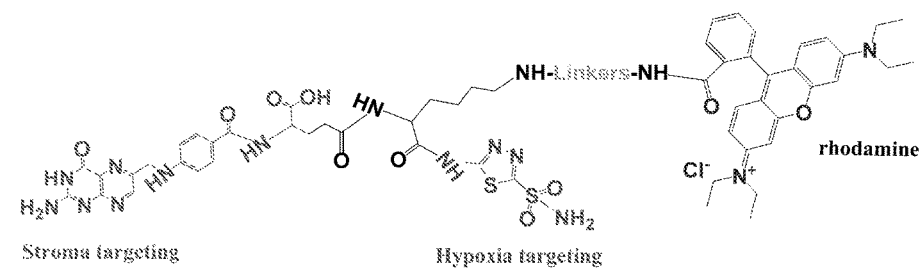
Figure 42:
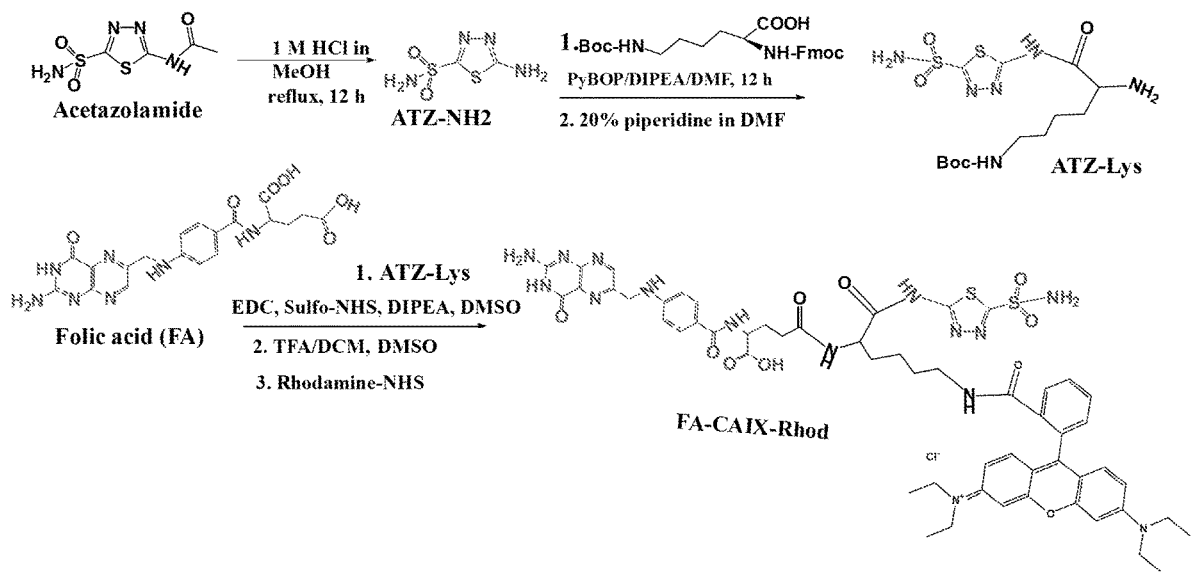

FIG. 42 is a scheme illustrating stepwise production of the compounds illustrated in FIGS. 41 & 41.

Figure 43:
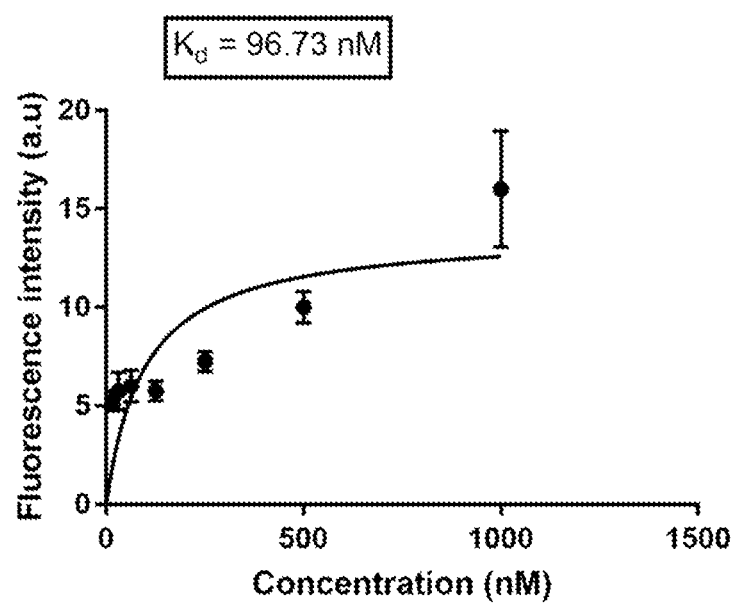

FIG. 43 is a graph showing that the high binding affinity of the small molecule imagining agent FA-CAIX-Rhod provides selectivity hypoxia and tumor stroma. The high binding affinity is due presence of dual hypoxia and tumor stroma targeting ligand. The high affinity will improve the tumor penetration with better and selective tumor treatment. This small molecule can change the paradigm of tumor imaging and imaging guided surgery in wide variety of tumor.

Figure 44A:
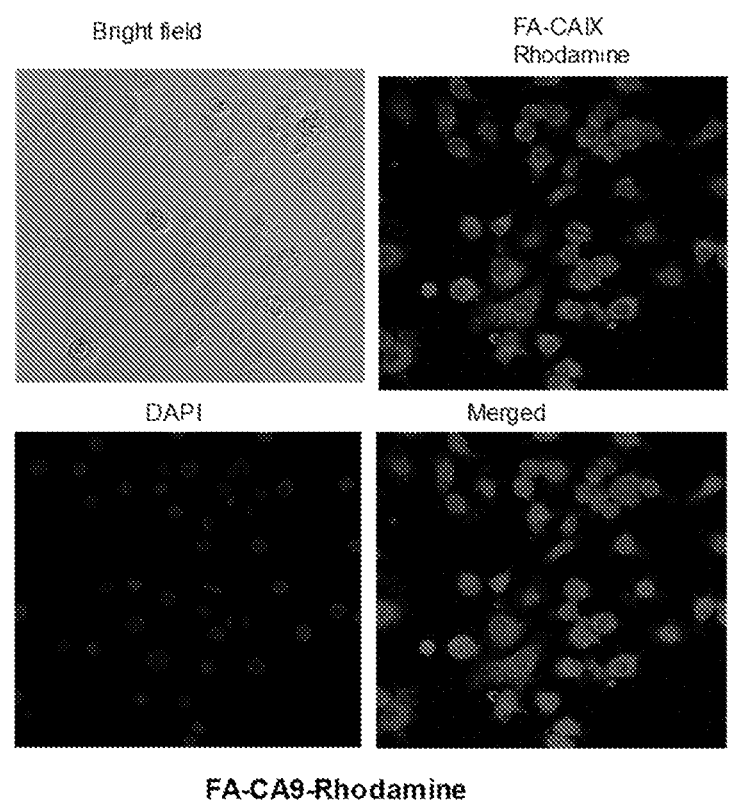
Figure 44B:
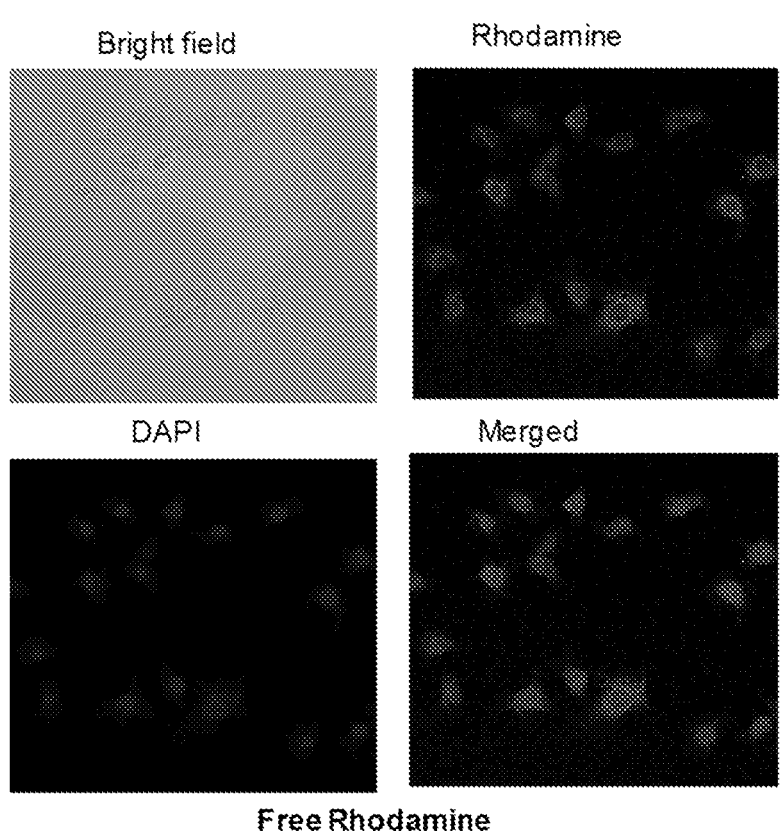

FIGS. 44A-44B are a series of micrographs illustrating results of a cell uptake study in folate receptor (overexpressed in tumor stroma) and CAIX (overexpressed in tumor hypoxia) positive activated RAW 264.7 cell indicates that FA-CAIX-Rhodamine (FIG. 44A) has higher cell accumulation compared to free rhodamine (FIG. 44B). Brighter the red color suggests the higher is the cell uptake.

Figure 45:
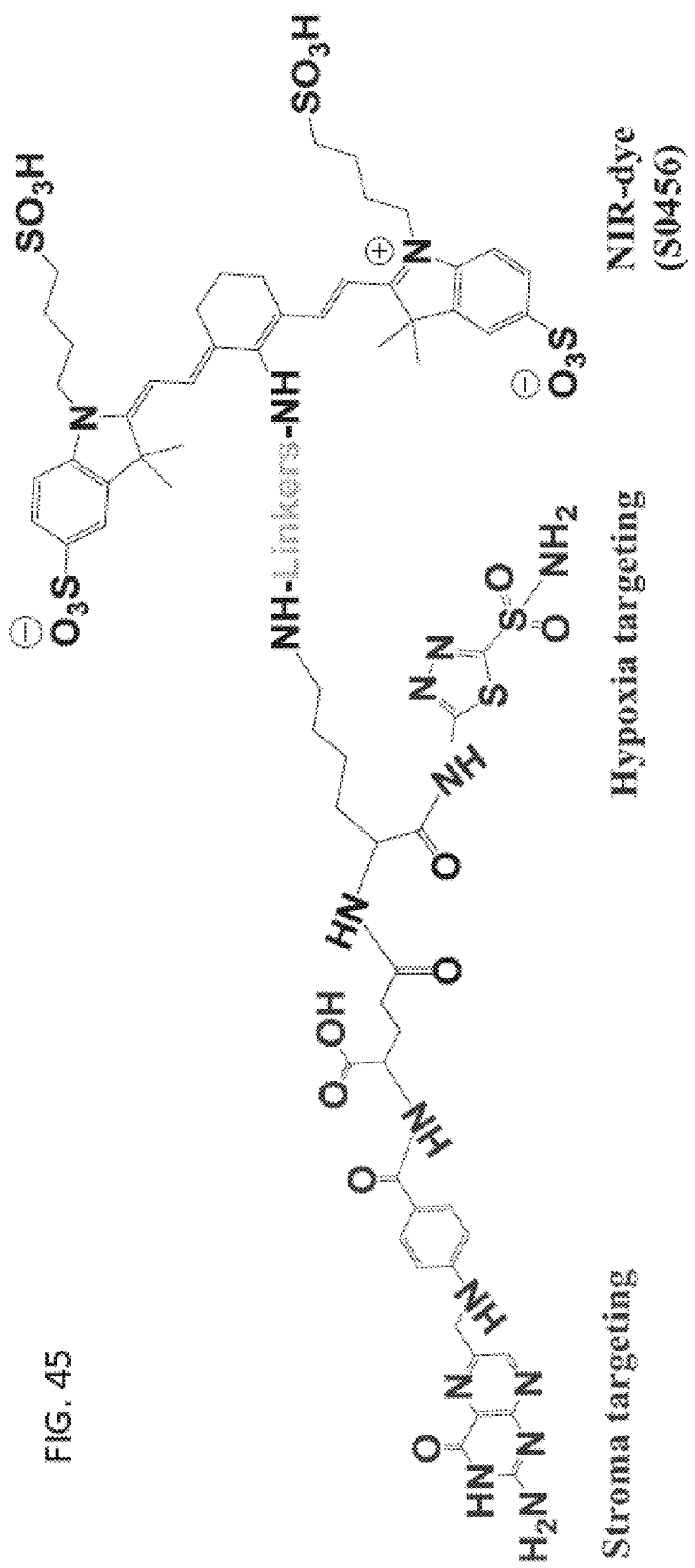

FIG. 45 is a representative hypoxia (targeting CAIX) and tumor stroma (folate receptor) targeting small molecule conjugated with near infrared dye (S0456) (namely FA-CAIX-S0456) for imaging and detection of tumor, pre-tumor, polyps and imaging guided surgery.

Figure 46A:
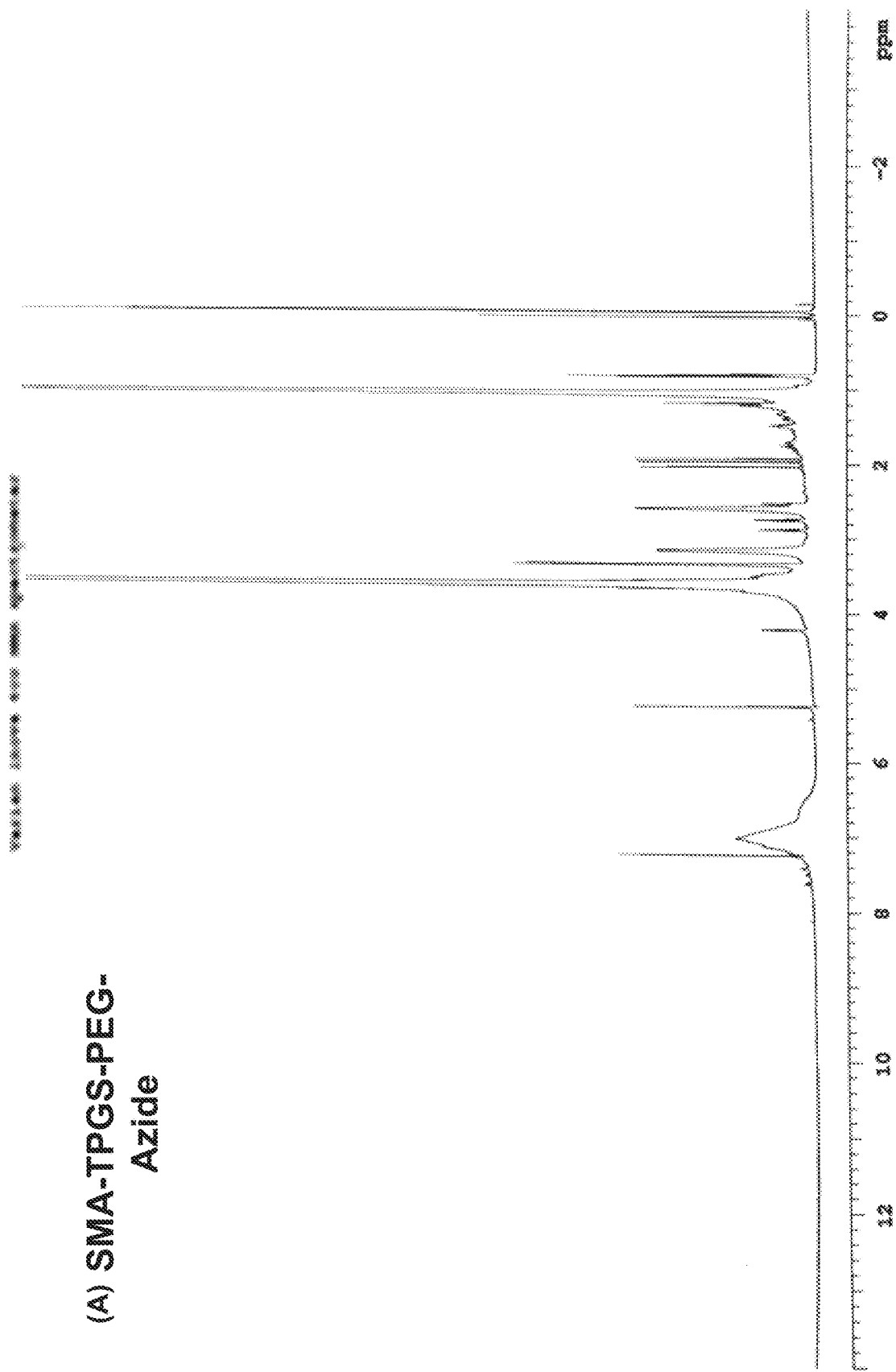

FIG. 46A-46C: Compounds were characterized by $^1$H-NMR to assure chemical identity. SMA-TPGS-PEG-N3 and ATZ-DBCO conjugates indicates the successful conjugation of ATZ to the SMA-TPGS polymers. $^1$H-NMR results confirmed the triazole ring formation as the characteristic peaks were found such as H-triazole ring around 7.9 ppm, O—CH$_2$ of triazole ring around 5.2 ppm, and CH2-N$_3$ peak around 4.2 ppm.

Figure 47:
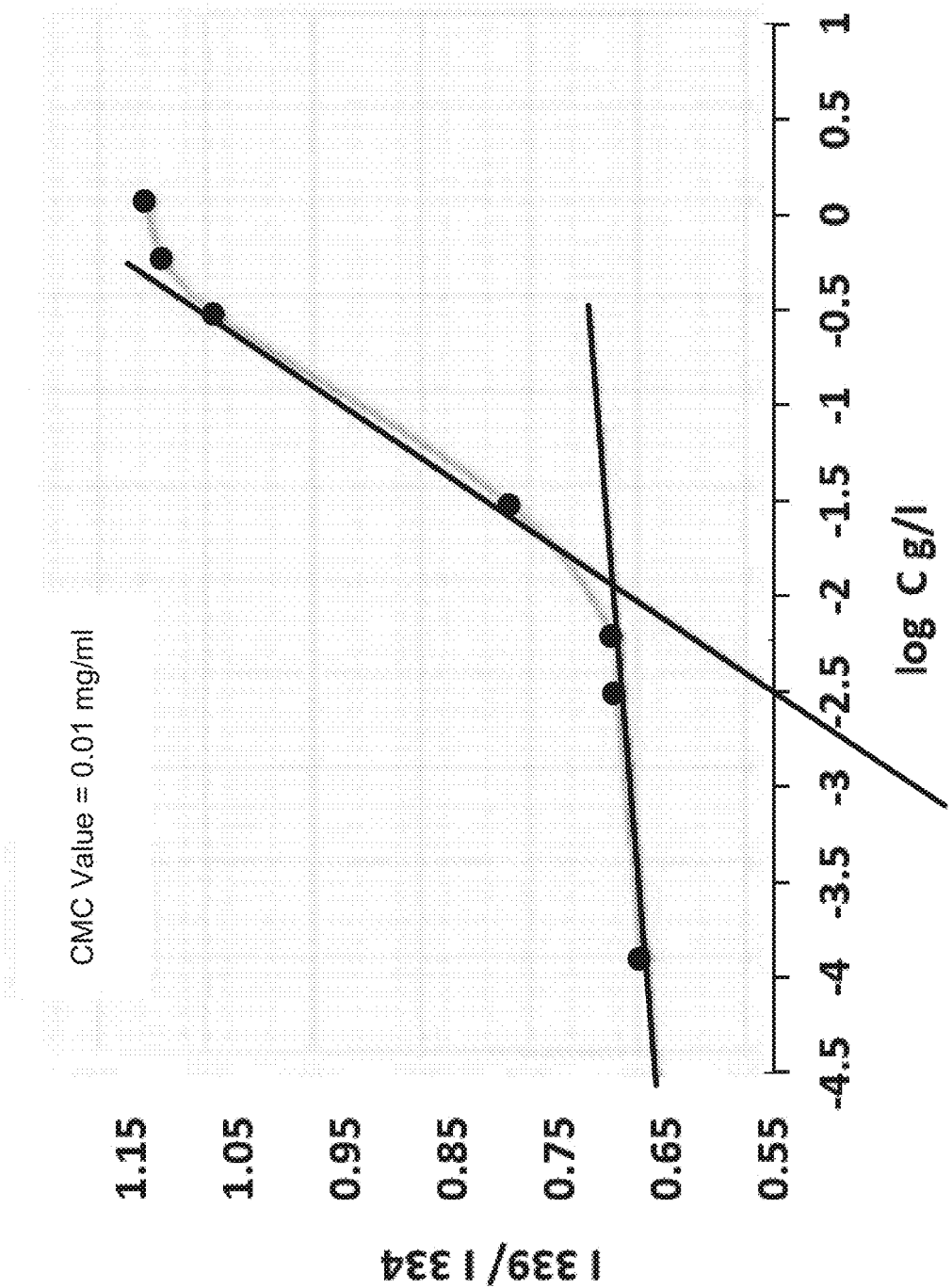

FIG. 47: Critical micellar concentration (CMC) for SMA-TPGS nanomicelles. The CMC of the formulations was 0.010 and 0.021 mg/ml for SMA-TPGS-C4.16 and SMA-TPGS-C4.16, respectively indicating high stability even on dilution of the sample in in vivo conditions such as blood or serum.

FIG. 48: Hydrodynamic particle size of the CAIX-C4.16 NP on reconstitution in 1× PBS after 2 months of storing the lyophilized powder in the −80° C. freezer. There has been a slight change of the particle size with narrow polydispersity index. This data supports the stability of the CAIX-C4.16 NP.

Figure 49A:
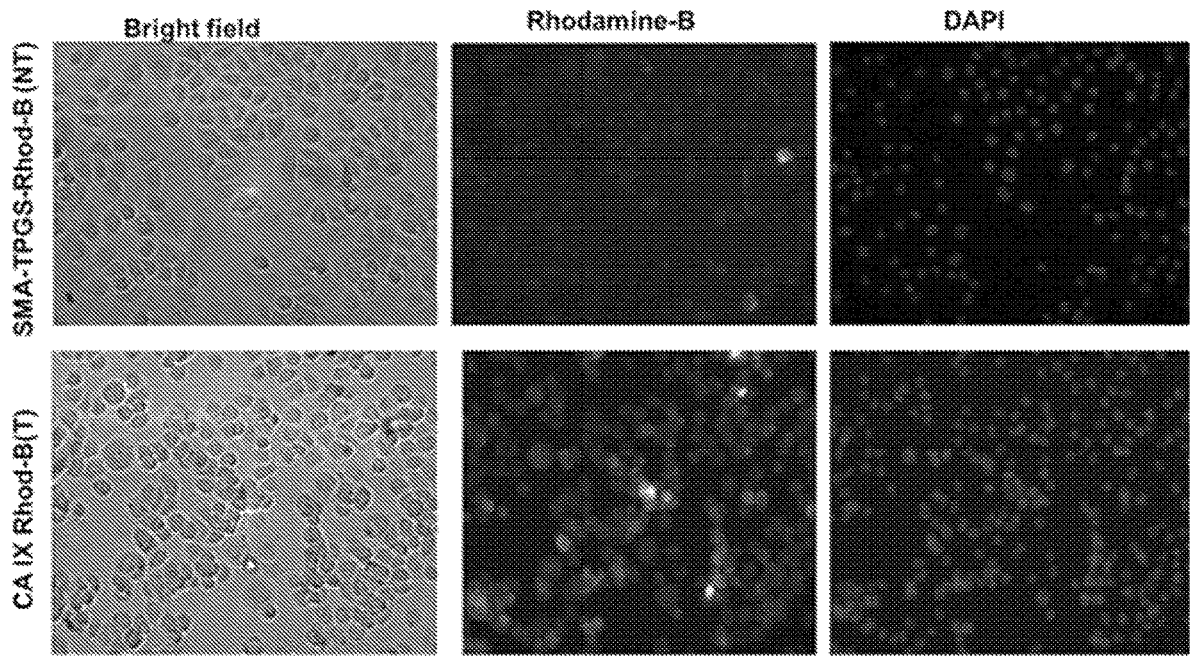
Figure 49B:
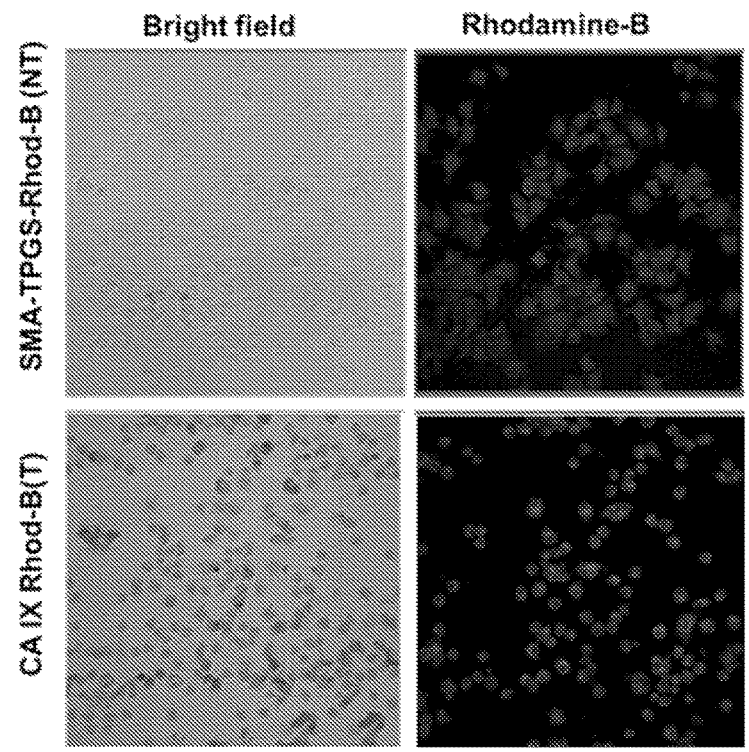

FIGS. 49A-49B Significantly high uptake of CAIX-Rhod-B (T) as compared to SMA-TPGS-Rhod-B (NT) was observed in both (FIG. 49A) epi-fluorescence microscopic study, and (FIG. 49B) Confocal Microscopy imaging. The hypoxic EVR-res A498 cells were treated with Rhodamine B labeled targeted oligomers for 2 h. Gray images and Red fluorescence indicate bright field and Rhodamine B, images respectively.

Figure 50A:
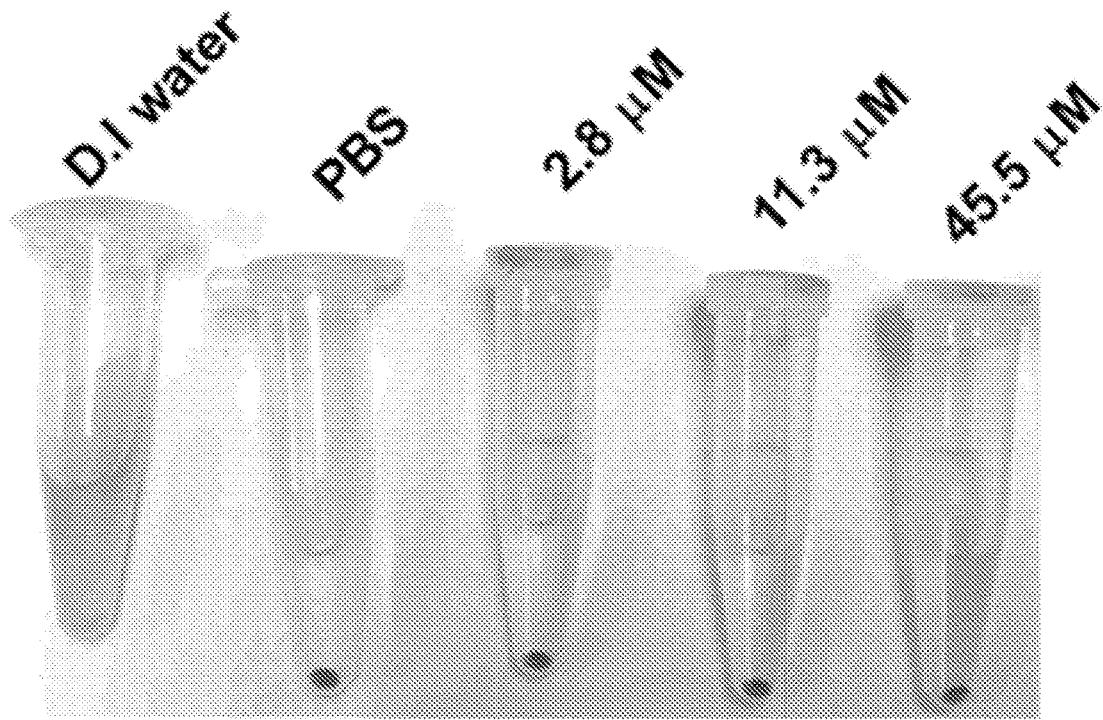
Figure 50B:
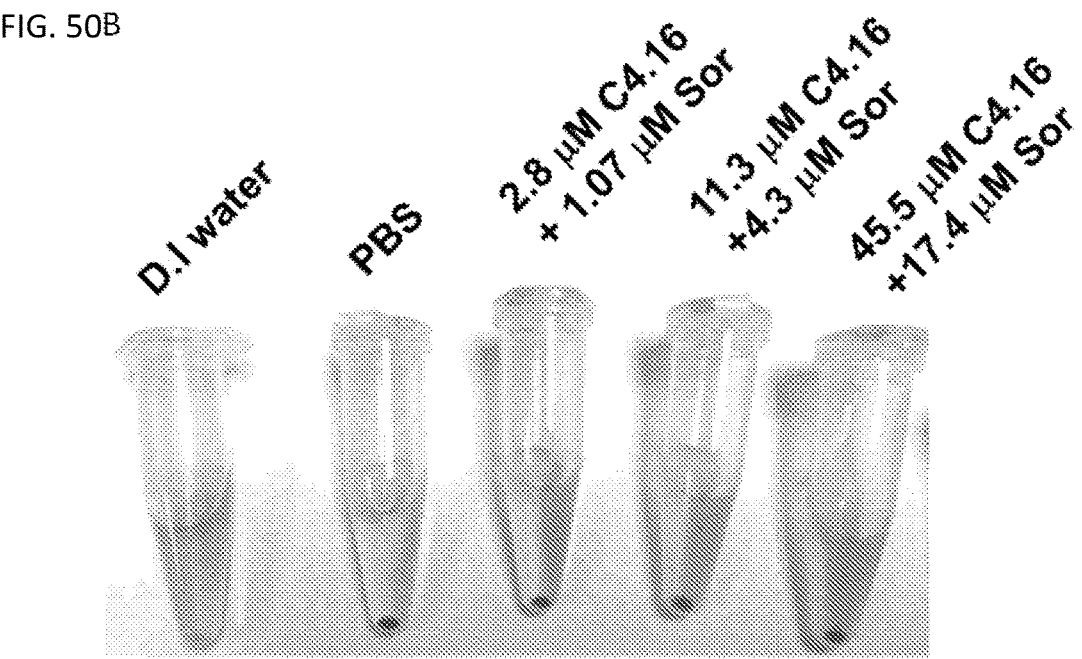

FIGS. 50A-50B: The hemolysis assay of mouse blood treated with (FIG. 50A) CA IX-C4.16 in a range of concentration of C4.16 is 2.8, 11.3, 45.5 µM, PBS as a negative control and DI water as a positive control. The data from this figure clearly indicates there is insignificant hemolysis in all three concentrations of C4.16 with respect PBS and DI water treated blood was completely hemolyzed. (FIG. 50B) Samples treated with CAIX-C4.16 containing C4.16 2.8, 11.3, 45.5 µM in combination with Sor in range of concentration such as 1.07, 4.3, 17.4 µM, PBS as a negative control and DI water as a positive control. All the treatment and control have same amount of DMSO that was added to solubilize in making Sor stock. The data from this figure indicates there no major change in hemolysis for all three concentrations of C4.16+Sor with respect PBS, whereas DI water completely hemolyzed the blood.

Figure 51:
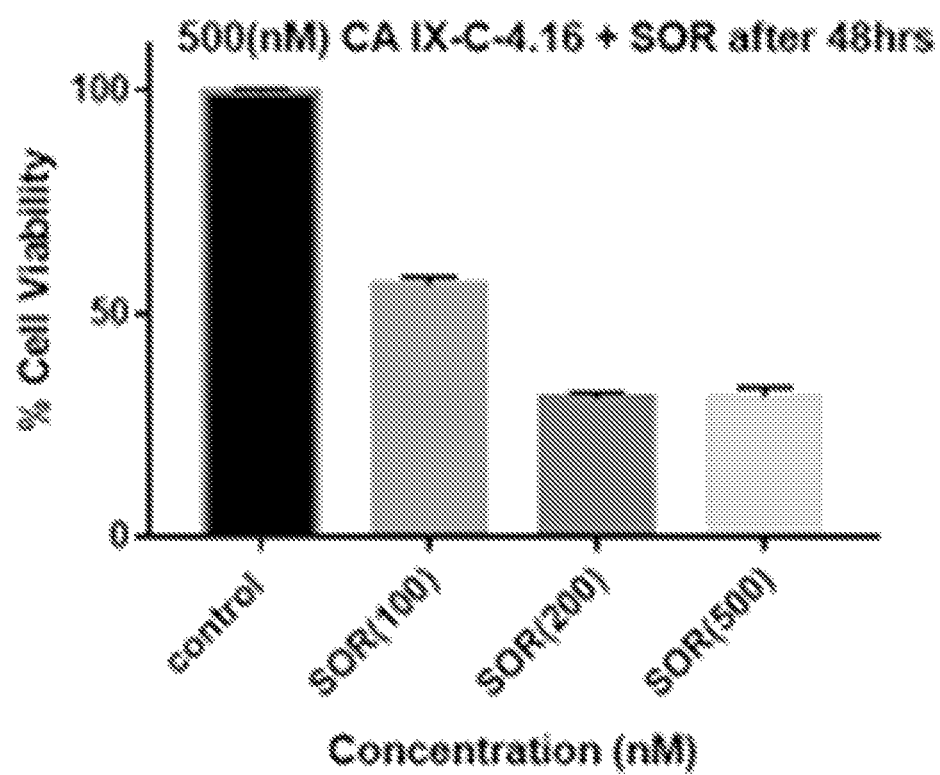

FIG. 51 is a graph showing in vitro cytotoxicity assay of CA IX-C4.16 (500 nM) in combination with different doses of sorafenib on Ev-res A498 RCC cell lines indicates that low dose of CA IX-C4.16 NPs sensitize sorafenib for inhibiting growth of RCC cell line.

DETAILED DESCRIPTION

There is provided herein a first embodiment that is a substantially rod-shaped nanoformulation including: up to 30% CFM-4.16; a styrene maleic anhydride (SMA)—vitamin E tocopheryl polyethylene glycol succinate (TPGS) co-polymer; and one or more of: the CAIX targeting ligand acetazolamide (ATZ); the folate receptor targeting ligand folic acid; both ATZ and folic acid; one or more of sorafenib, everolimus, and/or cabozantinib; and/or a tumor cell stimuli-responsive linker.

Another embodiment is a nanoformulation including up to 30% w/w of a CARP-1 functional mimetic (CFM) and a styrene maleic anhydride (SMA)—vitamin E tocopheryl polyethylene glycol succinate (TPGS) co-polymer. Optionally, such nanoformulations may further include one or more of: a carbonic anhydrase-IX (CAIX; CA9) targeting ligand; the CAIX targeting ligand acetazolamide (ATZ); a folate receptor targeting ligand; the folate receptor targeting ligand folic acid; a CAIX targeting ligand and a folate receptor targeting ligand; one or more of sorafenib, everolimus, and/or cabozantinib; and/or a tumor cell stimuli-responsive linker. In various embodiments of the nanoformulations, one or more of: the CFM is CFM-4.16; the nanoformulation is rod-shaped; the nanoformulation is rod-shaped and 100-200 nm in length; the nanoformulation is spherical; the nanoformulation is within a population of such nanoformulations having: a mean diameter of 144.6 nm±20 nm; a polydispersity index of 0.275±0.05; a Zeta potential of −7.86±4 mV; and/or a critical micelles concentration of 0.010 mg/ml.

Also provided are rod-shaped nanoformulation including: CFM-4.16; a CAIX targeting ligand (such as ATZ); a folate receptor targeting ligand (such as folic acid); and one or more polymer(s) selected from the group consisting of: DBCO-conjugated vitamin E TPSG, SMA-TPGS; 2-hydroxypropyl-β-cyclodextrin (HP-β-CD), sulfobutylether-β-cyclodextrin (SBE-β-CD), phosphatidylethanolamine (PC), ceramide, Pluronic® F127, and PLA-PEG.

Yet additional embodiments are nanoformulations including: a polymer selected from one or more of: DBCO-conjugated vitamin E TPSG, SMA-TPGS; HP-β-CD, SBE-β-CD, PC, ceramide, Pluronic® F127, and PLA-PEG; a CAIX-targeting ligand (such as ATZ); and a dye (such as S0456 NIR dye). The provided nanoformulations may further include one or more of: a folate receptor targeting ligand; a folate receptor targeting ligand including folic acid; a CARP-1 functional mimetic (CFM); a CFR including CFM-4.16; or sorafenib, everolimus, and/or cabozantinib. For instance, in one specific embodiment, the nanoformulation further includes CFM-4.16 and at least one of sorafenib, everolimus, or cabozantinib.

The nanoformulations provided herein include nanoformulation that are rod-shaped (wherein the rod-shaped nanoformulation is 100-200 nm in length, and nanoformulations that are spherical.

Additional embodiments provide pharmaceutical compositions including at least one nanoformulation described herein, as well as uses of such pharmaceutical compositors to treat a solid tumor in a subject in need thereof. By way of example, such uses include instances where the treatment is a prophylactic treatment and/or a therapeutic treatment; and/or uses that overcome drug resistance in the subject in need thereof.

Also provided are imaging composition including any nanoformulation described herein, as well as use of such imaging compositions to visualize a solid tumor in a subject in need thereof. By way of example, such uses include visualizing a solid tumor that is renal cell carcinoma (RCC).

Yet another embodiment is a method of treating a subject with a solid tumor exhibiting hypoxia and/or stromal components, including administering to the subject a nanoformulation described herein, or a pharmaceutical composition including such a nanoformulation.

Another embodiment is a method of treating a subject with a solid tumor (such as a carcinoma, a sarcoma, a lymphoma, a melanoma, a mesothelioma, or an adenocarcinoma) exhibiting hypoxia and/or stromal components, which method includes administering to the subject: (i) a nanoformulation encapsulated with a chemotherapeutic agent (such as a kinase inhibitor) for therapy; and/or (ii) a small molecule-based imaging agent for early diagnosis of tumor, pre-tumor/pre-cancerous lesion, polyp and imaging guided surgery. In specific examples of this method of treatment embodiment the cancer expresses one or more of carbonic anhydrase-IX, XII in a hypoxia/hypoxic region; folate receptor isotypes in tumor and tumor immune cells; and/or CD44 in cancer stem cells or stem like cells.

In further examples of such method of treatment embodiments, the solid tumor is lung cancer, clear cell renal cell carcinoma, non-clear cell renal cell carcinoma, pancreatic cancer, bone cancer, skin cancer, head and neck cancer, cutaneous melanoma, intraocular melanoma uterine cancer, ovarian cancer, endometrial cancer, rectal cancer, stomach cancer, colon cancer, breast cancer, triple negative breast cancer, ovarian cancer, ovarian dysplasia, colorectal polyps, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, oral cancer, laryngeal cancer, testicular cancer, liver cancer, non-small cell lung cancer, cancer of the adrenal gland, cancer of the urethra, prostate cancer, pleural mesothelioma, nasopharyngeal carcinoma, cancer of the bladder, cancer of the ureter, kidney cancer, brain cancer, or pituitary adenoma.

In examples of the methods of treatment, the nanoformulation includes a liposome, lipid-polymer hybrid nanoparticle, or multivesicular liposome including polymers, lipids, and/or natural oils. Further examples include methods wherein the nanoformulation includes one or more of: carbonic anhydrase-IX, XII targeting ligand including imidazole, sulfoimidazole derivative, acetazolamide; methazolamide; ethoxzolamide; dichlorphenamide; dorzolamide; brinzolamide; benzolamide; topiramate; zonisamide; sulpiride; indisulam; celecoxib; valdecoxib; an antibody; or a peptide.

In specific examples of the treatment methods the nanoformulation includes a folate receptor isotype targeting ligand selected from folic acid, methotrexate, aminopterin, antibodies, and peptides; the nanoformulation includes one or more CD44 targeting ligands selected from hyaluronic acid (HA), hyaluronan, antibodies, and peptides; the nanoformulation includes one, two, or more than two different types of receptor targeting ligands that selectively deliver nanoformulation to a tumor microenvironment; the nanoformulation includes at least one: CARP-1 functional mimetic compound (CFM), receptor tyrosine kinase inhibitor (such as axitinib, cediranib, erlotinib, gefitinib, grandinin, lapatinib, lestaurtinib, lucitanib, neratinib, olmutinib, osimertinib, pazopanib, quizartinib, regorafenib, rociletinib, semaxanib, sorafenib, sunitinib, taselisib, tivozanib, toceranib, or vandetanib), cycle dependent kinase inhibitor (such as abemaciclib, ribociclib or trilaciclib), serine-threonine kinase inhibitor (such as Bisindolylmaleimide I, Dihydrochloride(H-89), ML-7, KN-93, or Staurosporine), or mammalian targeting rapamycin (mTOR) inhibitor; and/or the nanoformulation includes up to 30% w/w of anticancer compound including CARP-1 functional mimetic (CFM) (such as CFMs is CFM4, CFM-4.16, CFM-4.20 or CFM-4.17) and a styrene maleic anhydride (SMA)—vitamin E tocopheryl polyethylene glycol succinate (TPGS) co-polymer.

In further method of treatment embodiments, the nanoformulation includes a hypoxia or a stroma component receptor; and//or one, two, or more than two different types of receptor targeting ligands.

Additional method of treatment embodiments include nanoformulations that include spherical, non-spherical, rod shaped, worm-like, and/or flagella like shape liposomes or micelles. For instance, in some instances the rod-shaped nanoformulation is 100-200 nm in length. Additional examples include methods using a nanoformulation that includes a population of liposomes or micelles having a diameter of 40-200±20 nm; or a nanoformulation that includes a population of liposomes or micelles within a population thereof having a polydispersity index of 0.275±0.05.

In specific examples of the treatment methods, the nanoformulation includes a population of liposomes or micelles within a population thereof having a Zeta potential of −7.86±4 mV. In further examples, the nanoformulation includes a population of liposomes or micelles within a population thereof having a critical micelles concentration of 0.010 mg/ml. Optionally, the nanoformulation may include one or more tumor cell stimuli-responsive, antifouling, rigid, flexible, zwitterionic, or pegylated linker.

In specific examples of the method of treating a subject with a solid tumor, the nanoformulation overcomes a drug resistance in the subject in need thereof.

Another provided embodiment is a method of treating a subject with a solid tumor using a nanoformulation, wherein the nanoformulation is a rod-shaped nanoformulation including CFM-4.16, a CAIX targeting ligand, a folate receptor targeting ligand, and a polymer selected from one or more of: DBCO-conjugated vitamin E TPSG, SMA-TPGS; 2-hydroxypropyl-β-cyclodextrin (HP-β-CD), sulfobutylether-β-cyclodextrin (SBE-β-CD), phosphatidylethanolamine (PC), ceramide, Pluronic® F127, or PLA-PEG. Optionally, the nanoformulation further includes one or more of Valine-citrulline (Val-Cit); Hydrazone; alpha-dialky substituted hydrazine; polyethylene glycol unit 2-30 (PEG2-30), (PEG2-40); rigid cyclic hexyl, pentyl groups; non-rigid alkyl groups; Saccharo-peptides; Dithiol (S—S); alpha-dialky substituted [(R1R2HC—S—S—), R1 or R2 are alkyl groups)]; Zwitterionic; or Thiol-maleimide.

Also provided herein are methods of treating a subject with a solid tumor, wherein the small molecule-based imaging agent used for the treatment provides early diagnosis of a tumor, a pre-tumor, or a polyp, and/or enables imaging guided surgery. In examples of such embodiments, the small molecule-based imaging agent includes one, two, or more than two different types of receptor targeting ligand(s) (such as ligand(s) that target hypoxia, stromal components, epithelial cell components, and/or angiogenic blood vessel cell components). In additional examples, the small molecule-based imaging agent includes: one or more rigid cyclic hexyl, pentyl groups; non-rigid alkyl groups; saccharo-peptides; oligomeric, polymeric, Zwitterionic; or Thiol-maleimide linkers; one or more of carbonic anhydrase-IX, XII targeting ligand including imidazole, sulfoimidazole derivative, acetazolamide; methazolamide; ethoxzolamide; dichlorphenamide; dorzolamide; brinzolamide; benzolamide; topiramate; zonisamide; sulpiride; indisulam; celecoxib; valdecoxib; antibody, or peptides; one or more of folate receptor isotypes targeting ligands including folic acid, methotrexate, aminopterin, antibody, or peptides; one or more of CD44 targeting hyaluronic acid (HA), hyaluronan, antibody, or peptides; a CMET targeting GE137 peptide; and/or a near infrared (NIR-I) dye (such as S0456), a near-infrared NIR (NIR-II) dye, or a maleimide, dibenzocyclooctyne (DBCO), thiol, carboxylic acid (—COOH), amine (—$NH_2$), or azide ($N_3$) functionalized derivative thereof.

The following section is illustrative but not limiting to the remainder of the disclosure. For example, methods of treatment are not limited to RCC, but instead include treating numerous other conditions (including specifically other solid tumors) as described elsewhere herein.

Methods disclosed herein include treating subjects (humans, veterinary animals (dogs, cats, reptiles, birds, etc.) livestock (horses, cattle, goats, pigs, chickens, etc.) and research animals (monkeys, rats, mice, fish, etc.) with therapeutic compositions disclosed herein. Treating subjects includes delivering therapeutically effective amounts. Therapeutically effective amounts include those that provide effective amounts, prophylactic treatments and/or therapeutic treatments.

An "effective amount" is the amount of a compound necessary to result in a desired physiological change in the subject. Effective amounts are often administered for research purposes. Effective amounts disclosed herein can cause a statistically-significant effect in an animal model or in vitro assay relevant to the assessment of RCC development or progression.

A "prophylactic treatment" includes a treatment administered to a subject who does not display signs or symptoms of RCC or displays only early signs or symptoms of RCC such that treatment is administered for the purpose of diminishing or decreasing the risk of developing RCC further. Thus, a prophylactic treatment functions as a preventative treatment against RCC. In particular embodiments, prophylactic treatments reduce, delay, or prevent metastasis from a primary RCC tumor site from occurring.

A "therapeutic treatment" includes a treatment administered to a subject who displays symptoms or signs of RCC and is administered to the subject for the purpose of diminishing or eliminating those signs or symptoms of RCC. The therapeutic treatment can reduce, control, or eliminate the presence or activity of RCC and/or reduce control or eliminate side effects of RCC.

Particular embodiments include suppressing RCC in a subject by administering an anti-RCC compound disclosed herein. RCC suppression includes one or more of decreasing the number of RCC cells in a subject, decreasing the number of metastases in as subject, decreasing tumor volume in a subject, increasing life expectancy in a subject, inducing chemo- or radiosensitivity in RCC cells in a subject, inhibiting RCC cell proliferation in a subject, inhibiting tumor growth in a subject, preventing, reducing, or delaying metastases in a subject, prolonging a subject's life, reducing cancer-associated pain in a subject, and/or reducing or delaying relapse or re-occurrence of RCC following treatment in a subject.

In particular embodiments, compositions are administered following the emergence of drug resistance, and can overcome drug resistance. Drug resistance refers to a clinical stage when cancer cell(s) do not respond to the cell-killing effects of administered drugs. Cancer cells may be drug resistant at the beginning of treatment, or may become resistant during the course of treatment.

For administration, therapeutically effective amounts (also referred to herein as doses) can be initially estimated based on results from in vitro assays and/or animal model studies. The actual dose amount administered to a particular subject can be determined by a physician, veterinarian or researcher taking into account parameters such as physical and physiological factors including target, body weight, severity of RCC, type of RCC, stage of RCC, previous or concurrent therapeutic interventions, idiopathy of the subject and route of administration.

Useful doses can range from 0.01 to 500 µg/kg or from 0.01 to 500 mg/kg. Therapeutically effective amounts can be achieved by administering single or multiple doses during the course of a treatment regimen (e.g., daily, every other day, weekly, monthly, every 6 months, or yearly).

The compositions described herein can be administered by, a variety of routes, however, intravenous injection is currently preferred.

For injection, compositions can be made as aqueous solutions, such as in buffers such as Hanks' solution, Ringer's solution, or physiological saline. The solutions can contain formulatory agents such as suspending, stabilizing and/or dispersing agents. Alternatively, the composition can be in lyophilized and/or powder form for constitution with a suitable vehicle, e.g., sterile pyrogen-free water, before use.

Compositions can advantageously include any pharmaceutically acceptable carriers which include those that do not produce significantly adverse, allergic or other untoward reactions that outweigh the benefit of administration, whether for research, prophylactic and/or therapeutic treatments. Exemplary pharmaceutically acceptable carriers and formulations are disclosed in Remington's Pharmaceutical Sciences, 18th Ed. Mack Printing Company, 1990. Moreover, compositions can be prepared to meet sterility, pyrogenicity, general safety and purity standards as required by United States FDA Office of Biological Standards and/or other relevant foreign regulatory agencies.

Exemplary generally used pharmaceutically acceptable carriers include any and all bulking agents or fillers, solvents or co-solvents, dispersion media, coatings, surfactants, antioxidants (e.g., ascorbic acid, methionine, vitamin E), preservatives, isotonic agents, absorption delaying agents, salts, stabilizers, buffering agents, chelating agents (e.g., EDTA), gels, binders, disintegration agents, and/or lubricants.

For imaging, in addition to S0456 NIR dye, exemplary fluorescent dyes include xanthene dyes, fluorescein dyes, rhodamine dyes, fluorescein isothiocyanate (FITC), 6 carboxyfluorescein (FAM), 6 carboxy-2',4',7',4,7-hexachlorofluorescein (HEX), 6 carboxy 4',5' dichloro 2',7' dimethoxyfluorescein (JOE or J), N,N,N',N' tetramethyl 6 carboxyrhodamine (TAMRA or T), 6 carboxy X rhodamine (ROX or R), 5 carboxyrhodamine 6G (R6G5 or G5), 6 carboxyrhodamine 6G (R6G6 or G6), and rhodamine 110; cyanine dyes, e.g. Cy3, Cy5 and Cy7 dyes; Alexa dyes, e.g., Alexa-fluor-555; coumarin, Diethylaminocoumarin, umbelliferone; benzamide dyes, e.g. Hoechst 33258; phenanthridine dyes, e.g. Texas Red; ethidium dyes; acridine dyes; carbazole dyes; phenoxazine dyes; porphyrin dyes; polymethine dyes, BODIPY dyes, quinoline dyes, Pyrene, Fluorescein Chlorotriazinyl, R110, Eosin, Tetramethylrhodamine, Lissamine, ROX, Napthofluorescein, and the like. See, for instance, Lv et al. (*Mol. Pharm* 13(5):1618-1625, 2016) and Mahalingam et al. (*Bioconjugate Chem* 29(10):3320-3331, 2018) for further discussion about S0456. Also specifically contemplated are far-NIR dyes with an NIR-II excitation window (such as CH1055), and their maleimide, thiol, carboxylic acid (—COOH), amine (—NH$_2$), dibenzocyclooctyne (DBCO) or azide (N$_3$) functionalized derivatives. See, for instance, Ding et al. (*Chem Sci.* 9(19):4370-4380, 2018); Zhu et al. (*Theranostics,* 8(15):4141-4151, 2018); Deng et al. (*Theranostics,* 8(15):4116-4128, 2018); Starosolski et al. (*PLoS One* 2017, doi.org/10.1371/journal.pone.0187563). Further imaging agent description is provided below.

The disclosure describes, in various embodiments, (a) synthesis, characterization and optimization of carbonic anhydrase-IX (CAIX) conjugated targeted polymer-lipid nanoformulation (PLNP) using copper-free click chemistry; (b) in vitro testing of CAIX-targeted-PLNP loaded with CFM-4.16 or sorafenib and their combination in inhibiting RCCs and (c) In vivo pre-clinical testing of CFM-4.16, sorafenib and their nanoformulation alone or in combination in mice models of RCCs.

Within the disclosure, the following terms can be used interchangeably: nanoformulation, nanomicelle, organomicelle, polymer-lipid nanoformulation (PLNP), and polymeric nanoparticle.

In particular embodiments, the nanoformulation can be functionalized with targeting ligands that bind CAIX. These embodiments can improve delivery specificity and efficiency.

Aspects of the current disclosure are now described in more detail. The description is organized into the following sections: (i) Liposome Nanoparticles; (ii) Targeting Ligand(s); (iii) Formulations; (iv) Methods of Treatment; (v) Diagnostic/Detection Agents; and (vi) Kits.

(i) Liposome Nanoparticles: Described Herein is the Preparation and Characterization of Liposomes which Encapsulate As illustrated in FIG. 20, drug encapsulated liposome can be prepared with click chemistry reacting functional group (such as DBCO) that can be reacted with FR-CA9 dual targeting ligand with azide (—N$_3$) functional group for selectively delivery of payload in tumor stroma and hypoxia.

Though specific useful lipid compositions are described herein the, the liposomes and lipid nanoparticles of the present disclosure can contain any suitable lipid, including cationic lipids, zwitterionic lipids, neutral lipids, or anionic lipids as described above. Suitable lipids can include fats, waxes, steroids, cholesterol, fat-soluble vitamins, monoglycerides, diglycerides, phospholipids, sphingolipids, glycolipids, cationic or anionic lipids, derivatized lipids, and the like.

Suitable phospholipids include phosphatidylcholine (PC), phosphatidic acid (PA), phosphatidylethanolamine (PE), phosphatidylglycerol (PG), phosphatidylserine (PS), and phosphatidylinositol (PI), dimyristoyl phosphatidyl choline (DMPC), distearoyl phosphatidyl choline (DSPC), dioleoyl phosphatidyl choline (DOPC), dipalmitoyl phosphatidyl choline (DPPC), dimyristoyl phosphatidyl glycerol (DMPG), distearoyl phosphatidyl glycerol (DSPG), dioleoyl phosphatidyl glycerol (DOPG), dipalmitoyl phosphatidyl glycerol (DPPG), dimyristoyl phosphatidyl serine (DMPS), distearoyl phosphatidyl serine (DSPS), dioleoyl phosphatidyl serine (DOPS), dipalmitoyl phosphatidyl serine (DPPS), dioleoyl phosphatidyl ethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), 1,2-dielaidoyl-sn-glycero-3-phophoethanolamine (transDOPE), and cardiolipin. Lipid extracts, such as egg PC, heart extract, brain extract, liver extract, and soy PC, are also useful. In some embodiments, soy PC can include Hydro Soy PC(HSPC). In certain embodiments, the lipids can include derivatized lipids, such as PEGylated lipids. Derivatized lipids can include, for example, DSPE-PEG2000, cholesterol-PEG2000, DSPE-polyglycerol, or other derivatives generally known in the art.

Liposomes and lipid nanoparticles of the present disclosure may contain steroids, characterized by the presence of a fused, tetracyclic gonane ring system. Examples of steroids include cholesterol, cholic acid, progesterone, cortisone, aldosterone, estradiol, testosterone, dehydroepiandrosterone. Synthetic steroids and derivatives thereof are also contemplated for use in methods and compositions of the present disclosure.

Cationic lipids contain positively charged functional groups under physiological conditions. Cationic lipids include N, N-dioleyl-N, N-dimethylammonium chloride (DODAC), N, N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N-[1-(2,3,-ditetradecyloxy)propyl]-N, N-dimethyl-N-hydroxyethylammonium bromide (DMRIE), N-[1-(2,3,dioleyloxy)propyl]-N,N-dimethyl-N-hydroxy ethylammonium bromide (DORI E), 3β-[N—(N', N'-dimethylaminoethane)carbamoyl]cholesterol (DC-Chol), dimethyldioctadecylammonium (DDAB) and N,N-dimethyl-2,3-dioleyloxy)propylamine (DODMA).

Any suitable combination of lipids can be used to provide the liposomes and lipid nanoparticles of the disclosure. The lipid compositions can be tailored to affect characteristics such as leakage rates, stability, particle size, zeta potential, protein binding, in vivo circulation, and/or accumulation in tissues or organs. For example, DSPC and/or cholesterol can be used to decrease leakage from liposomes. Negatively or positively lipids, such as DSPG and/or DOTAP, can be included to affect the surface charge of a liposome or lipid nanoparticle. In some embodiments, the lipid compositions can include ten or fewer types of lipids, or five or fewer types of lipids, or three or fewer types of lipids. In some embodiments, the molar percentage (mol %) of a specific type of lipid present typically includes from 0% to 10%, from 10% to 30%, from 30% to 50%, from 50% to 70%, from 70% to 90%, from 90% to 100% of the total lipid present in a liposome or lipid nanoparticle.

The lipid nanoparticles of the present disclosure can contain surfactants including non-ionic surfactants, some of which can act as triggering agents to facilitate release of the therapeutic liposome's cargo. Examples of non-ionic surfactants include ethoxylated alkylphenols, ethoxylated fatty esters, sorbitan derivatives, and tocopherol derivatives. Surfactants contemplated for use in the present disclosure include D-α-tocopherol polyethylene glycol succinate (TPGS), which is available having different polyethylene glycol sizes. Other useful non-ionic surfactants include: polyethylene glycol p-(1,1,3,3-tetramethylbutyl)-phenyl ether, polyoxyethylene (2) isooctylphenyl ether, polyoxyethylene (150) dinonylphenyl ether, dodecanoic acid 2,3-dihydroxypropyl ester, polyoxyethylene (20) sorbitan monolaurate, polyoxyethylene (20) sorbitan monopalmitate, polyoxyethylene (20) sorbitan monostearate, polyoxyethylene (20) sorbitan monooleate, and the like.

The term "liposome" encompasses any compartment enclosed by a lipid bilayer. The term liposome includes unilamellar vesicles which are composed of a single lipid bilayer and generally have a diameter in the range of 20 to 400 nm. Liposomes can also be multilamellar, which generally have a diameter in the range of 1 to 10 μm. In some embodiments, liposomes can include multilamellar vesicles (MLV), large unilamellar vesicles (LUV), and small unilamellar vesicles (SUV); mixtures are also contemplated.

"Micelle" refers to an aggregate of amphiphilic molecules such as lipids, assembled to form a particle with a hydrophobic interior and a hydrophilic exterior. Micelles are generally spherical assemblies with diameters below 100 nm, although a range of micelle diameters and varying micelle shapes, such as discoid micelles, are known in the art.

As used herein, the term "lipid" refers to lipid molecules that can include fats, waxes, steroids, cholesterol, fat-soluble vitamins, monoglycerides, diglycerides, phospholipids, sphingolipids, glycolipids, cationic or anionic lipids, derivatized lipids, and the like, as described in detail below. Lipids can form micelles, monolayers, and bilayer membranes. The lipids can self-assemble into liposomes.

As used herein, the terms "molar percentage" and "mol %" refer to the number of a moles of a given lipid or other component of a liposome divided by the total number of moles of all lipid or other components. Unless explicitly stated, the amounts of active agents, diluents, or other components are not included when calculating the mol % for a lipid or surfactant component of a liposome.

(ii)Targeting Ligand(s): Particular embodiments of the therapeutic and/or diagnostic nanoparticles include one or more targeting ligands to provide for more selective delivery to a desired (target) site. See FIGS. 33A and 33B, for instance, which illustrate example possible targets.

Solid tumor includes heterogenous cell populations, thus effective therapy may be carried out using targeting and selectively delivery of the drugs to multiple components of a target tumor. Thus, use of multi-component targeting ligands (or ligand libraries) be decorated on the nanoparticle for tumor selective therapy.

For example, particular embodiments can be done by exploiting the folate receptor beta (FRβ), toll-like receptor (TLR), hyaluronan receptor (CD44), T cell receptor (TCR)

of immune cells of tumor. Tumor epithelial cells overexpressing receptors such as folate receptors (FR), HER-2, and several types of G-protein-coupled receptor (GPCR); tumor angiogenic blood vessel targeting, vascular endothelial growth factor receptor (VEGFR-2) and tumor necrosis factor (TNF)-a; tumor hypoxia marker targeting using antibodies or small molecules; cancer stem cell (CSC) biomarker targeting using CD44; tumor stroma, fibroblast and extracellular matrix marker targeting fibroblast-activated protein (FAP); and programmed death-1 (PD-1) and programmed death ligand-1 (PD-L1) overexpressed in tumor associated immune cells, such as tumor-associated macrophages (TAMs), myeloid-derived suppressor cells (MDSCs) and inflammatory leukocytes (Sau et. al., *Drug Discovery Today* 23(7): 1344-1356, 2018). The FR receptor can be targeted with folic acid; TLR can be targeted with lipopeptides, lipoprotein, small oligonucleotide sequence; prostate specific membrane antigen (PSMA), VEGFR-2 and TNF-a can be targeted with antibody and small molecule inhibitors; CD44 can be targeted with hyaluronic acid (HA); fibroblast activation protein (FAP) of wound fibroblast cells can be targeted by linagliptin, and other xanthine scaffold (Jansen et al., *Med. Chem. Commun.* 5:1700-1707, 2014). Such targeting ligand(s) can be conjugated to nanoformulation for selective tumor multicomponent targeting based on tumor phenotype and biomarker expression.

Particular embodiments can include carbonic anhydrase (CA) enzyme subtypes targeting ligands. CA-ligands, such as acetazolamide and other sulfonamide and sulfamates derivatives, such as acetazolamide; methazolamide; ethoxzolamide; dichorophenamide; dorzolamide; brinzolamide; benzolamide; topiramate; zonisamide; sulpiride; indisulam; celecoxib; valdecoxib; as well as antibody(s) and/or peptides that have high affinity for CA enzymes (Supuran, *Front. Pharmacol.* 2011; doi:10.3389/fphar.2011.00034).

(iii) Formulations: Nanoparticles can be provided as part of compositions formulated for administration to subjects.

Various embodiments employ one or more of lipid, polymeric micelles, polymeric micelle encapsulated liposome, metal nanoparticles, spherical and non-spherical nanoparticles, polymer-lipid hybrid nanoparticles.

The compositions can be formulated for administration by, for example, injection, inhalation, infusion, perfusion, lavage, ingestion, or topical administration. For injection, compositions can be formulated as aqueous solutions, such as in buffers including Hanks' solution, Ringer's solution, or physiological saline. For oral administration, the compositions can be formulated as tablets, pills, dragees, capsules, liquids, gels, syrups, slurries, suspensions and the like.

In particular embodiments, the compositions can be applied as topical agents (e.g., gels, ointments, pastes, creams, lotions, sprays, powders, or salves), by subcutaneous or sub-dermal injections and/or as additives to wound dressings.

The gels, ointments, pastes, creams, lotions, sprays, powders, or salves may contain, in addition to compositions of the disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays particularly may benefit from the inclusion of excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compositions of the disclosure can be alternatively administered by aerosol. This is accomplished by preparing an aqueous aerosol, liposomal preparation or solid particles containing a composition of the disclosure. A non-aqueous (e.g., fluorocarbon propellant) suspension could be used. Sonic nebulizers can be preferred because they minimize exposing the compositions to shear, which can result in degradation of the composition.

Ordinarily, an aqueous aerosol is made by formulating an aqueous solution or suspension of the composition together with conventional pharmaceutically-acceptable carriers and stabilizers. The carriers and stabilizers vary with the requirements of the particular composition, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Compositions can also be formulated as depot preparations. Depot preparations can be formulated with suitable polymeric or hydrophobic materials (for example as an emulsion in an acceptable oil) or ion exchange resins, or as sparingly soluble derivatives, for example, as a sparingly soluble salt.

Additionally, compositions can be formulated as sustained-release systems utilizing semipermeable matrices of solid polymers containing at least one active ingredient. Various sustained-release materials have been established and are well known by those of ordinary skill in the art. Sustained-release systems may, depending on their chemical nature, release active ingredients following administration for a few weeks up to over 100 days.

Compositions can also be incorporated into transdermal patches and/or wound dressings. Generally, in these embodiments, compositions are embedded within puffs, gauzes, fleeces, gels, powders, sponges or other materials that are associated with a second layer to form an adhesive transdermal patch or wound dressing. Absorption enhancers can also be used to increase the flux of the composition across the skin. The rate of such flux can be controlled by either providing a rate controlling membrane or dispersing the composition in a polymer matrix or gel.

In particular embodiments, the second layer of transdermal patch or wound dressing a can be, without limitation, an elastomeric layer, vapor-permeable film, waterproof film, a woven or nonwoven fabric, mesh, or the like. The composition-containing and second layers can be bonded using any suitable method (e.g., the application of adhesives, such as pressure sensitive adhesives, hot melt adhesives, curable adhesives; the application of heat or pressure, such as in lamination, a physical attachment through the use of stitching, studs, other fasteners; or the like).

Although any adhesive suitable for forming a bond with the skin or other tissue can be used, in certain embodiments a pressure sensitive adhesive is used. Pressure sensitive adhesives are generally defined as adhesives that adhere to a substrate when a light pressure is applied but leave little to no residue when removed. Pressure sensitive adhesives include solvent in solution adhesives, hot melt adhesives, aqueous emulsion adhesives, calenderable adhesives, and radiation curable adhesives.

The most commonly used elastomers in pressure sensitive adhesives can include natural rubbers, styrene-butadiene latexes, polyisobutylene, butyl rubbers, acrylics, and silicones. In particular embodiments, acrylic polymer or silicone-based pressure sensitive adhesives can be used. Acrylic polymers can often have a low level of allergenicity, be cleanly removable from skin, possess a low odor, and exhibit low rates of mechanical and chemical irritation. Medical grade silicone pressure sensitive adhesives can be chosen for their biocompatibility.

Amongst the factors that influence the suitability for a pressure sensitive adhesive for use in wound dressings of particular embodiments is the absence of skin irritating components, sufficient cohesive strength such that the adhesive can be cleanly removed from the skin, ability to accommodate skin movement without excessive mechanical skin irritation, and good resistance to body fluids.

In particular embodiments, the pressure sensitive adhesive can include a butyl acrylate. While butyl acrylate pressure sensitive adhesives can generally be used for many applications, any pressure sensitive adhesive suitable for bonding skin can be used. Such pressure sensitive adhesives are well known in the art.

Any composition formulation disclosed herein can advantageously include any other pharmaceutically acceptable carriers which include those that do not produce significantly adverse, allergic or other untoward reactions that outweigh the benefit of administration, whether for research, prophylactic and/or therapeutic treatments. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety and purity standards as required by United States FDA Office of Biological Standards and/or other relevant foreign regulatory agencies.

Exemplary generally used pharmaceutically acceptable carriers include any and all bulking agents or fillers, solvents or co-solvents, dispersion media, coatings, surfactants, antioxidants (e.g., ascorbic acid, methionine, vitamin E), preservatives, isotonic agents, absorption delaying agents, salts, stabilizers, buffering agents, chelating agents (e.g., EDTA), gels, binders, disintegration agents, and/or lubricants.

Once formed, the compositions can be administered to subjects. Subjects include human subjects, veterinary animals (dogs, cats, reptiles, birds, etc. and also including animals found within zoos), livestock (horses, cattle, goats, pigs, chickens, etc.), and research animals (monkeys, rats, mice, fish, etc.).

(iv) Methods of Treatment: Therapeutic treatments include treating, reducing or eliminating a cancer. Specifically contemplated are liposomal compositions for use as chemotherapeutics, targeted therapeutics, radiotherapeutics, photoactivatable therapeutics, cancer immune therapeutics, antibody therapeutics, antibody-drug conjugates, and cancer vaccines, Prophylactic treatments prevent or reduce the occurrence or severity of, or slow down or lessen the development of cancer, or to reduce the likelihood of metastasis.

Treatments can provide an anti-cancer effect. Anti-cancer effects can reduce the number of cells that become cancerous, increase the time before cells become immortalized, prevent a higher level of or faster instance of metastasis, decrease the number of tumors, decrease the volume of cancerous tissue (e.g., tumor volume), increase life expectancy, induce sensitivity of cancerous cells to immune clearance, reduce cancer-associated pain, and/or prevent, reduce, delay, or eliminate a symptom associated with the treated cancer.

Therapeutically effective amounts provide therapeutic treatments and/or prophylactic treatments. Therapeutically effective amounts as well as dosing regimens can be determined by an attending physician or veterinarian, considering various factors such as the age, condition, the severity of the cancer, type of cancer, resistance of cancer cells to treatments, time of administration, and other clinical factors.

Therapeutic agents can include an anticancer agent or cytotoxic agent including avastin, doxorubicin, cisplatin, oxaliplatin, carboplatin, 5-fluorouracil, gemcitibine or taxanes, such as paclitaxel and docetaxel. Additional anticancer agents can include 20-epi-1,25 dihydroxyvitamin D3,4-ipomeanol, 5-ethynyluracil, 9-dihydrotaxol, abiraterone, acivicin, aclarubicin, acodazole hydrochloride, acronine, acylfulvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisaziridinyl-spermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caracemide, carbetimer, carboplatin, carboxamide-amino-triazole, carboxyamidotriazole, carest M3, carmustine, cam 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexonnaplatin, dexrazoxane, dexverapamil, dezaguanine, dezaguanine mesylate, diaziquone, didemnin B, didox, diethylnorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflomithine, eflomithine hydrochloride, elemene, elsamitrucin, emitefur, enloplatin, enpromate, epipropidine, epirubicin, epirubicin hydrochloride, epristeride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, fluorocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilmofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-$N_3$, interferon beta-IA, interferon gamma-IB, interferons, interleukins, iobenguane, iododoxorubicin, iproplant, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide 7, lobaplatin, lombricine, lometrexol, lometrexol sodium, lomustine, lonidamine, losoxantrone, losoxantrone hydrochloride, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, 06-benzylguanine, octreotide, okicenone, oligonucleotides, onapristone, ondansetron, oracin, oral cytokine inducer, orinaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazofurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RII retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI 1 mimetics, semustine, senescence derived inhibitor 1, sense oligonucleotides, signal transduction inhibitors, signal transduction modulators, simtrazene, single chain antigen binding protein, sizofuran, sobuzoxane, sodium borocaptate, sodium phenylacetate, solverol, somatomedin binding protein, sonermin, sparfosate sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride. Also contemplated are all known and to-be-developed immune check point inhibitors.

In some embodiments, the therapeutic agents can be part of cocktail of agents that includes administering two or more therapeutic agents.

In addition, the therapeutic agents can be delivered before, after, or with immune stimulatory adjuvants, such as aluminum gel or salt adjuvants (e.g., aluminum phosphate or aluminum hydroxide), calcium phosphate, endotoxins, toll-like receptor adjuvants and the like.

The compositions optionally can also be administered with one or more anti-infective agents such as anthelmintics (mebendazole), antibiotics including aminoclycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin, clindamycin, colistimethate sodium, polymyxin b sulfate, antivirals including acyclovir, amantadine, didanosine, efavirenz, foscarnet, ganciclovir, indinavir, lamivudine, nelfinavir, ritonavir, saquinavir, stavudine, valacyclovir, valganciclovir, zidovudine, quinolones (ciprofloxacin, levofloxacin), sulfonamides (sulfadiazine, sulfisoxazole), sulfones (dapsone), furazolidone, metronidazole, pentamidine, sulfanilamidum crystallinum, gatifloxacin, and sulfamethoxazole/trimethoprim. In particular embodiments, vancomycin can be replaced with an antibiotic disclosed within this paragraph. In particular embodiments, cefazolin can be replaced with an antibiotic disclosed within this paragraph.

Compositions optionally can also be administered with anesthetics such as ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and phenazopyridine.

In therapeutic use for the treatment of cancer, the liposome compositions including a therapeutic and/or diagnostic agent utilized in the pharmaceutical compositions of the present disclosure can be administered at the initial dosage of 0.001 mg/kg to 1000 mg/kg daily. A daily dose range of 0.01 mg/kg to 500 mg/kg, or 0.1 mg/kg to 200 mg/kg, or 1 mg/kg to 100 mg/kg, or 10 mg/kg to 50 mg/kg, can be used. The dosages, however, may be varied depending upon the requirements of the patient, the severity of the condition being treated, and the liposome composition(s) being employed. For example, dosages can be empirically determined considering the type and stage of cancer diagnosed in a particular patient. The dose administered to a patient, in the context of the present disclosure, should be sufficient to affect a beneficial therapeutic response in the patient over time. Determination of the proper dosage for a particular situation is within the skill of the practitioner. Optionally, treatment is initiated using lower dosages that may be less than the optimum dose of the liposome composition. Thereafter, the dosage may be increased by small increments until an optimum effect is reached. For convenience, the total daily dosage may be divided and administered in portions during the day, if desired.

(v) Diagnostic/Detection Agents

Tumor diagnosis and detection can be performed by administering to a tumor a multicomponent binding (targeted) imaging agent delivery conjugate (such as a liposome including an imaging agent and at least one targeting moiety).

For example, tumor multi-component homing imaging agent delivery conjugates, such as for example a FR/CA9 binding imaging agent, or a CD44/CA9 binding imaging agent, can be administered as a single dose or can be divided and administered as a multiple-dose regimen for primary tumor, pre-tumor or tumor metastatic tumor imaging, diagnosis, and/or detection.

The imaging agents can be used for tumor imaging-guided surgery. During surgical resection of a tumor, use of tumor multi-component binding imaging liposome can help the surgeon to visualize the tumor lesion, and/or tumor associated tissue. Thus, the surgeon can more precisely resect the tumor mass and leave healthy tissue untouched. See, e.g., Alsaab et al., *Biomaterials,* 183: 280-294, 2018; Wang et al., *Nanomedicine: Nanotechnology, Biology and Medicine* 14(4):1441-1454, 2018).

The therapeutic liposomes of the present disclosure may also contain diagnostic agents. A diagnostic agent used in the present disclosure can include any diagnostic agent known in the art, as provided, for example, in the following references: Armstrong et al., Diagnostic Imaging, 5th Ed., Blackwell Publishing (2004); Torchilin, V. P., Ed., Targeted Delivery of Imaging Agents, CRC Press (1995); Vallabhajosula, S., Molecular Imaging: Radiopharmaceuticals for PET and SPECT, Springer (2009). A diagnostic agent can be detected by a variety of ways, including as an agent providing and/or enhancing a detectable signal that includes gamma-emitting, radioactive, echogenic, optical, fluorescent, absorptive, magnetic or tomography signals. Techniques for imaging the diagnostic agent can include single photon emission computed tomography (SPECT), magnetic resonance imaging (MRI), optical imaging, positron emission tomography (PET), computed tomography (CT), x-ray imaging, gamma ray imaging, and the like.

In some embodiments, a diagnostic agent can include chelators that bind to metal ions to be used for a variety of diagnostic imaging techniques. Exemplary chelators include ethylenediaminetetraacetic acid (EDTA), [4-(1,4,8,11-tetraazacyclotetradec-1-yl)methyl]benzoic acid (CPTA), cyclohexanediaminetetraacetic acid (CDTA), ethylenebis-(oxyethylenenitrilo)tetraacetic acid (EGTA), diethylenetriaminepentaacetic acid (DTPA), citric acid, hydroxyethyl ethylenediamine triacetic acid (HEDTA), iminodiacetic acid (IDA), triethylene tetraamine hexaacetic acid (TTHA), 1,4,7,10-tetraazacyclododecane-1,4,7,10-tetra(methylene phosphonic acid) (DOTP), 1,4,8,11-tetraazacyclododecane-1,4,8,11-tetraacetic acid (TETA), 1,4,7,10-tetraazacyclododecane-1,4,7,10-tetraacetic acid (DOTA), and derivatives thereof.

A radioisotope can be incorporated into some of the diagnostic agents described herein and can include radionuclides that emit gamma rays, positrons, beta and alpha particles, and X-rays.

In other embodiments, the diagnostic agents can include optical agents such as fluorescent agents, phosphorescent agents, chemiluminescent agents, and the like. Numerous agents (e.g., dyes, probes, labels, or indicators) are known in the art and can be used in the present disclosure. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives having the general structure of 4,4-difluoro-4-bora-3a,4a-diaza-s-indacene, and/or conjugates and/or derivatives of any of these. Other agents that can be used include, for example, fluorescein, fluorescein-polyaspartic acid conjugates, fluorescein-polyglutamic acid conjugates, fluorescein-polyarginine conjugates, indocyanine green, indocyanine-dodecaaspartic acid conjugates, indocyanine-polyaspartic acid conjugates, isosulfan blue, indole disulfonates, benzoindole disulfonate, bis(ethylcarboxymethyl)indocyanine, bis(pentylcarboxymethyl)indocyanine, polyhydroxyindole sulfonates, polyhydroxybenzoindole sulfonate, rigid heteroatomic indole sulfonate, indocyaninebispropanoic acid, indocyaninebishexanoic acid, 3,6-dicyano-2,5-[(N,N,N',N'-tetrakis(carboxymethyl)amino]pyrazine, 3,6-[(N, N, N', N'-tetrakis(2-hydroxyethyl)-amino]pyrazine-2,5-dicarboxylic acid, 3,6-bis(N-azatedino)pyrazine-2,5-dicarboxylic acid, 3,6-bis(N-morpholino)pyrazine-2,5-dicarboxylic acid, 3,6-bis(N-piperazino)pyrazine-2,5-dicarboxylic acid, 3,6-bis(N-thiomorpholino)pyrazine-2,5-dicarboxylic acid, 3,6-bis(N-thiomorpholino)-pyrazine-2,5-dicarboxylic acid S-oxide, 2,5-dicyano-3,6-bis(N-thiomorpholino)pyrazine S,S-dioxide, indocarbocyaninetetrasulfonate, chloroindocarbocyanine, and 3,6-diaminopyrazine-2,5-dicarboxylic acid. Also specifically contemplated are far-NIR dyes with an NIR-II excitation window (such as CH1055), and their maleimide, thiol, carboxylic acid (—COOH), amine (—NH$_2$), dibenzocyclooctyne (DBCO) or azide (N$_3$) functionalized derivatives. See, for instance, Ding et al. (*Chem Sci.* 9(19):4370-4380, 2018); Zhu et al. (*Theranostics,* 8(15):4141-4151, 2018); Deng et al. (*Theranostics,* 8(15):4116-4128, 2018); Starosolski et al. (*PLoS One* 2017, doi.org/10.1371/journal.pone.0187563).

One of ordinary skill in the art will appreciate that particular optical agents used can depend on the wavelength used for excitation, depth underneath skin tissue, and other factors generally well known in the art. For example, optimal absorption or excitation maxima for the optical agents can vary depending on the agent employed, but in general, the optical agents of the present disclosure will absorb or be excited by light in the ultraviolet (UV), visible, or infrared (IR) range of the electromagnetic spectrum. For imaging, dyes that absorb and emit in the near-IR (~700-900 nm, e.g., indocyanines) are preferred. For topical visualization using an endoscopic method, any dyes absorbing in the visible range are suitable.

In some embodiments, the non-ionizing radiation employed in the process of the present disclosure can range in wavelength from 350 nm to 1200 nm. In one exemplary embodiment, the fluorescent agent can be excited by light having a wavelength in the blue range of the visible portion of the electromagnetic spectrum (from 430 nm to 500 nm) and emits at a wavelength in the green range of the visible portion of the electromagnetic spectrum (from 520 nm to 565 nm). For example, fluorescein dyes can be excited with light with a wavelength of 488 nm and have an emission wavelength of 520 nm. As another example, 3,6-diaminopyrazine-2,5-dicarboxylic acid can be excited with light having a wavelength of 470 nm and fluoresces at a wavelength of 532 nm. In another embodiment, the excitation and emission wavelengths of the optical agent may fall in the near-infrared range of the electromagnetic spectrum. For example, indocyanine dyes, such as indocyanine green, can be excited with light with a wavelength of 780 nm and have an emission wavelength of 830 nm.

In yet other embodiments, the diagnostic agents can include magnetic resonance (MR) and x-ray contrast agents that are generally well known in the art, including, for example, iodine-based x-ray contrast agents, superparamagnetic iron oxide (SPIO), complexes of gadolinium or manganese, and the like. (See, e.g., Armstrong et al., Diagnostic Imaging, 5th Ed., Blackwell Publishing (2004)). In some embodiments, a diagnostic agent can include a magnetic resonance (MR) imaging agent. Exemplary magnetic resonance agents include paramagnetic agents, superparamagnetic agents, and the like. Exemplary paramagnetic agents can include gadopentetic acid, gadoteric acid, gadodiamide, gadolinium, gadoteridol mangafodipir, gadoversetamide, ferric ammonium citrate, gadobenic acid, gadobutrol, or gadoxetic acid. Superparamagnetic agents can include superparamagnetic iron oxide and ferristene. In certain embodiments, the diagnostic agents can include x-ray contrast agents as provided, for example, in the following references: H. S Thomsen, R. N. Muller and R. F. Mattrey, Eds., Trends in Contrast Media, (Berlin: Springer-Verlag, 1999); P. Dawson, D. Cosgrove and R. Grainger, Eds., Textbook of Contrast Media (ISIS Medical Media 1999); Torchilin, V. P., Curr. Pharm. Biotech. 1:183-215 (2000); Bogdanov, A. A. et al., Adv. Drug Del. Rev. 37:279-293 (1999); Sachse, A. et al., Investigative Radiology 32(1):44-50 (1997). Examples of x-ray contrast agents include, without limitation, iopamidol, iomeprol, iohexyl, iopentol, iopromide, iosimide, ioversol, iotrolan, iotasul, iodixanol, iodecimol, ioglucamide, ioglunide, iogulamide, iosarcol, ioxilan, iopamiron, metrizamide, iobitridol and iosimenol. In certain embodiments, the x-ray contrast agents can include iopamidol, iomeprol, iopromide, iohexyl, iopentol, ioversol, iobitridol, iodixanol, iotrolan and iosimenol.

As for the therapeutic agents described above, the diagnostic agents can be associated with the therapeutic liposome in a variety of ways, including for example being embedded or encapsulated in the liposome. Similarly, loading of the diagnostic agents can be carried out through a variety of ways known in the art, as disclosed for example in the following references: de Villiers, M. M. et al., Eds., Nanotechnology in Drug Delivery, Springer (2009); Gregoriadis, G., Ed., Liposome Technology: Entrapment of drugs and other materials into liposomes, CRC Press (2006).

(vi) Kits: Also provided herein are kits. As used herein, the term "kit" refers to a set of two or more components necessary for employing a method as described herein. Kit components can include liposomes of the present disclosure, reagents, buffers, containers and/or equipment. Active component(s), including particularly at least one liposome loaded with at least one therapeutic compound, or containing at least one targeting/imaging compound, can be provided as kits. Specifically contemplated are kits that include liposomes loaded with (containing) or decorated with, both a therapeutic agent and a targeting or imaging agent.

Examples of kit include two or more components, one of which is an Azide (—N$_3$) functionalized targeting ligand for targeting tumor component(s) (such as tumor stroma, hypoxic tissue, angiogenic blood vessel, tumor immune cells, and so forth); and another of which is a Dibenzocyclooctyne (DBCO) functionalized nanoparticle containing one or more DBCO-functionalized imaging agents, and optionally also including one or more therapeutic agent(s). The —N$_3$ functionalized targeting ligand can be reacted with DBCO-functionalized nanoparticle using copper-free click chemistry (as described herein) to obtain a tumor multicomponent selective drug delivery system for therapy and/or imaging system for tumor diagnosis. This enables mixing and matching different targeting agent(s) with drug delivery agent(s), providing an off-the-self medicine for therapeutic and diagnostic use. For instance, when a cancer patient is in need of treatment, based on their tumor biomarker expression, the targeting ligand and drug delivery counterpart can be mixed together, and the patient can be treated using this personalized off-the-self medicine.

Disclosed kits include material(s) and reagent(s) useful in the administration of a therapeutic and/or diagnostic liposomal composition to a subject to treat a diseases or condition (such as cancer). The materials and reagents can include those necessary to administer any of the therapeutic compositions disclosed herein according to any method described herein and/or known to one of ordinary skill in the art.

Kits can include one or more containers including one or more or more compounds as described herein, optionally along with one or more agents for use in therapy. For instance, some kits will include an amount of at least one non-liposome encapsulated anti-cancer agent, or one anti-inflammatory component.

Any active component in a kit may be provided in premeasured dosages, though this is not required; and it is anticipated that certain kits will include more than one dose.

Kits can also include a notice in the form prescribed by a governmental agency regulating the manufacture, use, or sale of pharmaceuticals or biological products, which notice reflects approval by the agency of manufacture, use, or sale for human administration. The notice may state that the provided active ingredients can be administered to a subject. The kits can include further instructions for using the kit, for example, instructions regarding administration; proper disposal of related waste; and the like. The instructions can be in the form of printed instructions provided within the kit or the instructions can be printed on a portion of the kit itself. Instructions may be in the form of a sheet, pamphlet, brochure, CD-ROM, or computer-readable device, or can provide directions to instructions at a remote location, such as a website. In particular embodiments, kits can also include some or all of the necessary medical supplies needed to use the kit effectively, such as applicators, ampules, sponges, sterile adhesive strips, Chloraprep, gloves, and the like. Variations in contents of any of the kits described herein can be made. The instructions of the kit will direct use of the active ingredient(s) included in that kit to effectuate a clinical and/or therapeutic use described herein.

Polymer Nanoparticles for Combination Therapy against Drug-Resistant Renal Cell Carcinoma A promising library of a novel class of anticancer compounds termed CARP-1 functional mimetics (CFMs) that inhibit cell growth by various mechanisms such as inducing apoptosis has been developed. CARP-1 (Cell cycle and apoptosis regulator 1, aka CCAR1) is a peri-nuclear phospho-protein and a regulator of cell growth and apoptosis signaling (Rishi et al., *J. Biol. Chem.* 281, 13188-13198, 2006; Rishi et al., *J. Biol. Chem.* 278, 33422-33435, 2003; Puliyappadamba et al., *J. Biol. Chem.* 286, 38000-38017, 2011; Muthu et al., *Oncotarget* 6, 6499-510, 2015). CARP-1 not only functions as a transcriptional co-activator of steroid family of nuclear receptors and a regulator of adipogenesis through the glucocorticoid receptor (GR), it also regulates Adriamycin (ADR)-dependent apoptosis in part through co-activation of p53 (Kim et al., *Mol. Cell* 31, 510-519, 2008; Ou et al., *J. Biol. Chem.* 289(24):17078-17086, 2014). CARP-1 expression is often elevated in cells experiencing stress due to growth factor withdrawal or chemotherapy-induced cell cycle arrest and apoptosis (Rishi et al., *J. Biol. Chem.* 281, 13188-13198, 2006; Rishi et al., *J. Biol. Chem.* 278, 33422-33435, 2003; Kim et al., *Mol. Cell* 31, 510-519, 2008). Knockdown of CARP-1 resulted in resistance to apoptosis by ADR or EGFR tyrosine kinase inhibitors demonstrating a requirement for CARP-1 in cell growth inhibitory and apoptosis signaling by these agents (Rishi et al., *J. Biol. Chem.* 281, 13188-13198, 2006; Rishi et al., *J. Biol. Chem.* 278, 33422-33435, 2003; Kim et al., *Mol. Cell* 31, 510-519, 2008). CARP-1 also functions as a co-activator of the APC/C E3 ligase (Puliyappadamba et al., *J. Biol. Chem.* 286, 38000-38017, 2011). APC/C is a multi-subunit ubiquitin E3 ligase protein that plays a distinct role in cell cycle transitions, and misregulation of APC/C substrates such as securin, polo-like kinase (Plk) has been demonstrated to correlate with tumor progression (Lehman et al., *Am. J. Pathol.* 170, 1793-805, 2007; Peters, *Molecular Cell* 9, 931-943, 2002). A chemical biology-based high-throughput screening of a chemical library resulted in identification of a number of novel, small molecule inhibitors (SMIs) of CARP-1 binding with APC/C subunit APC2. These compounds, CFMs, inhibit cell growth by inducing apoptosis in various cancer types. For example, NCI 60-panel screening indicated CFM efficacy against non-small cell lung cancers (NSCLC), triple negative breast cancers (TNBC) and renal cell carcinomas (RCC) (Ashour et al., *PLoS One* 8, 2013).

In the case of RCC, antiangiogenic drugs that block the vascular endothelial growth factor receptor (VEGFR) pathway are now standard first-line treatment in metastatic RCC. They are also used sequentially to prolong clinical benefit in patients with recurrent disease (Rini et al., *The Lancet* 373, 1119-1132, 2009). However, resistance to therapy ultimately emerges in most patients, and further understanding of the underlying biology and potential therapeutic targets are urgently needed for clinical translation (Rini & Atkins, *The Lancet Oncology* 10, 992-1000, 2009). Everolimus is one such drug that was recently developed as a secondary treatment option for resistant RCCs (Motzer et al., *Lancet* 372, 449-456, 2008; Minguet et al., *Cancer Chemotherapy and Pharmacology* 76, 219-233, 2015). However, resistance to newer drugs (including Everolimus) continues to emerge. Therefore, newer drug molecules with different mechanism of action and novel targeted drug delivery approaches need to be developed to address the safety and efficacy of newer therapies.

Carbonic anhydrase IX (CAIX or CA9) is a membrane bound protein overexpressed on the surface of many cancer cells in a hypoxic environment (Mcdonald & Dedhar, *Subcell Biochem.* 255-269, 2014). Carbonic anhydrase enzymes tightly control the acid-base balance in the kidney (Mcdonald & Dedhar, *Subcell Biochem.* 255-269, 2014). CAIX is involved in tumor cell survival and metastasis, and increased expression correlates with poor clinical outcome. The overexpression of CAIX has been demonstrated in 93-97% of clear cell renal cell carcinomas (ccRCCs) with limited expression in normal tissues/organs (Parkkila et al. PNAS 97(5):2220-2224, 2000). Numerous studies have confirmed the CAIX distribution on normal tissues and malignancies (Jiang et al., *Nan fang yi ke da xue xue bao* (*J. South. Med. Univ.*) 32, 412-414, 2012; López et al., *Cancer* 10, 262-270, 2012; Liao et al., *Cancer Res.* 57, 2827-2831, 1997; Peña et al., *Clin. Cancer Res.* 16(19):4853-4363, 2010; Choueiri et al., *Urologic Oncology: Seminars and Original Investigations* 31, 1788-1793, 2013 Choueiri et al., *BJU Int.* 106, 772-778, 2010). For renal cancer, CAIX is almost homogeneously expressed in the ccRCC subtype (Jiang et al., *Nan fang yi ke da xue xue bao* (*J. South. Med. Univ.*) 32, 412-414, 2012; López et al., *Cancer* 10, 262-270, 2012; Liao et al., *Cancer Res.* 57, 2827-2831, 1997; Peña et al., *Clin. Cancer Res.* 16(19):4853-4363, 2010; Choueiri et al., *Urologic Oncology: Seminars and Original Investigations* 31, 1788-1793, 2013 Choueiri et al., *BJU Int.* 106, 772-778, 2010; Oosterwijk-Wakka et al., *BJU Int.* 107, 118-125, 2011; Escudier et al., *Nat. Rev. Clin. Oncol.* 9, 327-337, 2012). Given the favorable tissue distribution, the potential of CAIX targeting of RCC for diagnosis or therapy has been studied extensively (Minn et al., Oncotarget. 7:56471-56479, 2016; Muselaers et al., *J Nucl Med.* 55(6):1035-

1041, 2014). Due to the unique molecular basis of ccRCC, CAIX is regarded as an excellent target for diagnosis and possibly for therapy (McDonald et al., *Oncotarget* 3, 84-97, 2012; Liao et al., *Cancer Res.* 57, 2827-2831, 1997; Peña et al., *Clin. Cancer Res.* 16(19):4853-4363, 2010; Choueiri et al., *Urologic Oncology: Seminars and Original Investigations* 31, 1788-1793, 2013; Oosterwijk-Wakka et al., *BJU Int.* 107, 118-125, 2011). Clinical trials have unambiguously demonstrated that CAIX can be targeted to RCC tissues without damage to normal tissues expressing CAIX (Krall et al., J Nucl Med. 57(6):943-950, 2016). However, there are no approved therapies against CAIX (Brouwers, *J Clin Oncol.* 26(22): 3808-3809, 2008). Monoclonal antibodies have been used to target CAIX, but their large molecular weight limits penetration throughout a poorly vascularized tumor, and their slow blood clearance minimizes their utilization as tumor imaging agents or radiotherapeutics because of high background and toxicity (McDonald et al., *Oncotarget* 3, 84-97, 2012). Finally, the new therapeutic options have led to investigations that examine whether small molecules CAIX-inhibitors can be used in serum assays or as imaging target to study whether CAIX monitoring can be useful to predict responses (Peña et al., *Clin. Cancer Res.* 16(19):4853-4363, 2010; Choueiri et al., *Urologic Oncology: Seminars and Original Investigations* 31, 1788-1793, 2013; Choueiri et al., *BJU Int.* 106, 772-778, 2010).

In addition, the introduction of several anticancer small molecule drugs (e.g. sunitinib, pazopanib, axitinib, temsirolimus, and everolimus) has rapidly changed the treatment of metastatic RCC (Calvo et al., *Cancer Treat. Rev.* 50, 109-117, 2016; Krusch et al., *J Immunol.* 183(12):8286-8294, 2009; Arranz et al., *Crit Rev Oncol Hematol.* 80(2): 314-322, 2011; Bellmunt et al., *Efficacy and Toxicity. Clin. Genitourin. Cancer* 12, 262-269, 2014). Although the impact on disease progression is encouraging, a substantial proportion of patients do not respond adequately, and therapy resistance almost inevitably occurs (Juengel et al., *Oncotarget* 7:85208-85219, 2016). Possibly combination treatments aimed at different, non-related pathways may be advantageous (Calvo et al., *Cancer Treat. Rev.* 50, 109-117, 2016; Krusch et a/., *J Immunol.* 183(12):8286-8294, 2009; Bellmunt et al., *Efficacy and Toxicity. Clin. Genitourin. Cancer* 12, 262-269, 2014). Due to their increasing in vascular nature and high level of vascular permeability factor or vascular endothelial growth factor (VEGF) expression, ccRCC patients show promising success with anti-VEGF cancer therapy. Unfortunately, the majority of cancer patients ultimately develop a refractory response to anti-VEGF treatment over time.

Moreover, there is a critical need to develop safe and effective delivery vehicles that can carry the payload to the right target tissue and cell. Different types of nanoparticles recently emerged as an excellent delivery system. The CFM compounds have poor aqueous solubility and consequent poor bioavailability for their use and development as potential anti-cancer agents. To address this issue, in Example 1 nanolipid formulations (NLFs) of CFM-4 and CFM-4.16 compounds were generated using chemically conjugated SMA-TPGS block polymer, then addition DMSO contained drug to aqueous phase of polymer, followed by stirring, separation of unencapsulated drugs using Tangential Flow Filtration and tested (Peña et al., *Clin. Cancer Res.* 16(19): 4853-4363, 2010; Oosterwijk-Wakka et al., *BJU Int.* 107, 118-125, 2011). These NLFs resulted in significant improvements in overall bio-availabilities of CFM-4 and CFM-4.16 when compared with the respective free compound (Peña et al., *Clin. Cancer Res.* 16(19):4853-4363, 2010; Oosterwijk-Wakka et al., *BJU Int.* 107, 118-125, 2011). Nanoparticles are useful to encapsulate CFMs and protect them from clearance and degradation.

The Exemplary Embodiments and Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

First Set of Exemplary Embodiments

1. A method of treating a subject with a solid tumor exhibiting hypoxia and/or stromal components, including: (i) a nanoformulation encapsulated with a chemotherapeutic agent; and/or (ii) a small molecule based imaging agent for early diagnosis of tumor, pre-tumor/pre-cancerous lesion, polyp and imaging guided surgery.

such as kinase inhibitors for therapy

2. The method of embodiment 1, wherein the cancer is expressing carbonic anhydrase-IX, XII in hypoxia/hypoxic region; folate receptor isotypes in tumor and tumor immune cells; CD44 in cancer stem cells or stem like cells.
3. The method of embodiment 1, wherein the solid tumor is a carcinoma, a sarcoma, a lymphoma, a melanoma, a mesothelioma, or an adenocarcinoma.
4. The method of embodiment 1, wherein the solid tumor is lung cancer, clear cell renal cell carcinoma, non-clear cell renal cell carcinoma, pancreatic cancer, bone cancer, skin cancer, head and neck cancer, cutaneous melanoma, intraocular melanoma uterine cancer, ovarian cancer, endometrial cancer, rectal cancer, stomach cancer, colon cancer, breast cancer, triple negative breast cancer, ovarian cancer, ovarian dysplasia, colorectal polyps, carcinoma of the fallopian tubes, carcinoma of the endometrium, carcinoma of the cervix, carcinoma of the vagina, carcinoma of the vulva, cancer of the esophagus, cancer of the Small intestine, cancer of the endocrine system, cancer of the thyroid gland, cancer of the parathyroid gland, oral cancer, laryngeal cancer, testicular cancer, liver cancer, non-Small cell lung cancer, cancer of the adrenal gland, cancer of the urethra, prostate cancer, pleural mesothelioma, nasopharyngeal carcinoma, cancer of the bladder, cancer of the ureter, kidney cancer, brain cancer, or pituitary adenoma.
5. The method of embodiment 1, wherein the nanoformulation is a liposome, lipid-polymer hybrid nanoparticle, or multivesicular liposome including polymers, lipids, and/or natural oils.
6. The method of embodiment 1, wherein the nanoformulation includes: carbonic anhydrase-IX, XII targeting ligand including imidazole, sulfoimidazole derivative, acetazolamide; methazolamide; ethoxzolamide; dichorophenamide; dorzolamide; brinzolamide; benzolamide; topiramate; zonisamide; sulpiride; indisulam; celecoxib; valdecoxib; antibodies and peptides.
7. The method of embodiment 1, wherein the nanoformulation includes: folate receptor isotypes targeting ligands including folic acid, methotrexate, aminopterin, antibodies and peptides.

8. The method of embodiment 1, wherein the nanoformulation includes one or more: CD44 targeting ligands including hyaluronic acid (HA), hyaluronan, antibodies and peptides.

9. The method of embodiment 1, wherein the nanoformulation includes: single, dual or multiple types of receptor targeting ligands to deliver the single or polypharmacy payload to the tumor microenvironment.

10. The method of embodiment 1, wherein the nanoformulation includes: CARP-1 functional mimetic compounds (CFMs), receptor tyrosine kinase inhibitors, cycle dependent kinase inhibitors, serine-threonine kinase inhibitors or mammalian targeting rapamycin (mTOR) inhibitors.

11. The method of embodiment 1, wherein the nanoformulation includes up to 30% w/w of anticancer compound including CARP-1 functional mimetic (CFM) and a styrene maleic anhydride (SMA)—vitamin E tocopheryl polyethylene glycol succinate (TPGS) co-polymer.

12. The method of embodiment 11, wherein the CFMs is CFM4, CFM-4.16, CFM-4.20 or CFM-4.17

13. The method of embodiment 1, wherein receptor tyrosine kinase inhibitors are either axitinib, cediranib, erlotinib, gefitinib, grandinin, lapatinib, lestaurtinib, lucitanib, neratinib, olmutinib, osimertinib, pazopanib, quizartinib, regorafenib, rociletinib, semaxanib, sorafenib, sunitinib, taselisib, tivozanib, toceranib or vandetanib.

14. The method of embodiment 1, wherein cycle dependent kinase inhibitors is abemaciclib, ribociclib or trilaciclib.

15. The method of embodiment 1, wherein serine-threonine kinase inhibitors are Bisindolylmaleimide I, Dihydrochloride(H-89), ML-7, KN-93, Staurosporine 16. The method of embodiment 1, wherein the nanoformulation containing hypoxia, stroma components receptors.

17. The method of embodiment 1, wherein the nanoformulation containing single, dual and multiple receptor targeting ligands 18. The method of embodiment 1, wherein the nanoformulation containing spherical, non-spherical, rod shaped, worm-like, flagella like shape 19. The method of embodiment 18, wherein the rod-shaped nanoformulation is 100-200 nm in length.

20. The method of embodiment 18, wherein the nanoformulation within a population of nanoformulations of embodiment 1 diameter is (40-200)±20 nm.

21. The method of embodiment 18, wherein the nanoformulation is within a population of nanoformulations of embodiment 1 having a polydispersity index of 0.275±0.05.

22. The method of embodiment 18, wherein the nanoformulation is within a population of nanoformulations of embodiment 1 having a Zeta potential of −7.86±4 mV.

23. The method of embodiment 18, wherein the nanoformulation is within a population of nanoformulations of embodiment 1 having a critical micelles concentration of 0.010 mg/ml.

24. The method of embodiment 1, where in a nanoformulation including a tumor cell stimuli-responsive, antifouling, rigid, flexible, zwitterionic, pegylated linkers.

25. The method of embodiment 1, wherein the nanoformulation overcomes drug resistance in the subject in need thereof.

26. The method of embodiment 1, wherein a rod-shaped nanoformulation including CFM-4.16, a CAIX targeting ligand, a folate receptor targeting ligand, and a polymer selected from one or more of: DBCO-conjugated vitamin E TPSG, SMA-TPGS; 2-hydroxypropyl-β-cyclodextrin (HP-β-CD), sulfobutylether-β-cyclodextrin (SBE-β-CD), phosphatidylethanolamine (PC), ceramide, Pluronic® F127, or PLA-PEG.

27. The method of embodiment 26, wherein a nanoformulation of nanoformulations of embodiment 1 containing Valine-citrulline (Val-Cit); Hydrazone; alpha-dialky substituted hydrazine; Polyethylene glycol unit 2-30 (PEG2-40); rigid cyclic hexyl, pentyl groups; non-rigid alkyl groups; Saccharo-peptides; Dithiol (S—S); alpha-dialky substituted [(R1R2HC—S—S—), R1 or R2 are alkyl groups)]; Zwitterionic; Thiol-maleimide.

28. The method of embodiment 1, wherein small molecule-based imaging agent used for early diagnosis of tumor, pre-tumor, polyp and imaging guided surgery.

29. The method of embodiment 26, wherein a small molecule of embodiment 1 containing single, dual, multiple targeting ligands to target hypoxia, stromal components, epithelial cell components, angiogenic blood vessel targeting agents.

30. The method of embodiment 1, where in small molecule-based imaging agent containing rigid cyclic hexyl, pentyl groups; non-rigid alkyl groups; saccharo-peptides; oligomeric, polymeric, Zwitterionic; Thiol-maleimide linkers.

31. The method of embodiment 1, where in small molecule-based imaging agent containing carbonic anhydrase-IX, XII targeting ligand including imidazole, sulfoimidazole derivative, acetazolamide; methazolamide; ethoxzolamide; dichlorphenamide; dorzolamide; brinzolamide; benzolamide; topiramate; zonisamide; sulpiride; indisulam; celecoxib; valdecoxib; antibody, peptides.

32. The method of embodiment 1, wherein where in small molecule-based imaging agent containing folate receptor isotypes targeting ligands including folic acid, methotrexate, aminopterin, antibody, peptides.

33. The method of embodiment 1, wherein where in small molecule-based imaging agent containing CD44 targeting hyaluronic acid (HA), hyaluronan, antibody, peptides 34. The method of embodiment 1, wherein where in small molecule-based imaging agent containing CMET targeting GE137 peptides.

35. The method of embodiment 1, wherein where in small molecule-based imaging agent, wherein the S0456 is the near infrared (NIR) dye and their maleimide, dibenzocyclooctyne (DBCO) or azide ($N_3$) functionalized derivative.

Second Set of Exemplary Embodiments

1. A substantially rod-shaped nanoformulation including: up to 30% CFM-4.16; a styrene maleic anhydride (SMA)—vitamin E tocopheryl polyethylene glycol succinate (TPGS) co-polymer; and one or more of: the CAIX targeting ligand acetazolamide (ATZ); the folate receptor targeting ligand folic acid; both ATZ and folic acid; one or more of sorafenib, everolimus, and/or cabozantinib; and/or a tumor cell stimuli-responsive linker.

2. A nanoformulation including up to 30% w/w of a CARP-1 functional mimetic (CFM) and a styrene maleic anhydride (SMA)—vitamin E tocopheryl polyethylene glycol succinate (TPGS) co-polymer.
3. The nanoformulation of embodiment 2, further including one or more of: a carbonic anhydrase-IX (CAIX; CA9) targeting ligand; the CAIX targeting ligand acetazolamide (ATZ); a folate receptor targeting ligand; the folate receptor targeting ligand folic acid; a CAIX targeting ligand and a folate receptor targeting ligand; one or more of sorafenib, everolimus, and/or cabozantinib; and/or a tumor cell stimuli-responsive linker.
4. The nanoformulation of embodiment 2 or embodiment 3, wherein one or more of: the CFM is CFM-4.16; the nanoformulation is rod-shaped; the nanoformulation is rod-shaped and 100-200 nm in length; the nanoformulation is spherical; the nanoformulation is within a population of such nanoformulations having: a mean diameter of 144.6 nm±20 nm; a polydispersity index of 0.275±0.05; a Zeta potential of −7.86±4 mV; and/or a critical micelles concentration of 0.010 mg/ml.
5. A rod-shaped nanoformulation including: CFM-4.16; a CAIX targeting ligand; a folate receptor targeting ligand; and one or more polymer(s) selected from the group consisting of: DBCO-conjugated vitamin E TPSG, SMA-TPGS; 2-hydroxypropyl-β-cyclodextrin (HP-β-CD), sulfobutylether-β-cyclodextrin (SBE-β-CD), phosphatidylethanolamine (PC), ceramide, Pluronic® F127, and PLA-PEG.
6. The rod-shaped nanoformulation of embodiment 5 wherein; the CAIX targeting ligand is ATZ; and/or the folate receptor targeting ligand is folic acid.
7. A nanoformulation including: a polymer selected from one or more of: DBCO-conjugated vitamin E TPSG, SMA-TPGS; HP-β-CD, SBE-β-CD, PC, ceramide, Pluronic® F127, and PLA-PEG; a CAIX-targeting ligand; and a dye.
8. The nanoformulation of embodiment 7, wherein: the CAIX-targeting ligand is ATZ; and/or the dye is S0456 NIR dye.
9. The nanoformulation of embodiment 7, further including one or more of: a folate receptor targeting ligand; a folate receptor targeting ligand including folic acid; a CARP-1 functional mimetic (CFM); a CFR including CFM-4.16; or sorafenib, everolimus, and/or cabozantinib.
10. The nanoformulation of embodiment 7, further including CFM-4.16 and at least one of sorafenib, everolimus, or cabozantinib.
11. The nanoformulation of embodiment 7, wherein the nanoformulation is rod-shaped.
12. The nanoformulation of embodiment 11, wherein the rod-shaped nanoformulation is 100-200 nm in length.
13. The nanoformulation of embodiment 7, wherein the nanoformulation is spherical.
14. A pharmaceutical composition including a nanoformulation of any of embodiments 1-13.
15. Use of a pharmaceutical composition of embodiment 1 or embodiment 14 to treat a solid tumor in a subject in need thereof.
16. The use of embodiment 15, wherein the treatment: is a prophylactic treatment and/or a therapeutic treatment; and/or overcomes drug resistance in the subject in need thereof.
17. An imaging composition including the nanoformulation of any of embodiments 1-13.
18. Use of the imaging composition of embodiment 17 to visualize a solid tumor in a subject in need thereof.
19. The use of any one of embodiments 15, 16, or 18, wherein the solid tumor is renal cell carcinoma (RCC).
20. A method of treating a subject with a solid tumor exhibiting hypoxia and/or stromal components, including administering to the subject a nanoformulation of any one of embodiments 1-13, or the pharmaceutical composition of embodiment 14.
21. A method of treating a subject with a solid tumor exhibiting hypoxia and/or stromal components, including: (i) a nanoformulation encapsulated with a chemotherapeutic agent for therapy; and/or (ii) a small molecule-based imaging agent for early diagnosis of tumor, pre-tumor/pre-cancerous lesion, polyp and imaging guided surgery.
22. The method of embodiment 21, wherein the chemotherapeutic agent includes a kinase inhibitor.
23. The method of embodiment 21, wherein the cancer is expressing carbonic anhydrase-IX, XII in a hypoxia/hypoxic region; folate receptor isotypes in tumor and tumor immune cells; and/or CD44 in cancer stem cells or stem like cells.
24. The method of embodiment 21, wherein the solid tumor is a carcinoma, a sarcoma, a lymphoma, a melanoma, a mesothelioma, or an adenocarcinoma.
25. The method of embodiment 21, wherein the solid tumor is lung cancer, clear cell renal cell carcinoma, non-clear cell renal cell carcinoma, pancreatic cancer, bone cancer, skin cancer, head and neck cancer, cutaneous melanoma, intraocular melanoma uterine cancer, ovarian cancer, endometrial cancer, rectal cancer, stomach cancer, colon cancer, breast cancer, triple negative breast cancer, ovarian cancer, ovarian dysplasia, colorectal polyps, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, oral cancer, laryngeal cancer, testicular cancer, liver cancer, non-small cell lung cancer, cancer of the adrenal gland, cancer of the urethra, prostate cancer, pleural mesothelioma, nasopharyngeal carcinoma, cancer of the bladder, cancer of the ureter, kidney cancer, brain cancer, or pituitary adenoma.
26. The method of embodiment 21, wherein the nanoformulation is a liposome, lipid-polymer hybrid nanoparticle, or multivesicular liposome including polymers, lipids, and/or natural oils.
27. The method of embodiment 21, wherein the nanoformulation includes one or more of: carbonic anhydrase-IX, XII targeting ligand including imidazole, sulfoimidazole derivative, acetazolamide; methazolamide; ethoxzolamide; dichorophenamide; dorzolamide; brinzolamide; benzolamide; topiramate; zonisamide; sulpiride; indisulam; celecoxib; valdecoxib; an antibody; or a peptide.
28. The method of embodiment 21, wherein the nanoformulation includes a folate receptor isotype targeting ligand selected from folic acid, methotrexate, aminopterin, antibodies, and peptides.
29. The method of embodiment 21, wherein the nanoformulation includes one or more CD44 targeting ligands selected from hyaluronic acid (HA), hyaluronan, antibodies, and peptides.

30. The method of embodiment 21, wherein the nanoformulation includes one, two, or more than two different types of receptor targeting ligands that selectively deliver nanoformulation to a tumor microenvironment.
31. The method of embodiment 21, wherein the nanoformulation includes at least one: CARP-1 functional mimetic compound (CFM), receptor tyrosine kinase inhibitor, cycle dependent kinase inhibitor, serine-threonine kinase inhibitor, or mammalian targeting rapamycin (mTOR) inhibitor.
32. The method of embodiment 21, wherein the nanoformulation includes up to 30% w/w of anticancer compound including CARP-1 functional mimetic (CFM) and a styrene maleic anhydride (SMA)—vitamin E tocopheryl polyethylene glycol succinate (TPGS) copolymer.
33. The method of embodiment 32, wherein the CFMs is CFM4, CFM-4.16, CFM-4.20 or CFM-4.17
34. The method of embodiment 31, wherein receptor tyrosine kinase inhibitor is axitinib, cediranib, erlotinib, gefitinib, grandinin, lapatinib, lestaurtinib, lucitanib, neratinib, olmutinib, osimertinib, pazopanib, quizartinib, regorafenib, rociletinib, semaxanib, sorafenib, sunitinib, taselisib, tivozanib, toceranib, or vandetanib.
35. The method of embodiment 31, wherein cycle dependent kinase inhibitor is abemaciclib, ribociclib or trilaciclib.
36. The method of embodiment 31, wherein serine-threonine kinase inhibitor is Bisindolylmaleimide I, Dihydrochloride(H-89), ML-7, KN-93, Staurosporine
37. The method of embodiment 21, wherein the nanoformulation includes a hypoxia or a stroma component receptor.
38. The method of embodiment 21, wherein the nanoformulation includes one, two, or more than two different types of receptor targeting ligands.
39. The method of embodiment 21, wherein the nanoformulation includes spherical, non-spherical, rod shaped, worm-like, and/or flagella like shape liposomes or micelles.
40. The method of embodiment 39, wherein the rod-shaped nanoformulation is 100-200 nm in length.
41. The method of embodiment 39, wherein the nanoformulation includes a population of liposomes or micelles having a diameter of 40-200±20 nm.
42. The method of embodiment 39, wherein the nanoformulation includes a population of liposomes or micelles within a population thereof having a polydispersity index of 0.275 ±0.05.
43. The method of embodiment 39, wherein the nanoformulation includes a population of liposomes or micelles within a population thereof having a Zeta potential of −7.86±4 mV.
44. The method of embodiment 39, wherein the nanoformulation includes a population of liposomes or micelles within a population thereof having a critical micelles concentration of 0.010 mg/ml.
45. The method of embodiment 21, where the nanoformulation includes one or more tumor cell stimuli-responsive, antifouling, rigid, flexible, zwitterionic, or pegylated linker.
46. The method of embodiment 21, wherein the nanoformulation overcomes drug resistance in the subject in need thereof.
47. The method of embodiment 21, wherein the nanoformulation is a rod-shaped nanoformulation including CFM-4.16, a CAIX targeting ligand, a folate receptor targeting ligand, and a polymer selected from one or more of: DBCO-conjugated vitamin E TPSG, SMA-TPGS; 2-hydroxypropyl-β-cyclodextrin (HP-β-CD), sulfobutylether-β-cyclodextrin (SBE-β-CD), phosphatidylethanolamine (PC), ceramide, Pluronic® F127, or PLA-PEG.
48. The method of embodiment 47, wherein the nanoformulation includes one or more of Valine-citrulline (Val-Cit); Hydrazone; alpha-dialky substituted hydrazine; polyethylene glycol unit 2-30 (PEG2-30), (PEG2-40); rigid cyclic hexyl, pentyl groups; non-rigid alkyl groups; Saccharo-peptides; Dithiol (S—S); alpha-dialky substituted [(R1R2HC—S—S—), R1 or R2 are alkyl groups)]; Zwitterionic; or Thiol-maleimide.
49. The method of embodiment 21, which is a small molecule-based imaging agent used early diagnosis of tumor, pre-tumor, polyp, and imaging guided surgery.
50. The method of embodiment 49, wherein the small molecule-based imaging agent includes one, two, or more than two different types of receptor targeting ligand(s).
51. The method of embodiment 50, wherein the receptor targeting ligand(s) target hypoxia, stromal components, epithelial cell components, and/or angiogenic blood vessel cell components.
52
30. The method of embodiment 21, wherein the small molecule-based imaging agent includes one or more rigid cyclic hexyl, pentyl groups; non-rigid alkyl groups; saccharo-peptides; oligomeric, polymeric, Zwitterionic; or Thiol-maleimide linkers.
53. The method of embodiment 21, wherein the small molecule-based imaging agent includes one or more of carbonic anhydrase-IX, XII targeting ligand including imidazole, sulfoimidazole derivative, acetazolamide; methazolamide; ethoxzolamide; dichlorphenamide; dorzolamide; brinzolamide; benzolamide; topiramate; zonisamide; sulpiride; indisulam; celecoxib; valdecoxib; antibody, or peptides.
54. The method of embodiment 21, wherein the small molecule-based imaging agent includes one or more of folate receptor isotypes targeting ligands including folic acid, methotrexate, aminopterin, antibody, or peptides.
55. The method of embodiment 21, wherein the small molecule-based imaging agent includes one or more of CD44 targeting hyaluronic acid (HA), hyaluronan, antibody, or peptides.
56. The method of embodiment 21, wherein the small molecule-based imaging agent includes a CMET targeting GE137 peptide.
57. The method of embodiment 21, wherein the small molecule-based imaging agent includes: a near infrared (NIR) dye; a near-infrared NIR (NIR-II) dye; or a maleimide, dibenzocyclooctyne (DBCO), thiol, carboxylic acid (—COOH), amine (—NH$_2$), or azide (N$_3$) functionalized derivative thereof.
58. The method of embodiment 57, wherein the NIR dye is S0456.

Example I

Polymer Nanoparticles for Combination Therapy Against Drug-Resistant Renal Cell Carcinoma This Example utilizes a nanotechnology-based approach to address the poor aqueous solubility of CFM derivatives, such as the potent CFM compound (CFM-4.16), that has restricted their clinical utility as therapeutic agents. This disclosure successful overcomes the solubility concerns of CFM-4.16, particularly by encapsulating it in water-soluble vitamin E tocopheryl polyethylene glycol succinate (TPGS)-based nanoformulation. This formulation enables high drug loading (up to 30% w/w of drug equivalent) and intravenous administration. At least some of the material included in this Example was published as Cheriyan et al., *Oncotarget.* 8(62): 104928-104945, 2017.

Renal cell carcinoma (RCC) is one of the most common malignancies, and its occurrence is expected to rise in coming years (Cairns, *Cancer Biomarkers* 9, 461-473, 2011; Rini et al., *The Lancet* 373, 1119-1132, 2009; Cohen & Mcgovern, *N. Engl. J. Med* 353, 2477-2490, 2005). RCC is tough to treat as the cells are largely resistant to many current therapies.

Surgery remains the best treatment option (Amato, *Semin. Oncol.* 27, 177-186, 2000), although 20-30% of patients progress to develop metastatic disease. If diagnosed early, there is a better chance of the cancer going into remission but if the cancer does not respond to first line therapies there are very limited secondary options (Rini et al., *The Lancet* 373, 1119-1132, 2009; Amato, *Semin. Oncol.* 27, 177-186, 2000). Currently, FDA approved agents for treatment of metastatic RCC include tyrosine kinase inhibitors (TKIs) such as sorafenib and sunitinib and mammalian target of rapamycin (mTOR) inhibitors such as temsiorlimus and everolimus. In patients with an advanced form of RCC, targeted therapies including the ones using the new drug, Everolimus resulted in improved clinical outcomes. However, patients ultimately develop resistance to targeted therapies as well.

Carbonic anhydrase IX (CAIX) is an enzyme expressed on the surface of kidney cancer cells with a restricted expression in normal cells. Here, the utility of carbonic anhydrase IX (CAIX) targeting small molecules conjugated to the surface of Nanomicelles loaded with CARP-1 Functional Mimetic CFM4.16 (CAIX CFM4.16-PLNPs), to promote the therapeutic effects for kidney cancer via systemic administration was explored. CFMs inhibited RCC cell viability in a dose-dependent manner that was comparable to Everolimus treatments as well as the combination with sorafenib. CFM-4.16 inhibited viabilities of Everolimus resistant RCC cells albeit CFM-4.16 combined with sorafenib was more effective than CFM-4.16 alone. Without being bound by theory, CFM-dependent loss of RCC cell viabilities was due to activation of pro-apoptotic, stress-activated protein kinases (SAPKs), and apoptosis. However, CFMs and sorafenib are hydrophobic and their dose escalation for in-vivo studies remain challenging. The solubility and delivery concerns of CFM-4.16 and sorafenib were overcome by utilizing a nanotechnology-based approach. The data disclosed herein reveal successful overcoming of the solubility concerns of CFM-4.16 and sorafenib by encapsulating it in water-soluble vitamin E TPGS based micellar nanoformulation that enabled high drug loading (up to 30% w/w of drug equivalent) and affords its intravenous administration. The disclosed polymeric NP formulations were also used to assess in vitro efficacy in parental, wild-type and everolimus-resistant RCC. It was found that the CAIX-CFM-PLNPs significantly improved the cellular uptake efficiency in both CAIX-positive human clear renal cells carcinoma (RCC-A498) and RCC-A498-Everolimus resistant tumor spheroids, resulting in the efficient cell killing compared with free CFM4.16 and non-targeted CFM-PLNPs. After confirming the anticancer activity of CFM-4.16 loaded nanoformulations in vitro, intravenous (i.v.) administration of the CFM-4.16 loaded polymeric NPs in a clinically relevant RCC mouse model was examined. The CFM-4.16 formulation inhibited viability of parental and Everolimus-resistant RCC cells in vitro, and suppressed growth of parental A498 RCC-cell-derived xenografts in part by stimulating apoptosis. After optimizing its potency and biological stability imaging of animal inoculated with RCC tumor by conjugation with NIR dye was performed. The results showed high binding affinity and specific tumor uptake, faster normal tissue clearance and less non-target organ uptake. These findings show efficacy of CFM-4.16 in combination with sorafenib using nanoformulation in treatment of RCCs. In vivo, CAIX-targeted-PLNPs via intravenous delivery showed specificity and a sustained release property, both of which improved the efficiency of CFM formulations in restraining tumor growth. Significantly the results show that CAIX-targeted nanoparticles can be used as an effective therapeutic strategy for RCC.

Figure 1:
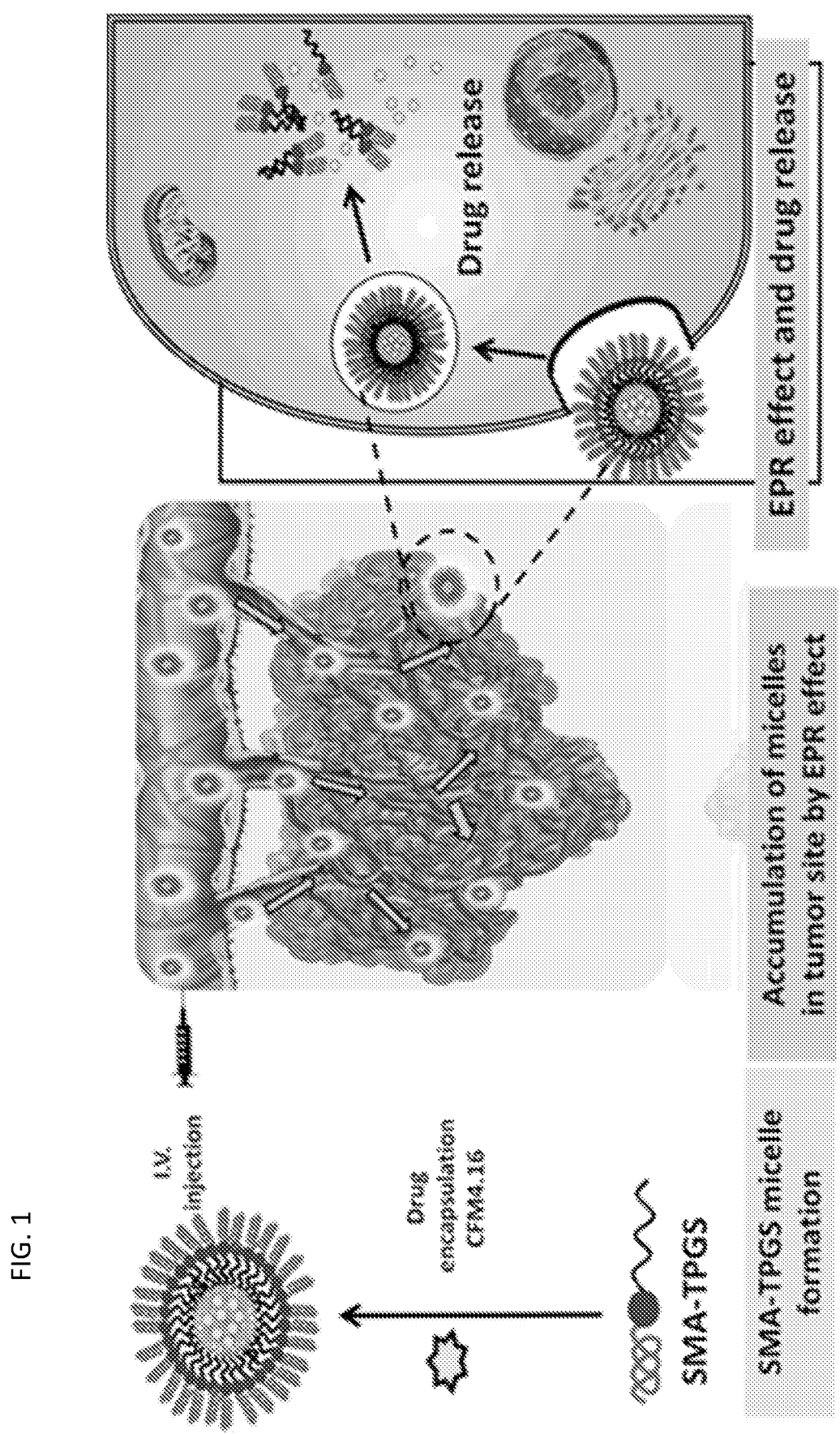
FIG. 1 is a drawing illustrating that nanoformulations can utilize either passive or active targeting approaches for drug delivery.
Figure 2:
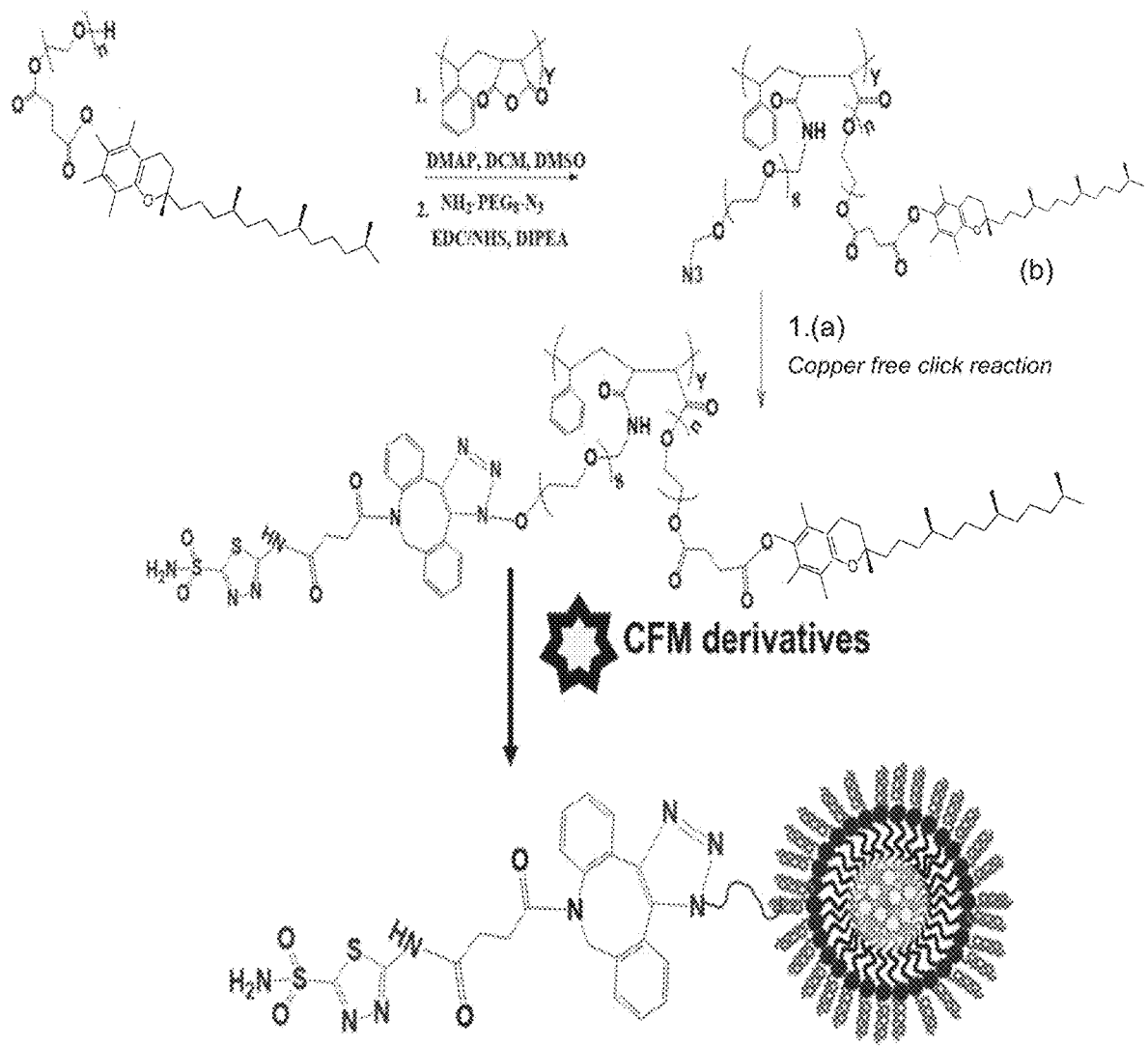
FIG. 2 shows a scheme for synthesis of CAIX-targeted-PLNPs, showing the chemical conjugation of acetazolamide-SMA-TPGS oligomer (namely CA IX-SMA-TPGS). Final 'click' reaction product, compound c, has been used to encapsulate C4.16 or to conjugate with S0456 or Rhodamine dye with —SH functional group to obtain CA IX-oligomer.
Figure 3:
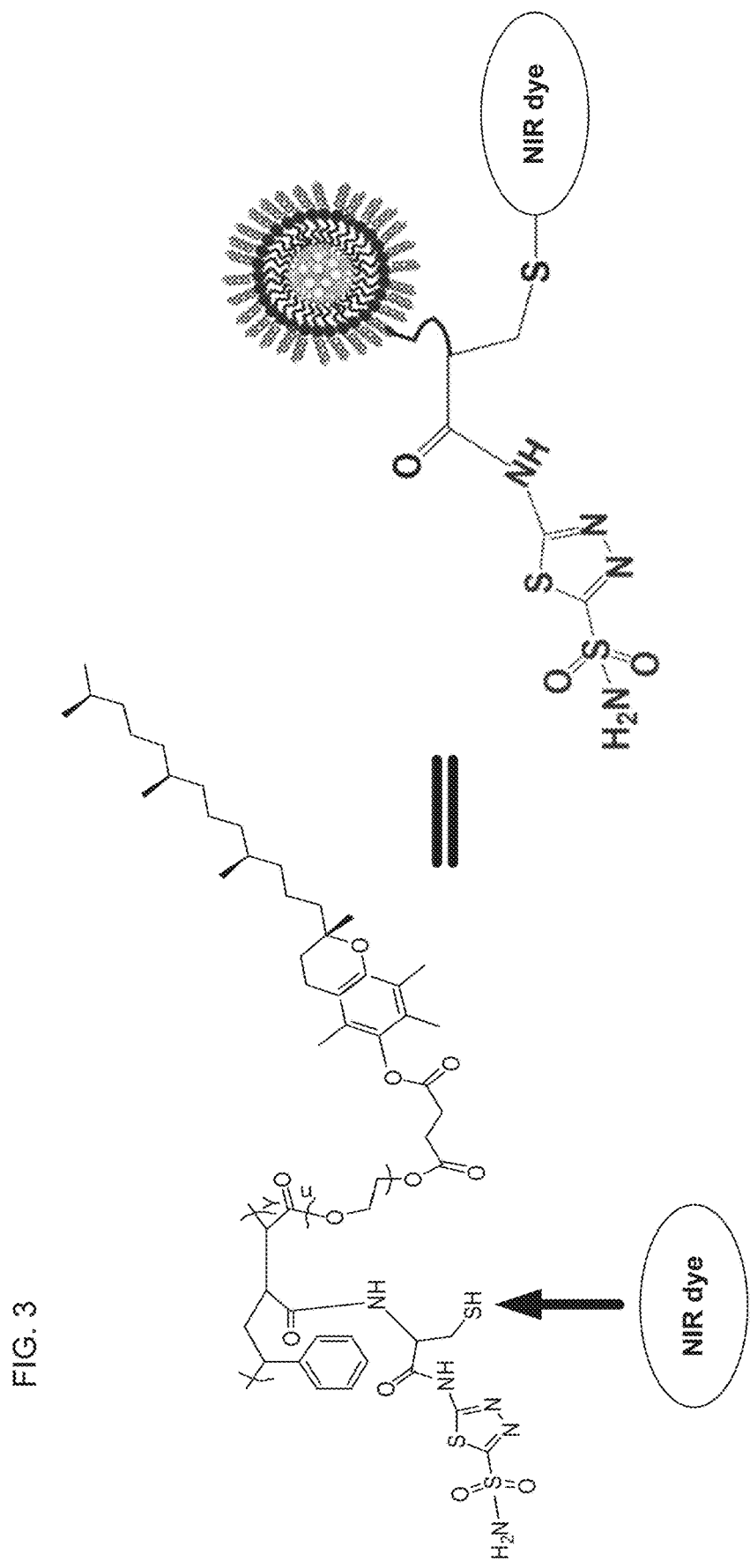
FIG. 3 shows a scheme for synthesis of CAIX-targeted-PLNPs plus NIR dye (for imaging)

Different types of TPGS polymer-based nanoformulations were synthesized and purified using a modular copper free "click" chemistry-based approach that allows for the development of the CFM-4.16 and sorafenib encapsulated PLNPs formulations as shown in FIGS. 2 and 3. CAIX is a superior targeting ligand that has been proven to be specifically overexpressed in 93 to 97% of both clear cell renal cell carcinoma (ccRCC) and some papillary RCC, with a limited expression in normal tissues. CAIX is an important biomarker for RCC, and it plays a pivotal role in tumor progression, acidification, metastasis, and the inside hypoxic condition. Many clinical trials are ongoing using CAIX linked inhibitors or antibodies for monotherapy or diagnostic imaging.

Polymer-lipid hybrid nanoparticles were synthesized with the CAIX targeted nanoplatforms conjugated with near-infra red (NIR) dye for targeted imaging of tumor sites with reduced off-target effects. This aspect of the disclosure expands upon previous success in the design, synthesis, and development of SMA-TPGS-CFM-4.16 and SMA-CFM-4.16 nanomicellar formulations. See FIGS. 2 and 3.

Proton nuclear magnetic resonance spectroscopy ($^1$H NMR) and Fourier transform infrared spectroscopy (FTIR) analysis revealed that the SMA-TPGS copolymer was a conjugate and not a physical mixture of TPGS with SMA. Next, SMA-CFM-4.16 and SMA-TPGS-CFM-4.16 formulations were generated and characterized. The mean diameter, the polydispersity index, and the Zeta potential of SMA-TPGS-CFM-4.16 formulation were 144.6 nm±20 nm, 0.275 ±0.05, and −7.86±4 mV, respectively. The mean diameter, the polydispersity index, and the Zeta potential of SMA-CFM-4.16 formulation however were 123 nm±31 nm, 0.163±0.07, and −18±5 mV, respectively. The slight increase in the particle size of the TPGS containing formulations is understandable, due to the hydrophilic PEG chains protruding out thereby increasing the hydrodynamic diameter. The critical micelles concentration (CMC) of the formulations was 0.010 and 0.023 mg/ml for SMA-TPGS-CFM-4.16 and SMA-CFM-4.16, respectively indicating high stability even on dilution of the sample. The Transmission Electron Microscopic (TEM) analyses did not indicate any morphological differences between CFM-4.16 loaded and unloaded nanomicelles. The loading of CFM-4.16 also had insignificant effect on the nanomicellar mean diameter, polydispersity index, or Zeta potential in comparison to the unloaded nanomicelles.

The type of polymer and the drug loading levels are critical factors that often influence drug release kinetics, cellular uptake and the therapeutic efficacy of the drug-loaded nanoparticles (Escudier et al., *Nat. Rev. Clin. Oncol.* 9, 327-337, 2012). The encapsulation efficiency (EE) and drug loading content (DLC) for the disclosed formulations was determined as detailed in the materials and methods section. The EE and DLC for the SMA-CFM-4.16 was 77% and 17%, respectively. The EE and DLC parameters for SMA-TPGS-CFM-4.16 preparation were 85.55 and 29%, respectively, suggesting improved loading due to the inclusion of emulsifier, TPGS. The stability of the formulations was next determined by their extended (2 months) storage at 4° C., 25° C., or 35° C. with light protection. CFM-4.16 remained encapsulated in the SMA-TPGS nanomicelles with a recovery percentage of 99.73±1.10 at 4° C., 94.9±7.2 at 25° C., and 92.88±1.78 at 35° C. The recovery percentage of CFM-4.16 in SMA encapsulated formulation was 101.41±0.53 at 4° C., 96.42±0.42 at 25° C., and 90.81±1.32 at 35° C. Altogether, the results indicate that the CFM-4.16 micellar formulations have suitable drug loading and particle characteristics, and can be stored at 4° C. or at room temperature (25° C.).

Figure 8:
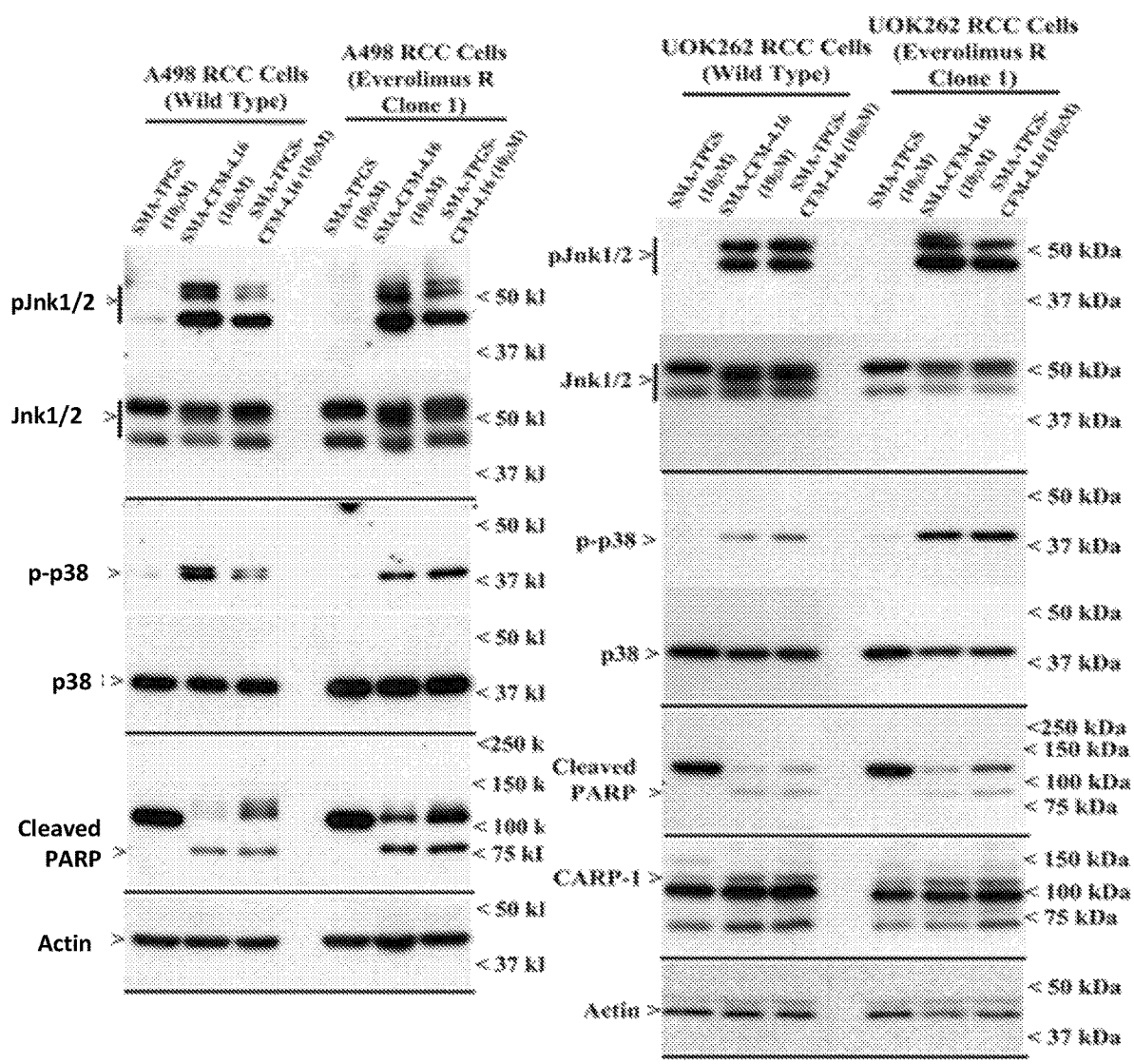
FIG. 8 illustrates Western blot data indicating that nanofromulations works effectively in treating RCC.

Parental RCC cells and their respective, Everolimus-resistant sublines were treated with various doses of block co-polymer (SMA-TPGS), free CFM-4.16, SMA-CFM-4.16, and SMA-TPGS-CFM-4.16 for 24 h. The RCC cell viabilities were determined as described in the materials and methods below. As shown in Cheriyan et al. (Oncotarget. 8(62): 104928-104945, 2017), the treatments of cells with various doses of block co-polymer alone elicited a very modest to no loss of their viabilities when compared with their untreated counterparts. The free CFM-4.16 or its nanomicellar formulations, on the other hand, inflicted a significant loss of viabilities of the parental as well as Everolimus-resistant RCC cells when compared with their respective, untreated counterparts. Of note is the fact that the free compound or its formulations at the three respective doses of each provoked a generally similar degree of reduction in RCC cell viabilities that ranged between 40-80%. A498 parental and resistant RCC cells albeit were more sensitive to the 10 µM dose of either of the micellar formulations when compared with their CFM-4.16 treated counterparts, overall a similar range of reduction in the viabilities of cells that were treated with free compound or its micellar formulations would suggest for an excellent in vitro activity of CFM-4.16 formulations. Consistent with the data, the Western blot analysis further revealed that treatments of parental or Everolimus-resistant RCC cells with 10 µM dose of SMA-CFM4.16 and SMA-TPGS-CFM4.16 (micellar formulations of CFM-4.16) also caused activation of pro-apoptotic cleaved caspase 3, P38α/β and JNK1/2, CARP-1 expression, and PARP cleavage when compared with their respective block co-polymer (SMA-TPGS)-treated cells (FIG. 8).

Figure 10A:
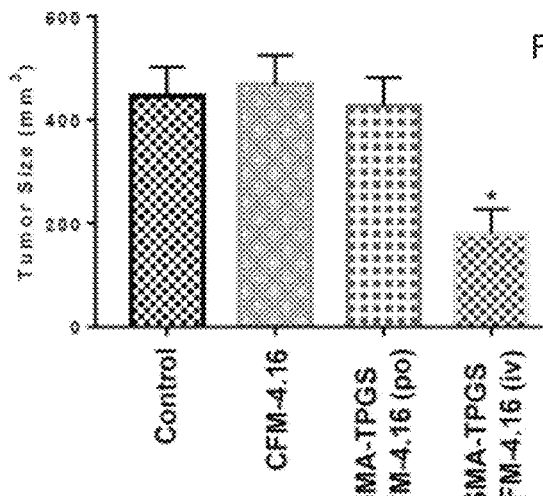
FIG. 10A Nanomicellar formulation of CFM-4.16 inhibits growth of A498 RCC cell-derived xenografts.
Figure 10B:
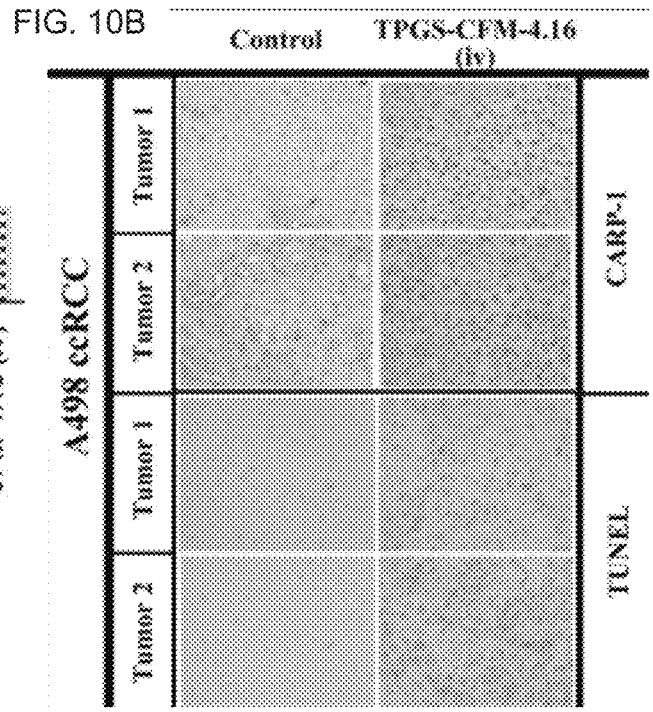
(FIG. 10B) SMA-TPGS-CFM-4.16 treatments (iv) induce CARP-1 expression and apoptosis in RCC tumor xenografts. Representative tumor tissues from two animals each from the vehicle-treated (noted as Control) or SMA-TPGS-CFM-4.16 treated groups. Photomicrographs (400× magnification) are shown for apoptosis (by TUNEL assay), and levels CARP-1 protein.
Figure 10C:
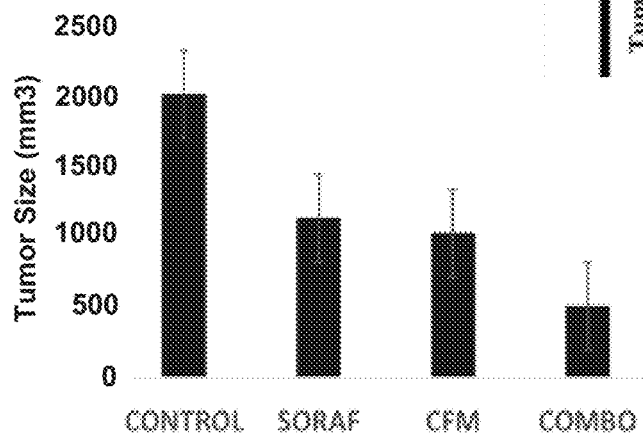
(FIG. 10C) Sorafenib in combination with CFM4.16 works very effectively in inhibiting tumor growth of A498 RCC in xenograft animal model.
Figure 10D:
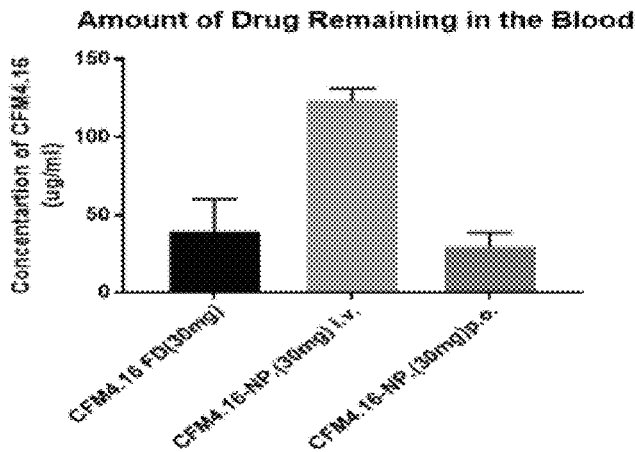
(FIG. 10D) Amount of drug remaining in the blood indicates higher bioavailability of iv injected nanoformulations.
Figure 12:
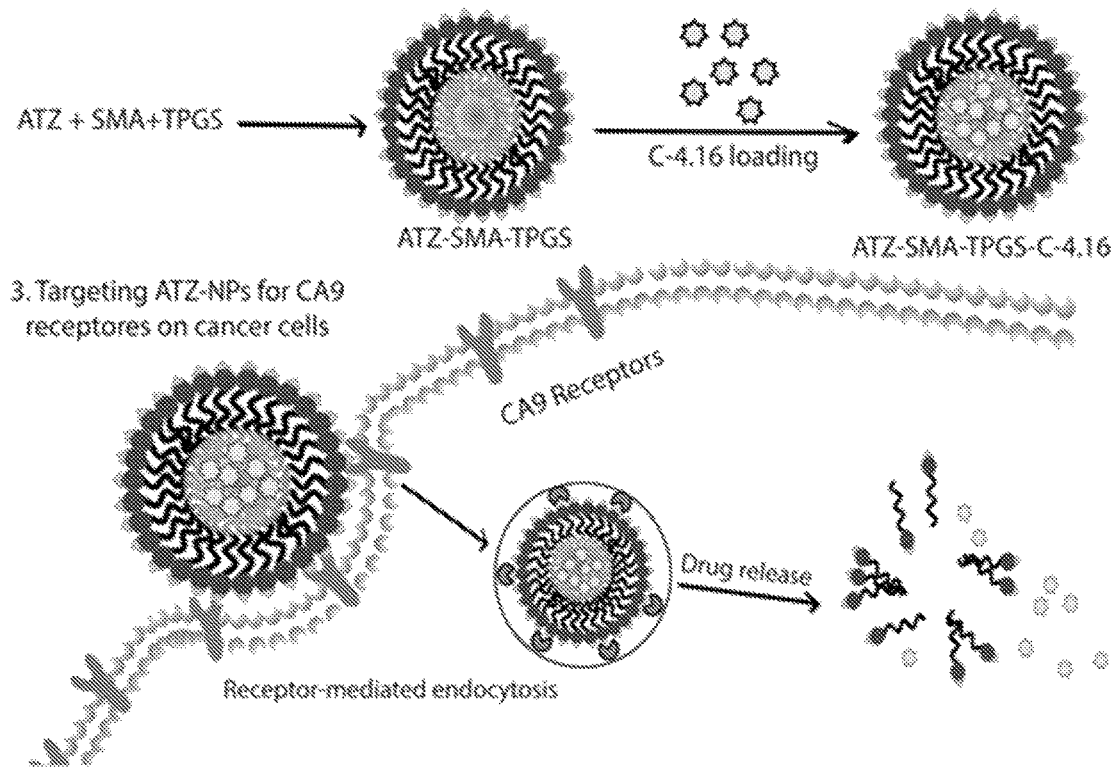
FIG. 12 is an illustration of CA9 receptor mediated cancer cell uptake of ATZ-SMA-TPGS with C-4.16 drug.

The in vivo anti-tumor efficacy of nanomicellar formulation of CFM-4.16 (SMA-TPGS-CFM-4.16) was examined in a highly aggressive RCC A498 orthotopic xenograft tumor bearing SCID mice as described in methods and published protocols in (Pena et al., *Clin. Cancer Res.* 16(19):4853-4363, 2010; Oosterwijk-Wakka et al., *BJU Int.* 107, 118-125, 2011). In previous studies, CFM-4.16 was prepared by dissolving it in 10% DMSO/cremophor plus sterile, distilled water with a pH of 4.5. A dose of 30 mg/kg/day of this preparation was administered by intravenous (tail vein) injections for a total dose of 482 mg/kg in SCID mice bearing human TNBC cell-derived xenografts. With the exception of a mild, <2% loss in body weight, the preparation did not cause any histological abnormalities in the treated animals, and lacked a therapeutic T/C values (Peña et al., *Clin. Cancer Res.* 16(19):4853-4363, 2010). On this basis, a 30 mg/kg/day dose of CFM-4.16 (free compound as DMSO/cremophor preparation or nanomicellar formulation) was chosen for use in the in vivo experiments described herein. As shown in FIG. 10A, intravenous (iv) administration of vehicle (Control) SMA-TPGS (total dose of 120 mg/animal), DMSO/cremophor preparation of CFM-4.16 (total dose of 240 mg/animal), or administration of SMA-TPGS-CFM-4.16 (total dose of 210 mg/animal) by oral gavage failed to inhibit tumor growth. However, only two i.v. injections of 30 mg/kg/day of SMA-TPGS-CFM-4.16 (total dose of 60 mg/animal) caused a significant reduction in tumor size when compared with the tumor sizes noted in the other treatment groups FIG. 10A. The HPLC analysis of the tumors from animals treated with i.v. injections of SMA-TPGS-CFM-4.16 revealed presence of CFM-4.16 in tumors. In addition, after the completion of the animal experiment, tumors from treatment and control groups were dissected, and cryosectioned for imaging of apoptotic signs using TUNEL (Terminal deoxynucleotidyl transferase dUTP nick end labeling) and CARP-1. The immuno-histological analysis of tumors from animals treated with i.v. injections of SMA-TPGS-CFM-4.16 showed elevated levels of CARP-1 and TUNEL-positive cells when compared with the tumors derived from the animals of control group (FIG. 10B). Thus, the data show that nanomicellar formulation of CFM-4.16 enhance anti-tumor efficacy of CFM-4.16 when administered i.v. but not orally, at a significantly lower total dose when compared with the free compound.

Materials and Methods. Cell Culture, Reagents and Chemicals. Structure and synthesis of CFM-4, -4.16, and -4.17 compounds have been recently described (Peña et al., *Clin. Cancer Res.* 16(19):4853-4363, 2010). A stock solution of 50 mM of each CFM was prepared in dimethyl sulfoxide (DMSO) and stored at −20° C. Styrene maleic anhydride (SMA, MW 1600), D-alpha-tocopheryl polyethylene glycol succinate (Vitamin E-TPGS), and 3-[4,5-Dimethylthiazol-2-yl]-2,5diphenyltetrazolium bromide (MTT) were obtained from Sigma-Aldrich, St Louis, MO. Everolimus was purchased from SelleckChem, Boston, MA and a 50 mM stock solution was prepared in DMSO and stored at −20° C., while clinical grade Adriamycin (ADR) was obtained from the Karmanos Cancer Institute pharmacy, Detroit, MI. All other analytical grade reagents were purchased from Sigma-Aldrich (St Louis, Mo.) and used without further purification.

DMEM, EMEM medium and antibiotics (penicillin and streptomycin) were purchased from Invitrogen Co. (Carlsbad, CA). Fetal bovine serum (FBS) and DMSO were obtained from Denville Scientific Inc. (Metuchen, NJ), and Fisher Scientific (Fair Lawn, NJ), respectively. The Protein Assay Kit was purchased from Bio-Rad Laboratories (Hercules, CA). The mouse monoclonal antibodies for β-actin were acquired from Sigma-Aldrich (St. Louis, Mo.). Rabbit polyclonal antibodies for α-tubulin, Cyclin B1, Cleaved Caspase-8, PARP, phospho and total p38α/β. phospho-and total JNK1/2 SAPKs were purchased from Cell Signaling Technology (Beverly, MA). Generation and characterization of the anti-CARP-1 rabbit polyclonal antibodies has been previously described (Rishi et al., *J. Biol. Chem.* 278, 33422-33435, 2003).

The human RCC A498, CAKI-1, CAKI-2, and ACHN cells were from ATCC. The HLRCC (UOK 268 and UOK 262) cells were from NCI. All the cells were routinely maintained as described before (Beljanski et al., *Invest New*

Drugs. 29(6):1132-1142, 2011; Roulin, et al., *Mol. Cancer* 10, 90, 2011). All the cell culture media were supplemented with 10% FBS, 100 units/ml of penicillin, and 100 µg/ml of streptomycin, and the cells were kept at 37° C. and 5% $CO_2$. For cell growth and MTT studies, the cells were cultured in fresh media with 10% FBS prior to their treatments with various agents.

Generation of Everolimus-resistant RCC cells. The human RCC A498, UOK262, and UOK268 cells were cultured in the chronic presence (>6 months) of Everolimus. The parental A498 cells were initially treated with 500 nM Everolimus for 3-4 weeks, followed by escalation to 1.0, 2.0, 4.0 and 10.0 UM doses. The cells were cultured in continuous presence of each of the dose for 3-4 weeks until resistance was developed, and cells became adapted to growth in 2 µM Everolimus. In the case of UOK262 and 268 RCC cells, the parental cells were initially cultured in 10 nM Everolimus for 3-4 weeks. For selection of the resistant cells, everolimus dose was escalated to 20, 50, 100, 200, 500, 1000, and 2000 nM. The UOK cells were cultured in continuous presence of each of the dose for 2-3 weeks until resistance developed, and cells adapted to growth in 2 µM Everolimus. Subsequent, routine maintenance of the resistant cells in the presence of 2 µM Everolimus was continued and multiple, resistant sublines for each of the RCC cells were isolated and characterized for their growth inhibitory ($GI_{50}$) dose of Everolimus by the MTT-based viability assays as detailed below.

Generation of CARP-1 knock-down RCC cells. The human RCC UOK262 parental cells were transfected with vector plasmid pcDNA3/hygro or plasmid expressing CARP-1 anti-sense (Clone 1.6; Rishi et al., *J. Biol. Chem.* 278, 33422-33435, 2003). Multiple, stable sublines for hygromycin resistance were selected in the presence of 400 µg/ml hygromycin (#10687010, InVitrogen Inc) following methods described before (Rishi et al., *J. Biol. Chem.* 278, 33422-33435, 2003). The levels of CARP-1 in the parental, and vector or CARP-1 antisense plasmid-transfected RCC cells and their viabilities in the presence of CFM compounds were determined by western blot and MTT assays, respectively, as described below.

Cell Viability Assays. The cytotoxicity of CFM-4, -4.6, -4.16, -4.17, Everolimus, ADR, SMA-TPGS co-polymer, SMA-CFM-4.16, SMA-TPGS-CFM-4.16 in the RCC cells (A498, UOK262, and UOK268) was assessed by MTT assay. First, $5 \times 10^3$ cells were seeded in a 96-well plate in triplicate and allowed to grow in fresh culture media for another 24 h. Cells were then treated with respective agents for the noted doses and times. Control cells were treated with 0.1% DMSO in culture medium. After treatment, an MTT assay was performed. Briefly, 20 µL of 1 mg/ml of MTT was added to each well and cells were incubated for 2-4 h at 37° C. MTT was removed, and the resulting formazan products were dissolved by adding 50 µl DMSO/well followed by colorimetric analysis using a multi-label plate reader at 570 nm (Victor3; PerkinElmer, Wellesley, MA).

Flow Cytometry Analysis. Apoptosis induction in A498 RCC cells by the free and micellar formulations of CFM-4.16 was determined by flow cytometry with Annexin V/7-AAD dual staining. The percentages of Annexin V−/7-AAD− (R5), Annexin V+/7-AAD− (R6) and Annexin V−/7-AAD+ (R4) and Annexin V−/7-AAD+ (R3) were obtained to determine the number of live cells, as well as early and late apoptotic, and necrotic cells.

Western Blot Analysis. For protein expression analysis, western blot experiments were conducted. The RCC cells were treated with DMSO/Vehicle (Control) or the indicated doses and times of the noted compounds, and were lysed to prepare protein extracts. Cells were harvested and lysed in RIPA buffer (50 mM Tris-HCl, pH 8.0, 150 mM sodium chloride, 1.0% NP-40, 0.5% sodium deoxycholate, 0.1% sodium dodecyl sulfate (SDS), and 0.1% of protease inhibitor cocktail) for 20 min at 4° C. The lysates were then centrifuged at 14,000 rpm at 4° C. for 15 min to get rid of debris. The protein concentrations of whole cell lysates were then determined using the Protein Assay Kit. Supernatant proteins, 50 µg from each sample, were separated by SDS-10% polyacrylamide gel electrophoresis (SDS-PAGE) and transferred to polyvinylidene difluoride (PVDF) membrane (Bio-Rad, Hercules, CA) by standard procedures. The membranes were hybridized with primary antibodies followed by incubation with appropriate secondary antibodies. The antibody-bound proteins were visualized by treatment with the chemiluminescence detection reagent (Amersham Biosciences) according to the manufacturer's instructions, followed by exposure to X-ray film (Kodak X-Omat). The same membranes were then re-probed with either the anti-β actin or anti-α tubulin antibody, which was used as an internal control for protein loading.

SMA-TPGS Synthesis and Micellar Nanoformulation Fabrication. SMA-TPGS block copolymer (SMA-TPGS) was first synthesized by adding known amounts of TPGS in $NaHCO_3$ buffer at pH 8.9 with fixed amounts of anhydrous SMA to permit its anhydride ring opening reaction with the alcohol group of TPGS. All unconjugated reagents were removed by ultrafiltration (Millipore TFF, Milford, MA) of the SMA-TPGS conjugate prior to its lyophilization. For Morphology, Transmission Electron Microscopy (TEM) of the nanoparticles was assessed using JEOL JEM-1000 instrument (JEOL Ltd, Tokyo, Japan). Then, the products obtained were stored in the freezer until further use. Nanomicelles were characterized by proton nuclear magnetic resonance spectroscopy ($^1H$ NMR) and Fourier transform infrared spectroscopy (FTIR). The structure of the synthesized SMA-TPGS copolymer was detected by $^1H$ NMR in $D_2O$. The —CH protons and methyl protons of SMA segment had signals at 5.2 and 1.69 ppm, respectively. The —CH2 protons of PEO part of TPGS had the peak at 3.65 ppm. The lower peaks were noted in the aliphatic region that belong to various moieties of vitamin E tails (not shown and Liao et al., *Cancer Res.* 57, 2827-2831, 1997). The proper synthesis of the SMA-TPGS co-polymer was also confirmed by FTIR analysis, and was not found to be a physical mixture of TPGS with SMA as all measurements indicated the absence of any free crystalline particles in nanomicelles preparation. Both SMA and TPGS inhibited crystallization of CFM-4.16 during nanomicelles formulation. CFM loaded micelles were then fabricated according to earlier published protocols (Sosman & Puzanov, *Cancer.* 115(10 Suppl):2368-2375, 2009; Maeda et al., *J. Control. Release* 65, 271-284, 2000; Iyer et al., *J. Drug Target.* 15, 496-506, 2007), followed by characterization of micelles for size, charge, critical micelles concentration (CMC), and drug loading as described below. See FIGS. 4A-4F and 5A-5D.

Figure 4D:
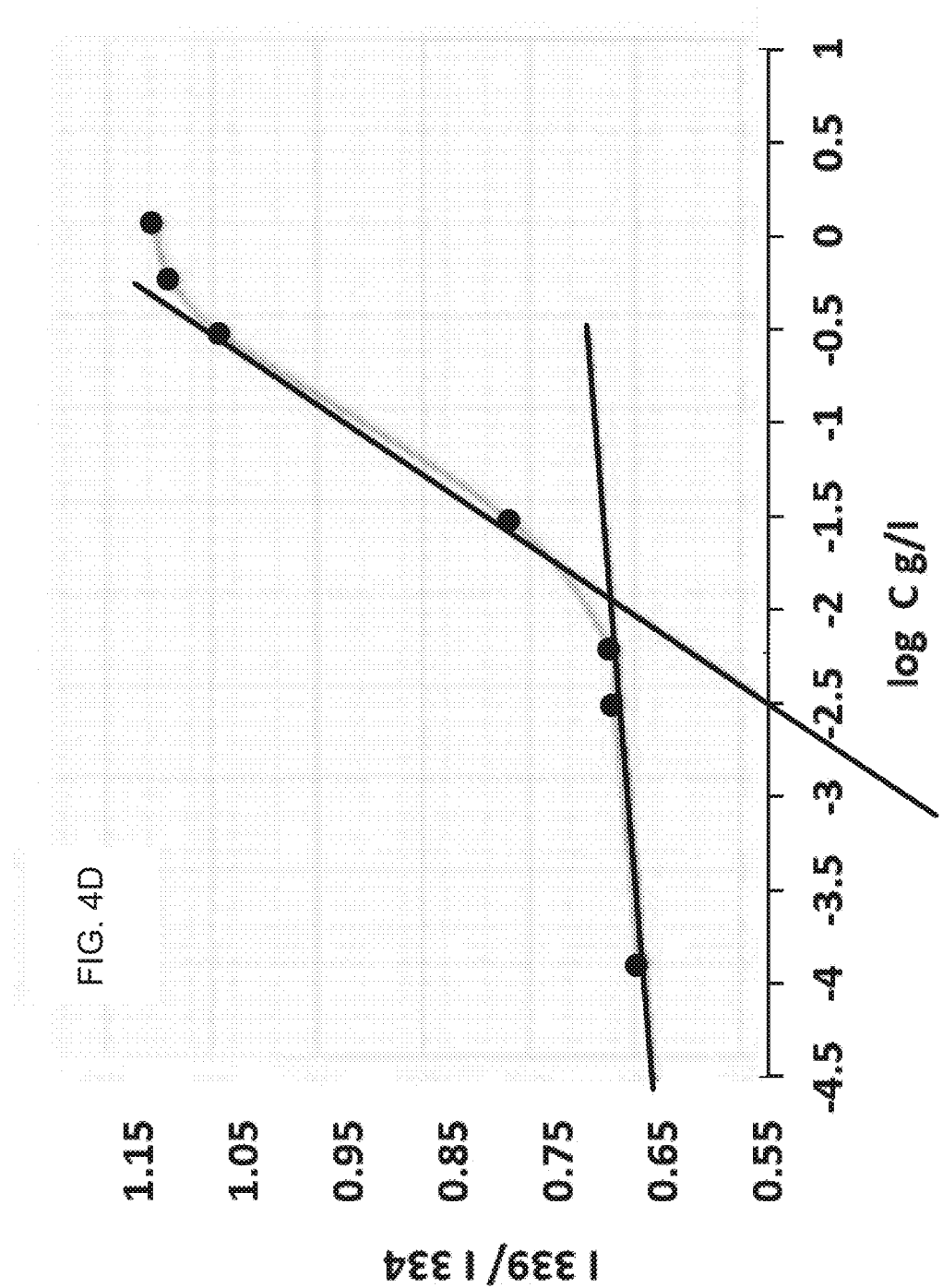
Figure 4E:
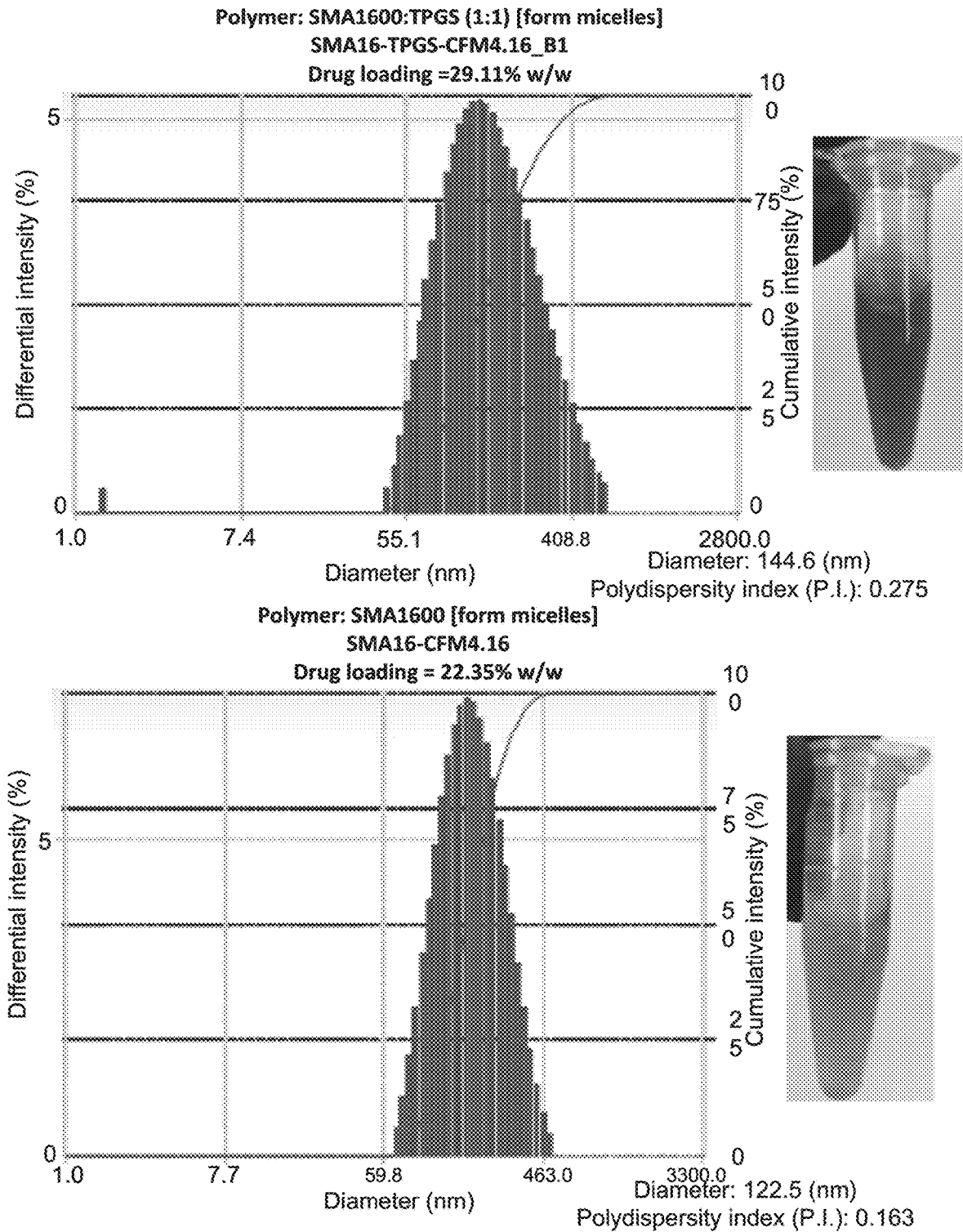
Figure 4F:
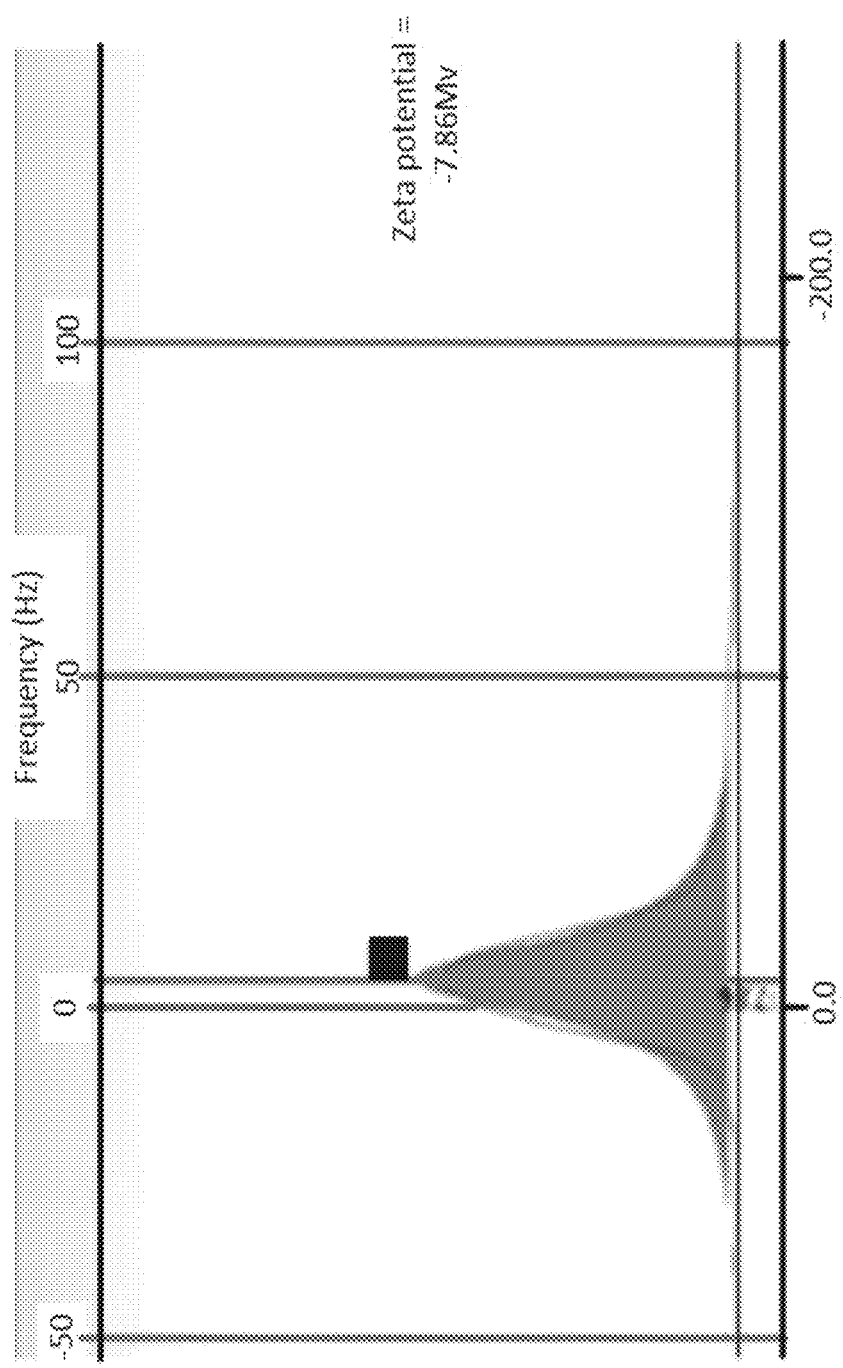
Figure 5A:
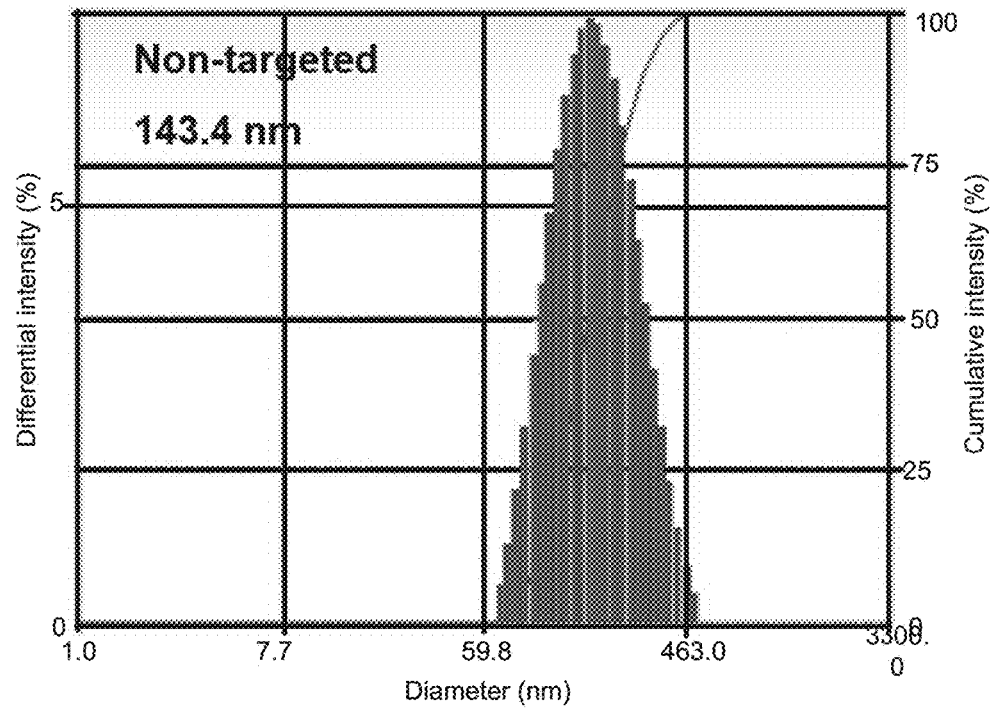
FIG. 5A and FIG. 5B illustrate distribution of particle size and zeta potential for non-targeted nano-formulation, respectively.
Figure 5B:
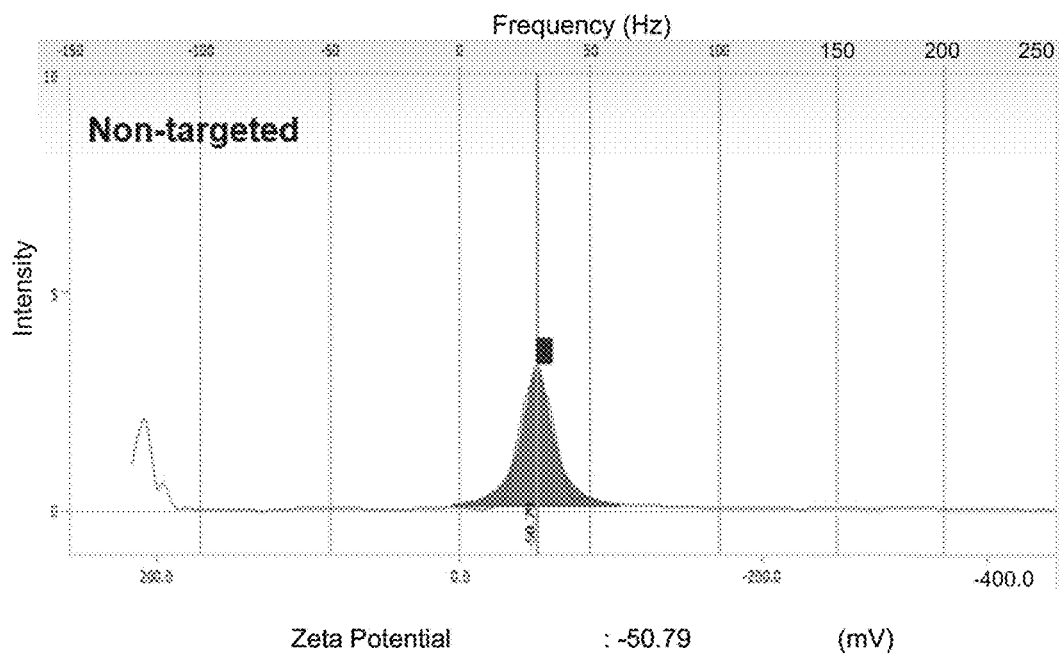
Figure 5C:
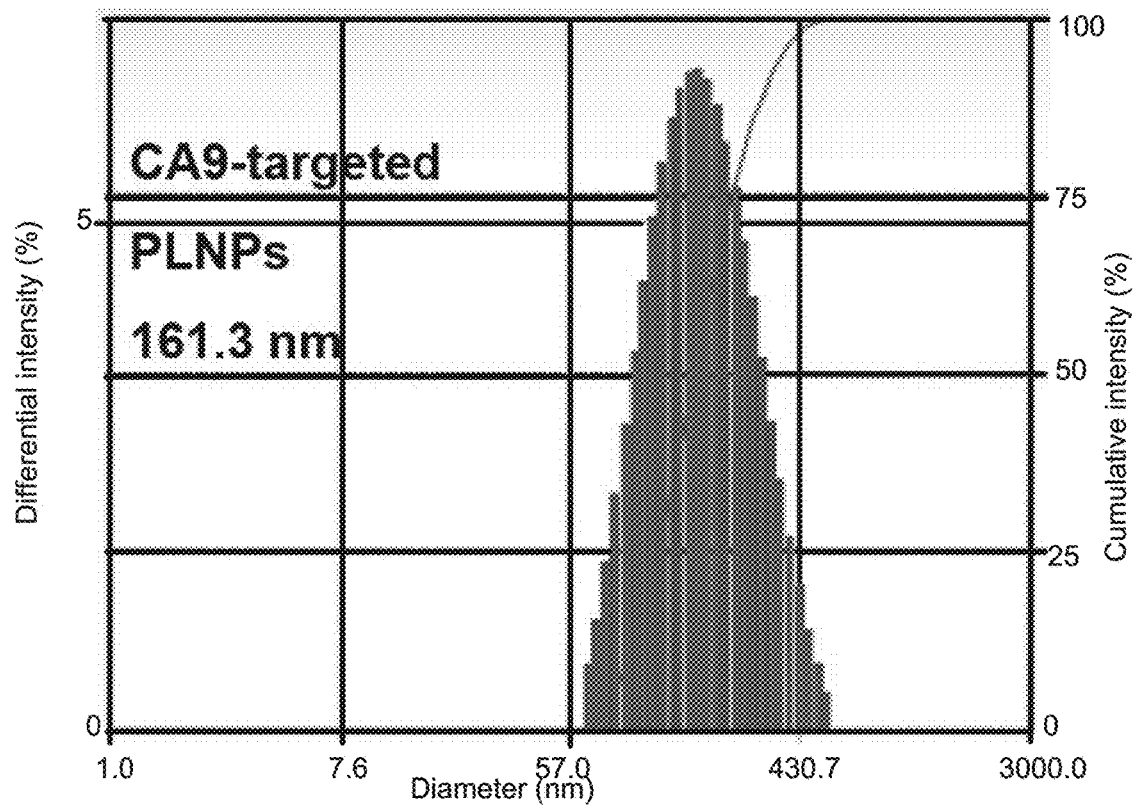
FIG. 5C and FIG. 5D illustrate the particle size and zeta potential of CAIX-targeted formulation, respectively.
Figure 5D:
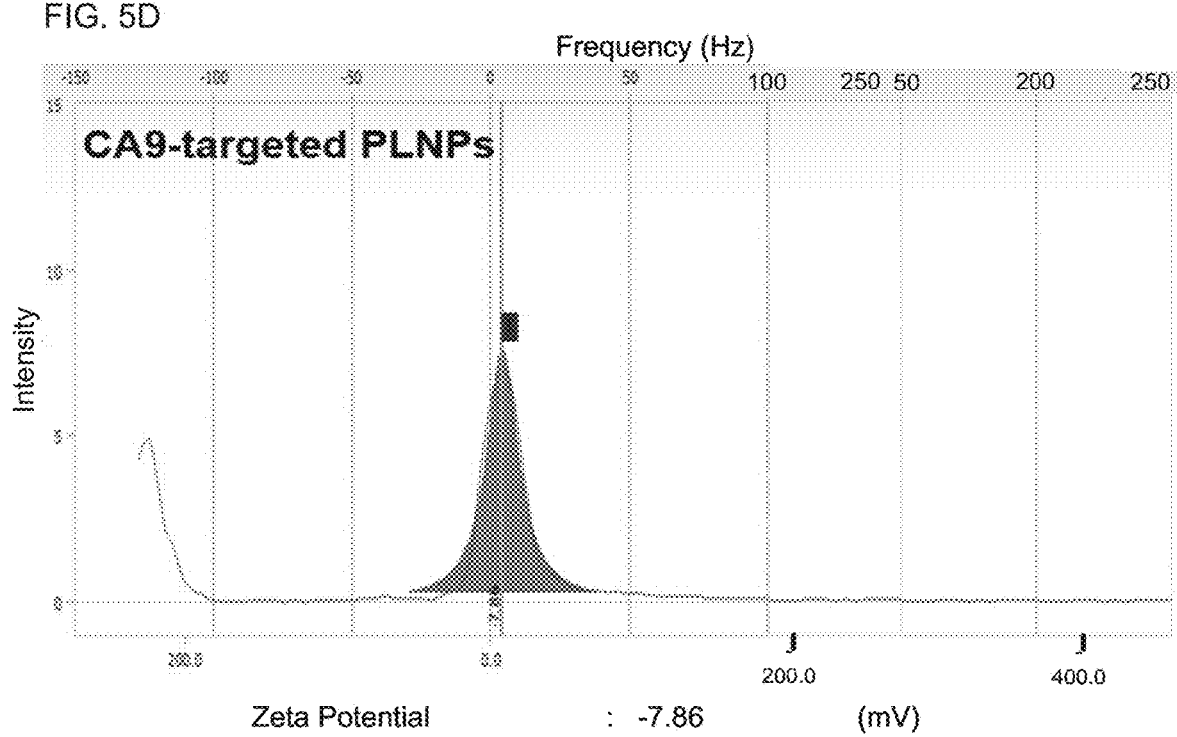
Figure 6C:
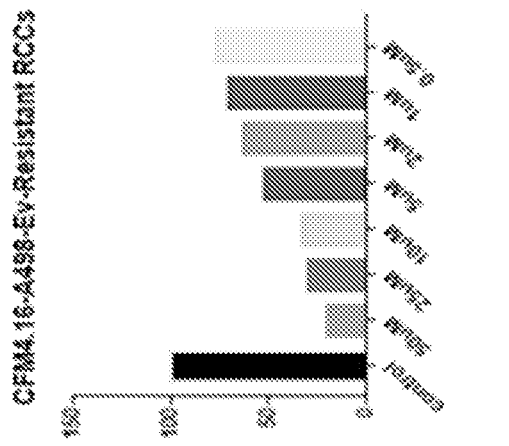
FIGS. 6A-6E are a series of graphs, showing CFM4.16 works in good synergism with sorafenib in Everolimus-resistant (EV-resistant) renal cell carcinoma cell lines. MTT study of CFM4.16 (FIG. 6A) and Sorafenib (Sor or SORF) (FIG. 6B) in EV-resistant A498 cells and individual treatment of CFM4.16 or SoRF (FIG. 6C) in wild-type A498 cells. The combination of CFM4.16 (1 µM) with different concentration of Sorafenib (FIG. 6D), and combination CFM4.16 and SOR at variable concentration (FIG. 6D) in A498 cells indicate CFM4.16+Sorafenib is synergistically killing the drug resistant (EV-resistant and wild type) RCC cells. 100% DMSO was used as positive control. Control indicates cell were left untreated.
Figure 6B:
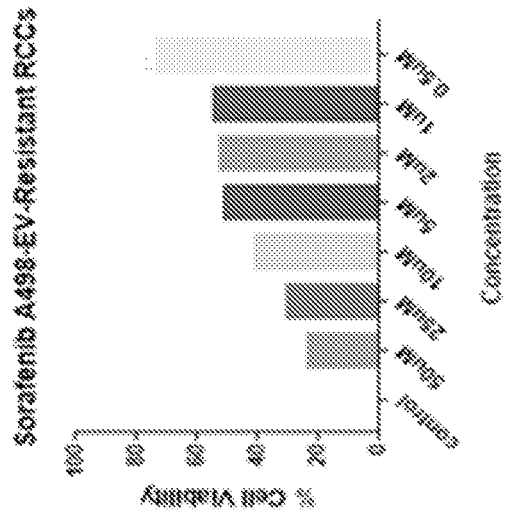
Figure 6A:
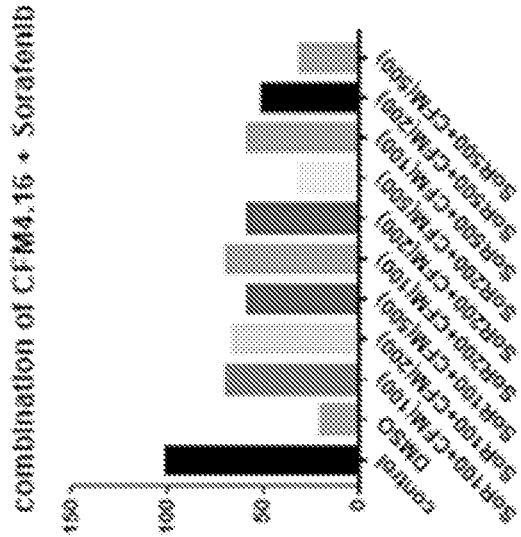
Figure 6E:
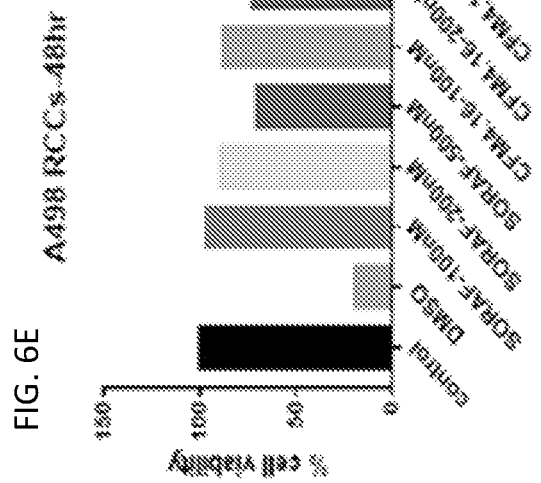
Figure 6D:
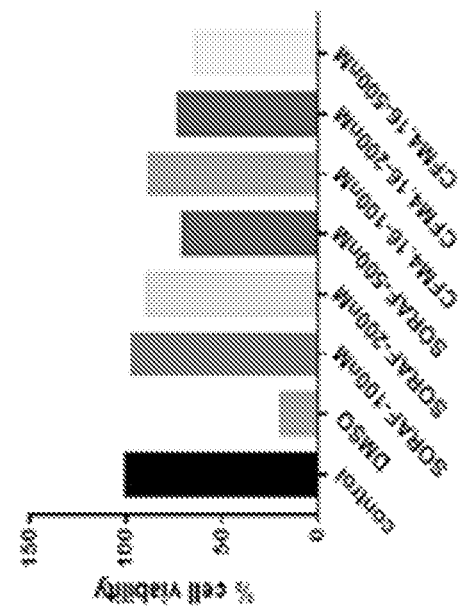
Figure 7:
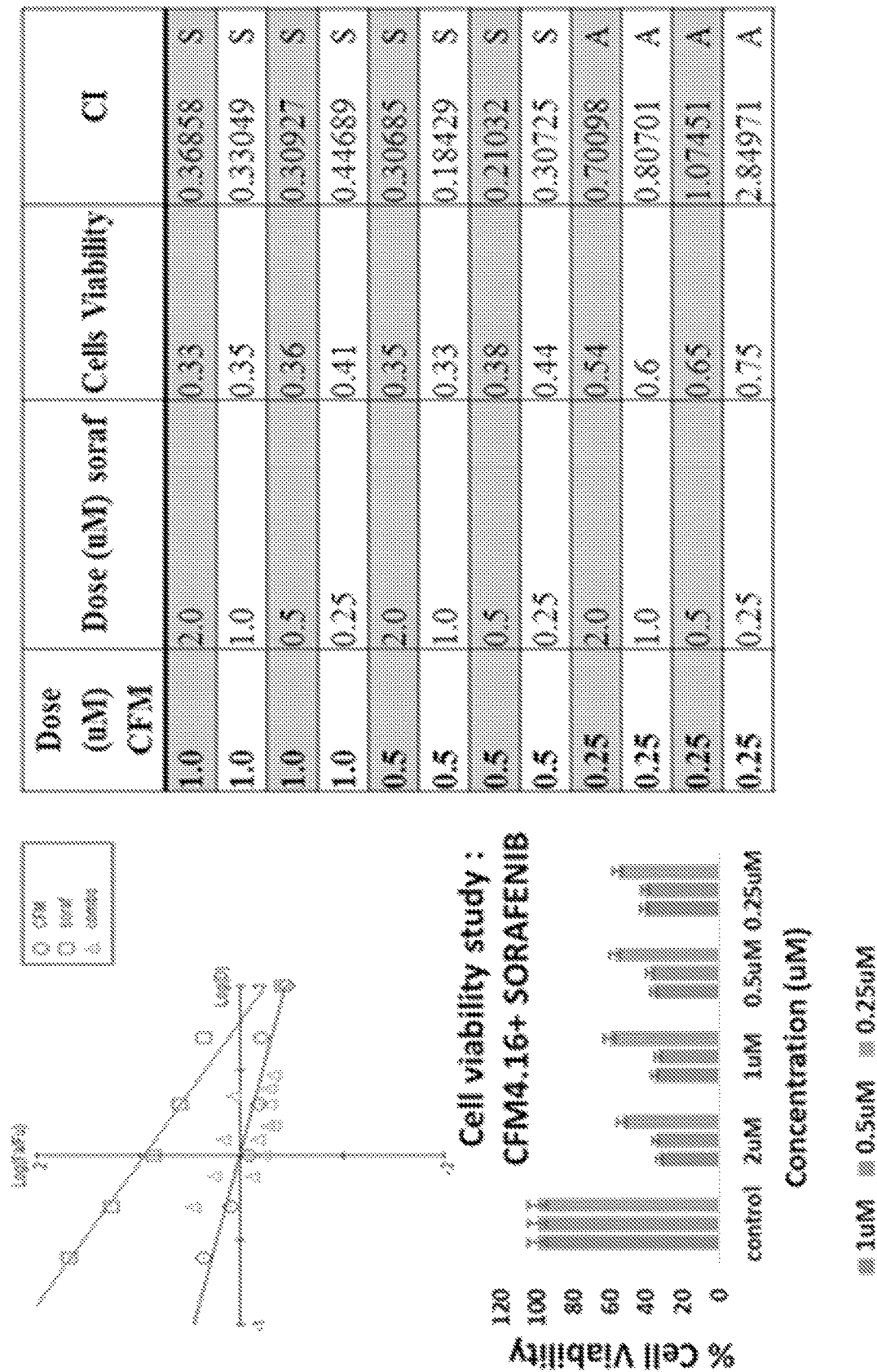
FIG. 7 shows that CFM4.16 works in good synergism with sorafenib in EV-resistant renal cell carcinoma cell lines and combination index table. Synergistic combination of CFM4.15 with Sorafenib (Soraf) in RCC cell killing was determined by combination index (CI) value obtaining from CompuSyn program. CI value<1 indicates synergistic cell killing, CI=1 means additive and CI>1 means antagonistic. The data indicate in most cased CI<1, thus CFM4.16+Soraf is working in synergy.

Particle Size and Zeta Potentials. Particle size and surface charge (zeta potential), measurements were performed using a Beckman Coulter Delsa NanoC-DLS Particle analyzer (Miami, FL) equipped with a 658 nm He—Ne laser. For particle size, the nanomicelles were suspended in de-ionized (DI) water, and the scattered light detected at 165° angle. The peak average histograms were then obtained from the intensity, volume and number from 70 scans to calculate the average diameter of the particles. The zeta potentials were evaluated by measuring the electrophoretic mobility of the charged particles under an applied electric field. The obtained results, of particle size of CFM4-16 loaded nanomicelles was 144.5 nm (FIG. 4E) and surface charge was −7.86 mV (FIG. 4F). These results indicate that the size and surface properties are optimal and safe for intravenous injection as well as ideal for tumor delivery.

Loading Efficiency of SMA-CFM Nanomicelles. The CFM-4.16 loading content percentage in SMA-TPGS nanomicelles was evaluated by High Performance Liquid Chromatography (HPLC). First, a method for analyzing drug content was developed and validated according to ICH guidelines Oyer et al., Drug Discov. Today 11, 812-818, 2006). The standard curve of CFM-4.16 in DMSO and its successive dilutions were measured with mobile phase at 309 nm (A max). The calibration curve was linear in the range of 50-50,000 ng/ml with a correlation coefficient (R2)=0.9999. The loading efficiency of micelles was calculated by dissolving a known amount of nanomicelles directly in DMSO and further dilution of drugs with the mobile phase followed by determination of the absorbance at 309 nm with respect to the standard curve as described previously (Maeda et al., J. Control. Release 65, 271-284, 2000).

Drug Encapsulation Efficiency (EE). Free drug (non-incorporated in the SMA-TPGS) was separated by an ultra-filtration centrifugation technique. Briefly, 1 mL of CFM-4.16 and SMA-TPGS-CFM 4.16 colloidal solution were placed in the upper chamber of a centrifuge tube matched with an ultrafilter and centrifuged for 15 min at 4000 rpm. The total drug content in CFM-4.16 nanoformulation was determined as follows. Aliquots of 1 mL formulation dispersion were diluted appropriately by ethanol to dissolve the TPGS-SMA ingredient, and the resulting suspension was then filtrated through 0.45 μm membrane filters. The filtered solution was analyzed by Waters® Alliance e2695 HPLC using Symmetry® C18 column (250 mm×4.6 mm, 5 μm). The mobile phase was a mixture of Acetonitrile, Methanol, 10 mM $KH_2PO_4$ buffer (65:20:15 v/v) with pH adjusted to 2, and the flow rate was maintained at 1.0 ml/min. All the samples were analyzed at 309 nm using empower PDA software. The encapsulation efficiency (EE) and drug loading content (DLC) were then calculated by the following equations:

Drug loading content (DLC)

$$\% \text{ drug loading} = \frac{\text{(Weight of CFM4.16 encapsulated in micelles)}}{\text{(Total weight of CFM4.16 loaded in micelles)}} \times 100 \quad \text{Equation (1)}$$

Encapsulation Efficiency (EE)

$$\% \text{ encapsulation efficacy} = \frac{\text{(Mass of CFM4.16 encapsulated in micelles)}}{\text{(Total mass of CFM4.16 initially loaded in micelles)}} \times 100 \quad \text{Equation (2)}$$

Three-dimensional Renal Sphere Assays. The RCC cells were obtained from xenograft tumors derived from parental cells or from the parental and Everolimus-resistant RCC cells from a two-dimensional culture plate with 70-80% confluence. Three-dimensional renal sphere cultures were performed by essentially following the methods in (Pena et al., Clin. Cancer Res. 16(19):4853-4363, 2010). Briefly, the cells were washed twice in 1× PBS and trypsinized following established protocols. The cells were then pelleted at 200×g at room temperature, and re-suspended in 5 ml of sphere media (DMEM/F12 supplemented with 2 mM L-glutamine, 100 U/ml penicillin, 100 U/ml streptomycin, 1×B27 supplement, 20 ng/ml recombinant human epidermal growth factor (EGF; Sigma), and 10 ng/ml recombinant human basic fibroblast growth factor (bFGF; R&D Systems). 5000 viable cells were seeded per ml in an ultra-low adherent 60 mm plate and incubated them at 37° C. and 5% $CO_2$ for two weeks without disturbing the plates. After the spheres formed, fresh media was added with or without 10 μM CFM-4.16. Incubation then continued for an additional 24 h at 37° C. and 5% $CO_2$. At the end of the incubation period, the spheres in the untreated and treated plates were photographed as described in (Greish et al., J. Control. Release 97, 219-30, 2004).

Establishment of RCC Cell-Derived Xenografts in Immunocompromised Mice. The experiments involving generation of RCC cell-derived sub-cutaneous xenografts were performed according to previously published methods and protocols approved by the Institutional Laboratory Animal Care & Use Committee (IACUC). Female, 5-week old NCR SCID mice with were purchased from Charles River Laboratories (Horsham, PA).

For subcutaneous (s.c.) tumor xenograft studies, maximal tolerated doses for CFM-4.16 (prepared in 10% DMSO/cremophor+distilled, sterile water, and pH adjusted to 4.5), SMA-TPGS co-polymer, SMA-TPGS-CFM-4.16, and SMA-CFM-4.16 preparations were first determined. The MTD for free CFM-4.16 (prepared in DMSO/cremophor) have been described before, and a 30 mg/kg/day iv injection was judged safe; a total dose of 482 mg/kg provoked a mild ataxia with some tail and leg twitching that resolved within 1-2 minutes. This dose/schedule of free CFM-4.16 produced a mild weight loss of 1.6% body weight by day 7 (recovery by day 18). No other histological abnormalities were noted (Pena et al., Clin. Cancer Res. 16(19):4853-4363, 2010). A 30 mg/kg/day dose of SMA-TPGS, was injected (iv) while a 30 mg/kg/day of SMA-TPGS-CFM-4.16 was administered by oral gavage in two female, NCR SCID mice for 10 days. The animals did not show any signs of toxicity, discomfort, or any histological abnormalities. These observations indicate a suitable toxicity profile of SMA-TPGS co-polymer and its CFM-4.16 formulation. However, the iv injections of a 30 mg/kg were best tolerated when administered on alternate days. Accordingly, for the efficacy studies the block co-polymer was administered daily by iv route while the micellar formulation with CFM-4.16 was administered by oral gavage. The iv administration of the CFM-4.16 micellar formulation was conducted on every alternate day.

For efficacy studies, after a suitable period of acclimation, a suspension of 1×10⁶ A498 RCC cells in 200 μl of serum-free Hank's balanced salt solution were subcutaneously implanted in flanks of each animal using a 27-gauge needle. Tumors were allowed to grow unperturbed for 10-14 days. When tumors became palpable (200 mm³), the mice were randomly assigned to treatment or control groups of eight animals each. Mice were treated with Control, PBS only, SMA-TPGS co-polymer (30 mg/kg; i.v.), SMA-TPGS-CFM-4.16 formulation (30 mg/kg/day) by oral gavage for 10 days. In the case of the group of mice treated with iv administration of SMA-TPGS-CFM-4.16 formulation (30 mg/kg), only two injections were administered where the first dose was followed by the second dose on the alternate day. The tumor weight and volume were measured daily, and mice were observed for changes in weight and side effects. The end points for assessing antitumor activity consisted of tumor weight, tumor growth inhibition (% T/C), and tumor cell kill Log10. Tumor weight (mg)=(A×B2)/2 where A and B are the tumor length and width (in mm), respectively. Tumor growth inhibition (T/C) was the median tumor weight in the treated group (T) when the median tumor weight in the control group reached 750 mg. Results were expressed as percentage. According to NCI-accepted criteria, a treatment is considered effective if T/C is <42%. Tumor growth delay (T-C) is the difference between the median time (in days) required for the treatment group tumors (T) to reach 1000 mg and the median time (days) for the control group tumors to reach the same weight. The animals were sacrificed on day 10 and tumor tissues were collected immediately after tumor volume measurement. Tumor volumes were calculated by the modified ellipsoidal formula. Tumor volume=1/2(length×width$^2$). Representative tumor samples were stored at −80° C. for subsequent analysis.

In Vivo Imaging Studies. S0456 a reactive near-infra-red fluorochrome, was covalently linked with PLNPs and used for in vivo near-IR optical imaging of selected nanoparticle formulations. The formulations were injected intravenously in female nude mice bearing tumor xenografts. The distribution and tumor targeted delivery were imaged by tracking the fluorescent output of IRDye 800® with in vivo Imaging System (see FIG. 11).

Statistical Analysis. The statistical analysis was done using Prism 6.0 software (Graph Pad Software Inc., San Diego, CA). The data were expressed as mean±SEM and analyzed using a two-tailed Student t-test or one-way ANOVA followed by a post hoc test. A p value of <0.05 was considered statistically significant.

Table 1 illustrates that the combination index (CI) of non-encapsulated CFM 4.16 with addition of different non-encapsulated anticancer agents demonstrates effective synergism between CFM 4.16 and sorafenib in RCC. The combination of CFM4.16 was performed with various clinically approved drugs, such as Sorafenib, Everolimus, Olaparip, Palbociclib, Dabrafenib. All the clinically drugs were treated in combination with CFM4.16 with a range of concentrations using MTT assay in the specified RCC cell line, and the data were feed to CompuSyn program to obtain the CI-value. The data indicates CFM4.16 is highly synergistic with Sorafenib, Dabrafenib and moderately synergy with Everolimus and Palbociclib in RCC cells. Based on these data, novel nanoparticle-formulation of these drugs have been developed, improving tumor targetability as an individual or combination treatment.

TABLE 1

Summary of combination index (CI) value of anticancer drugs

| Cell Line | Type | Combination Index (CI) Drug + CFM4.16 | | | | |
| --- | --- | --- | --- | --- | --- | --- |
| | | Sorafenib | Everolimus | Olaparip | Palbociclib | Dabrafenib |
| A498 | wild type | 0.53 | 0.7 | 1.0978 | 0.7 | 0.13850 |
| | Everolimus resistant type | 0.6 | 1.3 | 1.121 | 0.971 | 0.677 |
| OUK262 | wild type | 0.76 | 0.67 | 0.9878 | 0.897 | 0.234 |
| | Everolimus resistant type | 0.8 | 1.45 | 1.312 | 1.0023 | 0.587 |

Example II

Tumor Hypoxia Targeting Oligomicelles with Polypharmacy Payload for Treating and Overcoming Drug Resistance in Renal Cell Carcinoma This Example describes synergistic therapeutic strategies to deliver a variety of therapeutic agents to target the hypoxic tumor microenvironments. Particular embodiments use oligomicelles that target carbonic anhydrase 9 (CA9) and deliver a combination of sorafenib and CARP-1 protein activator CFM4.16 (C-4.16; U.S. Pat. No. 9,598,441) for overcoming drug resistance for RCC therapy. This Example focuses on multimodal approaches, including (a) optimization of hypoxia marker conjugated targeted nanoformulation (PLNPs) using copper-free click chemistry; and (b) In vitro and in vivo pre-clinical testing of CA9 and/or folate receptor (FR) targeted-PLNP loaded with polypharmacy in inhibiting RCCs using mice bearing resistant RCCs and patient-derived xenografts (PDX). At least some of the material in this Example was published as Alsaab et al., *Biomaterials* 183: 280-294, 2018.

The most common form of RCC (more than 95%) is clear cell renal cell carcinoma (ccRCC). The mutation and inactivation of tumor suppressor Von Hippel-Lindau (VHL) gene is frequently observed in this malignancy that leads to higher intracellular level of hypoxia-inducible factors 1α and 2α (HIF1α and HIF2α). The increased level of HIF-1α in RCC effectively regulates the tumorigenesis by secreting vascular endothelial growth factor (VEGF) and hepatocyte growth factor (HGF), modifying the cellular metabolism, inhibiting apoptosis pathway, acclimatizing to acidic pH, and up-regulating metastasis associated proteins. All these factors promote RCC to develop resistance against radiotherapy and conventional chemotherapy (Strese et al., *BMC Cancer* 13:331, 2013. doi: 10.1186/1471-2407-13-331). Several receptor tyrosine kinase inhibitors (RTKIs), mammalian target of rapamycin inhibitors (mTOR) and serine-threonine kinase (STK) inhibitors are clinically approved for the treatment of RCC, although the benefit of overall progression-free survival is very poor (5-year survival rate of <10%). Thus there is an urgent unmet need for targeted combination therapies with novel mechanisms (Voss et al., *Hematol Oncol Clin North Am* 2011; 25:835-52. doi: 10.1016/j.hoc.2011.04.008).

To overcome the critical problem of current RCC treatment, a tumor penetrating nanosized oligomicelles of spherical shape that can localize and penetrate tumor tissues effectively and interrogate tumor hypoxia and deliver the combination drug cocktail to shut down vital tumorigenic signaling were developed. Several studies have identified the key players that are responsible for drug resistance and immune evasion leading to poor prognosis of RCC, categorized based on their specific roles: (i) RTK-mTOR are the key tumorigenic signalling for tumor survival, immune suppression and stroma formation. More than 5 FDA-approved kinase inhibitors have been used in clinic, but resistance to anti-kinase therapy almost always occurs with RCC patients and requires new treatment regimens (Sánchez-Gastaldo et al., *Cancer Treatment Reviews,* 60:77-89, 2017). (ii) Impairment of intrinsic and extrinsic apoptotic signaling is an important player of drug resistance and the role of CARP-1 protein (cell cycle and apoptosis protein-1) have been discovered for inducing apoptosis in cancer cells (Cheriyan et al., *Oncotarget.* 9(51):29680-29697, 2018). (iii) Carbonic anhydrase-9 (CA9) is a tumor hypoxia marker for the maintenance of extracellular acidosis and cancer stemness, thus facilitating tumor growth and metastases. More than 7 clinical trials are underway to target CA9 in RCC and other solid tumors (Clinical Trial Identifiers: NCT00059735, NCT00884520). Thus, the strategy described in Part II is to further establish tumor penetrating oligomicelles that target tumor-multi-components (such as CA9 targeting hypoxia) and co-delivery of RTK-inhibitors and CARP-1 activators for effective RCC therapy.

Carbonic anhydrase 9 (CA9, also referred to herein as CAIX) is an enzyme expressed on the surface of kidney cancer cells with a restricted expression in normal cells. Here, the utility of anti-carbonic anhydrase 9 (CA9) small molecules conjugated to the surface of oligomicelles loaded with CARP-1 Functional Mimetics or C4.16 (CAIX-C4.16-PLNPs) were explored to promote the therapeutic effects for kidney cancer via systemic administration. Thus, the strategy was to establish tumor penetrating oligomicelle to target tumor-multi-components (such as CA9 targeting hypoxia) and co-delivery of RTK-inhibitors and CARP-1 activators for effective RCC therapy. C-4.16 inhibited RCC cell viability in a dose-dependent manner that was comparable to Everolimus treatments as well as the combination with sorafenib. C-4.16 inhibited viabilities of Everolimus resistant RCC cells albeit C-4.16 combined with sorafenib was more effective than C-4.16 alone. The oligomicelles formulations were also used for in vitro efficacy in parental, wild-type and everolimus-resistant RCC. It was found that the CA9-C4.16-PLNPs significantly improved the cellular uptake efficiency in both CAIX-positive human clear cell renal cells carcinoma (RCC-A498) and RCC-A498-Everolimus resistant tumor spheroids, resulting in the efficient cell killing compared with free C-4.16 and non-targeted C-4.16-PLNPs. After confirming the anticancer activity of C-4.16 loaded nanoformulations in vitro, the intravenous (i.v.) administration of the C-4.16 loaded PLNPs in a clinically relevant RCC mouse model was examined. After optimizing its potency and biological stability imaging of animals inoculated with A498 RCC tumor in a xenograft model and a PDX model by conjugation with NIR dye was performed. The results showed high binding affinity and specific tumor uptake, faster normal tissue clearance and less non-target organ uptake. These findings portent promising therapeutic potential of C-4.16 in combination with sorafenib using nanoformulation in treatment of RCCs.

1-Cu free click chemistry utilized oligomer for tumor hypoxia penetration. The objective was to synthesize formulations for tumor hypoxia targeting containing ATZ oligomers for targeting the CA9 enzyme on the surface of kidney cancer. As illustrated in FIG. 23, first ATZ-NH$_2$ is synthesized from ATZ by acid hydrolysis, then it is functionalized with an NH2 group and is conjugated to DBCO-NHS Ester to obtain the ATZ-DBCO compound (a). On the other hand, in FIG. 23 scheme 2 SMA-TPGS block copolymer (SMA-TPGS) was synthesized by adding known amounts of TPGS in NaHCO$_3$ buffer at pH 8.9 with fixed amounts of anhydrous SMA to permit its anhydride ring opening reaction with the alcohol group of TPGS and later on reacted with NH2-PEG8 with terminal N3 group to get compound (b). Finally, compound a and b are coupled to arrive at ATZ-SMA-TPGS oligomer by CU-free click chemistry. All compounds were characterized by $^1$H-NMR and FTIR to assure chemical identity. This ATZ-SMA-TPGS is loaded either with water insoluble C4.16 to produce ATZ-C4.16 oligomicelles. The oligomicelles were prepared with different methods, such as solvent evaporation, and oil/water emulsion methods to formulate spherical micelles with TPGS, SMA-TPGS.

Preparation and characterization of CA9 targeting oligomicelles. FIG. 20 provides a pictorial overview of how the oligomicelles were made, and how they are expected to operate in vivo.

Materials and Methods. Cell culture, reagents and chemicals. The structure and synthesis of C-41.6 compound has been previously described (Pena et al., *Clin. Cancer Res.* 16(19):4853-4363, 2010; U.S. Pat. No. 9,598,441). A stock solution of 10 mM of C-41.6 was solubilized in dimethyl sulfoxide (DMSO) and stored at −20° C. for further use. Sorafenib was obtained from LC Laboratories, Boston, MA and a 10 mM stock solution was prepared in DMSO and stored at −20° C. Everolimus was obtained from Selleck-Chem, Boston, MA and a 10 mM stock solution was prepared in DMSO and stored at −20° C., while clinical grade Adriamycin (ADR) was obtained from Karmanos Cancer Institute pharmacy, Detroit, MI. Acetazolamide, click chemistry reagents, Styrene maleic anhydride (SMA, MW 1600), D-alpha-tocopheryl polyethylene glycol succinate (Vitamin E-TPGS), and 3-[4,5-Dimethylthiazol-2-yl]-2,5diphenyltetrazolium bromide (MTT) were purchased from Sigma-Aldrich, St Louis, MO. All other analytical grade reagents were obtained from Sigma-Aldrich (St Louis, Mo.) and used without further purification. DMEM, RPMI medium and antibiotics (penicillin and streptomycin) utilized in this work were purchased from Invitrogen Co. (Carlsbad, CA). Fetal bovine serum (FBS) and DMSO were purchased from Fisher Scientific (Fair Lawn, NJ). All the Protein Assay Kit was obtained from Bio-Rad Laboratories (Hercules, CA). The rabbit monoclonal antibodies for β-actin were acquired from Sigma-Aldrich (St. Louis, Mo.). Rabbit monoclonal antibodies phospho-and total AKT were purchased from Cell Signaling Technology (Beverly, MA). Carbonic Anhydrase-IX (CA9), rabbit monoclonal antibodies were purchased from Cell Signalling (Danvers, MA).

Cell line development and culturing condition. The human RCC A498 cells were from ATCC. The HLRCC (UOK 268 and UOK 262) cells were from NCI. All the cells were regularly maintained as published before (Beljanski et al., *Invest New Drugs.* 29(6):1132-1142, 2011; Roulin, et al., Mol. Cancer 10, 90, 2011). All the cell culture media were supplemented with 10% FBS, 100 units/ml of penicillin, and 100 μg/ml of streptomycin, and the cells were cultured at 37° C. and 5% $CO_2$. For cell viability and MTT studies, the cells were cultured in fresh media supplemented with 10% FBS prior to their treatments with various agents. Resistant RCC cell-lines, including Evr-res A498 and Evr-res UOK262 have been already established and validated. For inducing hypoxia, cells will be treated with 200 μM Cobalt Chloride ($CoCl_2$) in normal growth media for 72 h prior to experiment. RCC 3D-spheroid cell lines will be grown in low density with 2% FBS containing culture media.

General procedure for synthesis of compound SMA-TPGS and ATZ-SMA-TPGS by Copper free 'click' chemistry. As illustrated in FIG. 23 Scheme 1, SMA-TPGS block copolymer (SMA-TPGS) was first synthesized by adding known amounts of TPGS in $NaHCO_3$ buffer at pH 8.9 with fixed amounts of anhydrous SMA to permit its anhydride ring opening reaction with the alcohol group of TPGS. Then, cystine was conjugated by acid-amine coupling (EDC/NHS). Then, COOH of conjugated SMA-Cystine-TPGS is coupled to DBCO-amine for click chemistry reaction to obtain (compound a). In step 2, $ATZ-NH_2$ was synthesized from ATZ by acid hydrolysis into acetazolamide-amine as previously described. Subsequently, it was being functionalized with —COOH group of Fmoc protected 6-aminohexanoic acid, then reacted with protected form of acetazolamide to finally arrive at ATZ-C6-azide (compound b) which is a CA9 (hypoxia) targeting ligand. Finally, the CU free click chemistry reaction will occur by reacting (compound a) with (compound b) to form triazole ring. All unconjugated reagents were removed by dialysis prior to its lyophilization.

Preparation and Characterization of C-4.16-loaded micellar nanoformulation. After final click chemistry reaction, ATZ-SMA-TPGS (CA9-targeted polymer) was obtained and SMA-TPGS (non-targeted polymer) is obtained in parallel. Both, (SMA-TPGS and ATZ-SMA-TPGS-C4.16) nanomicelles were developed using the previous reported method with slight modification. In brief, 100 mg of conjugates polymer was dissolved in 100 ml of DI water under stirring. Then C-4.16 (30 mg) were dissolved in 1 ml of DMSO and mixed with the polymer solution. Subsequently, 40 mg of EDC was added dropwise into solution and pH was kept at 5.0 to stir for 30 min. Then, the pH raised to 11 and kept for other 30 min. Finally, the pH was adjusted to 7.8-8.0 and the free drug C-4.16 were removed by dialysis bag for 4-5 h (MW 2 kDa). Then, the products obtained were lyophilized to obtain the final powder and were stored in the freezer until further use. Subsequently, the particle size and surface charge (zeta potential) measurements were performed using a Beckman Coulter Delsa NanoC-DLS Particle analyzer (Miami, FL) equipped with a 658 nm He—Ne laser. For particle size, the nanomicelles were suspended in de-ionized (DI) water, and the scattered light was detected at 165° angle. The peak average histograms were then obtained from the intensity, volume and number from 70 scans and the average diameter of the particles was calculated. The zeta potentials were evaluated by measuring the electrophoretic mobility of the charged particles under an applied electric field. For Morphology, Transmission Electron Microscopy (TEM) of the nanoparticles was evaluated using JEOL JEM-1000 instrument (JEOL Ltd, Tokyo, JP). Nanomicelles were also characterized by proton nuclear magnetic resonance spectroscopy ($^1H$ NMR) and Fourier transform infrared spectroscopy (FTIR). The structure of the synthesized SMA-TPGS and ATZ-SMA-TPGS copolymer was detected by $^1H$ NMR in D2O as previously described (https://doi.org/10.18632/oncotarget.2065). The proper synthesis of the SMA-TPGS and ATZ-SMA-TPGS co-polymers was also confirmed by the FTIR analysis, and was not found to be a physical mixture of TPGS with SMA as all measurements indicated the absence of any free crystalline particles in nanomicelles preparation.

The Drug Loading (DL) and Encapsulation efficiency (EE) of C4.16-loaded nanomicelles. The C-4.16 loading content percentage and the encapsulation efficiency (EE %) were evaluated in both nanomicelles by High-Performance Liquid Chromatography (HPLC). Samples of the C-4.16 micelles preparations were taken and the unentrapped C-4.16 was quantified using a previously published HPLC method (Cheriyan et al., *Oncotarget.* 8(62): 104928-104945, 2017). The loading efficiency of micelles was calculated by dissolving a known amount of nanomicelles directly in DMSO and further dilution of drugs with the mobile phase followed by determination of the absorbance at 309 nm (A max) with respect to the standard curve as described previously (Id.). Free drug (non-incorporated in the SMA-TPGS or ATZ-SMA-TPGS) was separated by ultrafiltration centrifugation technique. Briefly, 1 mL of CFM-4.16 and SMA-TPGS-CFM 4.16 colloidal solution were placed in the upper chamber of a centrifuge tube matched with an ultrafilter and centrifuged for 15 minutes at 4000 rpm. The total drug content in CFM-4.16 nanoformulation was determined as follows. Aliquots of 1 mL formulation dispersion were diluted appropriately by ethanol to dissolve the TPGS-SMA ingredient, and the resulting suspension was then filtrated through 0.45 μm membrane filters. The filtered solution was analyzed by Waters® Alliance e2695 HPLC using Symmetry® C18 column (250 mm×4.6 mm, 5 μm). The mobile phase was a mixture of Acetonitrile, Methanol, 10 mM KH2PO4 buffer (65:20:15 v/v) with pH adjusted to 2, and the flow rate was maintained at 1.0 mL/min. All the samples were analyzed using empower PDA software. The encapsulation efficiency (EE) and drug loading content (DLC) were then calculated by the Equations (1) and (2), above.

Expression of CAIX by A498 RCC cells and A498 RCC tumor models. RCC A498 cells were cultured in Dulbecco's modified Eagle's medium (DMEM) with GlutaMAX supplemented with 10% fetal bovine serum, 100 U/Ml penicillin, and 100 μg/Ml streptomycin. The expression of CAIX on the surface of A498 and EV-A498 cells was investigated under a normoxic or hypoxic condition 45: A498 cells were exposed to normoxia (no treatment) or hypoxia (Cobalt chloride treatment) for 72 h, followed by CAIX detection using immunofluorescence analysis or western blot 48. A498 cells were fixed with 4% cold paraformaldehyde for 15 min after incubation for 24 h under normoxic or hypoxic condition. Cells were washed three times with DPBS and blocked with 10% bovine serum albumin for 1 h at room temperature, then incubated with primary rabbit monoclonal anti-CAIX antibody (20 μg/mL) overnight at 4° C. Cells were washed three times followed by incubation with FITC-conjugated rabbit anti-mouse secondary antibody for 1 h at room temperature. A498 cells under normoxic or hypoxic condition, only treated with FITC-conjugated goat anti-mouse secondary antibody served as controls to avoid interference of cell auto-fluorescence. Nuclei were stained with Hoechst 33342 for 15 min after washing three times with DPBS. Cells were observed using a CLSM. Mice were implanted with A498 cells using the technique previously reported by Onn et al. 39. A498 cell suspensions ($1\times10^7$ cells/mL) were prepared in Matrigel Matrix (4.35 mg/mL) (BD Biosciences, San Jose, CA). The mice (7-8 weeks) were anesthetized and placed in the right lateral decubitus position. Syringes with 29-gauge needles were used to inject $1\times10^6$ cells percutaneously into the right lateral thorax, at the lateral dorsal 1 mL axillary line, 1.5 cm above the lower rib line just below the inferior border of the scapula. On day 56 after tumor cell implantation, three mice were sacrificed, and RCC tumor tissue was collected. Protein was extracted from tumor tissues using RIPA buffer with the Halt Protease and Phosphatase Inhibitor Cocktail. CAIX expression in tumor extract samples was confirmed by Western blot.

In vitro cytotoxicity assay. MTT assay was used to evaluate the anti-cancer effects of CAIX-targeted (ATZ-SMA-TPGS-C-4.16) and non-targeted (SMA-TPGS-C-4.16) nanoformulations and free anticancer drugs (C-4.16, Everolimus, and Sorafenib) in CAIX-positive (A498 RCC cells) and CAIX-negative (UOK-268 RCC cells). First, the cells were seeded in a 96-well multiwell plate at a density of $5\times10^3$ cells per well. The cells were allowed to grow in fresh culture media overnight. CAIX-positive and CAIX-negative cells were generated by parallel treatments with hypoxia and normoxia as described above. After 20 h, the medium was removed, and the wells were washed twice with PBS. The cells were then treated them with various concentrations of respective agents for the noted doses and times. Control cells were treated with 0.1% DMSO in culture medium. After treatment, an MTT assay was performed. Briefly, 20 μL of 1 mg/ml of MTT was added to each well and cells were incubated for 2-4 h at 37° C. MTT was removed, and the resulting formazan products were dissolved by adding 50 μl DMSO/well followed by colorimetric analysis using a multilabel plate reader and the absorbance was measured at 595 nm (Victor3; PerkinElmer, Wellesley, MA).

Cellular uptake of CAIX-targeted (ATZ-SMA-TPGS-C-4.16) and non-targeted (SMA-TPGS-C-4.16) nanoformulations. The cellular uptake of CAIX-targeted (ATZ-SMA-TPGS-C-4.16) and non-targeted (SMA-TPGS-C-4.16) nanoformulations after 4 h treatment was examined by CLSM. A498 cells were seeded at a density of $1\times10^5$ onto a glass bottom dish, and grown overnight followed by incubation in normoxia or hypoxia for 24 h. Thereafter, the medium was replaced with serum-free medium and the cells were incubated with Rhodamine B conjugated CAIX-targeted-nanomicelles or non-targeted nanomicelles. Cells were subsequently washed three times and fixed with 4% paraformaldehyde. The cells were washed three times with DPBS and treated with 2.5 μg/mL of Hoechst 33342 for 15 min at 37° C. to stain nuclei. Finally, the cells were washed three times with DPBS and visualized by CLSM. For the quantitative study, A498 cells were seeded in 6-well plates at a density of $7.5\times10^5$ cells per well and cultured for 24 h under normoxia or hypoxia. Different formulations of with Rhodamine B conjugated CAIX-targeted-nanomicelles were added to the plates as described above. After 4 h incubation, the cells were washed three times with cold DPBS followed by trypsin treatment, and finally resuspended in 0.5 mL DPBS. The fluorescent intensity of the treated cells was determined using F-2500/F-4500 Fluorescence Spectrophotometer Instruction Apoptosis analysis by flow cytometry and Caspase 3/7 Glo assay.

Apoptosis induction in A498 RCC cells was determined by the free and micellar formulations of CFM-4.16 by flow cytometry with Annexin V/7-AAD dual staining. The percentage of Annexin V–/7-AAD –(R5), Annexin V+/7-AAD –(R6) and Annexin V–/7-AAD+(R4) and Annexin V–/7-AAD+(R3) were obtained to determine the number of live cells, as well as early and late apoptotic, and necrotic cells.

GBM tumorspheres were dissociated into single cells and $1\times10^5$ cells were seeded per well (12-well plates) and 24 hours later treated with NAMPT inhibitors. After 96 hr incubation, cells were collected and stained with propidium iodide (PI) and APC-conjugated Annexin V (Annexin V apoptosis detection kit APC, eBioscience), and analyzed by an ACCURI™ flow cytometer and the BD CSampler software (BD Biosciences). To evaluate caspase-3/7 activities, cells were treated with DMSO or inhibitors (12.5 nM) for 24 hrs and were tested by Caspase-Glo 3/7 Assay (Promega) according to the manufacturer's recommendations.

Western Blot analysis. For protein expression analysis, western blot experiments were conducted. The RCC cells were treated with DMSO/Vehicle (Control) for the indicated doses and times of the noted compound, and were lysed to prepare protein extracts. Cells were harvested and lysed in RIPA buffer (50 mM Tris-HCl, pH 8.0, 150 mM sodium chloride, 1.0% NP-40, 0.5% sodium deoxycholate, 0.1% sodium dodecyl sulfate (SDS), and 0.1% of protease inhibitor cocktail) for 20 min at 4° C. The lysates were then centrifuged at 14,000 rpm at 4° C. for 15 min to remove debris. The protein concentrations of whole cell lysates were then determined using the Protein Assay Kit. Supernatant proteins, 50 μg from each sample, were separated by SDS-10% polyacrylamide gel electrophoresis (SDS-PAGE) and transferred to polyvinylidene difluoride (PVDF) membrane (Bio-Rad, Hercules, CA) by standard procedures. The membranes were hybridized with primary antibodies followed by incubation with appropriate secondary antibodies. The antibody-bound proteins were visualized by treatment with the chemiluminescence detection reagent (Amersham Biosciences) according to the manufacturer's instructions, followed by exposure to X-ray film (Kodak X-Omat). The same membranes were then re-probed with either the anti-β actin antibody, which was used as an internal control for protein loading.

A-498 Three-dimensional RCC tumor spheroids uptake. CAIX expression of tumor spheroids was checked by immunofluorescence. The RCC cells were obtained from xenograft tumors derived from parental cells or from the parental and Everolimus-resistant RCC cells from a two-dimensional culture plate with 70-80% confluence. The three-dimensional renal sphere cultures were performed by essentially following the methods described by in Cheriyan et al. (*Oncotarget.* 8(62): 104928-104945, 2017). Briefly, the cells were washed twice in 1× PBS and trypsinized following established protocols. The cells were then pelleted at 200×g at room temperature, and re-suspended in 5 ml of sphere media (DMEM/F12 supplemented with 2 mM L-glutamine, 100 U/ml penicillin, 100 U/ml streptomycin, 1×B27 supplement, 20 ng/ml recombinant human epidermal growth factor (EGF; Sigma), and 10 ng/ml recombinant human basic fibroblast growth factor (bFGF; R&D Systems)). 5000 viable cells were seeded per ml in an ultra-low adherent 60 mm plate and incubated at 37° C. and 5% CO2 for two weeks without disturbing the plates. After the spheres formed, fresh media was added with or without 1 μM Rhodamine B conjugated CAIX-targeted-nanomicelles. Cell incubation continued for an additional 4 h at 37° C. and 5% CO2. At the end of the incubation period, the spheroids were washed with cold DPBS and scanned began from the top to the equatorial plane to obtain the Z-stack images by CLSM for the spheres in the untreated and treated plates as described in Alsaab et al. (*Biomaterials* 183:280-294, 2018 and Example 1.

Animal: Establishment of RCC cell-derived xenografts in immunocompromised mice. The experiments involving generation of RCC cell-derived sub-cutaneous xenografts were performed according to previously published methods and protocols approved by the Institutional Laboratory Animal Care & Use Committee (IACUC). Female, 5-weeks old NCR SCID mice with Lc (Horsham, PA) were used. For efficacy studies, after a suitable period of acclimation, a suspension of $1 \times 10^6$ A498 RCC cells in 200 μl of serum-free Hank's balanced salt solution purchased from Charles River Laboratories were subcutaneously implanted in flanks of each animal using a 27-gauge needle. Tumors were allowed to grow unperturbed for 10-14 days. When tumors became palpable (200 mm$^3$), the mice were randomly assigned to treatment or control groups of five animals each. Mice were treated with Control, PBS only, ATZ-SMA-TPGS-C-4.16 NF (24 mg/kg; iv), Sorafenib (10 mg/kg/day), and with combination of ATZ-SMA-TPGS-C-4.16 plus sorafenib with iv administration for 10 days. In the case of the group of mice treated with iv administration of nanoformulations and combination, only two injections were administered where the first dose was followed by the second dose on the alternate day. The tumor weight and volume were measured daily, and mice were observed for changes in weight and side effects. The end points for assessing antitumor activity consisted of tumor weight, tumor growth inhibition (% T/C), and tumor cell kill Log10. Tumor weight (mg)=(A×B2)/2 where A and B are the tumor length and width (in mm), respectively. Tumor growth inhibition (T/C) was the median tumor weight in the treated group (T) when the median tumor weight in the control group reached 750 mg. Results were expressed as percentage. According to NCI-accepted criteria, a treatment is considered effective if T/C is <42%. Tumor growth delay (T-C) is the difference between the median time (in days) required for the treatment group tumors (T) to reach 1000 mg and the median time (days) for the control group tumors to reach the same weight. The animals were sacrificed on day 10 and tumor tissues were collected immediately after tumor volume measurement. Tumor volumes were calculated by the modified ellipsoidal formula. Tumor volume=1/2(length×width$^2$). Representative tumor samples were stored at −80° C. for subsequent analysis.

PDX animal imaging and bio-distribution of CAIX-targeted-nanoformulation. A CAIX-targeted-nanomicelles conjugated with Near-infrared dye was administered directly via iv administration to 5-weeks old NCR SCID mice and the distribution behavior in the mice was monitored at different time points after administration using an in vivo imaging system. The bio-distribution and tumor-targeting properties of CAIX-targeted-nanomicelles in Patient Derived Xenograft (PDX) animal model of Kidney cancer was investigated using a Carestream In Vivo MS FX PRO, Light Source: 400 W Xenon, Monochrome interlined, fixed lens (10x), cooled (−29 C, absolute), CCD camera (13.8×13.8 cm/2048×2048 px, 67 μmpx, 16 bit), excitation 760 nm, emission 790 nm wavelength for fluorescence, and X-ray images were captured. Both fluorescence and X-ray images of mouse was merged to demonstrate the localization of nanoparticles.

Statistical analysis. The statistical analysis was done using Prism 7.0 software (Graph Pad Software Inc., San Diego, CA). The data were expressed as mean±SEM and analyzed using a two-tailed Student t-test or one-way ANOVA followed by a post hoc test, unless specified otherwise. A p value of <0.05 was considered statistically significant.

TABLE 2

Characterization of Oligomicelles Nano-formulations

| Sample | CMC (mg/ml) | Hydrodynamic size (nm) | PDI | Zeta potential (mV) | EE (%) |
|---|---|---|---|---|---|
| ATZ-SMA-TPGS-C-4.16 | 0.021 | 179.5 ± 20 nm | 0.094 ± 0.05 | −10.21 ± 4 | 75.5 ± 12 |
| SMA-TPGS-CFM-4.16 | 0.010 | 105.2 ± 31 nm | 0.165 ± 0.07 | −7.86 ± 4 | 85 ± 9.8 |

Abbreviations:
SMA, styrene maleic acid;
TPGS, d-α-tocopheryl polyethylene glycol succinate;
ATZ, Acetazolamide;
CMC, critical micelle Rationale for choosing CA9 protein for RCC therapy. CA9 expression on the cell surface is associated with induction of tumor hypoxia through regulation of HIF1. The clinicopathological analysis have supported the fact that overexpression of CA9 in RCC is linked to poor disease prognosis and resistance to chemo and immunotherapy. Accumulated literature and clinical trial data indicate that CA9 expression is 95-99% for both primary and metastatic RCC (Tostain et al., *Eur J Cancer* 46:3141-3148, 2010), whereas it has restricted expression in normal tissues (including non-cancerous renal tissue). CA9 is significantly overexpressed in RCC cell lines and tumor (FIG. 14; see also FIG. 19). These results signify that CA9 is an excellent target for site specific delivery of therapeutic payloads to renal tumors. As reported earlier, a small molecule, acetazolamide (ATZ), has high affinity (Kd 8.3 nM) to CA9 (Bao et. al., *PLoS One* 2012;7) and can deliver the payload into the inner core (more than the periphery) of the tumor (Hashem et al., *Biomaterials Volume* 183:280-294, 2018). Along these lines, for the first time, development of an ATZ-conjugated oligomicelle library for selective delivery of drug cocktail to the hypoxic region including the tumor core of therapy resistance RCC is described. It is well established that the hypoxic tumor core harbors aggressive and drug resistant stem like cells can persist after initial drug therapy, that have the ability to invade normal tissues and metastasize to distant sites forming secondary tumors. Targeting the hypoxic core using CA9 is disclosed.

In addition to acetazolamide, other CA-ligands can include Sulfonamide and Sulfamate derivatives, such as methazolamide; ethoxzolamide; dichorophenamide; dorzolamide; brinzolamide; benzolamide; topiramate; zonisamide; sulpiride; indisulam; celecoxib; and valdecoxib.

Conjugation of ATZ and folic acid (FA): In 1952, ATZ was approved for treating low oxygen associated high altitude sickness, glaucoma, periodic paralysis, epilepsy, and heart failure (Smith & Friedman, *Headache.* 57:1303-1310, 2017). As per World Health Organization (WHO), ATZ is considered as one of the safest and most effective medicines.

However, despite several attempts there is still no approved therapy for targeting CA9 in tumors (Skapa, et al., *J. Clin. Oncol.* 26:3809-3811, 2008). Girentuximab, a CA9 targeting monoclonal antibody (mAb), entered phase-3 trial for RCC patients but the study was suspended as a single therapy (Clinical Trial Identifier: NCT00087022) due to limited efficacy. Currently, [177]Lu-Girentuximab is being investigated for radiotherapy and it has been reported to cause myelotoxicity in patients (Muselaers, et al., *Eur. Urol.* 69:767-770, 2016). To improve the toxicity and efficacy of current therapies, ATZ for targeting CA9 is used with the following advantages: (i) ATZ has selective and high binding affinity (Kd 8.3 nM) for CA9 active site and does not compete with other CA isoforms; (ii) ATZ facilitates internalization of receptors to deliver drug cargo into the cytoplasm and recycles the receptor back to the cell surface to be available for reuse; (iii) ATZ does not function as a suicide inhibitor of CA9, in contrast to compounds such as coumarin/thiocoumarin (Maresca et al., J. Med. Chem. 53:335-344, 2010). Due to all of the above favorable features, ATZ represent an excellent targeting ligand for resistant RCC therapy.

The FA-conjugated tumor imaging agent, OTL38 is in phase 3 clinical trial for RCC image guided surgery (Clinical Trial Identifier: NCT02645409). High affinity (Kd 1 nM) of FA to both FR-α/β and the ease of chemical functionalization at the γ-COOH group indicates FA is an excellent dual targeting agent. Clinicopathological analysis has indicated that the poor response of anti-VEGF therapy to advanced RCC is associated with the richness of tumor stroma (Mitsunari et al., *Oncol. Lett.* 13:834-840, 2017). The tumor stroma is composed of anti-inflammatory macrophages (TAM, M-2 subtype), fibroblasts, T-regulatory cells (Treg), and ineffective CD8+T cells (Martignoni, et al., *Mod. Pathol.* 27:765-774, 2014). To resurrect the immune surveillance immune-check point inhibitors such as Nivolumab (anti-PD1) have been approved for RCC (Xu, et al., *Oncologist.* 22:311-317, 2017). However, the response rate of Nivolumab to RCC patients is only 5% higher than Evr. Thus, an FA-ATZ oligomer platform engineered to target major components of the renal tumor environment, such as cancer epithelial cells, tumor stroma and hypoxia rich tumor regions will yield better therapeutic outcome with reduced toxicity to patients in the clinical setting.

Deep tumor penetration and hypoxia targeting ability of FA-ATZ oligomer and anti-cancer effect with drug combination: rhodamine conjugated FA-ATZ oligomer has deep tumor matrix penetration and superior uptake in A489-spheroid model. Interestingly, Z-stacking (confocal microscopy) of FA-ATZ oligomer treated cells indicate that the rhodamine-signal is significantly higher in the core of the spheroid than the periphery. This is a clear indication that oligomicelles (OM) penetrate deep into the tumor spheroid and reach the hypoxic regions very effectively in tumor.

Encapsulation of C4.16 in polymer/lipid micelles and conjugating them with FA-ATZ oligomer, namely FA-ATZ-C4.16 oligomicelles (OMs) provides a functional approach for resolving the challenges to deliver them selectively to resistant RCC. RTK-mTOR axis: As RCC is highly vascularized, the use of drugs to inhibit RTK, such as MET, AXL and VEGFR signaling are used as first-line therapies. Clinically, CB (FDA approved, 2015), a frontline therapy to inhibit RTK activity of RCC, showed significant progression free survival (>36 months) than other RTKIs, Sorafenib (12 months), Axitinib (20 months) and anti-PD-1 (program cell death-1) inhibitor, Nivolumab (32 months) (Alsaab et al., *Front. Pharmacol.*, 2017, doi.org/10.3389/ fphar.2017.00561). Alongside, mTOR inhibitors, such as Evr and Temsirolimus were approved as second-line single agent therapy. All these kinase inhibitors are poorly water soluble, only orally available, and approved for single therapy. Thus, these tumors eventually become resistant to RTK/mTOR inhibitors and require newer therapies to overcome resistance. The nanoformulation of the inhibitors will be a worthwhile strategy to provide multiple benefits such as (i) amenable for i.v. injection leading to lowering of drug dose; (ii) higher stability and bioavailability; (iii) sustain drug release and reduced toxicity. Literature reports and clinical experience have revealed that inhibiting RCC proliferation with polypharmacy specific to different targets is superior to monotherapy approaches. However, such approaches tend to produce severe on-target and off-target toxicities. To achieve the maximum therapeutic benefits and reduce the toxicity, cabozantinib (CB) is encapsulated in polymer/lipid micelles and which are conjugated with FA-ATZ oligomer to arrive at FA-ATZ-CB oligomicelles (OMs). This i.v. administrable FA-ATZ-C4.16 and FA-ATZ-CB OM combination is an excellent approach to precisely target the convergent pathways of RCC activity with resistant and tumor stroma features.

RCC PDX tumor specific uptake and bio-distribution of CA9 oligomers. Clinically small molecule NIR imaging agents have excellent ability to distinguish the tumor lesion from healthy tissue in imaging guided surgery (Clinical Trial Identifiers: NCT02317705, NCT01778933) (Zhang et al., *Nat Rev Clin Oncol* 14:347-64, 2017). To demonstrate CA9 and FR targeting ability, FA-ATZ small molecule fragment (compound b, scheme 2, FIG. 23) was conjugated with S0456 NIR dye (namely FA-ATZ-S0456) to use it for tumor imaging and bio-distribution. The reason for choosing the FA-ATZ-S0456 small molecule fragment is that they will excrete out of the body faster, thus reducing non-specific toxicity. S0456 is clinically approved dye (Clinical Trial Identifier: NCT02317705) with signature features such as ease of chemical functionalization, high photo stability, cost effectiveness, and high stoke shift (Wang et. al., *Nanomedicine: Nanotechnology, Biology and Medicine* 14(4): 1441-1454, 2018).

In vivo, CAIX-targeted-PLNPs via intravenous delivery showed specificity and a sustained release property, both of which improved the efficiency of CFM formulations in restraining tumor growth and significantly the results suggest that CAIX-targeted nanoparticles can be used as an effective therapeutic strategy for RCC.

The results of efficacy and bio-distribution of targeted PLNPs in animals bearing RCC xenografts and PDX model showed higher accumulation of drugs at tumor sites with higher tumor growth inhibition. Also, the targeted formulation showed high binding affinity and specific tumor uptake, faster normal tissue clearance, and less non-target organ uptake. These findings portent promising therapeutic potential of hypoxia-targeted-PLNPs for treating RCCs.

Example III

Copper Free Click Chemistry Utilized Dual Folate Receptor (FR-α/β) and Carbonic Anhydrase-9 (CA9) Receptor Targeting Nanoparticle and Small Molecule Library for Combination Therapy and Fluorescence Image Guided Surgery of Cancer This Example provides a tumor penetrating and tumor multicomponent targeting library of nanosized oligomicelles (OMs) of spherical and non-spherical geometry, with tunable surface properties. This strategy can overcome the delivery barriers and reach tumor tissues and the tumor core effectively, as well as interrogate tumor hypoxia, tumor associated immune cells, and cancer epithelial cells. The OMs are further engineered to deliver combination drug cocktail to shut down vital tumorigenic signaling. Folate Receptor α and β (FR-α/β) is a leading factor for macrophage infiltration, cell metabolism and DNA synthesis in a rapidly proliferating tumor environment (Shen et al., *Oncotarget.* 6:14700-14709, 2015; Puig-Kröger et al., *Cancer Res.* 69:9395-9403, 2009). Several clinical trials are being investigated for targeting FR ("Farletuzumab (MORAb-003)" is in phase 3 for solid tumor therapy; Clinical Trial Identifier: NCT00849667) (Fisher et al., *J. Nucl. Med.* 49:899-906, 2008). The combination OM strategy overcomes the drug resistance by targeting hypoxia and reprogramming pro-oncogenic tumor associated macrophages (TAM) in the RCC tumor environment.

CA9 expression on the cell surface is associated with the induction of tumor hypoxia through regulation of HIF1a. The clinicopathological analysis has supported the fact that overexpression of CA9 in RCC is linked to poor disease prognosis and resistance to therapy. The accumulated literature and clinical trial data indicate that CA9 expression is 95-99% for both primary and metastatic RCC (Tostain et al., *Eur. J. Cancer.* 46:3141-3148, 2010; Uemura et al., *Clin. Cancer Res.* 12:1768-1775, 2006), whereas it has restricted expression in healthy tissues (including non-cancerous renal tissue). CA9 is significantly overexpressed in RCC tumors section (FIG. 9A) and cell lysates (FIG. 9B) as obtained from western blot analysis. These results signify that CA9 is an excellent target for site specific delivery of therapeutic payloads to renal tumors (Soyupak et al., *Urol. Int.* 74:68-73, 2005). As reported earlier, a small molecule, ATZ, has high affinity (Kd 8.3 nM) to CA9 (Bao et al., *PLoS One.* 7, 2012 doi:10.1371/journal.pone.0050860) and it can deliver the payload into the inner core (more than the periphery) of the tumor (Dal Corso & Neri, *J. Control. Release.* 246:39-45, 2017; Lv et al., *Mol. Pharm.* 13:1618-1625, 2016). Along these lines, for the first time, development of an ATZ-conjugated OM library for the selective delivery of a drug cocktail to the hypoxic region of therapy resistant RCC was proposed. It is well established that the hypoxic tumor (core) harbors aggressive and drug resistant stem-like cells that can persist after initial drug therapy and have the ability to invade normal tissues and metastasize to distant sites forming secondary tumors.

FRα and β: Overexpression of FR has a diverse role in folate management for DNA synthesis in rapidly dividing cancer cells (O'Shannessy et al., *Oncotarget.* 2:1227-1243, 2011). Among the four isoforms of the FR-family (FR-α, β, γ, δ), FRα has been extensively explored in the clinical arena for targeted therapy and imaging of various solid tumors including renal cell carcinoma (Clinical Trial Identifier: NCT01689662) (Fisher et al., *J. Nucl. Med.* 49:899-906, 2008). In contrast, the less recognized FRβ isoform has a pronounced role in tumor stroma formation, as well as tumor associated macrophage (TAM) maturation and infiltration in various tumors including RCC (Shen et al., *Oncotarget.* 6:14700-14709, 2015). The histology of patient tumor sections indicated that FRβ is 90% positive in kidney tumor stroma samples (Shen et al., *Oncotarget.* 6:14700-14709, 2015). Both FRα and FRβ isoforms have high affinity (Kd 1 nM) to FA (O'Shannessy et al., *Oncotarget.* 2:1227-1243, 2011). Thus, use of FA is an excellent approach for targeting the multi-components of renal cancer, such as tumor epithelial cells and tumor stroma. To achieve this, linkage of FA with the ATZ-conjugated oligomers (called as FA-ATZ) is proposed so that the whole construct can deliver the cytotoxic payload to hypoxia, epithelial and stromal components of the tumor milieu.

Strategy to Deliver C4.16 and Multi-Kinase Inhibitor Combination Payload:

Encapsulation of C4.16 in polymer/lipid micelles and conjugating them with the FA-ATZ oligomer, namely FA-ATZ-C4.16 OMs provides a functional approach to deliver drugs selectively to resistant RCC. See also Example 2.

The disclosed nanoformulations of RCC inhibitors provide a strategy to provide multiple benefits such as (i) amenability for i.v. injection leading to lowering of drug dose and better suited for metastatic RCCs; (ii) higher stability and bioavailability; (iii) sustained drug release and reduced toxicity. Literature reports and clinical experience have revealed that inhibiting RCC proliferation with polypharmacy specific to different targets is superior to monotherapy approaches (Hsieh et al., *Semin. Cell Dev. Biol. doi:*10.1016/j.semcdb.2016.09.002, 2016).

Combination delivery of multi-kinase inhibitor Sorafenib or Cabozantinib (CB) and C4.16. CB will be used in combination with the potent apoptosis inducer, C4.16 (Gibney et al., *Ann. Oncol.* 24:343-349, 2013; Rivet et al., *Cancer.* 112:433-442, 2008). First, the two agents will be encapsulated into polymer/lipid micelles followed by conjugation of the micelles with FA-ATZ-oligomers to arrive at FA-ATZ-C4.16 and FA-ATZ-CB OMs respectively. In order to selectively deliver the payload in tumor environment as well as to penetrate the tumor tissue, various sizes, shapes and compositions will be developed based on the OM-library. For simplicity, the conjugation of FA-ATZ oligomers onto the drug carrier will be achieved through copper free 'click' reaction (FIG. 20). The synthesis of OMs can be divided into two parts, (I) $N_3$-terminal oligomer component: synthesis of cholesterol (Chol) attached, variable cancer cell stimuli-responsive linkers containing FA-ATZ with azide ($N_3$) terminal group; (II) preparation of dibenzocyclooctyne (DBCO) containing various biocompatible micelle forming lipids, and polymer encapsulated either with CB or C4.16.

One of the major clinical limitation of nanoparticles (NPs) is that they have tendency to accumulate in the liver and spleen upon systemic administration. Thus, the use of anti-fouling agents such as PEGn (n=2-40) (Ernsting et al., *J. Control. Release.* 206:122-130, 2015), zwitterionic (Natrajan et al., *Org. Biomol. Chem.* 10:1883, 2012) and saccharopeptides (Leamon et al., *J. Pharmacol. Exp. Ther.* 336:336-343, 2011) that will help the OMs to avoid undesirable hepatic and splenic uptake and maintain sustained drug accumulation in the tumor will be used. To specifically effect sequential release of ligand and payload in the tumor microenvironment, functionally variable cancer cell stimuli-responsive linkers, such as valine-citrulline (val-cit) (Fujiwara et al., *Sci. Rep.* 6:24954, 2016); Polyethylene glycol unit 2-30 (PEG2-40); rigid cyclic hexyl, pentyl groups; non-rigid alkyl groups; dithiol (S—S); alpha-dialky substituted [(R1R2HC—S—S—), R1 or R2 are alkyl groups)] (Wayua et al., *Mol. Pharm.* 12:2477-2483, 2015); Zwitterionic and thiol-maleimide will be employed for synthesizing FA-ATZ oligomers. The purpose of using thiol-maleimide linker chemistry is to ensure OMs stability in plasma during circulation (FDA approved "Kadcyla®" has high stability due to presence of thiol-maleimide linker). Use of alkyl chain will not only improve the self-assembly but also provide rotational flexibility (C—C bond) of the targeting ligand to efficiently interact with the receptors. In tumor cell cytoplasm the "val-cit" linkers will be cleaved due to abundance of cathepsin b, thereby releasing the cargo. (—CMe2-S—S—) will be used instead of (S—S) because of enhanced stability offered by the former linker to OMs from plasma associated glutathione and selective cleavage in reducing tumor cell cytoplasm. The use of saccharo-peptidic linkers in phase 1 trial (Clinical Trial Identifier: NCT03011320) EC1456 have shown low liver toxicity (Leamon et al., *J. Pharmacol. Exp. Ther.* 336:336-343, 2011). The presence of α-dimethyl group in (—CMe2-S—S—) increases steric hindrance thereby rendering these linkers more stable in plasma than unmethylated S—S versions (Vlahov & Leamon, *Bioconjug. Chem.* 23:1357-1369, 2012). To enhance the loading efficiency and stability of micelles, "Chol" will be employed as a common counterpart in all FA-ATZ-$N_3$ oligomers. On the other hand, micelle forming DBCO-linked lipid or polymer will be synthesized and they will be used to encapsulate either C4.16 or CB. Finally, FA-ATZ-$N_3$ oligomers will be coupled with drug encapsulated DBCO-micelles using strained promoted 'click' chemistry to arrive at FA-ATZ-C4.16 and FA-ATZ-CB OMs respectively (FIG. 20).

Engineering shape and size of OMs to avoid non-specific organ uptake and stepwise disintegration of OMs to enhance tumor extravasation, cellular internalization and immune cell infiltration: To penetrate the stroma, unique surface decorated nanosized OMs will be developed. The use of small molecular size PEG 6, 10, 20 linked Chol in FA-ATZ oligomers will help produce smaller diameter NPs, than the traditional amphiphilic block copolymers (Yu et al., *J. Pharm. Sci.* 102:1054-1062, 2013). To develop a library of formulations, DBCO-conjugated vitamin E TPGS, TPGS-styrene maleic anhydride (TPGS-SMA6-8), 2-hydroxypropyl-β-cyclodextrin (HP-β-CD) and sulfobutylether β-cyclodextrin (SBE-β-CD), phosphatidyl-ethanolamine (PC) and ceramide will be synthesized. Finally, DBCO micelles will be coupled with $N_3$-FA-ATZ. A wide variety of drug encapsulated polymers and lipids will not only increase the drug loading efficiency but also generate varied dimension of OMs. In vitro and in vivo testing of drug loaded OM library will provide a clear idea of synergistic therapeutic efficacy, immune modulation and reversal of drug resistance. All the proposed polymers and lipids are either in phase clinical trials or FDA approved. For example, cyclodextrin-polyethylene glycol NP (CRLX101) is being investigated in a phase-2 trial for treating solid tumors (Clinical Trial Identifier: NCT02769962) (Weiss et al., *Invest. New Drugs.* 31:986-1000, 2013). In spherical and non-spherical OMs (FIG. 20), dual stimuli-responsive linkers, such as (i) "succinic ester" linked with Chol, (ii) "α-dimethylated dithiol (S—S)" or "val-cit" linked with micelles part have been meticulously introduced. The extracellular tumor environment is highly abundant with carboxylesterase (Tobin et al., *Br. J. Clin. Pharmacol.* 62:122-129, 2006; Hatfield et al., *Expert Opin. Drug Metab. Toxicol.* 4:1153-1165, 2008). Thus, after in vivo administration of OMs, Chol will disintegrate from the OM and sequentially produce further smaller sized micelles. This will facilitate deep tumor penetration and enhance vascular extravasation through natural tropism. Following that, FA and ATZ will guide the fragmented NP for endocytosis to the cancer cells and macrophages. On internalization, the selective cleavage of S—S by glutathione or val-cit by cathepsin B into the cytoplasm will result in release of the drug cargo. Thus, the dual stimuli-responsive OMs will follow adaptive alterations of physicochemical properties (e.g. size, shape and drug release) in accordance with the extracellular and intracellular stimuli of the tumor cells (Li et al., *Proc. Natl. Acad. Sci.* 113:4164-4169, 2016). This strategy helps to overcome the bottleneck of tumor stromal barriers in RCC.

Interaction of spherical NPs with cells and tumor has received considerable attention, but the effects of shape of the NPs with tumor accumulation have received little attention. Spherical NPs are more vulnerable to be attacked by reticuloendothelial system (RES) of liver and spleen. Literature reports indicate that worm-like or rod-shaped micelles can avoid RES mediated liver/spleen uptake and selectively accumulate in tumor with sustained drug release (Geng et al., *Nat. Nanotechnol.* 2:249-255, 2007). A representative TEM images of spherical and rod-shaped OMs are shown in FIG. 21A, 21B. The data revealed that size of spherical OM was in the range of 30-70 nm and length of rod-shaped OM was in the range of 100-200 nm. The rod-shaped dual tumor hypoxia (CA9) and cancer stem cell (CSC) targeting OMs can predominantly accumulate within the tumor core compared to tumor periphery of various PDx tumor models (FIG. 22A-22E).

The non-spherical micelles of FA-ATZ-C4.16 and FA-ATZ-CB will be further developed by using solvent evaporation, precipitation and sonication method in presence of amphiphilic block copolymers, such as Pluronic® F127, PLA-PEG-PLA (Wang et al., *Mol. Pharm.* 11:3766-3771, 2014). Thus, non-spherical dual CA9 and FRα/β targeting OMs reduce non-specific organ uptake and enhance RCC selective accumulation. In oligomer synthesis, a zwitterionic linker can act as an antifouling agent can be used, thus OMs will enhance plasma circulation and stability by reducing non-specific protein adsorption (Jackson et al., *ACS Nano.* 11:5680-5696, 2017). The use of ceramide and PC will contribute to negative zeta potential, thus increasing receptor mediated tumor delivery. Also, presence of amide bond in ceramide will increase the stability and plasma circulation of OMs than the ester bond containing PC (Thuy et al., *Pharmaceutics.* 9:15, 2017).

Various tumor cell stimuli-responsive linkers containing OM library of FA-ATZ-C4.16 and FA-ATZ-CB will be synthesized using copper-free 'click' chemistry. The OM library compounds will be tested for physico-chemical characteristics, evaluated for synergistic cytotoxicity and mechanistic pathway kinase signaling, and interrogated for the role of M2-macrophages in immune-evasion using VVT and the drug resistant RCC. After evaluating the in vitro drug delivery efficiency and the molecular mechanistic pathway, in vivo anti-tumor efficacy and imaging studies with selected "hits" in RCC cells inoculated s.c., orthotopic kidney tumors and PDx models will be conducted. For this purpose, the in vivo efficacy of single and combination drug therapies, survival and preliminary safety studies will be evaluated.

Copper free 'click' chemistry-based synthesis of stepwise disintegrating OM library with dual CA9 and FR-α/β targeting ligand to deliver combination drug payload. Variable tumor cell stimuli-responsive linker containing FA-ATZ oligomers with terminal $N_3$ group will be synthesized. As illustrated in FIG. 23, ATZ-$NH_2$ will be synthesized from ATZ by acid hydrolysis; then it will be functionalized with the —COOH group of Fmoc protected 6-aminohexanoic acid, and finally it will be coupled with a protected form of lysine to finally arrive at ATZ-C6-lysine (compound a). On the other hand, γ-COOH of FA will be reacted with ATZ-C6-lysine (compound a) in the presence of EDC, and sulpho-NHS (Sahu et al., *J. Control. Release.* 253:122-136, 2017) will yield dual CA9 and FR-α/β targeting ligand (FIG. 23, compound b, scheme 2). In FIG. 23, scheme 3, Chol will be reacted to succinic anhydride; then the —COOH group of Chol-succinate will be coupled with the —$NH_2$ group of 6-azido-lysine, namely "Chol-lysine". This compound will be conjugated with various tumor cell stimuli-responsive linkers to arrive at the $N_3$-functionalized compound c (FIG. 23). Finally, compounds b and c will be coupled to arrive at the FA-ATZ-N3 oligomer. (ii) Synthesis of DBCO-modified polymer/lipid and encapsulation of C4.16 and CB in it. DBCO-NHS Ester will be used to couple with vitamin E TPGS, cyclodextrin, phosphatidylethanolamine and ceramide. All compounds will be characterized by $^1$H-NMR, $^{13}$C-NMR and elemental analysis to ensure chemical identity and purity. This will be tested with analytical HPLC. FIG. 23 reactions will be carried forward in DMSO and DMF solvents. Thus, instead of silica-gel chromatography, other purification methods, such as (i) single and/or double precipitation using bi-mixture organic solvents [petroleum ether/methyl-t-butyl ether (MTBE), ACN/MTBE, methanol/diethyl ether]; (ii) ion exchanged DEAE cellulose chromatography (Whatman® DE52); and (iii) RP preparative HPLC can be used. This DBCO-linked lipid or polymer will be loaded either with water insoluble C4.16 or CB to produce DBCO-C4.16 micelles and DBCO-CB micelles. The micelles will be prepared with different methods, such as solvent evaporation and oil/water emulsion to formulate spherical micelles with cyclodextrins, TPGS, TPGS-SMA, phospholipid (Cheriyan et al., *Oncotarget.* 8:104928-104945, 2017; Sahu et al., *J. Control. Release.* 253:122-136, 2017; Luong et al., *Colloids Surfaces B Biointerfaces.* 157:490-502, 2017). In contrast, for making non-spherical micelles, co-solvent evaporation, vortex and brief sonication of TPGS and SMA-TPGS polymers in the presence of amphiphilic block copolymers, such as PLA-PEG-PLA, Pluronic® F127 will be used (Hatfield et al., *Expert Opin. Drug Metab. Toxicol.* 4:1153-1165, 2008). Finally, various sizes and shapes of DBCO-C4.16 or DBCO-CB micelles will be coupled with N3-FA-ATZ oligomers using a copper free 'click' reaction to get a library of FA-ATZ-C4.16 and FA-ATZ-CB OMs.

For the synthesis of FA-ATZ-S0456, stable linkers, such as PEGn (n=2-40), zwitterionic and saccharo-peptidic will be introduced in between compound b (scheme 2 of FIG. 23) and S0456. These linkers will help to avoid liver metabolism and excrete through the kidney route (De Jesus et al., *Int. J. Mol. Imaging.* 2015:1-10, 2015).

Linker synthesis: All the linkers have been designed with one end containing the —NH2 group and other end containing the —COOH, so that they can easily be conjugated with Chol-lysine-$N_3$ and compound b. In general linkers will be synthesized by EDC/NHS, PyBOP/DIPEA chemistry with Boc and Fmoc-protected precursors. The Zwitterionic linker will be synthesized with Boc and Fmoc-protected N, N-Bis(3-aminopropyl) methylamine followed by alkylation with 1,3-propane sultone at the tertiary amine. Then selective deprotection of Boc and coupling with succinic acid will get —$NH_2$ and —COOH terminal zwitterionic linkers (Natrajan et al., *Org. Biomol. Chem.* 9:5092, 2011). Other linkers, such as Saccharo-peptide, α-dimethylated dithiol, will be custom synthesized from Creative Biolabs (Shirley, NY).

Characterization and screening of OMs: The synthesized OMs will be analyzed for the particle size, zeta potential and polydispersity index using a more accurate tRPS platform qNanosystem (Izon Science, Cambridge, MA) (Song et al., *Stem Cells.* 35:1208-1221, 2017) and the standard Zeta-sizer instrument (Malvern, USA). Drug loading (w/w), encapsulation efficiency will be determined by HPLC and UV-method. High drug loading up to 30% (w/w of drug) has been achieved (Kesharwani et al., *Biomacromolecules.* 16:3042-3053, 2015; Yang et al., *Sci. Rep.* 5:8509, 2015). Thus, high drug loaded FA-ATZ-C4.16 and FA-ATZ-CB OMs will be generated. The amount of FA and ATZ present in selected OMs will be quantified by the HPLC gradient method. The morphology of spherical and non-spherical OMs will be analyzed by TEM, and the size distribution of the particles will be evaluated by atomic force microscopy (AFM). Formulations with optimal parameters in terms of size, shape, surface charge, and drug loading will be carried forward for subsequent in vitro and in vivo evaluation. To evaluate the tumor cell specific release of the payload, a release study of self-immolative linkers conjugated OMs in presence of higher equivalent of specific enzymes at room temperature at 37° C. will be performed. Release of FA-ATZ fragments will be detected by LC-MS and HPLC.

The cell killing effect, reversal of drug resistance and macrophage modulation of dual tumor hypoxia and stroma targeting OMs containing combination drugs will be demonstrated. C4.16 is more potent than Evr, Sorafenib and CB in WT and Evr-res RCC cells, as well as the xenograft tumor model (Cheriyan et al., *Oncotarget.* 8:104928-104945, 2017).

Authenticated RCC cell lines such as WT (A498, UOK262), Evr-res (A498, UOK262), Caki-1, ACHN will be utilized as RCC cells, as well as Raw 264.7 (macrophage), and freshly isolated PBMCs from human blood for macrophage phenotyping studies. Based on the previous literature and metastatic in nature, Caki-1 and ACHN cells will be used for understanding the interaction of macrophages with cancer cells (Komohara et al., *Cancer Sci.* 102:1424-1431, 2011; Brodaczewska et al., *Mol. Cancer.* 15:83, 2016). The following will be established (i) a synergistic anticancer effect, (ii) the role of M2-macrophages in tumor immune evasion, and (iii) the mechanism of inhibiting tumorigenic cross-talk between RCC epithelial cells and M2-macrophages using OMs (FIG. 30A-30E). The tumor environment mimetic advance spheroid and transwell cell culture models will be used to establish efficacy.

Cell line development and culturing conditions: WT RCC and human umbilical vein endothelial (HUVEC) cells will be purchased from ATCC (Bethesda, MD). Drug resistant RCC cells, including Evr-res A498 and Evr-res UOK262 have been developed and validated. For inducing hypoxia, cells will be treated with 200 µM Cobalt Chloride in normal growth media at 72 h prior to experiment (Piret et al., *Ann N Y Acad Sci.* 973:443-447, 2002). The cells will be grown in 10% FBS, 100 units/ml of penicillin, and 100 µg/ml of streptomycin, and the cells will be kept at 37° C./5% CO2. HUVEC cells will be cultured in an EGM-Plus growth media (Lonza, MD, USA). RCC 3D-spheroid cultures will be grown in low density with 2% FBS containing culture media. An in vitro co-culture system with macrophage cells (upper chamber) in the presence of Caki-1, or ACHN cells (Komohara et al., *Cancer Sci.* 102:1424-1431, 2011) (lower chamber) will be used using a 0.4 um microporous membrane transwell plate (Corning, NY) (Zanganeh et al., *Nat. Nanotechnol.* 11:986-994, 2016). Peripheral blood mononuclear cell (PBMC) will be freshly isolated from human blood using FICOLL-PAQUE® (GE Healthcare, PA) by stepwise centrifugation with brakes (as per standard protocol). Then the PBMC will be incubated with human CD14 microbeads (Miltenyi Biotec, CA) to isolate the monocytes from the lymphocyte mixture. To generate human macrophages, isolated CD14+ monocytes will be cultured in complete growth media either with 10 ng/ml GM-CSF to polarize M1-macrophage or 50 ng/ml M-CSF to differentiate M2-macrophage for 7 days (Ball et al., *PLOS One.* 11, doi:10.1371/journal.pone.0149600, 2016).

The cell killing effect (MTT assay, and Promega's Live-Dead® assay) of FA-ATZ-C4.16 and FA-ATZ-CB as a single agent or in combination in WT, Evr-res RCC cells at a dose of 10-0.1 µM for 24-72 h will be screened. Treatment with cell culture media will be used as a negative control (0% cell death), 100 µg/mL 100 kDa poly(ethyleneimine) will be used as a positive control (100% cell death). A cell killing study of C4.16 in combination with either of CB or Sorafenib in WT and Evr-res A498 cell line was performed. The data show that C4.16+CB induced highest synergistic cell killing outcome in Evr-res A498 cell FIG. 15F). Thus, it builds the rationale of using combination of FA-ATZ-C4.16 and FA-ATZ-CB for overcoming drug resistance and synergistic tumor growth inhibition. The synergism will be further demonstrated with isobologram analysis (Sau et al., *Mol. Cell. Biochem.:* 1-18, 2017) and tested with factorial analysis of variance. Once the optimal dose of (FA-ATZ-C4.16+FA-ATZ-CB) treatment with lowest CI value is obtained, the combination OM in a Evr-res 3D-spheroid culture model will be challenged, and the reduction of spheroid volume quantified. This data will validate that the combination OM is efficient to disrupt the tumor stroma leading to better tumor inhibition compared to single agent. To evaluate the mechanism of cell killing, the increase of cell apoptosis (using Annexin V/PI and Histone DNA ELISA assays) in WT and Evr-res cells treated with combination OM compared with controls will be quantified (Sau et al., *Mol. Cell. Biochem.,* 43(1-2):119-136, 2017).

Mechanism underlying the reversal of drug resistance: Evr-res is a clinically observed phenomenon in renal tumor patients. Thus, the Evr-res cells and tumor will be challenged with OM combination treatment to evaluate the signaling pathway for overcoming the resistance. Significant research on C4.16 has demonstrated that it activates the CARP-1 protein, upregulates cleaved caspase 8 (C-Cas 8), cleaved PARP (C-PARP) and down-regulates total AKT (T-AKT), pAKT, cyclin B1 in WT, Evr-res A498 cell lines, resulting in the induction of apoptosis and reversal of drug resistance (FIG. 8) (Cheriyan et al., *Oncotarget.* 8:104928-104945, 2017). CB is an inhibitor of multi-tyrosine kinases including MET, VEGFRs, and AXL (Yakes et al., *Mol. Cancer Ther.* 10:2298-2308, 2011). The upregulation of MET and AXL produces HIF-1α mediated drug resistance, consequently causing a poor prognosis in RCC. The activation of MET is associated with recruitment of hepatocyte growth factor (HGF) to cancer cells from tumor stroma (Finisguerra et al., Oncogene. 35:5457-5467, 2016). Thus, western blot analysis of FA-ATZ-C4.16 and FA-ATZ-CB treated cell protein lysates in WT and Evr-res RCC cells will be performed to elucidate the down-regulation of MET, AXL kinase and their downstream signaling, such as Growth factor receptor-bound protein 2 (Grb-2) and PI3K/AKT. The HGF in OM-treated cell culture media will be quantified by enzyme linked immunosorbent assay (ELISA). As the CB is a VEGFR inhibitor, the VEGFR down-regulation will be evaluated in HUVEC cell line. This mechanistic study will establish the underlying reason for synergistic cell killing as well as overcoming drug resistance and deciphering tumor hypoxia in OM treated WT and drug resistant counterparts.

Effect of combination therapy to reprogram macrophages. It is reported that systemically administered NP are internalized by TAMs. Thus, use of FR-α/β (FA-ATZ-C4.16+FA-ATZ-CB) for targeted therapy will enhance tumor stroma penetration by several folds, resulting in significant destabilization of the immune-suppressive tumor environment. To evaluate the hypothesis that the downmodulation of M2-macrophages can induce the antitumor effect, the Raw264.7 cell line will be co-cultured with Caki-1, and ACHN in a 0.4 µm pore size transwell plate and the cells will be treated with the OM combination. To evaluate the resurrection of apoptosis in metastatic RCC cells, the lower part of the transwell plate will be stained with pro-apoptotic markers such as FITC-conjugated cleaved Caspase 3, Caspase 8 and PARP for visualization under a fluorescence microscope. To further determine whether (FA-ATZ-C4.16+FA-ATZ-CB) treatment can increase the M1 macrophage population and decrease M2 macrophages, human PBMC derived M1/M2-macrophages (as described above) will be co-cultured with ACHN/Caki-1 cells in the transwell system. After 24-48 h of treatment, mRNA of M1/M2 will be isolated, and their distinct markers will be quantified by real-time polymerase chain reaction (RT-PCR) (Ball et al., *PLoS One.* 11, doi:10.1371/journal.pone.0149600. 2016). Based on the literature, iNOS, TNFα, IL-12p40, CD86 (for M1 markers) and Arginase I, CD206, IL-10 (for M2 markers) will be quantified. This macrophage phenotyping analysis will provide a clear idea whether FRβ targeting OMs can suppress tumorigenic M2 function and redirect tumoricidal M1 to trigger the immune surveillance and lead to better killing and reversal of drug resistance. To find the direct role of macrophages in drug resistance to cancer cells, MET, AXL, VEGFR, GrB-2, AKT, p-AKT and HIF-1α protein expression in RCC cell lysates isolated from an M1/M2 co-cultured transwell flask treated with Oms will be investigated. All these data will validate the hypothesis that targeting tumor hypoxia, epithelial cells and stroma is a worthwhile approach to reverse the drug resistance of RCC through the resurrection of apoptosis, the inhibition of oncogenic signaling, and the reeducation of immune cells.

Development of tumor models: To further confirm the anti-tumor efficacy of the FA-ATZ-C4.16 and FA-ATZ-CB combination, three models will be used. S.c. nu/nu xenograft model: for preliminary screening and to evaluate reversal of drug resistance, inoculation will be: s.c. Evr-res A498 cell line with $10^5$ cells/mouse. Orthotopic RCC model: 30,000 luciferase-transfected Evr-res A498 cells with Matrigel (1:1) will be injected within the subrenal capsule in one side of the kidney of CD34+ humanized NOD-SCID gamma (Hu NSG) mouse and bioluminescence imaging (BLI) will be performed every 3-4 days after tumor engraftment to monitor tumor growth (Chang et al., *Mol. Cancer.* 14:119, 201). The most advanced CD34+ Hu NSG mice have several advantages compared to nu/nu or NOD-SCID gamma, such as robust T-cells, B-cells, macrophages, and other immune cell function, and they can recapitulate human tumors (Morton et al., *Cancer Res.* 76:6153-6158, 2016). Hu NSG mice are the best immuno-oncology platform for efficacy testing of novel immunotherapies targeting macrophages and T cells (Chang et al., *Mol. Cancer.* 14:119, 201). PDx model: a TM00387 metastatic RCC PDx model that grows in NOD-SCID mice will be used. TM00387 will be grown s.c. and the tumors will be established by trocaring tumor fragments according to standard methods (Guastella et al., *Mol. Imaging.* 15, pii:1536012116644881, 2016). In addition, there is access to lung and breast PDx models.

Maximum tolerated dose (MTD) analysis and experimental design: Healthy non-tumor mice will be used to establish the MTD of the combination OMs. The MTD of C4.16 is 30 mg/kg (Cheriyan et al., *Oncotarget.* 8:104928-104945, 2017; Cheriyan et al., *Oncotarget.* 2:73370-73388, 2016), thus the tolerance study will be initiated with 30 mg/kg for FA-ATZ-C4.16. It is reported that CB is well tolerated with 60 mg/kg dose (Yakes et al., *Mol. Cancer Ther.* 10:2298-2308, 2011). Thus, the starting dose of FA-ATZ-CB will be 60 mg/kg. In this dose de-escalation study, the MTD of the combination OMs with 4 cohorts of 5 mice each will be identified. The dose-limiting toxicity (DLT) is weight loss ≥10%. The study will begin at dose 30 mg/kg for FA-ATZ-C4.16 and 60 mg/kg for FA-ATZ-CB. If there are any DLTs, the level of FA-ATZ-C4.16 will be reduced to 25 mg/kg and another cohort evaluated. If there are any DLT in this cohort, then FA-ATZ-CB will be reduced by 20%.

Experimental design: Once the orthotopic RCC tumors are developed and s.c. tumor mass reaches a volume of 50 mm$^3$, the animals will be randomly assigned to test groups.

(a) Imaging to s.c. PDx and RCC orthotopic model: The dose FA-ATZ-S0456 fragment will be tested at 10 nmole/animal based on prior results obtained for NIR imaging and targeting to PDX tumor. Tumor hypoxia targeting OMs can efficiently penetrate deep into the tumor tissue and reach the tumor core and periphery in triple negative breast and non-small cell lung PDx model, and that they follow receptor competition. While the passively delivered non-targeted NP fails to reach deep into the tumor tissue and rather accumulate mostly at the tumor periphery (FIG. 22A-22D). Another limitation of conventional NPs is the non-specific liver and spleen uptake that the disclosure resolves using hypoxia targeting OMs. This supportive in vivo data opens a new paradigm for using hypoxia and tumor stroma targeting FA-ATZ-S0456 as a potent candidate for tumor imaging of RCC, harboring drug resistant and metastatic features. A preclinical optical imager (Bruker In-vivo Xtreme II, Bellirica, MA, USA) will be used for live mice NIR imaging at 1, 4, 12, 24, 48, 72 h of single post i.v. dose, based on prior experience and published literature (Lv et al., *Mol. Pharm.* 13:1618-1625, 2016). The following groups will be used. Group 1: targeted FA-ATZ-50456; group 2: non-targeted S0456 (NT) dye; group 3: competition studies for targeting FA-ATZ-50456 (pre-injection of 100-fold excess targeting ligand followed by injection of targeted NIR dye). This data will determine the tumor selective localization of FA-ATZ-50456 compared to NT dye. The competition study will support the receptor mediated tumor penetration of FA-ATZ-S0456. The bio-distribution analysis will be performed at the end of the experiment to evaluate whether the tumor vs. liver and tumor vs. blood uptake of NIR dye is higher in FA-ATZ-50456 treatment compared to controls. Sectioning at the surface will be performed, and the core of the tumor mass will be isolated from targeted and NT dye treated mice to visualize FA-ATZ-50456 penetration in the hypoxic region (co-stained with HIF-1α antibody) under an NIR fluorescence microscope. This time scale imaging of mice will demonstrate the selective binding, effective competition and retention of NIR dye in renal tumor.

(b) Therapy and survival study using S.c. Evr-res, s.c. PDx and orthotopic models: The antitumor therapeutic effect of CA9 targeting OMs of C4.16 in combination with Sorafenib in a VVT A498 xenograft nu/nu model (FIG. 18) was evaluated. Synergistic tumor growth inhibition of combination therapy was observed when compared to single agent treated or control group mice. Thus, the preliminary therapy study with the Evr-res s.c. RCC tumor model will be performed to understand the effect of combination therapy on macrophage reprogramming and reversing drug resistance. The therapy study will have two parts: (b1) optimal dose determination of (FA-ATZ-C4.16+FA-ATZ-CB): Evr-res A498 tumors bearing nu/nu xenograft mice (2 doses with 5 mice per group) and one control (5 mice) will be used. The 2 doses will be adjusted based on MTD results as obtained above. The optimal dose study will provide the effective dose of OMs with maximum tumor growth inhibition at lowest DLT. From this study, one dose will be selected for the final therapy study in Evr-res s.c., PDx and orthotopic RCC models: (b2) In the final therapy study, mice will be evaluated for efficacy and molecular effects: There will be 5 groups: Group 1: Vehicle control (no-drug containing OMs); group 2: targeted (FA-ATZ-C4.16+FA-ATZ-CB); group 3: free drug combination of (C4.16+CB); group 4: non-targeted OMs with C4.16; group 5: non-targeted OMs with CB. Orthotopic renal tumor growth inhibition will be monitored by BLI immediate after intraperitoneal injection of D-luciferin (150 mg/kg).

Statistical Considerations: Efficacy will be evaluated using tumor size, and tumor volume will be measured at multiple end points and tumor weight at sacrifice. As described above, tumor weight will be assessed using analysis of variance and tumor volume with mixed effects models. With 6 animals in each of 5 groups, in the ANOVA analysis, there will be 84% statistical power to detect medium size effect (0.73 sds) testing with 5% type I error. Kaplan-Meier method will be used to estimate overall survival from therapy study. As noted before, type I error will be controlled while making pair-wise comparisons.

Dosing schedule: For therapy studies, OMs will be administered i.v. with 2-3 doses per week (up to three weeks) with the dose obtained from MTD and optimal dose study (b1). In each case, after dosing, body weight and tumor volume will be recorded daily. The tumor volume will be calculated according to the NCI-recognized formula: Tumor Volume (in mm$^3$)=0.5 LD2, where L and D is the longer and shorter diameters in mm of the tumor, respectively. In addition, the weight of the tumor mass and the concentration of the drugs in the tumor and other organs will be measured by LC-MS/MS and HPLC after euthanizing the mice.

Evaluation of acute safety profiles: Most importantly, the objective is to develop safe clinically-translatable combination therapies, and, as such, it is critical to determine acute toxicity, if any, from systemic administration of the OMs. Body weight (BVV) changes: For safety studies, the BW changes will be recorded daily. The results will be normalized to baseline and reported as percent change in BW with time. Blood cell counts: Blood will be obtained from control and treated animals at midway during the treatment, and upon sacrifice. White blood cells and platelet counts will be measured using a hemocytometer. Liver enzyme levels and tissue histology analysis: Alanine aminotransferase (ALT) and aspartate aminotransferase (AST) will be measured in isolated plasma using a spectrophotometric assay as per supplier protocol (Pointe Scientific Inc. MI, USA). Mice with tumor blistering or dramatic health declines will be euthanized.

Evaluation of tumor growth suppression: Aside from tumor weight and volume calculations, the extent to which the combination attenuates tumor stroma in orthotopic tissue samples will be evaluated by assessing the reduction in trichrome staining and reduced stellate cell activation as determined by α-SMA (smooth muscle actin) staining. Since inflammatory cells can also modulate fibrosis, the tissue samples will be stained for T-lymphocytes, M1/M2 macrophages and neutrophils. T-lymphocytes will be stained using the CD3 antibody, M1 will be stained with (iNOS, CD80), and M2 will be stained with (CD163, CD204, CD206 and Arginase-1) and neutrophils using Gr-1 antibody. IHC staining for tumor apoptosis (TUNEL), proliferation (Ki67), and tumor vascularity (MECA-32) will be used to evaluate the effect of the combination on inhibiting tumor vasculature and inducing apoptosis. Pentachrome staining will be used to evaluate the collagen content and overall stroma structure in tumor tissues. To evaluate the effect of the treatment on tumor perfusion, Hoechst 33342 staining will be performed on 3 mice (kept for molecular effect analysis) from each treatment group. IHC slides will be examined by an expert pathologist.

This example provides new nanoformulations with the ability to penetrate tumor stroma and reach "deep" hypoxic regions of the tumor to deliver drugs for effective therapy of drug resistant RCC. In addition, the development of a small molecule dual targeting NIR imaging agent for image-guided intraoperative surgery in a clinical setting is provided.

Example IV

Tumor Hypoxia and/or Stromal Components, Including a Nanoformulation Encapsulated with Chemotherapeutic Agents such as Kinase Inhibitors for Therapy This example describes the synthesis and analysis of a versatile tumor hypoxia directed nanoplatform; at least some of the work reported herein was published as Alsaab et al. (*Biomaterials* 183:280-294, 2018) and overlaps with experiments described in Example 2.

Drug resistance is one of the significant clinical burdens in renal cell carcinoma (RCC). The development of drug resistance is attributed to many factors, including impairment of apoptosis, elevation of carbonic anhydrase IX (CA IX, a marker of tumor hypoxia), and infiltration of tumorigenic immune cells. To alleviate the drug resistance, we have used Sorafenib (Sor) in combination with tumor hypoxia directed nanoparticle (NP) loaded with a new class of apoptosis inducer, CFM 4.16 (C4.16), namely CA IX-C4.16. The NP is designed to selectively deliver the payload to the hypoxic tumor (core), provoke superior cell death in parental (WT) and Everolimus-resistant (Evr-res) RCC and selectively downmodulate tumorigenic M2-macrophage. Copper-free 'click' chemistry was utilized for conjugating SMA-TPGS with Acetazolamide (ATZ, a CA IX-specific targeting ligand). The NP was further tagged with a clinically approved NIR dye (S0456) for evaluating hypoxic tumor core penetration and organ distribution. Imaging of tumor spheroid treated with NIR dye-labeled CA IX-SMA-TPGS revealed remarkable tumor core penetration that was modulated by CA IX-mediated targeting in hypoxic-A498 RCC cells. The significant cell killing effect with synergistic combination index (CI) of CA IX-C4.16 and Sor treatment suggests efficient reversal of Evr-resistance in A498 cells. The CA IX directed nanoplatform in combination with Sor has shown multiple benefits in overcoming drug resistance through (i) inhibition of p-AKT, (ii) upregulation of tumoricidal M1 macrophages resulting in induction of caspase 3/7 mediated apoptosis of Evr-res A498 cells in macrophage-RCC co-culturing condition, (iii) significant in vitro and in vivo Evr-res A498 tumor growth inhibition as compared to individual therapy, and (iv) untraceable liver and kidney toxicity in mice. Near-infrared (NIR) imaging of CA IX-SMA-TPGS-S0456 in Evr-res A498 RCC model exhibited significant accumulation of CA IX-oligomer in tumor core with>3-fold higher tumor uptake as compared to control. In conclusion, this study demonstrates versatile tumor hypoxia directed nanoplatform that can work in synergy with existing drugs for reversing drug-resistance in RCC accompanied with re-education of tumor-associated macrophages, that could be applied universally for several hypoxic tumors.

FIG. 25 is an illustration of a representative tumor hypoxia directed nano-therapy in combination with Sorafenib for achieving multiple benefits against cancer, such as reversing drug resistance, inducing apoptosis and reprogramming macrophages.

Methods & Materials: See Alsaab et al. (*Biomaterials* 183:280-294, 2018).

Nanoparticle formulation and characterization. Chemical conjugation of was performed to obtain the CA IX-SMA-TPGS (CA IX-targeted oligomer), and SMA-TPGS (non-targeted oligomer) by using copper free 'click' reaction. Then C-4.16 drug was encapsulated either with SMA-TPGS or with CA IX-SMA-TPGS to obtain SMA-TPGS-C4.16 and CA IX-SMA-TPGS NP respectively, using nano-emulsion method. In brief, 100 mg of SMA-TPGS/CA IX-SMA-TPGS oligomer were dissolved in 100 mL of deionized (DI) water under stirring. Then C4.16 (30 mg) was dissolved in 1 mL of DMSO and mixed with the polymer solution. Subsequently, 40 mg of EDC was added dropwise into solution and pH was kept at 5.0 to stir for 30 min. Then, the pH was raised to 11 and kept for other 30 min. Finally, pH was adjusted to 7.8-8.0 and the free drug C4.16 were removed by dialysis for 4-5 h in a bag with a cut-off of MW 2 kDa. Then, the products obtained were lyophilized to obtain the final powder and stored in the freezer until further use. Subsequently, the particle size and surface charge (zeta potential) measurements were performed using a Beckman Coulter Delsa Nano-C-DLS Particle analyzer (Miami, FL) equipped with a 658 nm He—Ne laser. Hydrodynamic diameter histogram was obtained as differential intensity vs diameter of NPs. FIG. 26A shows hydrodynamic size of targeted non-targeted SMA-TPGS-C4.16 and hypoxia targeting CA IX-SMA-TPGS-C4.16 NP.

Morphology, Transmission Electron Microscopy (TEM) of the NP was evaluated using JEOL-JEM-1000 instrument (JEOL Ltd, Tokyo, Japan). The NPs were added on the copper grid and samples were negatively stained with Uranyl Acetate. FIG. 26B shows the Transmission electron microscopic morphology of non-targeted and targeted NP.

Figure 26C:
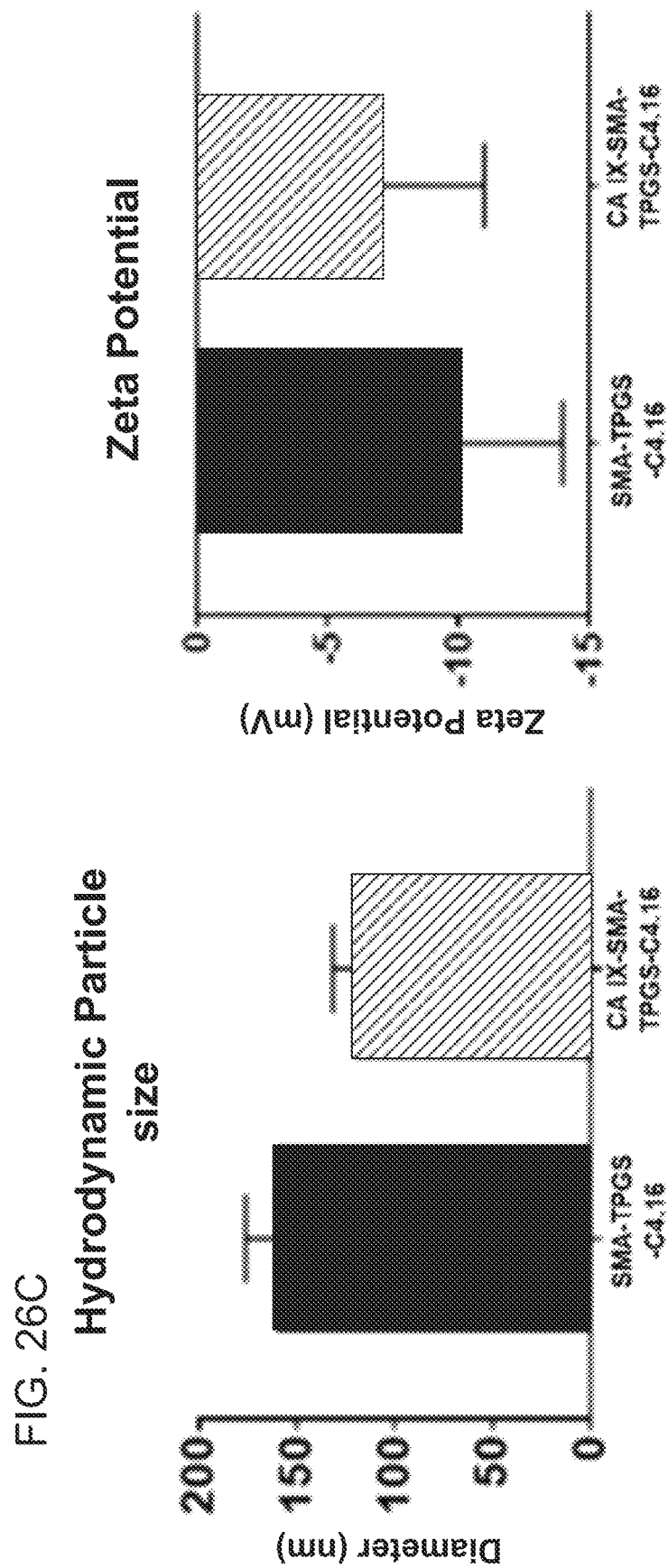

For particle size, we suspended the NPs in DI water and detected the scattered light at 165° angle. We then obtained the peak average histograms of intensity, volume and number from 70 scans to calculate the average diameter of the particles. The zeta potentials were evaluated by measuring the electrophoretic mobility of the charged particles under an applied electric field. FIG. 26C shows Zeta potential by Dynamic Light Scattering (DLS) is shown. Representative histogram of hydrodynamic particle size and zeta potential (n=3).

The chemical synthesis of the SMA-TPGS and CA IX-SMA-TPGS oligomer was also confirmed by the MALDI/MS and was found not to be a physical mixture of TPGS with SMA. We also characterized oligomer by proton nuclear magnetic resonance spectroscopy (1H NMR) and Fourier transform infrared spectroscopy (FTIR). The structure of the synthesized SMA-TPGS and CA IX-SMA-TPGS copolymer was detected by $^1$H NMR in D20. $^1$H NMR results confirmed the triazole ring formation in CA IX-SMA-TPGS as the characteristic peaks were found for the NH group of triazole ring around $\delta$7.9 ppm, peak of —CH2 of triazole ring around 5.2, and $CH_2$—$N_3$ peak around 4.2. FIG. 26D shows MALDI/MS analysis of CA IX-SMA-TPGS and SMA-TPGS are shown. The increment of molecular weight in CA IX-SMA-TPGS (m/z 3126) compared to SMA-TPGS (m/z 2399), and their corresponding fragmented peaks indicates the successful conjugation of ATZ to the SMA-TPGS polymers.

Figure 26E:
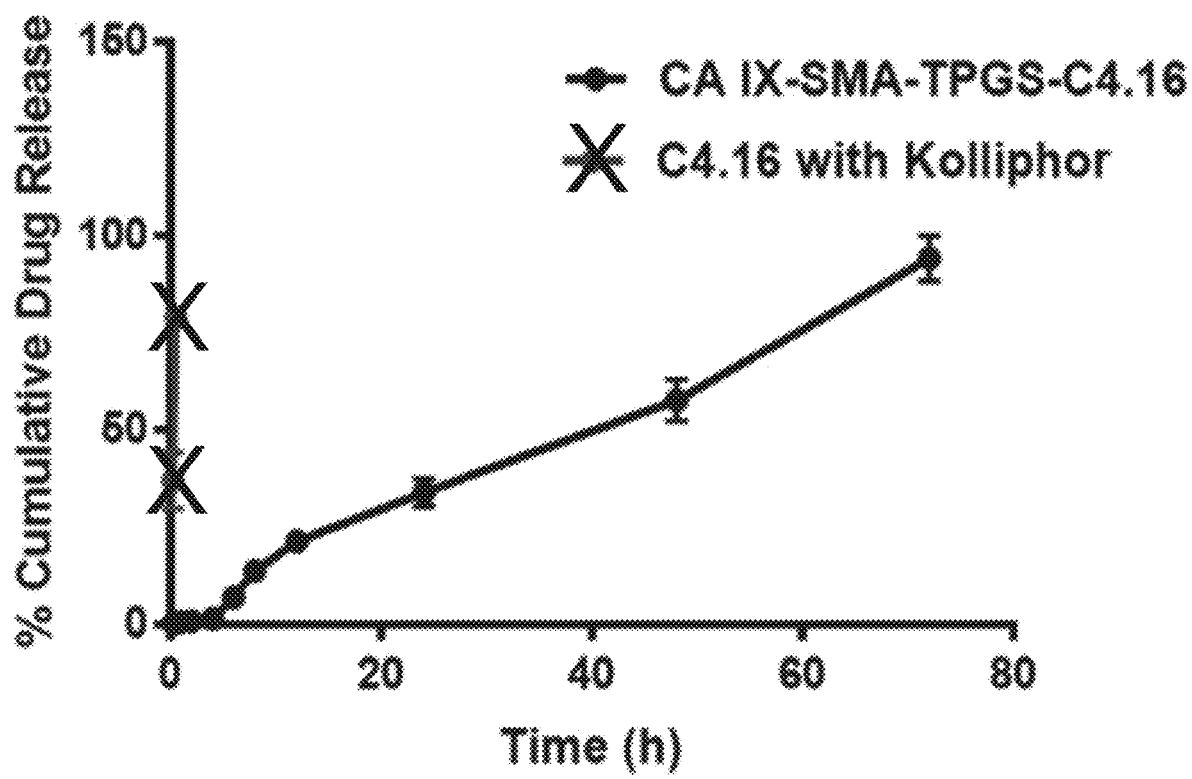

In vitro drug release kinetics of CAIX-SMA-TPGS-C4.16 in PBS indicates that the sustained release of C4.16 from the CAIX-SMA-TPGS-C4.16 NP as compared to free C4.16 with excipient, such as Kolliphor in PBS is shown in FIG. 26E.

Figure 9B:
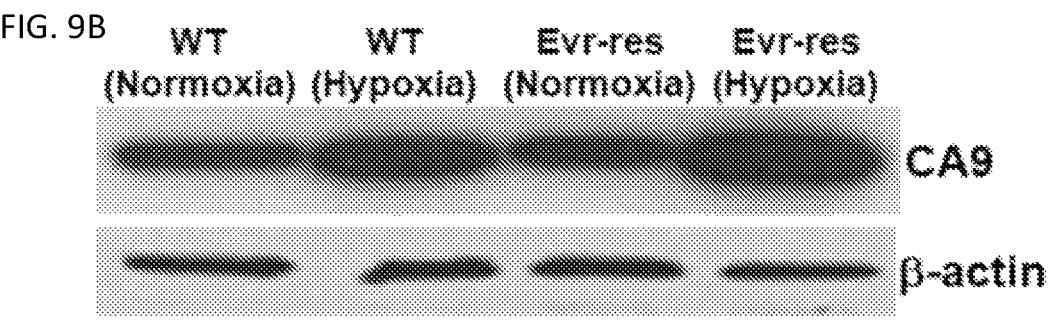

Rationale for choosing CA IX protein for RCC therapy. In this study, we have shown that CA IX was overexpressed in A498 and Evr-res A498 RCC cells and tumor. In FIGS. 9A, 9B, 16A, 16B, and 27A-27B, immunohistochemistry of CA IX-positive A498 RCC tumor xenografts collected from tumor tissue section is shown. The intense bright green fluorescence indicates the presence of CA IX. In FIG. 9B, Western blot data show levels of CA IX protein in A498 and Evr-res A498 RCC cells that were cultured under normoxic (no cobalt chloride treatment) or hypoxic conditions (treated with cobalt chloride for 72 h). Together with immunohistological localization of CA IX in RCC tumor, the upregulation of CA IX expression in hypoxic WT and Evr-res A498 RCC cells in comparison to their respective, normoxic counterparts provides a rational strategy for delivering the payload into the hypoxic core of RCC tumor. Moreover, CA IX has been shown to be specifically overexpressed in 93-97% of both ccRCC and some papillary RCCs, with limited expression in normal tissues (Takacova et al., *Oncol. Lett.*, 5(1):191-197, 2012). CA IX is also an important biomarker for RCC, and it plays a pivotal role in tumor progression, acidification, metastasis, and the intra-tumoral hypoxic condition. CA IX expression on the cell surface is associated with induction of tumor hypoxia through regulation of HIF1α. The clinicopathological analysis has supported the fact that overexpression of CA IX in RCC is linked to poor disease prognosis and resistance to chemo and immunotherapy. Many clinical trials are evaluating CA IX linked inhibitors or antibodies for monotherapy or diagnostic imaging. Recently, a small molecule, acetazolamide (ATZ), with high affinity (Kd~8.3 nM) to CA IX (Bao et al., *PLoS One* 7(11):e50860, doi: 10.1371/journal-.pone.0050860, 2012) has been reported to deliver the payload into the inner core (more than the periphery) of a tumor. These results signify that CA IX is an excellent target for site-specific delivery of therapeutic payloads to renal tumors. Along these lines, we developed ATZ-conjugated NPs for selective delivery of drug cocktail to the hypoxic region including the tumor core of therapy resistant RCC. It is well established that the hypoxic tumor core harbors aggressive and drug-resistant stem-like cells can persist after initial drug therapy, which can invade normal tissues and metastasize to distant sites forming secondary tumors. Targeting the hypoxic core using CA IX is thus a highly innovative approach needing immediate attention.

Figure 16A:
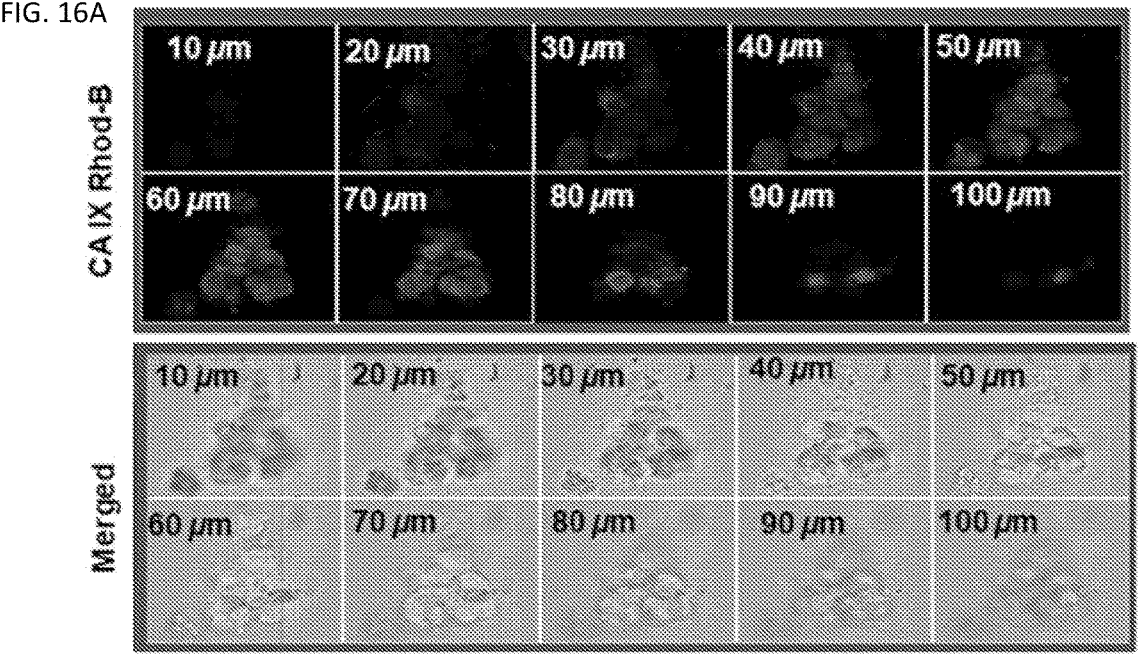
FIGS. 16A-16B illustrate cellular uptake (tumor matrix penetration) of CA9-Oligomicelles (see also FIG. 27 and related text). Confocal microscope images of ATZ-oligomer conjugated with rhodamine B and treated with hypoxic A498-spheroid. Z-stacking of the spheroid (FIG. 16A) indicates that fluorescence intensity is superior in 40-60 μm section. The highest fluorescence intensity at the center (as indicated by arrow) of 3D-plot (FIG. 16B) suggests ATZ-SMA-TPGS oligomer is efficient to reach the core of a tumor spheroid.
Figure 16B:
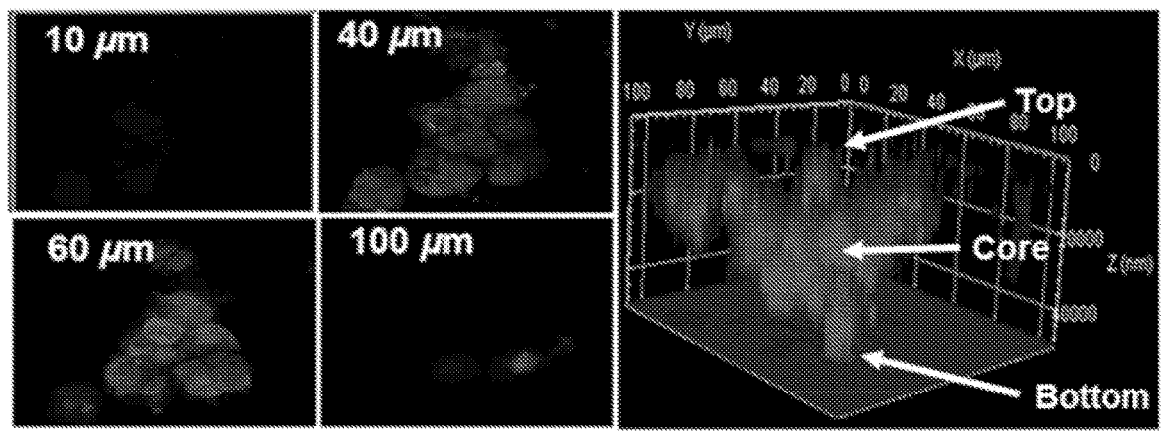

Hypoxia induced CA IX-overexpression in A498 cells and tumors enables tumor core penetration of CA IX oligomer. The 3D spheroid cell culture model is an in vivo mimetic study for testing NPs deep tumor core penetration ability. Thus, culturing A498 RCC cell lines with a spheroid model in hypoxic condition could be predictive of the tumor permeability of CA IX targeted NPs. In FIG. 16B, we found that the rhodamine-conjugated ATZ oligomer (CA IX-Rhod) has deep tumor matrix penetration and superior uptake in hypoxic Evr-res A498 spheroid model. The cell uptake study of CA IX targeted NPs was performed using Evr-res A498 spheroid model followed by imaging of spheroid using confocal microscopy. Interestingly, Z-stacking from 10, 40, 60, and 100 μm in confocal microscopy of CA IX targeted oligomer-treated cells indicate that rhodamine-signal is significantly higher in the core of the spheroid than the periphery (FIG. 16A, 16B). FIG. 49A, 49B shows the confocal microscopy of non-targeted SMATPGS-Rhod-B. The figure indicates that the non-targeted formulation has low cellular uptake as compared to CAIX-Rhod-B. This data supports the need of CAIX targeting ligand in oligomer for improving the hypoxic tumor core penetration. This also is a strong indication that CA IX targeted oligomer can penetrate deep into the tumor spheroid and likely reached the hypoxic regions very efficiently. The highest fluorescence intensity at the center (as indicated by arrow) of 3D-plot (FIG. 16B) suggests that CA IX targeted oligomer efficiently reached the core of tumor spheroid. Also, in FIG. 16B, with the lower range of Z-stacking from 40 to 60 μction (which is the core) has more fluorescence intensity than the periphery. Z-stacking of the spheroid at different sections from 10 to 100 μm with CA IX targeted formulations also shows superior fluorescence intensity from 40 to 60 μm sections representing organoid core. FIG. 27A showed the overall merged view of CA IX-Rhod-B oligomer with bright field and compared with untreated control. FIG. 27B shows the overall shape of the spheroid from along the three dimensions (x, y, and z) as another way of representation to demonstrate spheroid core penetration.

C4.16 anti-cancer effect and hypoxia targeting ability of CA IX NP. RCC is very difficult to treat as the cells are mostly resistant to many current therapies. Therefore, newer treatments including better ways of drug delivery are urgently needed to fight this malignant disease efficiently. Our previous work has demonstrated generation and characterization of RCC cells that are resistant to Evr, a frontline mTOR-targeted therapy, and revealed that a class of CARP-1 functional mimetic (CFM) compounds especially C-4.16 inhibited parental (VVT) and Evr-res RCCs (Cheriyan et al., *Oncotarget*. 8:104928-104945, 2017). In this study, we utilized C-4.16 and current clinical anti-RCC therapeutics Sor and Evr. First, we determined cytotoxicity of individual drugs C4.16, Sor, and Evr in both A498. Our results from FIG. 28A, 28B indicated that C4.16 was more effective in inhibiting growth of WT and Evr-res A498 compared with Sor. Evr, however, did not inhibit growth of Evr-res A498 RCC cells as previously published (Belmunt et al., *Clin Genitorin. Canc.* 12:262-296, 2015). In order to understand the safety of combination therapy, we performed the hemolysis assay using CAIX-C4.16 and combination of CAIX-C4.16+Sor. The data from FIG. 50A, 50B indicate concentrations as high as 45.5 μM of C4.16 and combination of (45.5 μM C4.16+17.4 μM Sor) have no significant effect in blood hemolysis (Dong et al., *Nanoscale* 6:120420-12049, 2014). We then clarified whether a combination of C4.16 and Sor were more effective when compared with individual treatment. In vitro cytotoxicity assay of C4.16 and Sor on FIG. 28A, 28B indicates C4.16 was more potent than FDA approved drug (Sor) and combining both drugs showed significantly lower the IC50 value. All the results indicate C4.16 and Sor inhibited viabilities of VVT and Evr-res RCC cells, and C4.16 when combined with Sor was more effective than C4.16 or Sor alone. However, C4.16's poor water solubility limits it's in vivo testing and clinical translation. We addressed the solubility and delivery concerns of C4.16 by utilizing a nanotechnology-based approach. Thus, encapsulation of C4.16 in NP and conjugating them with CA IX targeting oligomer was considered as a functional approach for resolving the challenges to deliver the compounds selectively to resistant RCC. The results as noted in FIG. 28C show that CA IX-C4.16 was more effective in inhibiting growth of A498 (VVT and Evr-res) compared to Sor and Evr and supported that CA IX-C4.16 nano-formulation was more potent compared to FDA approved drugs. The table in FIG. 28D summarizes IC50 values for all drugs with the WT and Evr-res RCC cell lines. The data in FIG. 28C, 28D showed that CA IX-C4.16 was more effective in inhibiting growth of A498 (VVT and Evr-res) compared to Sor and Evr and collectively indicate that CA IX-C4.16 was more potent compared to other drug options. Furthermore, to confirm the synergism, we utilized CompoSyn® software to evaluate the combination index (CI) value of C4.16 and Sor. As shown in FIG. 28E, C4.16 and Sor had CI value (less than 1) of 0.531 for A498 VVT and 0.654 for Evr-Res, which indicated synergism between the two compounds. FIG. 28F also demonstrated a combination of CA IX-C4.16 with Sor is synergistic in RCC cell killing as obtained from isobologram analysis. Thus, low dose of CA IX-C4.16 NP could potentially sensitize RCC cells for inhibition by Sor. Moreover, as shown in Figure S.6, a combination of 500 nM dose of CA IX-C4.16 with various doses of Sor further support their synergistic inhibition of RCC cells. A 500 nM dose of CA IX-C4.16 caused greater inhibition of RCC cell growth when combined with low doses of Sor (100, 200, 500 nM).

Figure 17:
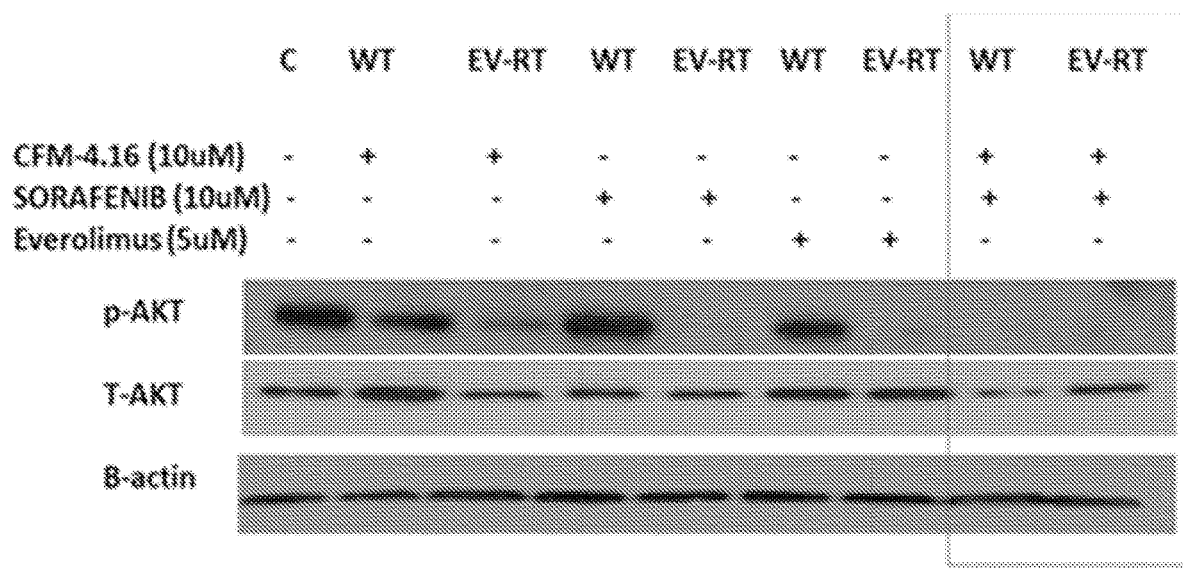
FIG. 17: Molecular mechanism of cell death and resurrection of apoptosis.

Mechanism of C4.16 for overcoming drug resistance. In this study, we determined how induction of apoptosis and inhibition of oncogenic survival signaling would reinforce the synergistic cell killing and reversal of drug resistance in VVT and Evr-res A498 cells when treated with CA IX C4.16+Sor. As shown in FIG. 17, we observed inhibition of AKT activation as indicated by downregulation of pAKT in C4.16 and Sor treatment compared to untreated control. We found that Evr-res RCC cells that were treated with C4.16 or Sor had a greater loss of AKT activities when compared with their VVT cells treated with respective agents. Interestingly though, a combination of C4.16 and Sor completely abolished AKT activity (pAKT) in both the WT and resistant cells. Therefore, it is likely that superior RCC growth inhibition by C4.16 and Sor is in part due to suppression of oncogenic AKT activity. Moreover, C4.16 cytotoxicity was mediated by apoptosis induction (FIG. 17) supporting our prior studies that have shown activation of apoptosis in C4.16 treated cells. Although, C4.16 or Sor induced caspase-3/7 activation, a significant upregulation of caspase-3/7 activity was noted in RCC cells treated with C4.16+Sor as compared to control (FIG. 29B). This finding was further supported by an increment of early and late apoptotic events in both WT and Evr-res A498 cells treated with CA IX-C4.16+Sor as compared to untreated control or CA IX-C4.16 (FIG. 29C). The fraction of cells that stained with Annexin V (+ve) or Annexin V (+ve) and 7-AAD (+ve) was higher in combination treatment than singular treatments as shown in FIG. 29D. In all the cases; combination always worked better than individual drugs in inhibiting RCC cells growth.

Reprogramming Macrophages to Modulate Combination Treatment. To overcome the critical problem of current RCC treatment, we developed a tumor-penetrating nano-sized NP of spherical shape that can localize and penetrate tumor tissues efficiently and target tumor hypoxia to deliver the combination drug cocktail to shut down vital tumorigenic signaling while simultaneously reprogramming macrophages for better therapeutic efficacy. Several studies have identified the key players that are responsible for drug resistance and immune evasion leading to the poor prognosis of RCC. These players are categorized based on their specific roles that include (i) RTK-mTOR that regulates critical tumorigenic signaling for tumor survival, immune suppression, and stroma formation, (ii) impairment of intrinsic and extrinsic apoptotic signaling is an essential player of drug resistance. Induction of CARP-1 protein has been well documented to induce apoptosis in cancer cells under the conditions of serum withdrawal or therapy stress. (iii) CA IX is a tumor hypoxia marker for the maintenance of extracellular acidosis and cancer stemness, thus facilitating tumor growth and metastases. More than seven clinical trials are underway to target CA IX in RCC and other solid tumors [NCT00059735, NCT00884520] (Bellmunt et al., *Glin Genitorin Canc* 12:262-269, 2014).

Figure 30A:
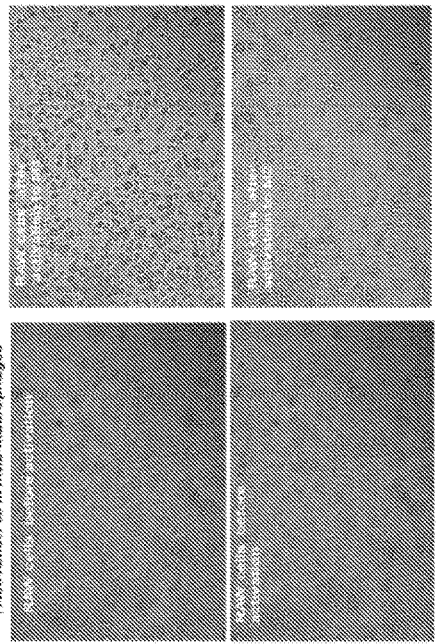
Figure 30B:
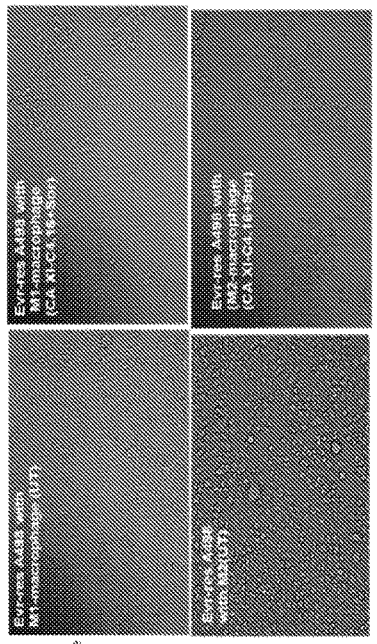
Figure 30C:
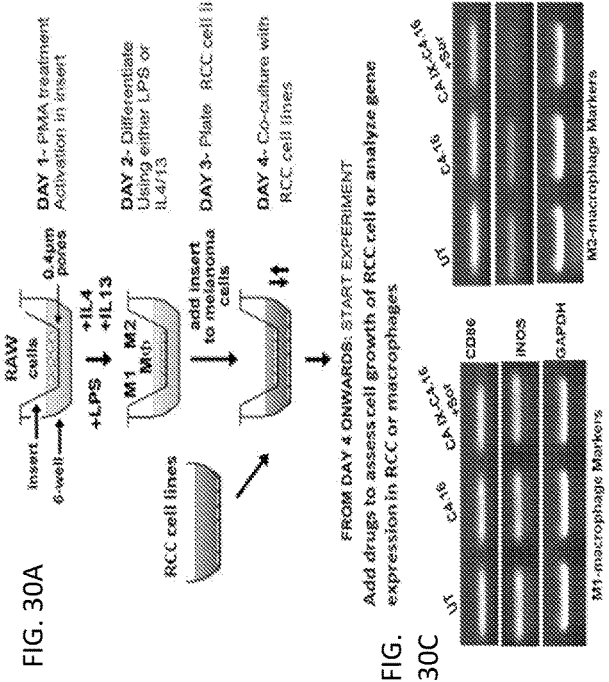
Figure 30D:
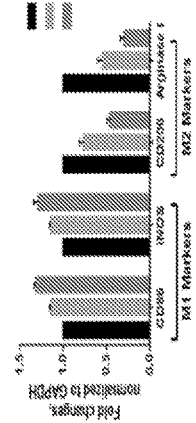
Figure 30E:
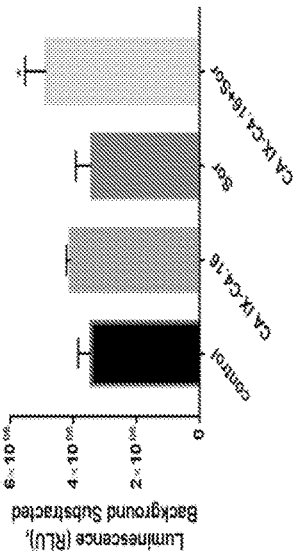

The delivery system engineered herein is a promising addition to clinical translation for better RCC treatment. FIG. 30A shows a schematic diagram as Raw264.7 cells were placed into the insert. Then, cells were polarized to M1-macrophage using IFN-γ and LPS, and to M2-macrophage using IL-4 recombinant protein. The change of morphology of Raw264.7 as shown in FIG. 30B supports the M1/M2 polarization of naïve Raw264.7 cells (Zajac et al., *Blood* 122:4054-4067, 2013) followed by treatment with C4.16 and CA IXC4.16+Sor for 24 h. The data in FIG. 30C clearly demonstrate the up-modulation of the tumoricidal M1-macrophage marker (CD86, iNOS) and down-modulation of the tumorigenic M2-macrophage marker (CD206, Arginase I) compared to untreated (UT) control and C4.16. The macrophage reprogramming ability of CA IX-targeting NP builds a rational of using (CA IX-C4.16+Sor) as a potent antitumor immune stimulatory agent of RCC. The treatment of CA IX+Sor to Evr-res A498 cells cocultured with M1-macrophage resulted in the growth inhibition and change of morphology that could be due to tumoricidal M-1 macrophage mediated cell death of RCC cells as shown in FIG. 30D.

To evaluate the macrophage induced RCC cell death, we analyzed up-modulation of caspase 3/7 in Evr-res A498 cell co-cultured with Raw 264.7 cell and treated with CA IX-C4.16+Sor or other treatments. The data from FIG. 30E clearly confirmed combination is significantly better in inducing apoptosis as compared to control or individual treatments. The mechanism of immune-modulation of CAIXC4.16+Sor can be attributed to inhibition of tumorigenic kinases, such as p-AKT (Sau et al., *J Contr Release* 274:24-34, 2018) and resurrection of apoptosis. As CAIX-04.16+Sor treatment is very effective in inhibiting P-AKT (FIG. 29A), the treatment of (CAIX-04.16+Sor) in Evr-res A498 and M1/M2 macrophage coculture condition is down-modulating the secretion of inflammatory cytokines, resulting in down-modulation of tumorigenic M2 macrophage function and up-modulation of M1 macrophage function. Another, possible explanation of immunomodulatory effect of (CAIXC4.16+Sor) could be suppression PD-1/PDL-1 cross talk. Prior literature has indicated that macrophages have elevated expression of PD-1 receptor that interacts with PDL-1 of cancer cells (Bally et al., *J. lmmunol.* 194:4545-4554, 2015). Thus, CAIXC4.16+Sor treatment can be inhibiting the PD-1/PDL-1 interaction, resulting in immune resurrection in co-culture condition as seen in FIG. 30. All these results demonstrate hypoxia targeting NP in combination with Sor is not only inducing chemotherapeutic effect but also reeducating macrophages to function as a tumoricidal agent, which could prove excellent for a combination of chemo-immune therapy to inhibit Evr-res RCC.

Figure 31A:
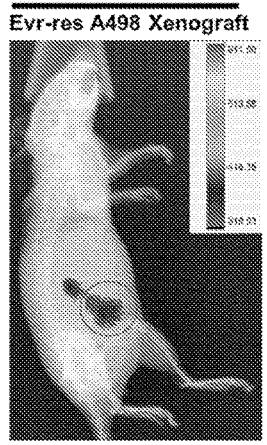
Figure 31B:
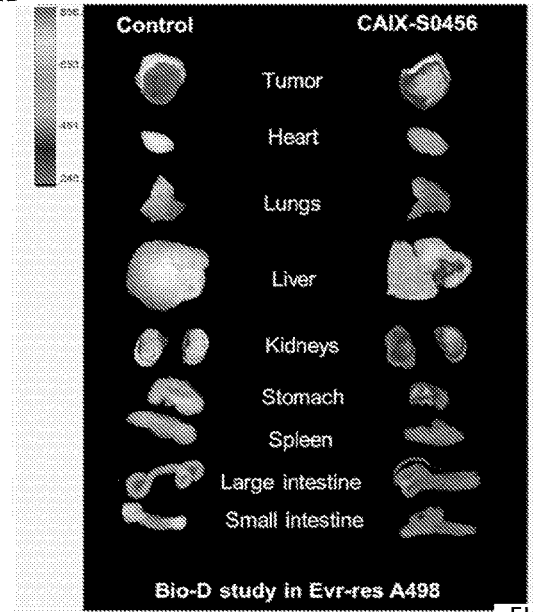
Figure 31C:
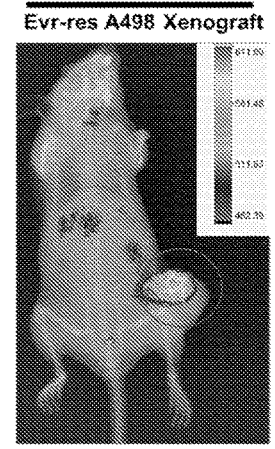
Figure 31D:
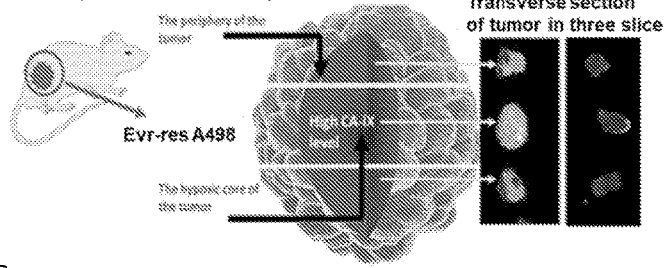
Figure 31E:
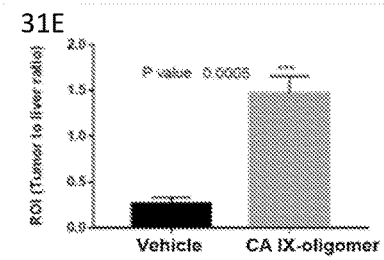
Figure 31F:
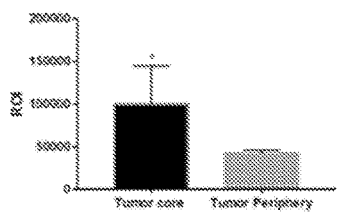

Superior tumor core penetration and high tumor uptake of CA IX oligomers in xenograft RCC model. After optimizing the anticancer effect of CA IX-C4.16 at the cellular level, we performed NIR imaging in animals inoculated with RCC tumor model following administration of CA IX-S0456. The idea of performing NIR-imaging with CA IX-oligomer will provide several advantages including its use as (i) agent for tumor image guided RCC surgery in the clinic, as well as (ii) meaningful insights into the therapeutic outcome and safety of nanoformulation in RCC model. It is well known that clinically small molecule NIR imaging agents have excellent ability to distinguish the tumor lesion from healthy tissue in imaging-guided surgery as noted in NCT02317705 and NCT01778933 (Zhang et al., *Nat Rev Clin Oncol* 14:347-365, 2017). The results show CA IX-S0456 selectively home to the orthotopic subcutaneous Evr-res A498 tumor as compared to control (FIGS. 31A and 31C). The biodistribution (Bio-D) study in FIG. 31B validates the prominent tumor selectivity of CA IX-S0456. The tumor selectivity of CA IX-S0456 in drug resistant RCC model builds a foundation for widespread applicability of CA IX-S0456 in Evr-res RCC tumor model that builds a rational platform for further investigation towards clinical translation of this technology. Herein, the reasons of using CAIX-S0456 oligomer compared to oligomicelles for tumor imaging is due to the fact that (i) small molecular weight oligomer, will help achieve deep tumor stroma penetration, (ii) hydrophilic nature of oligomer will assist faster clearance/excretion via the kidneys and healthy organs, while being selectively retained in the hypoxic tumor (Wilhelm et al., *Nat Rev Mater* 1, 2015; doi.org/10.1038/natrevmats.2016.14). In spheroid uptake study of CA IX-rhodamine (FIG. 16A) showed high localization of rhodamine in the core of the hypoxic Evr-res A498 spheroid. To ascertain core penetrating ability of CA IX-S0456 in a drug resistant tumor model, we performed three transverse sectioning of the isolated tumor after the bio-D study. FIG. 31D confirmed that CA IX-S0446 is very efficient in penetrating the core of tumor that predominantly harbors hypoxia and drug resistant features. As shown in FIG. 31E, more than 3-fold tumor ROI in CA IX-oligomer compared to control demonstrates the feasibility of CA IX-S0456 in clinical translation as an image-guided surgery tool. The findings in FIG. 31F suggest the ROI is >2-fold in CA IX-S0456 treated tumor core as compared to tumor periphery. These results support a high binding affinity and specific tumor uptake, faster normal tissue clearance, and low non-specific organ uptake of CA IX-oligomer.

Figure 31G:
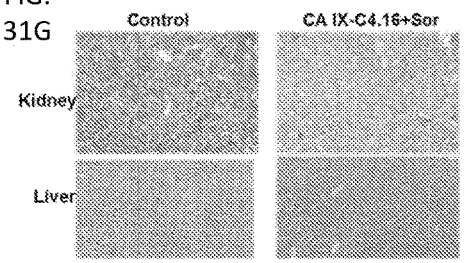

Tumor growth inhibition and excellent safety of CA IX-C4.16+Sor in Evr-res tumor. After confirming the in vitro anticancer activity, we finally examined the antitumor effect of CA IX-C4.16 NP in combination with Sor, to demonstrate the efficacy of combination regimen in reversing Evr-resistance in RCC. The CA IX-C4.16 NPs formulation inhibited the viability of VVT and Evr-res A498 cells in vitro by stimulating various tumoricidal pathways including induction of apoptosis, downregulation of pAKT and up-modulation and education of M1-macrophages. As shown in FIG. 18, CA IX-C4.16 significantly inhibited highly aggressive Evr-res A498 tumor in combination with Sor. The greater tumor growth inhibitory effect of CA IX-C4.16+Sor compared to control and individual treatments thus opens an avenue that CA IX-C4.16 nano-therapy can resurrect Sor as a more efficient anticancer therapeutic agent. Importantly, CA IX-C4.16+Sor did not cause any necrosis or morphological changes in tissue architecture of normal organs such as kidneys and liver (FIG. 31G). The superior tumor penetration of CAIX oligomer and efficient antitumor effect of CA IX-C4.16+Sor in different RCC tumor model underscore a viable strategy for developing a smart therapy against drug resistant tumors with high safety profile. The rationale of choosing the combination of C4.16 and Sor is to target the divergent pathway of RCC. C4.15 works through upregulation of CARP-1 protein, which is an inducer of apoptosis (Cheriyan et al., *Oncotarget.* 8:104928-104945, 2017). Whereas, Sor is a multi-kinase inhibitor. Thus, treatment of C4.16 resurrects the apoptosis pathway and Sor inhibits the tumor survival kinase signaling, resulting in the synergistic induction of anticancer effect and reversal of drug resistance of RCC. The current findings can support the claim that CA IX-NPs loaded with anticancer payload can play a universal role in overcoming drug resistance and repurposing current drugs in a more efficient way.

Conclusions: In this study, we have demonstrated elevated expression of CA IX in RCC that qualifies its use as an excellent biomarker for targeted therapy and imaging. The combination of C4.16 and Sor have a superior synergistic cell killing in Evr-res RCC, which is due in part to activation of caspase 3/7 protein and complete eradication of oncogenic AKT activation. Combination of CA IX-C4.16 with Sor showed targeted delivery of payload in hypoxic tumor resulting in induction of multimodal anticancer effects including, the resurrection of apoptosis, reversal of drug resistance, and reprogramming of malfunction macrophages. This NP could have a direct impact on developing newer therapies for treating RCC. We found that CA IX-C4.16 NP is suitable for intravenous administration with superior tumor accumulation of CA IX-oligomer as compared to liver and demonstrated effective antitumor response in Evr-res A498 tumor. Due to small molecular size and ease of chemical functionalization, CA IX-oligomer can potentially be further explored for selective CA IX tumor targeting for the diagnostic use and RCC image-guided surgery in the clinical setting. The tumor spheroid uptake study has clearly demonstrated excellent tumor core penetrating ability of CA IX-targeting oligomer, which is a critical indicator of tumor stromal disruption leading to better therapy response and immune modulation. In conclusion, the synergistic therapeutic potential of CA IX-C4.16 and Sor combination and selective NIR imaging of the CA IX anchored oligomer portend their promising potential towards developing better therapeutics and diagnostic tools for clinical translation against deadliest drug resistant RCC.

Example V

In Vivo Tumor Grown Inhibition Using CA IX-C4.16+CAIX-Everolimus

This example shows that tumor growth inhibition with CA IX-C4.16+CAIX-Everolimus is significantly higher compared to controls in breast patient derived tumor model.

Using subcutaneously implanted triple negative breast cancer (TNBC, BR1126 model) patient derived tumor xenograft (PDX) in NCR-Scid mice. Anti-tumor therapeutic effect of CA9-targeting nanomicelles of CFM-4.16 (CA9-C4.16) was treated either individually or in combination with CA 9-Everolimus. Everolimus (Evr) is an FDA approved mToR inhibitor and it was encapsulated with CA9-NPs (as made above) to obtain CA9-Evr. For combination treatment, a total of 7-intravenous doses (15 mg/kg/injection of CA9-CFM-4.16. 1 mg/kg/injection for 4-injection and 4 mg/kg/injection for last 3 injection of CA9-Evr) were administered via tail vein every fourth day (total dose CFM-4.16=105 mg; Everolimus=16 mg). The tumor sizes were measured 7 days post last injection. Results are shown

Example VI

Chemically Conjugated Carbonic Anhydrase IX and CD44 Directed Nanoformulation for Dual Targeting Tumor Hypoxia and/or Stromal Components The illustrations in FIGS. 33A and 33B represent tumor multicomponent targeting as innovative strategy for superior antitumor effect. FIG. 33A illustrates tumor microenvironment and overexpression of tumor cell type specific receptors that can be selectively targeted together for delivering therapeutic and diagnostic agents. FIG. 33B illustrates representative receptors that are overexpressed in tumor components. We are targeting multicomponent of tumor environment by using nanoformulation and small molecule imaging agent. This will improve the therapeutics outcome of cancer.

HA-Cysteine synthesis: For the synthesis of Carbonic anhydrase IX and CD44 directed nanoformulation: Firstly —COOH group of hyaluronic acid (HA, purchased from Lifecore Biomedical, MN, USA) was reacted with —NH$_2$ group of cysteine to obtain HA-Cysteine as per previously published literature (Fan et al., *J Controlled Release* 208: 121-129, 2015). Briefly, 100 mg HA (average molecular wt. of 6.7 Kda) was dissolved in 10 ml Milli-Q® water containing 10 mg EDC and Sulfo-NHS. The pH was then adjusted to 5-5.5 with 1 M HCl. The reaction mixture was stirred for 0.5 h, followed by addition of 200 mg L-cysteine and stirring at room temperature for another 12 h. In the reaction mixture 10 mM DTT was added to reduce the dithiol bond, if anything happens during the reaction. The HA-Cysteine was purified by dialysis (molecular weight cut-off 3.5 kDa) in water for overnight. Finally, the dialyzed HA-Cysteine was lyophilized and stored at −20° C. Positive Elliman test (yellow color) indicated the formation free thiol content of HA-SH.

ATZ-NH$_2$ and ATZ-C6-NH$_2$ synthesis: Acetazolamide was hydrolyzed to obtained ATZ-NH$_2$ based on our previously published literature Biomaterials Volume 183, November 2018, Pages 280-294. Briefly, 1 gm of Acetazolamide was hydrolyzed in 1M HCl with methanol under refluxing condition for overnight. Product formation was monitored by using thin layer liquid chromatography. ATZ-NH$_2$ was recovered after adding the NaOH beads to adjust the pH of the suspension to 7 and product was precipitated. ESI-MS data of ATZ-NH$_2$ [M+H]$^+$=180.9853. Then ATZ-NH$_2$ was coupled with 1-amino Fmoc heptanoic acid using EDC/NHS coupling and Fmoc was deprotected with 20% pieridine in DMF for 2 h. The positive ninhydrin charring indicates the free amine of ATZ-C6-NH$_2$. FT-IR spectra indicates that N—H stretching at 3000 cm−1 and presence of C—H bond stretching below 1000 cm−1 indicates the ATZ-C6-NH$_2$ formation.

HA-Cysteine-ATZ synthesis: 1 mole of HA-cysteine was coupled with 10 mole excess ATZ-C6-NH$_2$ in presence of EDC/NHS for overnight in DMSO/water condition and reaction mixture was dialyzed in MWCO 3.5 kDa. 3300-3500 cm−1 N—H bond stretch was obtained in HA-Cysteine-ATZ molecule.

HA and ATZ nanoformulation: HA-Cysteine-ATZ was mixed with fluoresce-dye maleimide (10:1 ratio) and paclitaxel loaded TPGS-SMA-SH was dithiolated (S—S) with HA-Cysteine-ATZ in presence of chloramine-T (8:10). Finally, reaction was dialyzed with 7.6 Kda MWCO. The product showed Elliman test negative indicates —SH groups were either dithiolated with TPGS-SMA-SH or coupled with Dye. NMR spectroscopy data indicates the presence of aromatic proton at δ7.7-7.8 ppm is coming from aromatic proton of SMA-TPGS polymer, thus support the formation of S—S bond in HA and ATZ nanoformulation. FT-IR analysis of showed C—O bond stretching at 1050-1150 cm−1 and N—H bond stretch at 3300-3500 cm−1 in the product.

Drug Loading: The drug loading in TPGS-SMA-SH was done under gradient pH conditions at room temperature as described earlier. The drug loading was calculated using HPLC at 227 nm for absorbance of paclitaxel (PTX). The amount of drug loaded was calculated by using a standard graph. The drug loading was found to be around 15% Wt./Wt. for PTX in this CD44 and CA IX dual targeting drug delivery system.

FIG. 34 illustrates carbonic anhydrase IX (for hypoxia) and CD44 (cancer stem cells) directed molecules using acetazolamide and hyaluronic acid nanoformulation for therapeutic drug delivery and tumor imaging. FIG. 35 illustrates the synthesis of the compound illustrated in FIG. 34, as described above.

Nanoparticle Morphology. For Morphology analysis, transmission electron microscopy (TEM) of the NPs was employed, using JEOL-JEM-1000 instrument (JEOL Ltd, Tokyo, Japan). The NPs were added on the copper grid and samples were negatively stained with Uranyl Acetate. The particles are non-spherical (and more specifically, rod-shaped) in shape, as illustrated in FIG. 21A, 21B.

In vitro Cytotoxicity. In-vitro cytotoxicity assay was performed using the MTT solution for the free drug Paclitaxel (PTX), the non-targeted formulation in the absence of the targeting ligands (NT-PTX), and the targeted formulation consisting of the two ligands, i.e., HA and ATZ (T-PTX). The cells were seeded in 96-well plates with a normal of 5000 cells in each well. After incubating these cells for 24 hours, they were treated with different concentrations of the formulations within a range of 65-1000 nM. The treated cells were further incubated in the presence of the formulations for 72 hours at 37° C., after which the MTT reagent solution (1 mg/ml) was added. The cells were incubated furthermore at 37° C. for 2 hours. Following this, the media was supplanted by DMSO and the plates were put on a shaker for 10 min. The absorbance was measured at 590 nm utilizing a high-performance multi-mode plate reader (Synergy 2, BioTek). The extent of surviving cells was calculated in terms of percentage by contrasting the absorbance of the treated cells and proper controls cells. The CAIX and CD44 targeting nanoformulation encapsulated paclitaxel demonstrated superior HT-29 tumor killing effect compared to control (FIG. 36).

In vivo Imaging and Organ Localization. Imaging study was performed using two sided subcutaneously implanted non-small cell lung cancer (NSCLC, LG1306 model, obtained from Jackson lab), triple negative breast cancer (TNBC, BR1126 model, obtained from Jackson lab), patient derived tumor xenograft (PDX) in NCR-Scid mice. Once tumor volume reached to 300-700 mm3, mice were injected with HA and ATZ nanoformulation containing NIR dye, namely HA-ATZ-S0456 NPs with a single 20 nmole dose of dye via intravenously injection and live mice were imaged at 4 h after dosing under anesthetic condition for LG1306 model and then bio-distribution of HA-ATZ-S0456 NPs was evaluated in different organs and tumor. For Br1126 model 10 nmole of dye was injected via i.v. and whole body was imaged after 4 h of dosing and biodistribution (bio-d) was performed in 24 h post dosing of the same mice. For control mice, they were treated with non-targeted dye and whole-body imaging of mice was performed at 4 h after dosing with 10 nmole dye and bio-d was performed in 24 h of post doing of the same mice. Fluorescence images were collected in Bruker Carestream Xtreme in vivo imaging system at excitation (750 nm) and emission (830 nm) wavelength. The instrument has dual fluorescence and X-ray imaging modalities with light source: 400 W Xenon illuminator. Both fluorescence and X-ray images of the mouse were merged to demonstrate the localization of NIR dye.

The CAIX and CD44 targeting nanoformulation conjugated with Nera infrared fluorescent dye showed superior tumor core penetration in (FIG. 37A) lung PDX tumor, (FIG. 37B) tumor targeting bio-distribution (Bio-D) in lung PDX tumor, (FIG. 37C) breast tumor, and (FIG. 37D) tumor targeting bio-distribution (Bio-D) in breast PDX tumor. CAIX and CD44 targeting nanoformulation demonstrated superior tumor core penetration.

Re-blocking of CAIX and CD44 receptor inhibits the tumor accumulation of CAIX-CD44 targeting nanoformulation, thus competing the receptor in (FIG. 38A) lung PDX tumor, (FIG. 38B) insignificant tumor accumulation of tumor targeting CAIX-CD44 targeting nanoformulation after receptor blocking in bio-distribution (Bio-D) study of in lung PDX tumor, (FIG. 38C) control dye treated mice has no-significant tumor uptake as compared to CAIX-CD44 targeting nanoformulation.

NIR Fluorescence Accumulation Intensity in Tumor Core vs. Periphery. Fluorescent intensities were quantified in tumor core and periphery using image j software and data represented. As illustrated in FIG. 39, the quantification of fluorescent intensities in CAIX and CD44 targeting nanoformulation treated tumor showed higher tumor core penetration than tumor periphery in lung, breast PDX tumor model, whereas control dye fails to reach tumor core as compared to its periphery.

Example VII

Production and Characterization of Imaging Agents

This example describes chemically conjugated carbonic anhydrase IX and folate receptor directed small molecule-based imaging agent for early diagnosis of tumor, pre-tumor/precancerous lesion, polyp and imaging guided surgery of tumor.

ATZ-$NH_2$ and ATZ-Lys synthesis: Acetazolamide was hydrolyzed to obtained ATZ-$NH_2$ based on our previously published literature *Biomaterials* Volume 183, November 2018, Pages 280-294. Briefly, 1 gm of Acetazolamide was hydrolyzed in 1M HCl with methanol under refluxing condition for overnight. Product formation was monitored by using thin layer liquid chromatography. ATZ-$NH_2$ was recovered after adding the NaOH beads to adjust the pH of the suspension to 7 and product was precipitated. ESI-MS data of ATZ-$NH_2$ $[M+H]^+$=180.9853. Then ATZ-$NH_2$ was coupled with —COOH group of Fmoc-Lys(Boc)-OH in presence of DMF/Pybop coupling agent. Then -Fmoc was deprotected using 20% piperidine in DMF to obtain ATZ-Lysine (ATZ-Lys) the compound was purified by precipitation method using diethyl ether. The compound showed ninhydrin charring, which indicates the presence of —$NH_2$ group and in NMR spectra also indicates presence of $CH_2$ proton at δ1.3-1.5 ppm is appearing from alkyl chain of lysine. FIG. 41 is a hypoxia and tumor stroma targeting small molecule imaging agent for imaging guided surgery. A synthesis scheme for this compound is shown in FIG. 42.

FA-CAIX-Rhod synthesis: First folic acid (FA) (100 mg, 1 mole) was activated with EDC/sulfo-NHS, DIPEA in presence of DMF for 30 min and ATZ-Lys (95.5 mg, 1 mole) was drop wisely added into the solution. The reaction was continued for overnight and product was separated by after brine wash, and precipitation with DCM/diethyl ether. Then -Boc was deprotected using TFA/DMF for 2-4 h and TFA was removed by Nitrogen flash and immediately reacted with rhodamine NHS for 12 h to obtain FA-CAIX-Rhod and product was separated by precipitation method and dialysis with 0.1-0.5 KDa MWCO. $^1$H-NMR spectroscopy indicates presence of aromatic proton δ 6.6-8 ppm that contributing from folic acid and rhodamine group of FA-CAIX-Rhod.

FIG. 41 is a hypoxia (targeting CAIX) and tumor stroma (folate receptor) targeting small molecule conjugated with rhodamine dye (namely FA-CAIX Rhodamine) for imaging and detection of tumor, pre-tumor, polyps and imaging guided surgery. A synthesis scheme for this compound is shown in FIG. 42.

Binding Affinity Analysis. The FA-CAIX-Rhod was used to determine the binding affinity in SKOV3 cell with positive folate receptor (Gawde et al., *Colloids and Surfaces B: Biointerfaces* 167: 8-19, 2018) and they were cultured with 100 μM $CoCl_2$ for 72 h to induce hypoxia that will increase CAIX expression. Then cells were platted with 50,000 cells per well of 24 well plate and treated with FA-CAIX-Rhod for 1 h and then cell were washed and lysed and rhodamine fluorescence intensity was measured and dissociation constant (Kd) was measured was calculated from a plot of cell bound fluorescence emission (a.u.) versus the concentration of FA-CAIX-Rhod fluorescent probes added using the GraphPad Prism program.

The high binding affinity of FA-CAIX-Rhod (FIG. 43) indicates the hypoxia and tumor stroma selectivity of the small molecule imagining agent.

Cell Uptake Analysis. Cell uptake study was performed RAW264.7 cell line having FR expression (*J Crohns Colitis.* 2018 Jan. 24; 12(2):217-229) with 100 μM $CoCl_2$ condition. Cells were treated them with 5 nM concentration of FA-CAIX-Rhod or with free Rhodamine for 1 h, cells were washed with PBS and images were collected in 20× objective with 2× zoom in confocal microscope with excitation (525 nm) and emission (575 nm). The nucleus was stained with Hoechst 33342 and merged with rhodamine images.

Cell uptake study in folate receptor (overexpressed in tumor stroma) and CAIX (overexpressed in tumor hypoxia) positive activated RAW 264.7 cell indicates that (FIG. 44A) FA-CAIX-Rhodamine has higher cell accumulation compared to (FIG. 44B) free rhodamine. Brighter red color suggests there is higher cell uptake.

FIG. 45 shows another hypoxia (targeting CAIX) and tumor stroma (folate receptor) targeting small molecule, this one conjugated with near infrared dye (S0456), (namely FA-CAIX-S0456) for imaging and detection of tumor, pre-tumor, polyps and imaging guided surgery.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in RCC cell killing according to a protocol utilized within the current disclosure.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the Examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed:

1. A rod-shaped encapsulated nanoparticle, oligomicelle, or nanomicelle comprising:
   CARP-1 functional mimetic (CFM) 4.16 (CFM-4.16);
   a carbonic anhydrase-IX (CAIX) targeting ligand;
   a folate receptor targeting ligand; and
   one or more polymer(s) selected from the group consisting of: DBCO-conjugated vitamin E TPSG, SMA- TPGS, 2-hydroxypropyl-β-cyclodextrin (HP-β-CD), sulfobutylether-β-cyclodextrin (SBE-β-CD), phosphatidylethanolamine (PC), ceramide, poloxamer 407, and PLA-PEG.

2. The rod-shaped encapsulated nanoparticle, oligomicelle, or nanomicelle of claim 1 wherein;
the CAIX targeting ligand is ATZ; and/or
the folate receptor targeting ligand is folic acid.

3. The rod-shaped encapsulated nanoparticle, oligomicelle, or nanomicelle of claim 1, comprising:
17% to 30% CFM-4.16;
a styrene maleic anhydride (SMA)—vitamin E tocopheryl polyethylene glycol succinate (TPGS) co-polymer; and
one or more of:
the CAIX targeting ligand acetazolamide (ATZ);
the folate receptor targeting ligand folic acid;
both ATZ and folic acid;
one or more of sorafenib, everolimus, and/or cabozantinib; and/or
a tumor cell stimuli-responsive linker.

4. A pharmaceutical composition comprising an encapsulated nanoparticle, oligomicelle, or nanomicelle of claim 1.

5. A method, comprising administering a pharmaceutical composition comprising the encapsulated nanoparticle, oligomicelle, or nanomicelle of claim 1 to a solid tumor in a subject.

6. The method of claim 5, wherein the administering:
is a prophylactic treatment and/or a therapeutic treatment; and/or
overcomes drug resistance in the subject in need thereof.

7. The method of claim 5, wherein the solid tumor is renal cell carcinoma (RCC).

8. An imaging composition comprising the encapsulated nanoparticle, oligomicelle, or nanomicelle of claim 1.

9. A method, comprising visualizing a solid tumor in a subject using the imaging composition of claim 8.

10. A method of treating a subject with a solid tumor exhibiting hypoxia and/or stromal components, comprising administering to the subject the encapsulated nanoparticle, oligomicelle, or nanomicelle of claim 1.

* * * * *